United States Patent
Dahlgren et al.

(10) Patent No.: US 10,968,236 B2
(45) Date of Patent: *Apr. 6, 2021

(54) TYK2 INHIBITORS AND USES THEREOF

(71) Applicant: Nimbus Lakshmi, Inc., Cambridge, MA (US)

(72) Inventors: Markus Dahlgren, Stratford, CT (US); Jeremy Robert Greenwood, Brooklyn, NY (US); Geraldine C. Harriman, Charlestown, RI (US); Joshua Jahmil Kennedy-Smith, New York, NY (US); Craig E. Masse, Cambridge, MA (US); Donna L. Romero, Chesterfield, MO (US); Mee Shelley, Tigard, OR (US); Ronald T. Wester, Ledyard, CT (US)

(73) Assignee: Nimbus Lakshmi, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/271,503

(22) Filed: Feb. 8, 2019

(65) Prior Publication Data

US 2019/0248810 A1  Aug. 15, 2019

Related U.S. Application Data

(60) Division of application No. 15/590,523, filed on May 9, 2017, now Pat. No. 10,253,046, which is a continuation of application No. 15/054,594, filed on Feb. 26, 2016, now abandoned.

(60) Provisional application No. 62/126,125, filed on Feb. 27, 2015.

(51) Int. Cl.
| | |
|---|---|
| *C07D 519/00* | (2006.01) |
| *C07F 5/02* | (2006.01) |
| *A61P 35/00* | (2006.01) |
| *A61P 37/00* | (2006.01) |
| *C07D 471/04* | (2006.01) |
| *C07D 487/04* | (2006.01) |

(52) U.S. Cl.
CPC ............ *C07D 519/00* (2013.01); *A61P 35/00* (2018.01); *A61P 37/00* (2018.01); *C07D 471/04* (2013.01); *C07D 487/04* (2013.01); *C07F 5/025* (2013.01); *C07F 5/027* (2013.01)

(58) Field of Classification Search
CPC .................................................. C07D 519/00
See application file for complete search history.

(56) References Cited

U.S. PATENT DOCUMENTS

| | | |
|---|---|---|
| 4,650,750 A | 3/1987 | Giese |
| 4,709,016 A | 11/1987 | Giese |
| 5,360,819 A | 11/1994 | Giese |
| 5,516,931 A | 5/1996 | Giese et al. |
| 5,602,273 A | 2/1997 | Giese et al. |
| 5,604,104 A | 2/1997 | Giese et al. |
| 5,610,020 A | 3/1997 | Giese et al. |
| 5,650,270 A | 7/1997 | Giese et al. |
| 7,390,799 B2 | 6/2008 | Bruncko et al. |
| 8,138,347 B2 | 3/2012 | Knight et al. |
| 8,440,689 B2 | 5/2013 | Arikawa et al. |
| 9,340,540 B2 | 5/2016 | Masse et al. |
| 10,023,571 B2 | 7/2018 | Masse et al. |
| 2004/0235867 A1 | 11/2004 | Bilodeau et al. |
| 2007/0112038 A1 | 5/2007 | Marlow et al. |
| 2010/0210623 A1 | 8/2010 | Guerin et al. |
| 2011/0152273 A1 | 6/2011 | Arikawa et al. |
| 2013/0034616 A1 | 2/2013 | Storck et al. |
| 2013/0090336 A1 | 4/2013 | Bourke et al. |
| 2013/0096104 A1 | 4/2013 | Lai et al. |
| 2013/0116260 A1 | 5/2013 | Arikawa et al. |
| 2013/0245031 A1 | 9/2013 | Arikawa et al. |
| 2018/0134700 A1 | 5/2018 | Greenwood et al. |
| 2018/0155349 A1 | 6/2018 | Greenwood et al. |
| 2018/0258086 A1 | 9/2018 | Greenwood et al. |
| 2019/0031664 A1 | 1/2019 | Masse et al. |

FOREIGN PATENT DOCUMENTS

| | | |
|---|---|---|
| JP | 2013032343 | 2/2013 |
| WO | 2001042246 | 6/2001 |
| WO | 2002088112 | 11/2002 |
| WO | 2003063794 | 8/2003 |
| WO | 2004019973 | 3/2004 |
| WO | 2004089925 | 10/2004 |
| WO | 2004106328 | 12/2004 |
| WO | 2005007623 | 1/2005 |
| WO | 2005051300 | 6/2005 |
| WO | 2005056524 | 6/2005 |
| WO | 2005113554 | 12/2005 |
| WO | 2006078846 | 7/2006 |
| WO | 2006122806 | 11/2006 |
| WO | 2007016176 | 2/2007 |
| WO | 2007044729 | 4/2007 |

(Continued)

OTHER PUBLICATIONS

Choy "Clinical significance of Janus Kinase inhibitor selectivity" Rheumatology 2018, pp. 1-10.*
Barnes "Kinases as Novel Therapeutic Targets in Asthma and Chronic Obstructive Pulmonary Disease" Pharmacological Reviews 68:788-815, Jul. 2016.*
Thoma "Selective inhibitors of the Janus kinase Jak3—Are they effective?" Bioorganic & Medicinal Chemistry Letters 24 (2014) 4617-462.*
Lin "A Novel Selective JAK2 Inhibitor Identified Using Pharmacological Interactions" Frontiers in Pharmacology Dec. 2018 | vol. 9 | Article 1379 pp. 1-14.*
O'Shea "Janus kinase Inhibitors in autoimmune diseases" Ann Rheum Dis. Apr. 2013 ; 72(0 2): ii111-ii115.*

(Continued)

*Primary Examiner* — David K O'Dell
(74) *Attorney, Agent, or Firm* — Andrea L. C. Reid; Paul R. Fleming; Dechert LLP

(57) ABSTRACT

The present invention provides compounds, compositions thereof, and methods of using the same for the inhibition of TYK2, and the treatment of TYK2-mediated disorders.

14 Claims, No Drawings

(56) References Cited

FOREIGN PATENT DOCUMENTS

| WO | 2007053452 | 5/2007 |
|---|---|---|
| WO | 2007070514 | 6/2007 |
| WO | 2007084786 | 7/2007 |
| WO | 2007129161 | 11/2007 |
| WO | 2008039218 | 4/2008 |
| WO | 2008109943 | 9/2008 |
| WO | 2008118802 | 10/2008 |
| WO | 2009114512 | 9/2009 |
| WO | 2011079051 | 6/2011 |
| WO | 2011090760 | 7/2011 |

OTHER PUBLICATIONS

Liang "Lead Optimization of a 4-Aminopyridine Benzamide Scaffold to Identify Potent, Selective, and Orally Bioavailable TYK2 Inhibitors" J. Med. Chem. 2013, 56, 4521-4536.*

Vardiman "The World Health Organization (WHO) classification of the myeloid neoplasms" Blood (2002), 100(7), 2292-2302.*

Pui "Treatment of Acute Lymphoblastic Leukemia" New England Journal of Medicine 2006, 354, 166-78.*

FS14 Myelofibrosis Facts I p. 1 Revised Apr. 2012, pp. 1-9.*

Ocana, A. "Preclinical development of molecular targeted agents for cancer" Nat. Rev. Clin. Oncol. 2011, 8, 200-209.*

Johnson, et. al. "Relationships between drug activity in NCI preclinical in vitro and in vivo models and early clinical trials." British Journal of Cancer 2001, 84, 1424-1431.*

Makrilakis "Pathophysiology of Type 2 diabetes" Chapter 3 in Diabetes in Clinical Practice: Questions and Answers from Case Studies, Nicholas Katsilambros et al. eds. John Wiley & Sons: 2006, pp. 43-58.*

University of Cambridge John van Geest Centre for Brain Repair School of Clinical Medicine "Alzheimer's disease and tauopathy" Online "http://www.brc.cam.ac.uk/research/alzheimers-disease-and-tauopathy/" accessed Sep. 10, 2015.*

Tomohiro Chiba "Emerging Therapeutic Strategies in Alzheimer's Disease" Intech 2013, 181-225.*

Wisclicenus, J. "Adolph Strecker's Short Textbook of Organic Chemistry" 1881, Spottiswoode: London, pp. 38-39.*

Teruel "The genetic basis of systemic lupus erythematosus: What are the risk factors and what have we learned" Journal of Autoimmunity 74 (2016) 161e175.*

Lin "Off-target toxicity is a common mechanism of action of cancer drugs undergoing clinical trials" Sci. Transl. Med. 11, eaaw8412 (2019) Sep. 11, 2019.*

Pociot "Type 1 diabetes genome-wide association studies: not to be lost in translation" Clinical & Translational Immunology (2017) 6, e162.*

Nagafuchi "TYK2 Promoter Variant and Diabetes Mellitus in the Japan" EBioMedicine (2015), 2(7), 744-9.*

Chaichian "Targeted Therapies in Systemic Lupus Erythematosus: A State-of-the-Art Review" J Clin Cell Immunol 2013, S6, 1-8.*

Skog "Revisiting the notion of type 1 diabetes being a T-cell-mediated autoimmune disease" Curr Opin Endocrinol Diabetes Obes 2013, 20:118-123.*

Mahieu "A critical review of clinical trials in systemic lupus erythematosus" Lupus (2016) 25, 1122-1140.*

McDonald-Hyman "Advances and challenges in immunotherapy for solid organ and hematopoietic stem cell transplantation" ScienceTranslationalMedicine Mar. 25, 2015 vol. 7 Issue 280, 2-14.*

Georg Pilz, "Modern multiple sclerosis treatment—what is approved, what is on the horizon" Drug Discovery Today Dec. 2008 , vol. 13, Nos. 23/24 1013-1025.*

Bieber "Allelic variation in the Tyk2 and EGF genes as potential genetic determinants of CNS repair" Proceedings of the National Academy of Sciences of the United States of America (2010), 107(2), 792-797.*

"Post-Transplant Lymphoproliferative Disease" NORD Rare Disease Database, 2018 pp. 1-16.*

Bacon et al., "Interleukin 12 (IL-12) induces tyrosine phosphorylation of JAK2 and TYK2: differential use of Janus family kinases by IL-2 and IL-12," The Journal of Experimental Medicine, vol. 181, No. 1, Jan. 1995 (pp. 399-404).

Ban et al., "Replication analysis identifies TYK2 as a multiple sclerosis susceptibility factor," European Journal of Human Genetics, vol. 17, Mar. 2009 (pp. 1309-1313).

Berge et al., "Pharmaceutical Salts," Journal of Pharmaceutical Sciences, vol. 66, No. 1, Jan. 1977 (pp. 1-19).

Cho et al., "Genomics and the multifactorial nature of human auto-immune disease," The New England Journal of Medicine, vol. 365, No. 17, Oct. 27, 2011 (pp. 1612-1623).

Cortes et al., "Identification of multiple risk variants for ankylosing spondylitis through high-density genotyping of immune-related loci," Nature Genetics, vol. 45, No. 7, Jul. 2013 (25 pages).

Duerr et al., "A Genome-Wide Association Study Identifies IL23R as an Inflammatory Bowel Disease Gene," Science, vol. 314, No. 5804, Dec. 2006 (pp. 1461-1463).

Finbloom et al., "IL-10 induces the tyrosine phosphorylation of tyk2 and Jak1 and the differential assembly of STAT1 and STAT3 complexes in human T cells and monocytes," The Journal of Immunology, vol. 155, No. 3, Aug. 1995 (pp. 1079-1090).

Fontan et al. "Discovering What Makes STAT Signaling TYK in T-ALL," Cancer Discovery, vol. 3, No. 5, May 2013 (pp. 494-496).

Graham et al., "Association of NCF2, IKZF1, IRF8, IFIH1, and TYK2 with Systemic Lupus Erythematosus," PLoS Genetics, vol. 7, No. 10, Oct. 2011 (9 pages).

Harel et al., "Pharmacologic inhibition of JAK-STAT signaling promotes hair growth," Science Advances, vol. 1, No. 9, Oct. 2015 (12 pages).

International Search Report and Written Opinion issued by the United States Patent and Trademark Office as International Searching Authority for International Application No. PCT/US2015/018071 dated Jun. 3, 2015 (7 pages).

International Search Report and Written Opinion issued by the United States Patent and Trademark Office as International Searching Authority for International Patent Application No. PCT/US2016/019724 dated May 3, 2016 (10 pages).

Ishizaki et al., "Tyk2 deficiency protects joints against destruction in anti-type II collagen antibody-induced arthritis in mice," International Immunology, vol. 23, No. 9, Sep. 2011 (pp. 575-582).

Ishizaki et al., "Tyk2 is a therapeutic target for psoriasis-like skin inflammation," International Immunology, vol. 26, No. 5, May 2014 (11 pages).

Jiang et al., "3,5-Disubstituted quinolones as novel c-Jun N-terminal kinase inhibitors," Bioorganic & Medicinal Chemistry Letters, vol. 17, Aug. 2007 (pp. 6378-6382).

Liang et al., "Lead identification of novel and selective TYK2 inhibitors," European Journal of Medicinal Chemistry, vol. 67, May 2013 (pp. 175-187).

Liang et al., "Lead Optimization of a 4-Aminopyridine Benzamide Scaffold to Identify Potent, Selective, and Orally Bioavailable TYK2 Inhibitors," Journal of Medicinal Chemistry, vol. 56, May 2013 (pp. 4521-4536).

Liu et al. "Synthesis and SAR of 1,9-dihydro-9-hydroxypyrazolo[3,4-b]quinolin-4-ones as novel, selective c-Jun N-terminal kinase inhibitors," Bioorganic & Medicinal Chemistry Letters, vol. 16, Mar. 2006 (pp. 2590-2594).

Michelotti et al., "Two classes of p38a MAP kinase inhibitors having a common diphenylether core but exhibiting divergent binding modes," Bioorganic & Medicinal Chemistry Letters, vol. 15, Sep. 2005 (pp. 5274-5279).

Miyazaki et al., "Design and effective synthesis of novel templates, 3,7-diphenyl-4-amino-thieno and furo-[3,2-c] pyridines as protein kinase inhibitors and in vitro evaluation targeting angiogenetic kinases," Bioorganic & Medicinal Chemistry Letter, vol. 17, No Month Listed 2007 (pp. 250-254).

Mulvihill et al., "Novel 2-phenylquinolin-7-yl-derived imidazo[1,5-α]pyrazines as potent insulin-like growth factor-I receptor (IGF-IR) inhibitors," Bioorganic & Medicinal Chemistry, vol. 16, No Month Listed 2008 (pp. 1359-1375).

(56) References Cited

OTHER PUBLICATIONS

Oyamada et al., "Tyrosine Kinase 2 Plays Critical Roles in the Pathogenic CD4 T Cell Responses for the Development of Experimental Autoimmune Encephalomyelitis," The Journal of Immunology, vol. 183, No. 11, Dec. 2009 (pp. 1539-7546).

Parham et al., "A receptor for the heterodimeric cytokine IL-23 is composed of IL-12Rβ1 and a novel cytokine receptor subunit, IL-23R," The Journal of Immunology, vol. 168, No. 11, Jun. 2002 (pp. 5699-5708).

Ramirez et al "Defining causative factors contributing in the activation of hedgehog signaling in diffuse large B-cell lymphoma," Leukemia Research, vol. 36, No. 10, Oct. 2012 (15 pages).

Remmers et al., "Genome-wide association study identifies variants in the MHC class I, IL10, and IL23R-IL12RB2 regions associated with Behçet's disease," Nature Genetics, vol. 42, No. 8, Aug. 2010 (20 pages).

Rostovetsev et al., "A Stepwise Huisgen Cycloaddition Process: Copper(I)-Catalyzed Regioselective "Ligation" of Azides and Terminal Alkynes," Angewandte Chemie International Edition, vol. 41, No. 14, Jul. 2002 (pp. 2596-2599).

Sanda et al. "TYK2-STAT1-BCL2 Pathway Dependence in T-Cell Acute Lymphoblastic Leukemia," Cancer Discovery, vol. 3, No. 5, May 2013 (pp. 564-577).

Sigurdsson et al., "Polymorphisms in the Tyrosine Kinase 2 and Interferon Regulatory Factor 5 Genes are Associated with Systemic Lupus Erythematosus," American Journal of Human Genetics, vol. 76, No. 3, Mar. 2005 (pp. 528-537).

Simma et al. "Identification of an Indispensable Role for Tyrosine Kinase 2 in CTL-Mediated Tumor Surveillance," Cancer Research, vol. 69, No. 1, Jan. 2009 (pp. 203-211).

Stahl et al., "Association and activation of Jak-Tyk kinases by CNTF-LIF-OSM-IL-6 beta receptor components," Science, vol. 263, No. 5143, Jan. 1994 (pp. 92-95).

Strange et al., "A genome-wide association study identifies new psoriasis susceptibility loci and an interaction between HLA-C and ERAP1," Nature Genetics, vol. 42, No. 11, Nov. 2010 (16 pages).

Sun et al., "Carbohydrate and Protein Immobilization onto Solid Surfaces by Sequential Diels-Alder and Azide-Alkyne Cycloadditions," Bioconjugate Chemistry, vol. 17, No. 1, Jan. 2006 (pp. 52-57).

Velazquez et al., "A protein tyrosine kinase in the interferon αβ signaling pathway," Cell, vol. 70, No. 2, Jul. 1992 (pp. 313-322).

Wan et al. "Tyk2/STAT3 Signaling Mediates β-Amyloid-Induced Neuronal Cell Death: Implications in Alzheimer's Disease," The Journal of Neuroscience, vol. 30, No. 20, May 2010 (pp. 6873-6881).

Welham et al., "Interleukin-13 signal transduction in lymphohemopoietic cells: similarities and differences in signal transduction with interleukin-4 and insulin," The Journal of Biological Chemistry, vol. 270, No. 20, May 1995 (pp. 12286-12296).

Wisclicenus, "Adolph Strecker's Short Textbook of Organic Chemistry," Spottiswoode, London, No Month Listed 1881 (pp. 38-39).

Xing et al., "Alopecia areata is driven by cytotoxic T lymphocytes and is reversed by JAK inhibition," Nature Medicine, vol. 20, No. 9, Sep. 2014 (17 pages).

Zhang et al., "Docking protein Gab2 regulates mucin expression and goblet cell hyperplasia through TYK2/STAT6 pathway," The FASEB Journal, vol. 26, No. 11, Nov. 2012 (pp. 4603-4613).

Akahane et al., "Anti-leukaemic activity of the TYK2 selective inhibitor NDI-031301 in T-cell acute lymphoblastic leukaemia," Br J Haematol. 2017; 177(2):271-282.

Dendrou et al., "Resolving TYK2 locus genotype-to-phenotype differences in autoimmunity," Sci Transl Med. 2016; 8 (363):363ra149.

Diogo et al., "TYK2 Protein-Coding Variants Protect against Rheumatoid Arthritis and Autoimmunity, with No Evidence of Major Pleiotropic Effects on Non-Autoimmune Complex Traits," PLoS One. 2015; 10(4):e0122271.

Li et al., "Two common disease-associated TYK2 variants impact exon splicing and TYK2 dosage," PLoS One. 2020; 15(1):e0225289.

Marroqui et al., "TYK2, a Candidate Gene for Type 1 Diabetes, Modulates Apoptosis and the Innate Immune Response in Human Pancreatic ß-Cells," Diabetes. 2015; 64(11):3808-17.

Mero et al., "A rare variant of the TYK2 gene is confirmed to be associated with multiple sclerosis," Eur J Hum Genet. 2010; 18(4):502-4.

Oksenberg, "Decoding multiple sclerosis: an update on genomics and future directions," Expert Rev Neurother. 2013; 13(2 Suppl):11-19.

Watford and O'Shea, "Human tyk2 kinase deficiency: another primary immunodeficiency syndrome," Immunity. 2006; 25(5):695-7.

Westra et al., "Fine-mapping and functional studies highlight potential causal variants for rheumatoid arthritis and type 1 diabetes," Nat Genet. 2018; 50(10):1366-1374.

* cited by examiner

TYK2 INHIBITORS AND USES THEREOF

CROSS-REFERENCE TO RELATED APPLICATIONS

The present application is a division of U.S. patent application Ser. No. 15/590,523, filed May 9, 2017, now issued as U.S. Pat. No. 10,253,046, which is a continuation of U.S. patent application Ser. No. 15/054,594, filed Feb. 26, 2016, which claims the benefit of U.S. Provisional Application No. 62/126,125, filed Feb. 27, 2015, the entirety of each of which is incorporated herein by reference.

TECHNICAL FIELD OF THE INVENTION

The present invention relates to compounds and methods useful for inhibiting non-receptor tyrosine-protein kinase 2 ("TYK2"), also known as Tyrosine kinase 2. The invention also provides pharmaceutically acceptable compositions comprising compounds of the present invention and methods of using said compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is the protein kinase family.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxins, and $H_2O_2$), cytokines (e.g., interleukin-1 (IL-1), interleukin-8 (IL-8), and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by kinase-mediated events. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

It has now been found that compounds of this invention, and pharmaceutically acceptable compositions thereof, are effective as inhibitors of TYK2 kinase.

Compounds of the present invention, and pharmaceutically acceptable compositions thereof, are useful for treating a variety of diseases, disorders or conditions, associated with regulation of signaling pathways implicating TYK2 kinases. Such diseases, disorders, or conditions include those described herein.

Compounds provided by this invention are also useful for the study of TYK2 enzymes in biological and pathological phenomena; the study of intracellular signal transduction pathways occurring in bodily tissues; and the comparative evaluation of new TYK2 inhibitors or other regulators of kinases, signaling pathways, and cytokine levels in vitro or in vivo.

DETAILED DESCRIPTION OF CERTAIN EMBODIMENTS

1. General Description of Certain Embodiments of the Invention

Compounds of the present invention, and compositions thereof, are useful as inhibitors of TYK2 protein kinase.

The binding pocket of TYK2 contains a plurality of hydration sites, each of which is occupied by a single molecule of water. Each of these water molecules has a stability rating associated with it. As used herein, the term "stability rating" refers to a numerical calculation which incorporates the enthalpy, entropy, and free energy values associated with each water molecule. This stability rating allows for a measurable determination of the relative stability of water molecules that occupy hydration sites in the binding pocket of TYK2.

Water molecules occupying hydration sites in the binding pocket of TYK2 having a stability rating of >2.5 kcal/mol are referred to as "unstable waters."

Without wishing to be bound by any particular theory, it is believed that displacement or disruption of an unstable water molecule (i.e., a water molecule having a stability rating of >2.5 kcal/mol), or replacement of a stable water (i.e., a water molecule having a stability rating of <1 kcal/mol), by an inhibitor results in tighter binding of that inhibitor. Accordingly, inhibitors designed to displace one or more unstable water molecules (i.e., those unstable water molecules not displaced by any known inhibitor) will be a tighter binder and, therefore, more potent inhibitor as compared to an inhibitor that does not displace unstable water molecules.

It was surprisingly found that provided compounds displace or disrupt one or more unstable water molecules. In some embodiments, a provided compound displaces or disrupts at least two unstable water molecules.

In certain embodiments, the present invention provides a compound of formula I:

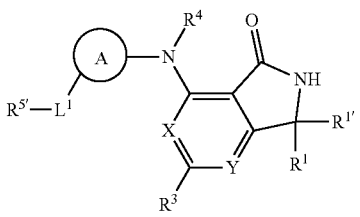

or a pharmaceutically acceptable salt thereof, wherein each of X, Y, Ring A, $L^1$, $R^1$, $R^{1'}$, $R^3$, $R^4$, and $R^5$ is as defined below and described in embodiments herein, both singly and in combination.

In certain embodiments, the present invention provides a compound of formula II:

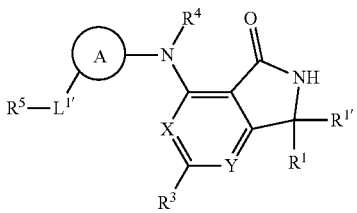

or a pharmaceutically acceptable salt thereof, wherein each of X, Y, Ring A, $L^{1'}$, $R^1$, $R^{1'}$, $R^3$, $R^4$, and $R^5$ is as defined below and described in embodiments herein, both singly and in combination.

In certain embodiments, the present invention provides a compound of formula III:

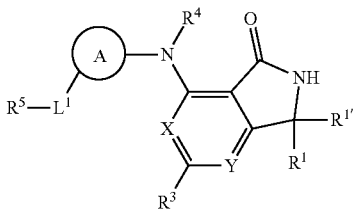

or a pharmaceutically acceptable salt thereof, wherein each of X, Y, Ring A, $L^1$, $R^1$, $R^{1'}$, $R^3$, $R^4$, and $R^5$ is as defined below and described in embodiments herein, both singly and in combination.

In certain embodiments, the present invention provides a compound of formula IV:

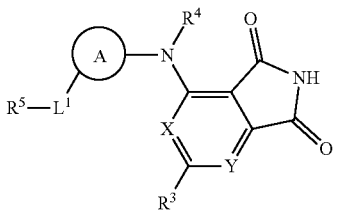

or a pharmaceutically acceptable salt thereof, wherein each of X, Y, Ring A, $L^1$, $R^3$, $R^4$, and $R^5$ is as defined below and described in embodiments herein, both singly and in combination.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

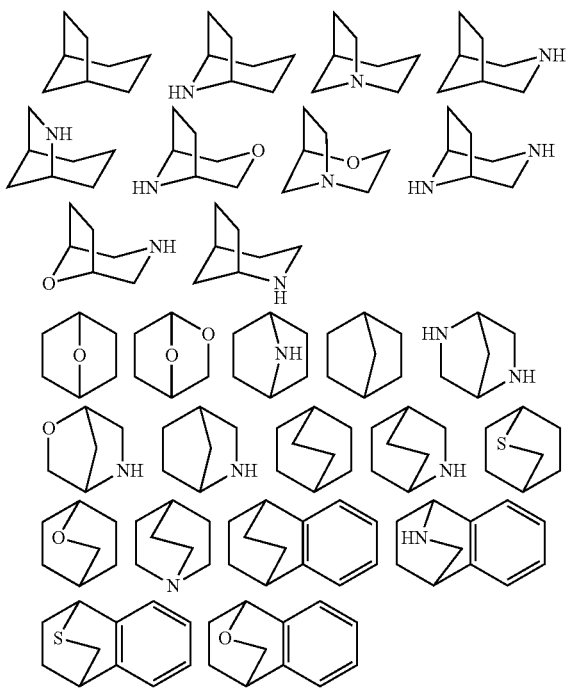

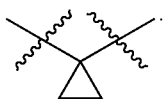

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH═CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ_2$; —N(R$^\circ$)C(S)NR$^\circ_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ_3$; —(CH$_2$)$_{0-4}$OC(O)R$^\circ$; —OC(O)(CH$_2$)$_{0-4}$SR$^\circ$; —SC(S)SR$^\circ$; —(CH$_2$)$_{0-4}$SC(O)R$^\circ$; —(CH$_2$)$_{0-4}$C(O)NR$^\circ_2$; —C(S)NR$^\circ_2$; —C(S)SR$^\circ$; —SC(S)SR$^\circ$, —(CH$_2$)$_{0-4}$OC(O)NR$^\circ_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ_2$; —(CH$_2$)$_{0-4}$S(O)R$^\circ$; —N(R$^\circ$)S(O)$_2$NR$^\circ_2$; —N(R$^\circ$)S(O)$_2$R$^\circ$; —N(OR$^\circ$)R$^\circ$; —C(NH)NR$^\circ_2$; —P(O)$_2$R$^\circ$; —P(O)R$^\circ_2$; —OP(O)R$^\circ_2$; —OP(O)(OR$^\circ$)$_2$; SiR$^\circ_3$; —(C$_{1-4}$ straight or branched alkylene)O—N(R$^\circ$)$_2$; or —(C$_{1-4}$ straight or branched)alkylene)C(O)O—N(R$^\circ$)$_2$, wherein each R$^\circ$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include ═O and ═S.

Suitable divalent substituents on a saturated carbon atom of an "optionally substituted" group include the following: ═O, ═S, ═NNR*$_2$, ═NNHC(O)R*, ═NNHC(O)OR*, ═NNHS(O)$_2$R*, ═NR*, ═NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(halon$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, —R˚, -(haloR˚), —OH, —OR˚, —O(haloR˚), —CN, —C(O)OH, —C(O)OR˚, —NH$_2$, —NHR˚, —NR˚$_2$, or —NO$_2$, wherein each R˚ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C— or $^{14}$C-enriched carbon are within the scope of this invention. Such compounds are useful, for example, as analytical tools, as probes in biological assays, or as therapeutic agents in accordance with the present invention. In certain embodiments, a warhead moiety, $R^1$, of a provided compound comprises one or more deuterium atoms. In certain embodiments, Ring B of a provided compound may be substituted with one or more deuterium atoms.

As used herein, the term "inhibitor" is defined as a compound that binds to and/or inhibits TYK2 with measurable affinity. In certain embodiments, an inhibitor has an IC$_{50}$ and/or binding constant of less than about 50 μM, less than about 1 μM, less than about 500 nM, less than about 100 nM, less than about 10 nM, or less than about 1 nM.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}$P, $^{33}$P, $^{35}$S, or $^{14}$C), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in a TYK2 protein kinase activity between a sample comprising a compound of the present invention, or composition thereof, and a TYK2 protein kinase, and an equivalent sample comprising an TYK2 protein kinase, in the absence of said compound, or composition thereof.

3. Description of Exemplary Embodiments

As described above, in certain embodiments, the present invention provides a compound of formula I:

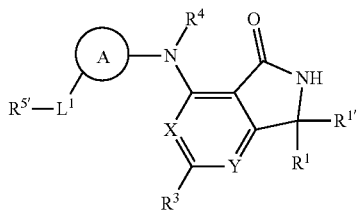

I or a pharmaceutically acceptable salt thereof, wherein:
each of X and Y is independently $=C(R^6)—$ or $=N—$, provided that X and Y are not simultaneously $=C(R^6)—$;

Ring A is phenyl; a 5-6 membered heteroaryl ring having 1-4 heteroatoms independently selected from nitrogen, oxygen, and sulfur; a 3-6 membered saturated or partially unsaturated heterocyclic ring having 1-2 heteroatoms independently selected from nitrogen, oxygen, and sulfur; or a 4-6 membered saturated or partially unsaturated carbocyclic ring; wherein Ring A is substituted with m instances of $R^7$;

each of $R^1$ and $R^{1'}$ is independently hydrogen, $—R^2$, halogen, $—CN$, $—NO_2$, $—OR$, $—SR$, $—NR_2$, $—S(O)_2R$, $—S(O)_2NR_2$, $—S(O)R$, $—C(O)R$, $—C(O)OR$, $—C(O)NR_2$, $—C(O)N(R)OR$, $—OC(O)R$, $—OC(O)NR_2$, $—N(R)C(O)OR$, $—N(R)C(O)R$, $—N(R)C(O)NR_2$, or $—N(R)S(O)_2R$; or $R^1$ and $R^{1'}$ are taken together to form an oxo group or with their intervening atoms to form an optionally substituted 3-7 membered spiro-fused ring having 0-2 heteroatoms independently selected from nitrogen, oxygen, and sulfur;

each $R^2$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$R^3$ is a group selected from $C_{1-6}$ alkyl, phenyl, a 3-7 membered saturated or partially unsaturated carbocyclic ring, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein $R^3$ is substituted with n instances of $R^8$;

$R^4$ is hydrogen or optionally substituted $C_{1-6}$ aliphatic; or $R^4$ and one instance of $R^7$ are taken together with their intervening atoms to form a 5-6 membered partially unsaturated or aromatic ring having 1-4 heteroatoms independently selected from nitrogen, oxygen and sulfur;

$R^{5'}$ is an 8-10 membered saturated or partially unsaturated heterocyclic ring having 1-2 heteroatoms independently selected from nitrogen, oxygen, and sulfur; wherein $R^5$ is substituted with p instances of $R^9$;

each instance of $R^6$, $R^7$, $R^8$, $R^{10}$, and $R^{11}$ is independently $—R^2$, halogen, $—CN$, $—NO_2$, $—OR$, $—SR$, $—NR_2$, $—S(O)_2R$, $—S(O)_2NR_2$, $—S(O)R$, $—C(O)R$, $—C(O)OR$, $—C(O)NR_2$, $—C(O)N(R)OR$, $—OC(O)R$, $—OC(O)NR_2$, $—N(R)C(O)OR$, $—N(R)C(O)R$, $—N(R)C(O)NR_2$, or $—N(R)S(O)_2R$;

each instance of $R^9$ is independently oxo, $C_{1-6}$ hydroxyaliphatic, $—R^2$, halogen, $—CN$, $—NO_2$, $—OR$, $—SR$, $—NR_2$, $—S(O)_2R$, $—S(O)_2NR_2$, $—S(O)R$, $—C(O)R$, $—C(O)OR$, $—C(O)NR_2$, $—C(O)N(R)OR$, $—OC(O)R$, $—OC(O)NR_2$, $—N(R)C(O)OR$, $—N(R)C(O)R$, $—N(R)C(O)NR_2$, or $—N(R)S(O)_2R$;

$L^1$ is a covalent bond or a $C_{1-6}$ bivalent saturated or unsaturated, straight or branched hydrocarbon chain wherein one or two methylene units of the chain are optionally and independently replaced by $—C(R^{10})_2—$, $—N(R)—$, $—N(R)C(O)—$, $—C(O)N(R)—$, $—N(R)S(O)_2—$, $—S(O)_2N(R)—$, $—O—$, $—C(O)—$, $—OC(O)—$, $—C(O)O—$, $—S—$, $—S(O)—$ or $—S(O)_2—$; or $L^1$ and one instance of $R^7$ are taken together with their intervening atoms to form a 5-10 membered partially unsaturated or aromatic ring having 1-4 heteroatoms independently selected from nitrogen, oxygen and sulfur; wherein said ring is substituted by q instances of R$^{11}$; and R$^5$ is attached to any position of the ring formed by L$^1$ and R$^7$;

m is 0-4;
n is 0-4;
p is 0-6;
q is 0-4; and
each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of formula II:

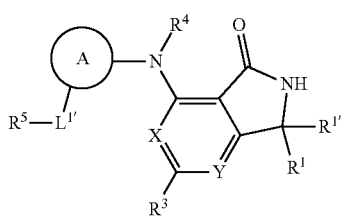

II or a pharmaceutically acceptable salt thereof, wherein:
each of X and Y is independently =C(R$^6$)— or =N—, provided that X and Y are not simultaneously =C(R$^6$)—;
Ring A is phenyl; a 5-6 membered heteroaryl ring having 1-4 heteroatoms independently selected from nitrogen, oxygen, and sulfur; a 3-6 membered saturated or partially unsaturated heterocyclic ring having 1-2 heteroatoms independently selected from nitrogen, oxygen, and sulfur; or a 4-6 membered saturated or partially unsaturated carbocyclic ring; wherein Ring A is substituted with m instances of R$^7$;
each of R$^1$ and R$^{1'}$ is independently hydrogen, —R$^2$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R; or
R$^1$ and R$^{1'}$ are taken together to form an oxo group or with their intervening atoms to form an optionally substituted 3-7 membered spiro-fused ring having 0-2 heteroatoms independently selected from nitrogen, oxygen, and sulfur;
each R$^2$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
R$^3$ is a group selected from C$_{1-6}$ alkyl, phenyl, a 3-7 membered saturated or partially unsaturated carbocyclic ring, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein R$^3$ is substituted with n instances of R$^8$;
R$^4$ is hydrogen or optionally substituted C$_{1-6}$ aliphatic; or
R$^4$ and one instance of R$^7$ are taken together with their intervening atoms to form a 5-6 membered partially unsaturated or aromatic ring having 1-4 heteroatoms independently selected from nitrogen, oxygen and sulfur;
R$^5$ is a group selected from hydrogen, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, phenyl, a 3-10 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein R$^5$ is substituted with p instances of R$^9$;
each instance of R$^6$, R$^7$, R$^8$, R$^{10}$, and R$^{11}$ is independently —R$^2$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;
each instance of R$^9$ is independently oxo, C$_{1-6}$ hydroxyaliphatic, —R$^2$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;
L$^{1'}$ is a C$_{1-6}$ bivalent saturated or unsaturated, straight or branched hydrocarbon chain wherein at least one methylene unit of the chain is replaced by —C(R$^{10}$)$_2$—; and one or two additional methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—; or
L$^{1'}$ and one instance of R$^7$ are taken together with their intervening atoms to form a 5-10 membered partially unsaturated or aromatic ring having 1-4 heteroatoms independently selected from nitrogen, oxygen and sulfur; wherein said ring is substituted by q instances of R$^{11}$; and R$^5$ is attached to any position of the ring formed by L$^{1'}$ and R$^7$;

m is 0-4;
n is 0-4;
p is 0-6;
q is 0-4; and
each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of formula III':

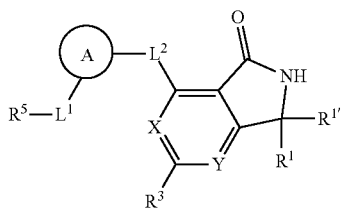

or a pharmaceutically acceptable salt thereof, wherein:
each of X and Y is independently =C(R$^6$)— or =N—, provided that X and Y are not simultaneously =C(R$^6$)—;
Ring A is phenyl; a 5-6 membered heteroaryl ring having 1-4 heteroatoms independently selected from nitrogen, oxygen, and sulfur; a 3-6 membered saturated or partially unsaturated heterocyclic ring having 1-2 heteroatoms independently selected from nitrogen, oxygen, and sulfur; or a 4-6 membered saturated or partially unsaturated carbocyclic ring; wherein Ring A is substituted with m instances of R$^7$;
each of R$^1$ and R$^{1'}$ is independently hydrogen, —R$^2$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R; or
R$^1$ and R$^{1'}$ are taken together to form an oxo group or with their intervening atoms to form an optionally substituted 3-7 membered spiro-fused ring having 0-2 heteroatoms independently selected from nitrogen, oxygen, and sulfur;
each R$^2$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
R$^3$ is a group selected from C$_{1-6}$ alkyl, phenyl, a 3-7 membered saturated or partially unsaturated carbocyclic ring, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein R$^3$ is substituted with n instances of R$^8$;
R$^{4'}$ and one instance of R$^7$ are taken together with their intervening atoms to form a 5-6 membered partially unsaturated or aromatic ring having 1-4 heteroatoms independently selected from nitrogen, oxygen and sulfur;
R$^5$ is a group selected from halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, phenyl, a 3-10 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein R$^5$ is substituted with p instances of R$^9$;
each instance of R$^6$, R$^7$, R$^8$, R$^{10}$, and R$^{11}$ is independently —R$^2$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;
each instance of R$^9$ is independently oxo, C$_{1-6}$ hydroxyaliphatic, —R$^2$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;
L$^1$ is a covalent bond or a C$_{1-6}$ bivalent saturated or unsaturated, straight or branched hydrocarbon chain wherein one or two methylene units of the chain are optionally and independently replaced by —C(R$^{10}$)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—; or
L$^1$ and one instance of R$^7$ are taken together with their intervening atoms to form a 5-10 membered partially unsaturated or aromatic ring having 1-4 heteroatoms independently selected from nitrogen, oxygen and sulfur; wherein said ring is substituted by q instances of R$^{11}$; and R$^5$ is attached to any position of the ring formed by L$^1$ and R$^7$;
L$^2$ is a C$_{2-6}$ bivalent saturated or unsaturated, straight or branched hydrocarbon chain wherein at least one methylene unit is replaced by —N(R$^4$)—; and one or two additional methylene units of the chain are optionally and independently replaced by —C(R$^{10}$)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—; or
L$^2$ is —N(R$^{4'}$)—;
m is 0-4;
n is 0-4;
p is 0-6;
q is 0-4; and
each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of formula of formula III' wherein L$^2$ is —N(R$^{4'}$)—, thereby forming a compound of formula III:

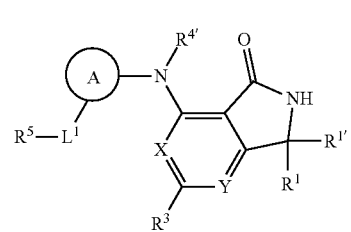

or a pharmaceutically acceptable salt thereof, wherein each of X, Y, Ring A, R$^1$, R$^{1'}$, L$^1$, R$^3$, R$^4$, R$^{4'}$, R$^5$, is as defined above and described in embodiments herein, both singly and in combination.

In certain embodiments, the present invention provides a compound of formula IV:

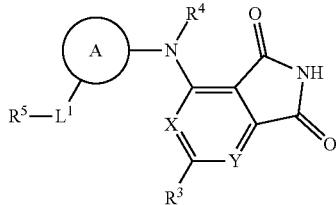

or a pharmaceutically acceptable salt thereof, wherein:
each of X and Y is independently =C($R^6$)— or =N—, provided that X and Y are not simultaneously =C($R^6$)—;
Ring A is phenyl; a 5-6 membered heteroaryl ring having 1-4 heteroatoms independently selected from nitrogen, oxygen, and sulfur; a 3-6 membered saturated or partially unsaturated heterocyclic ring having 1-2 heteroatoms independently selected from nitrogen, oxygen, and sulfur; or a 4-6 membered saturated or partially unsaturated carbocyclic ring; wherein Ring A is substituted with m instances of $R^7$;
each $R^2$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
$R^3$ is a group selected from $C_{1-6}$ alkyl, phenyl, a 3-7 membered saturated or partially unsaturated carbocyclic ring, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein $R^3$ is substituted with n instances of $R^8$;
$R^4$ is hydrogen or optionally substituted $C_{1-6}$ aliphatic; or
$R^4$ and one instance of $R^7$ are taken together with their intervening atoms to form a 5-6 membered partially unsaturated or aromatic ring having 1-4 heteroatoms independently selected from nitrogen, oxygen and sulfur;
$R^5$ is a group selected from halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)$S(O)_2R$, phenyl, a 3-10 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein $R^5$ is substituted with p instances of $R^9$;
each instance of $R^6$, $R^7$, $R^8$, $R^{10}$, and $R^{11}$ is independently —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$;
each instance of $R^9$ is independently oxo, $C_{1-6}$ hydroxyaliphatic, —$R^2$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$;
$L^1$ is a covalent bond or a $C_{1-6}$ bivalent saturated or unsaturated, straight or branched hydrocarbon chain wherein one or two methylene units of the chain are optionally and independently replaced by —C($R^{10})_2$—, —N(R)—, —N(R)C(O)—, —C(O)N(R)—, —N(R)$S(O)_2$—, —$S(O)_2N(R)$—, —O—, —C(O)—, —OC(O)—, —C(O)O—, —S—, —S(O)— or —$S(O)_2$—; or
$L^1$ and one instance of $R^7$ are taken together with their intervening atoms to form a 5-10 membered partially unsaturated or aromatic ring having 1-4 heteroatoms independently selected from nitrogen, oxygen and sulfur; wherein said ring is substituted by q instances of $R^{11}$; and $R^5$ is attached to any position of the ring formed by $L^1$ and $R^7$;
m is 0-4;
n is 0-4;
p is 0-6;
q is 0-4; and
each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

As defined generally above, each of X and Y is =C($R^6$)— or =N—, provided that X and Y are not simultaneously =C($R^6$)—. In some embodiments, both X and Y are =N—. In some embodiments, X is =N—, and Y is =C($R^6$)—. In some embodiments, X is =C($R^6$)—, and Y is =N—.

In some embodiments, each of X and Y is independently =C($R^6$)—, =N—, or =$N^+$(→$O^-$)—, provided that X and Y are not simultaneously =C($R^6$)—. In some embodiments, X is =C($R^6$)—, and Y is =$N^+$(→$O^-$)—.

As defined generally above, Ring A is phenyl; a 5-6 membered heteroaryl ring having 1-4 heteroatoms independently selected from nitrogen, oxygen, and sulfur; or a 3-6 membered saturated or partially unsaturated heterocyclic ring having 1-2 heteroatoms independently selected from nitrogen, oxygen, and sulfur; wherein Ring A is substituted with m instances of $R^7$.

In some embodiments, Ring A is phenyl. In some embodiments, Ring A is a 5-6 membered heteroaryl having 1-4 heteroatoms independently selected from nitrogen, oxygen, and sulfur. Ring A is a 5-membered heteroaryl having 1-4 heteroatoms independently selected from nitrogen, oxygen, and sulfur. In some embodiments, Ring A is a 6-membered heteroaryl having 1-4 nitrogens. In some embodiments, Ring A is pyridyl. In some embodiments, Ring A is pyrazolyl.

One of skill in the art will appreciate that a when Ring A is a 5-6 membered heteroaryl ring, multiple regioisomers are possible. Unless otherwise stated, all regioisomers are intended to be encompassed. In some embodiments, Ring A is 2-pyridyl. In some embodiments, Ring A is 3-pyridyl. In some embodiments, Ring A is 3-pyrazolyl. In some embodiments, Ring A is 4-pyrazolyl.

Likewise, when Ring A is phenyl, multiple attachment points are possible. In some embodiments, when Ring A is phenyl, $L^1$ is para to the point of attachment to the rest of the molecule. In some embodiments, $L^1$ is meta to the point of attachment to the rest of the molecule. In some embodiments, $L^1$ is ortho to the point of attachment to the rest of the molecule. In some embodiments, when Ring A is phenyl, and -$L^1R^5$ taken together is $C_{1-6}$ aliphatic, said -$L^1R^5$ group is para to the point of attachment to the rest of the molecule.

As defined generally above, the n group of formula I is 0-4. In some embodiments, n is 0. In some embodiments, n is 1-4. In certain embodiments, n is 1. In some embodiments, n is 2. In certain embodiments, n is 3. In certain embodiments, n is 4.

As defined generally above, each of $R^1$ and $R^{1'}$ is independently hydrogen, —$R^2$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —N(R)C(O)$NR_2$, or —N(R)$S(O)_2R$; or $R^1$ and $R^{1'}$ are taken together with their intervening atoms to form an optionally substituted 4-7 membered spiro-fused ring having 0-2 heteroatoms independently selected from nitrogen, oxygen, and sulfur.

In certain embodiments, each of $R^1$ and $R^{1'}$ are hydrogen. In some embodiments, each of $R^1$ and $R^{1'}$ is independently —$R^2$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —N(R)C(O)$NR_2$, —N(R)$S(O)_2R$. In certain embodiments, each of $R^1$ and $R^{1'}$ are methyl. In some embodiments, one of $R^1$ and $R^{1'}$ is methyl, and the other is hydrogen. In some embodiments, $R^1$ and $R^{1'}$ are taken together with their intervening atoms to form an optionally substituted 3-7 membered spiro-fused ring having 0-2 heteroatoms independently selected from nitrogen, oxygen, and sulfur. In some embodiments, $R^1$ and $R^{1'}$ are taken together with their intervening atoms to form an optionally substituted 3-7 membered spiro-fused carbocyclic ring. In some embodiments, $R^1$ and $R^{1'}$ are taken together with their intervening atoms to form an optionally substituted spirocyclopropyl ring. In some embodiments, $R^1$ and $R^{1'}$ are taken together with their intervening atoms to form an optionally substituted 3-7 membered spiro-fused heterocyclic ring having 1-2 heteroatoms independently selected from nitrogen, oxygen, and sulfur.

As defined generally above, $R^3$ is a group selected from $C_{1-6}$ alkyl, phenyl, a 3-7 membered saturated or partially saturated carbocyclic ring, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein $R^3$ is substituted with n instances of $R^8$.

In some embodiments, $R^3$ is a group selected from phenyl, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^3$ is phenyl. In some embodiments, when X is =N—, $R^3$ is phenyl.

In some embodiments, $R^3$ is a 3-7 membered saturated or partially unsaturated carbocyclic ring. In some embodiments, $R^3$ is a 3-7 membered saturated or partially unsaturated heterocyclic ring having 1-2 heteroatoms independently selected from nitrogen, oxygen, and sulfur. In some embodiments, $R^3$ is a 5-6 membered saturated heterocyclic ring having 1-2 heteroatoms independently selected from nitrogen, oxygen, and sulfur. In some embodiments $R^3$ is pyrrolidinyl. In some embodiments, $R^3$ is piperidinyl.

In some embodiments, $R^3$ is a 5-6 membered heteroaryl ring having 1-4 heteroatoms independently selected from nitrogen, oxygen, and sulfur. In some embodiments, $R^3$ is pyridinyl. In some embodiments, $R^3$ is a $C_{3-6}$ saturated or partially unsaturated carbocyclic ring. Exemplary $R^3$ groups include those depicted in Table 1.

As defined generally above, $R^4$ is hydrogen or optionally substituted $C_{1-6}$ aliphatic. In some embodiments, $R^4$ is hydrogen. In some embodiments, $R^4$ is optionally substituted $C_{1-6}$ aliphatic. In some embodiments, $R^4$ is unsubstituted $C_{1-6}$ aliphatic. In some embodiments, $R^4$ is optionally substituted $C_{1-6}$ alkyl. In some embodiments, $R^4$ is optionally substituted $C_{3-6}$ cycloalkyl.

As defined generally above, $L^1$ is a covalent bond or a $C_{1-6}$ bivalent saturated or unsaturated, straight or branched hydrocarbon chain wherein one or two methylene units of the chain are optionally and independently replaced by —N(R)—, —N(R)C(O)—, —C(O)N(R)—, —N(R)$S(O)_2$—, —$S(O)_2N(R)$—, —O—, —C(O)—, —OC(O)—, —C(O)O—, —S—, —S(O)— or —$S(O)_2$—; or $L^1$ and one instance of $R^7$ are taken together with their intervening atoms to form a 5-6 membered partially unsaturated or aromatic ring having 1-4 heteroatoms independently selected from nitrogen, oxygen and sulfur; wherein said ring is substituted by q instances of $R^{11}$; and $R^5$ is attached to any position of the ring formed by $L^1$ and $R^7$.

In some embodiments, $L^1$ is a covalent bond or a $C_{1-6}$ bivalent saturated or unsaturated, straight or branched hydrocarbon chain wherein one or two methylene units of the chain are optionally and independently replaced by —N(R)—, —N(R)C(O)—, —C(O)N(R)—, —N(R)$S(O)_2$—, —$S(O)_2N(R)$—, —O—, —C(O)—, —OC(O)—, —C(O)O—, —S—, —S(O)— or —$S(O)_2$—.

In some embodiments, $L^1$ and one instance of $R^7$ are taken together with their intervening atoms to form a 5-6 membered partially unsaturated or aromatic ring having 1-4 heteroatoms independently selected from nitrogen, oxygen and sulfur; wherein said ring is substituted by q instances of $R^{11}$; and $R^5$ is attached to any position of the ring formed by $L^1$ and $R^7$.

In some embodiments, when $L^1$ is a covalent bond, $R^5$ is not unsubstituted alkyl. In some embodiments, $L^1$ is a covalent bond. In other embodiments, $L^1$ is a $C_{1-6}$ bivalent hydrocarbon chain wherein one or two methylene units of the chain are optionally and independently replaced by —N(R)—, —N(R)C(O)—, —C(O)N(R)—, —N(R)$S(O)_2$—, —$S(O)_2N(R)$—, —O—, —C(O)—, —OC(O)—, —C(O)O—, —S—, —S(O)— or —$S(O)_2$—. In some embodiments, $L^1$ is a $C_{2-6}$ bivalent branched hydrocarbon chain. In some embodiments, $L^1$ is a $C_{3-6}$ bivalent branched alkylene chain.

In some embodiments, $L^1$ is a $C_2$ bivalent hydrocarbon chain wherein one methylene unit of the chain is replaced by —C(O)—. In some embodiments, $L^1$ is —$CH_2C(O)$— (wherein the carbonyl is adjacent to $R^5$). In some embodiments, $L^1$ is —C(O)—. In some embodiments, $L^1$ is a covalent bond or —C(O)—. Exemplary $L^1$ groups include those depicted in Table 1.

In some embodiments, $L^1$ is a covalent bond or a $C_{1-6}$ bivalent saturated or unsaturated, straight or branched hydrocarbon chain wherein one or two methylene units of the chain are optionally and independently replaced by —$C(R^{10})_2$—, —N(R)—, —N(R)C(O)—, —C(O)N(R)—, —N(R)$S(O)_2$—, —$S(O)_2N(R)$—, —O—, —C(O)—, —OC(O)—, —C(O)O—, —S—, —S(O)— or —$S(O)_2$—; or $L^1$ and one instance of $R^7$ are taken together with their intervening atoms to form a 5-10 membered partially unsaturated or aromatic ring having 1-4 heteroatoms independently selected from nitrogen, oxygen, sulfur, and boron; wherein said ring is substituted by q instances of $R^{11}$; and $R^5$ is attached to any position of the ring formed by $L^1$ and $R^7$. In some embodiments, $L^1$ and one instance of $R^7$ are taken together with their intervening atoms to form a 5-10 membered partially unsaturated or aromatic ring having 1-4 heteroatoms independently selected from nitrogen, oxygen, sulfur, and boron; wherein said ring is substituted by q instances of $R^{11}$; and $R^5$ is attached to any position of the ring formed by $L^1$ and $R^7$.

As defined generally above, $L^{1'}$ is a $C_{1-6}$ bivalent saturated or unsaturated, straight or branched hydrocarbon chain wherein at least one methylene unit of the chain is replaced by —$C(R^{10})_2$—; and one or two additional methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—; or $L^{1'}$ and one instance of $R^7$ are taken together with their intervening atoms to form a 5-10 membered partially unsaturated or aromatic ring having 1-4 heteroatoms independently selected from nitrogen, oxygen and sulfur; wherein said ring is substituted by q instances of $R^{11}$; and $R^5$ is attached to any position of the ring formed by $L^{1'}$ and $R^7$.

In some embodiments, $L^{1'}$ is —$C(R^{10})_2$—. In some embodiments, $L^{1'}$ and one instance of $R^7$ are taken together with their intervening atoms to form a 5-10 membered partially unsaturated or aromatic ring having 1-4 heteroatoms independently selected from nitrogen, oxygen and sulfur; wherein said ring is substituted by q instances of $R^{11}$; and $R^5$ is attached to any position of the ring formed by $L^{1'}$ and $R^7$. In some embodiments, $L^{1'}$ and one instance of $R^7$ are taken together with their intervening atoms to form a 5-6 membered partially unsaturated or aromatic ring having 1-4 heteroatoms independently selected from nitrogen, oxygen and sulfur; wherein said ring is substituted by q instances of $R^{11}$; and $R^5$ is attached to any position of the ring formed by $L^{1'}$ and $R^7$. In some embodiments, $L^{1'}$ and one instance of $R^7$ are taken together with their intervening atoms to form a 7-10 membered partially unsaturated or aromatic ring having 1-4 heteroatoms independently selected from nitrogen, oxygen and sulfur; wherein said ring is substituted by q instances of $R^{11}$; and $R^5$ is attached to any position of the ring formed by $L^{1'}$ and $R^7$. Exemplary $L^{1'}$ groups are depicted in Table 1.

In some embodiments, $L^{1'}$ is a $C_{1-6}$ bivalent saturated or unsaturated, straight or branched hydrocarbon chain wherein at least one methylene unit of the chain is replaced by —$C(R^{10})_2$—; and one or two additional methylene units of the chain are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—; or $L^{1'}$ and one instance of $R^7$ are taken together with their intervening atoms to form a 5-10 membered partially unsaturated or aromatic ring having 1-4 heteroatoms independently selected from nitrogen, oxygen, sulfur, and boron; wherein said ring is substituted by q instances of $R^{11}$; and $R^5$ is attached to any position of the ring formed by $L^{1'}$ and $R^7$. In some embodiments, $L^{1'}$ and one instance of $R^7$ are taken together with their intervening atoms to form a 5-10 membered partially unsaturated or aromatic ring having 1-4 heteroatoms independently selected from nitrogen, oxygen, sulfur, and boron; wherein said ring is substituted by q instances of $R^{11}$; and $R^5$ is attached to any position of the ring formed by $L^{1'}$ and $R^7$.

As defined generally above, $R^5$ is a group selected from halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, phenyl, 3-7 membered saturated or partially unsaturated heterocyclic ring having 1-2 heteroatoms independently selected from nitrogen, oxygen, and sulfur, and 5-6 membered heteroaryl ring having 1-4 heteroatoms independently selected from nitrogen, oxygen, and sulfur; wherein $R^5$ is substituted with p instances of $R^9$.

In some embodiments, $R^5$ is selected from —OR, —NR$_2$, and a 3-10 membered saturated or partially unsaturated heterocyclic ring having 1-2 heteroatoms independently selected from nitrogen, oxygen, and sulfur. In some embodiments, $R^5$ is selected from —OH, —OEt, —NH$_2$, NHEt, aziridinyl, azetidinyl, pyrrolidinyl, piperidinyl, morpholinyl, thiomorpholinyl, oxetanyl, tetrahydrothiopyranyl, and tetrahydrofuranyl. In some embodiments, $R^5$ is —OR. In some embodiments, $R^5$ is —NR$_2$. In some embodiments, $R^5$ is —NHEt or —NHiPr. Exemplary $R^5$ groups include those depicted in Table 1.

In some embodiments, $R^5$ is a 4-10 membered saturated or partially unsaturated heterocyclic ring having 1-2 heteroatoms independently selected from nitrogen, oxygen, and sulfur. In some embodiments, $R^5$ is an 4-membered saturated heterocyclic ring having 1 heteroatom selected from nitrogen, oxygen, and sulfur. In some embodiments, $R^5$ is an 5-membered saturated or partially unsaturated heterocyclic ring having 1-2 heteroatoms independently selected from nitrogen, oxygen, and sulfur. In some embodiments, $R^5$ is an 6-membered saturated or partially unsaturated heterocyclic ring having 1-2 heteroatoms independently selected from nitrogen, oxygen, and sulfur. In some embodiments, $R^5$ is an 7-membered saturated or partially unsaturated heterocyclic ring having 1-2 heteroatoms independently selected from nitrogen, oxygen, and sulfur. In some embodiments, $R^5$ is an 8-membered saturated or partially unsaturated heterocyclic ring having 1-2 heteroatoms independently selected from nitrogen, oxygen, and sulfur. In some embodiments, $R^5$ is an 9-membered saturated or partially unsaturated heterocyclic ring having 1-2 heteroatoms independently selected from nitrogen, oxygen, and sulfur. In some embodiments, $R^5$ is an 10-membered saturated or partially unsaturated heterocyclic ring having 1-2 heteroatoms independently selected from nitrogen, oxygen, and sulfur. In some embodiments, $R^5$ is an 8-membered saturated heterocyclic ring having 1-2 heteroatoms independently selected from nitrogen, oxygen, and sulfur. In some embodiments, $R^5$ is an 9-membered saturated heterocyclic ring having 1-2 heteroatoms independently selected from nitrogen, oxygen, and sulfur. In some embodiments, $R^5$ is an 10-membered saturated heterocyclic ring having 1-2 heteroatoms independently selected from nitrogen, oxygen, and sulfur. In some embodiments, $R^5$ is an 7-10 membered saturated or partially unsaturated spirocyclic heterocyclic ring having 1-2 heteroatoms independently selected from nitrogen, oxygen, and sulfur. In some embodiments, $R^5$ is an 7-10 membered saturated or partially unsaturated fused bicyclic heterocyclic ring having 1-2 heteroatoms independently selected from nitrogen, oxygen, and sulfur.

In some embodiments, $R^5$ is a group selected from halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, phenyl, 3-14 membered saturated or partially unsaturated heterocyclic ring having 1-4 heteroatoms independently selected from nitrogen, oxygen, and sulfur, and 5-6 membered heteroaryl ring having 1-4 heteroatoms independently selected from nitrogen, oxygen, and sulfur; wherein $R^5$ is substituted with p instances of $R^9$. In some embodiments, $R^5$ is a group selected from a 3-14 membered saturated or partially unsaturated heterocyclic ring having 1-4 heteroatoms independently selected from nitrogen, oxygen, and sulfur, and 5-6 membered heteroaryl ring having 1-4 heteroatoms independently selected from nitrogen, oxygen, and sulfur. In some embodiments, $R^5$ is a 3-14 membered saturated or partially unsaturated heterocyclic ring having 1-4 heteroatoms independently selected from nitrogen, oxygen, and sulfur. In some embodiments, $R^5$ is a group selected from a 10-14 membered saturated or partially unsaturated heterocyclic ring having 1-4 heteroatoms independently selected from nitrogen, oxygen, and sulfur. In some embodiments, $R^5$ is a group selected from a 10-14 membered saturated or partially unsaturated bicyclic heterocyclic ring having 1-4 heteroatoms independently selected from nitrogen, oxygen, and sulfur. In some embodiments, $R^5$ is a group selected from a 10-14 membered saturated or partially unsaturated tricyclic heterocyclic ring having 1-4 heteroatoms independently selected from nitrogen, oxygen, and sulfur. In some embodiments, $R^5$ is a group selected from a 10-14 membered saturated or partially unsaturated heterocyclic ring having 1-2 heteroatoms independently selected from nitrogen, oxygen, and sulfur. In some embodiments, $R^5$ is a group selected from a 10-14 membered saturated or partially unsaturated bicyclic heterocyclic ring having 1-2 heteroatoms independently selected from nitrogen, oxygen, and sulfur. In some embodiments, $R^5$ is a group selected from a 10-14 membered saturated or partially unsaturated tricyclic heterocyclic ring having 1-2 heteroatoms independently selected from nitrogen, oxygen, and sulfur.

In some embodiments, $R^{5'}$ is an 8-10 membered saturated or partially unsaturated bridged bicyclic heterocyclic ring having 1-2 heteroatoms independently selected from nitrogen, oxygen, and sulfur.

As defined generally above, $R^{5'}$ is an 8-10 membered saturated or partially unsaturated heterocyclic ring having 1-2 heteroatoms independently selected from nitrogen, oxygen, and sulfur; wherein $R^5$ is substituted with p instances of $R^9$. In some embodiments, $R^{5'}$ is an 8-membered saturated or partially unsaturated heterocyclic ring having 1-2 heteroatoms independently selected from nitrogen, oxygen, and sulfur. In some embodiments, $R^{5'}$ is an 9-membered saturated or partially unsaturated heterocyclic ring having 1-2 heteroatoms independently selected from nitrogen, oxygen, and sulfur. In some embodiments, $R^{5'}$ is an 10-membered saturated or partially unsaturated heterocyclic ring having 1-2 heteroatoms independently selected from nitrogen, oxygen, and sulfur. In some embodiments, $R^{5'}$ is an 8-membered saturated heterocyclic ring having 1-2 heteroatoms independently selected from nitrogen, oxygen, and sulfur. In some embodiments, $R^{5'}$ is an 9-membered saturated heterocyclic ring having 1-2 heteroatoms independently selected from nitrogen, oxygen, and sulfur. In some embodiments, $R^{5'}$ is an 10-membered saturated heterocyclic ring having 1-2 heteroatoms independently selected from nitrogen, oxygen, and sulfur. In some embodiments, $R^{5'}$ is an 8-10 membered saturated or partially unsaturated spirocyclic heterocyclic ring having 1-2 heteroatoms independently selected from nitrogen, oxygen, and sulfur. In some embodiments, $R^{5'}$ is an 8-10 membered saturated or partially unsaturated fused bicyclic heterocyclic ring having 1-2 heteroatoms independently selected from nitrogen, oxygen, and sulfur. In some embodiments, $R^{5'}$ is an 8-10 membered saturated or partially unsaturated bridged bicyclic heterocyclic ring having 1-2 heteroatoms independently selected from nitrogen, oxygen, and sulfur.

In some embodiments, $R^{5'}$ is an 8-14 membered saturated or partially unsaturated heterocyclic ring having 1-4 heteroatoms independently selected from nitrogen, oxygen, and sulfur; wherein $R^5$ is substituted with p instances of $R^9$. In some embodiments, $R^{5'}$ is an 8-12 membered saturated or partially unsaturated heterocyclic ring having 1-4 heteroatoms independently selected from nitrogen, oxygen, and sulfur. In some embodiments, $R^{5'}$ is an 10-14 membered saturated or partially unsaturated heterocyclic ring having 1-4 heteroatoms independently selected from nitrogen, oxygen, and sulfur. In some embodiments, $R^{5'}$ is an 8-14 membered saturated or partially unsaturated heterocyclic ring having 1-2 heteroatoms independently selected from nitrogen, oxygen, and sulfur. In some embodiments, $R^{5'}$ is an 8-14 membered saturated or partially unsaturated bicyclic heterocyclic ring having 1-4 heteroatoms independently selected from nitrogen, oxygen, and sulfur. In some embodiments, $R^{5'}$ is an 8-14 membered saturated or partially unsaturated tricyclic heterocyclic ring having 1-4 heteroatoms independently selected from nitrogen, oxygen, and sulfur.

As defined generally above each instance of $R^6$ is independently —$R^2$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$. In some embodiments $R^6$ is halogen or —CN. In some embodiments $R^6$ is halogen. In some embodiments, $R^6$ is fluoro. In some embodiments, $R^6$ is —CN.

In some embodiments, $R^6$ is hydrogen, —$R^2$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$. In some embodiments, $R^6$ is hydrogen. In some embodiments $R^6$ is halogen or —CN. In some embodiments $R^6$ is halogen. In some embodiments, $R^6$ is fluoro. In some embodiments, $R^6$ is —CN.

As defined generally above, each instance of $R^7$ is —$R^2$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$.

In some embodiments, $R^7$ is oxo, —$R^2$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$.

As defined generally above, each instance of $R^8$ is independently —$R^2$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$. In some embodiments, $R^8$ is a halogen. In some embodiments, $R^8$ is fluorine. In some embodiments, $R^8$ is chlorine. In some embodiments, $R^8$ is optionally substituted $C_{1-6}$ aliphatic. In some embodiments, $R^8$ is $C_{1-6}$ alkyl. In some embodiments, $R^8$ is methyl. In some embodiments, $R^8$ is alkyl substituted by one or more halogens. In some embodiments, $R^8$ is $CF_3$. In some embodiments, each $R^8$ is a halogen. In some embodiments, each $R^8$ is fluorine, chlorine, methyl, or $CF_3$.

In some embodiments, $R^8$ is oxo, —$R^2$, halogen, —CN, —$NO_2$, —OR, —SR, —$NR_2$, —$S(O)_2R$, —$S(O)_2NR_2$, —$S(O)R$, —$C(O)R$, —$C(O)OR$, —$C(O)NR_2$, —$C(O)N(R)OR$, —$OC(O)R$, —$OC(O)NR_2$, —$N(R)C(O)OR$, —$N(R)C(O)R$, —$N(R)C(O)NR_2$, or —$N(R)S(O)_2R$.

One of ordinary skill in the art will appreciate that an $R^8$ substituent on a saturated carbon of $R^3$ forms a chiral center. In some embodiments, that chiral center is in the (R) configuration. In other embodiments, that chiral center is in the (S) configuration.

As defined generally above, each instance of $R^9$ is independently oxo, $C_{1-6}$ hydroxyaliphatic, —$R^2$, halogen, —CN, —$NO_2$, —OR, —SR, —$NR_2$, —$S(O)_2R$, —$S(O)_2NR_2$, —$S(O)R$, —$C(O)R$, —$C(O)OR$, —$C(O)NR_2$, —$C(O)N(R)OR$, —$OC(O)R$, —$OC(O)NR_2$, —$N(R)C(O)OR$, —$N(R)C(O)R$, —$N(R)C(O)NR_2$, or —$N(R)S(O)_2R$.

In some embodiments, $R^8$ is oxo, —$R^2$, halogen, —CN, —$NO_2$, —OR, —SR, —$NR_2$, —$S(O)_2R$, —$S(O)_2NR_2$, —$S(O)R$, —$C(O)R$, —$C(O)OR$, —$C(O)NR_2$, —$C(O)N(R)OR$, —$OC(O)R$, —$OC(O)NR_2$, —$N(R)C(O)OR$, —$N(R)C(O)R$, —$N(R)C(O)NR_2$, or —$N(R)S(O)_2R$.

In some embodiments, $R^9$ is oxo. In some embodiments, $R^9$ is —$R^2$. In some embodiments, $R^9$ is optionally substituted $C_{1-6}$ aliphatic. In some embodiments, $R^9$ is $C_{1-6}$ hydroxyaliphatic. In some embodiments, $R^9$ is hydroxymethyl. In some embodiments, $R^9$ is hydroxyethyl. In some embodiments, $R^9$ is hydroxycyclobutyl. In some embodiments, $R^9$ is hydroxycyclobutyl. In some embodiments, $R^9$ is N,N-dimethylaminoethyl. In some embodiments, $R^9$ is a 3-7 membered saturated or partially unsaturated heterocyclic ring having 1-2 heteroatoms independently selected from nitrogen, oxygen, and sulfur. In some embodiments, $R^9$ is selected from —OH, —OEt, —$NH_2$, NHEt, aziridinyl, azetidinyl, pyrrolidinyl, piperidinyl, morpholinyl, thiomorpholinyl, oxetanyl, tetrahydrothiopyranyl, and tetrahydrofuranyl. In some embodiments, when $L^1$ is absent, at least one $R^9$ is oxo.

As defined generally above, each instance of $R^{10}$ is independently —$R^2$, halogen, —CN, —$NO_2$, —OR, —SR, —$NR_2$, —$S(O)_2R$, —$S(O)_2NR_2$, —$S(O)R$, —$C(O)R$, —$C(O)OR$, —$C(O)NR_2$, —$C(O)N(R)OR$, —$OC(O)R$, —$OC(O)NR_2$, —$N(R)C(O)OR$, —$N(R)C(O)R$, —$N(R)C(O)NR_2$, or —$N(R)S(O)_2R$.

In some embodiments, $R^{10}$ is oxo, —$R^2$, halogen, —CN, —$NO_2$, —OR, —SR, —$NR_2$, —$S(O)_2R$, —$S(O)_2NR_2$, —$S(O)R$, —$C(O)R$, —$C(O)OR$, —$C(O)NR_2$, —$C(O)N(R)OR$, —$OC(O)R$, —$OC(O)NR_2$, —$N(R)C(O)OR$, —$N(R)C(O)R$, —$N(R)C(O)NR_2$, or —$N(R)S(O)_2R$.

As defined generally above, m is 0-4. In some embodiments, m is 0. In some embodiments, m is 1-4. In some embodiments, m is 1. In some embodiments, m is 2. In some embodiments, m is 3. In some embodiments, m is 4.

As defined generally above, n is 0-4. In some embodiments, n is 0. In some embodiments, n is 1-4. In some embodiments, n is 1. In some embodiments, n is 2. In some embodiments, n is 3. In some embodiments, n is 4. In some embodiments, n is 0-1. In some embodiments, n is 0-2. In some embodiments, n is 0-3.

As defined generally above, p is 0-6. In some embodiments, p is 0. In some embodiments, p is 1-6. In some embodiments, p is 1. In some embodiments, p is 2. In some embodiments, p is 3. In some embodiments, p is 1-3. In some embodiments, p is 4. In some embodiments, p is 5. In some embodiments, p is 6.

As defined generally above, q is 0-4. In some embodiments, q is 0. In some embodiments, q is 1-4. In some embodiments, q is 1. In some embodiments, q is 2. In some embodiments, q is 3. In some embodiments, q is 4. In some embodiments, q is 0-1. In some embodiments, q is 0-2. In some embodiments, q is 0-3.

In certain embodiments, the present invention provides a compound of formula I, wherein when X is =N—, $R^3$ is phenyl.

In certain embodiments, the present invention provides a compound of formulas I, II, or III, wherein $R^1$ and $R^{1'}$ are each hydrogen, thereby forming a compound of formulas I-a, II-a, or III-a respectively:

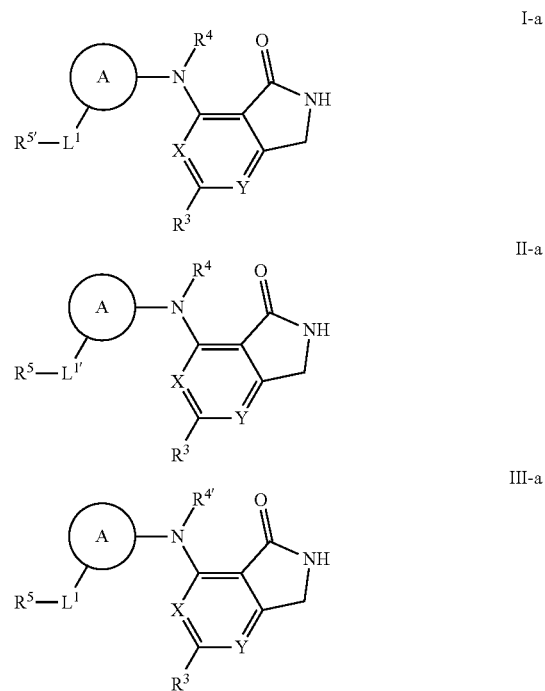

or a pharmaceutically acceptable salt thereof, wherein each of X, Y, Ring A, $L^1$, $L^{1'}$, $R^3$, $R^4$, $R^{4'}$, $R^5$, and $R^{5'}$ is as defined above and described in embodiments herein, both singly and in combination.

In certain embodiments, the present invention provides a compound of formulas I, II, III, or IV wherein X is =N— and Y is =C($R^6$)—; thereby forming a compound of formula I-b, II-b, III-b, or IV-b respectively:

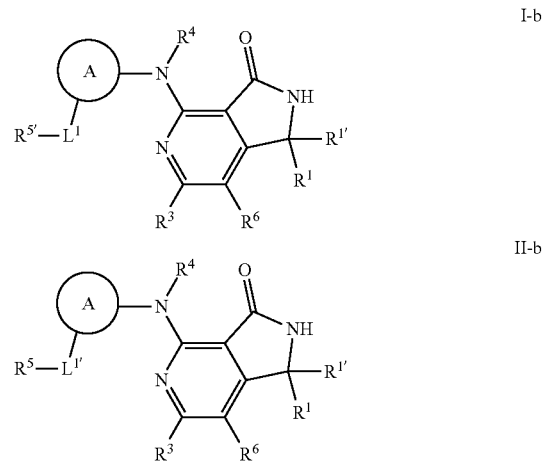

-continued

III-b

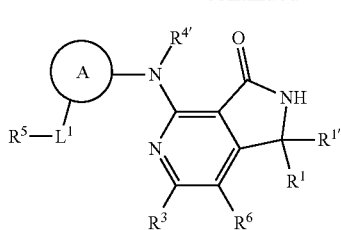

IV-b

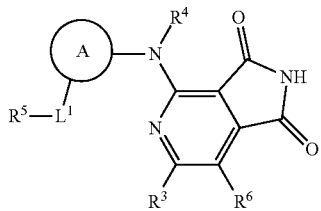

or a pharmaceutically acceptable salt thereof, wherein each of Ring A, $L^1$, $L^{1'}$, $R^1$, $R^{1'}$, $R^3$, $R^4$, $R^{4'}$, $R^5$, $R^{5'}$, and $R^6$ is as defined above and described in embodiments herein, both singly and in combination.

In certain embodiments, the present invention provides a compound of formulas I, II, III, or IV wherein X is $=C(R^6)-$; and Y is $=N-$, thereby forming a compound of formula I-c, II-c, III-c, or IV-c respectively:

I-c

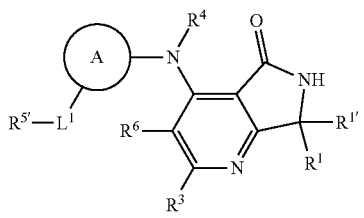

II-c

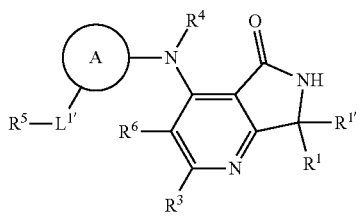

III-c

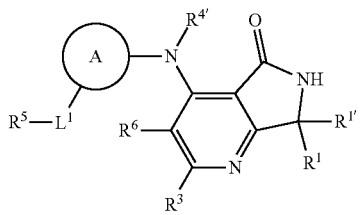

IV-c

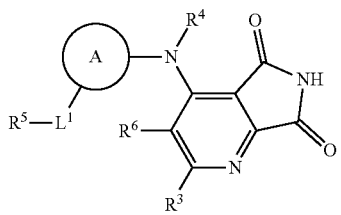

or a pharmaceutically acceptable salt thereof, wherein each of Ring A, $L^1$, $L^{1'}$, $R^1$, $R^{1'}$, $R^3$, $R^4$, $R^{4'}$, $R^5$, $R^{5'}$, and $R^6$ is as defined above and described in embodiments herein, both singly and in combination.

In certain embodiments, the present invention provides a compound of formulas I, II, III, or IV wherein X is $=C(R^6)-$; and Y is $=N^+(\rightarrow O^-)-$, thereby forming a compound of formula I-c-i, II-c-i, III-c-i, or IV-c-i respectively:

I-c-i

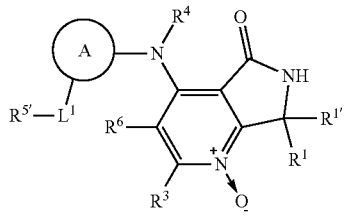

II-c-i

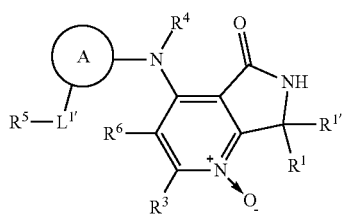

III-c-i

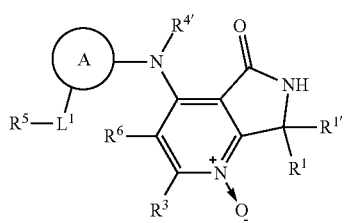

IV-c-i

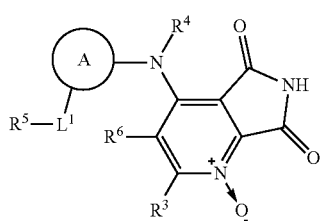

or a pharmaceutically acceptable salt thereof, wherein each of Ring A, $L^1$, $L^{1'}$, $R^1$, $R^{1'}$, $R^3$, $R^4$, $R^{4'}$, $R^5$, $R^{5'}$, and $R^6$ is as defined above and described in embodiments herein, both singly and in combination.

In certain embodiments, the present invention provides a compound of formulas I, II, III, or IV wherein X and Y are each $=N-$, thereby forming a compound of formula I-d, II-d, III-d, or IV-d respectively:

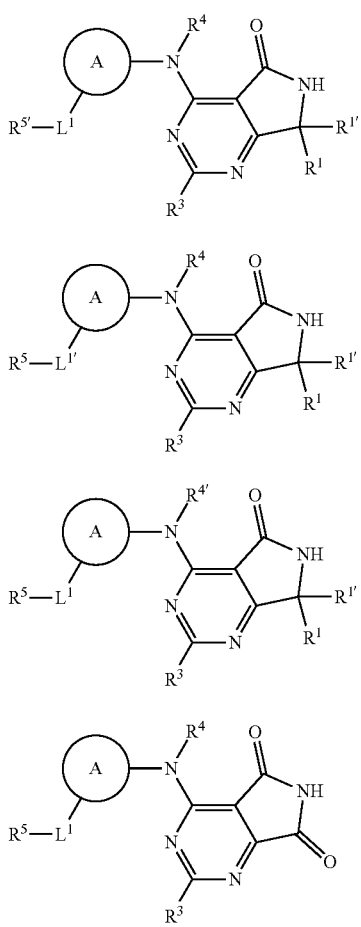

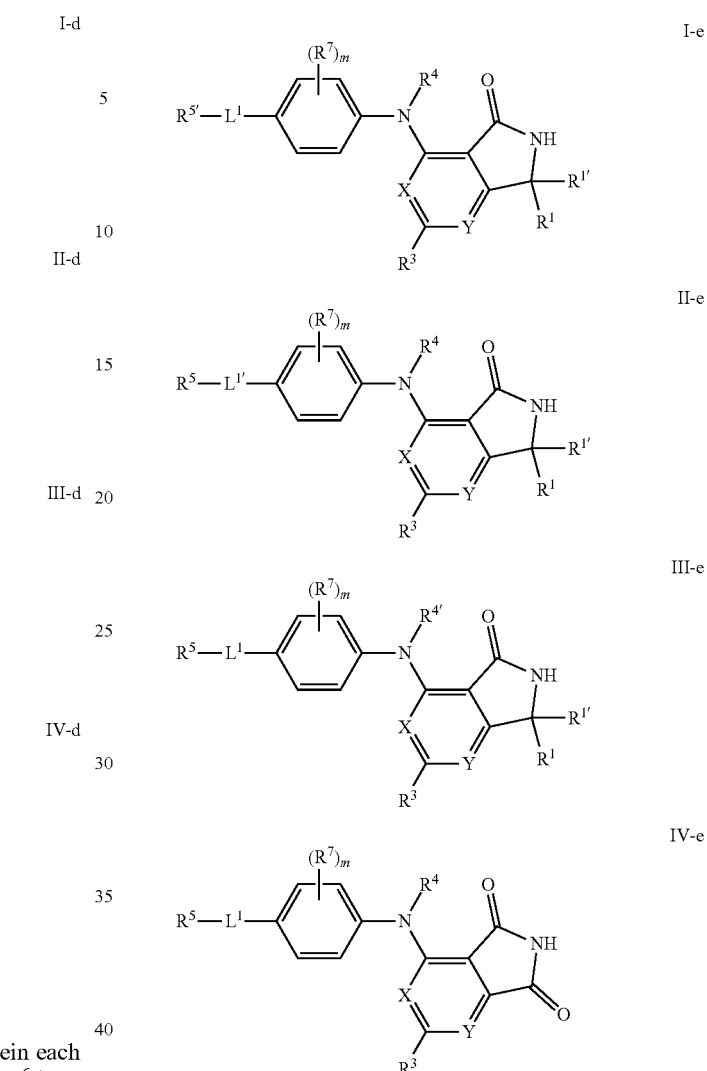

or a pharmaceutically acceptable salt thereof, wherein each of Ring A, $L^1$, $L^{1'}$, $R^1$, $R^{1'}$, $R^3$, $R^4$, $R^{4'}$, $R^5$, $R^{5'}$, and $R^6$ is as defined above and described in embodiments herein, both singly and in combination.

In some embodiments, the present invention provides a compound of any one of formulas I-b, I-c, II-b, II-c, III-b, III-c, IV-b, or IV-c wherein $R^6$ is hydrogen. In some embodiments, the present invention provides a compound of any one of formulas I-b, I-c, II-b, II-c, III-b, III-c, IV-b, or IV-c wherein $R^6$ is halogen. In some embodiments, the present invention provides a compound of any one of formulas I-b, I-c, II-b, II-c, III-b, III-c, IV-b, or IV-c wherein $R^6$ is fluoro. In some embodiments, the present invention provides a compound of any one of formulas I-b, I-c, II-b, II-c, III-b, III-c, IV-b, or IV-c wherein $R^6$ is —CN.

In certain embodiments, the present invention provides a compound of any one of formulas I, II, III, IV, I-a, II-a, III-a, I-b, II-b, III-b, IV-b, I-c, II-c, IV-c, I-d, II-d, III-d, or IV-d, wherein Ring A is phenyl, pyridin-2-yl, pyridine-3-yl, pyrazinyl, pyridazinyl, or pyrazol-4-yl.

In certain embodiments, the present invention provides a compound of one of formulas I, II, III, or IV wherein Ring A is phenyl, and $L^1$ is para to —N($R^4$)— or —N($R^{4'}$)—, thereby forming a compound of one of formulas I-e, II-e, III-e, and IV-e respectively:

or a pharmaceutically acceptable salt thereof, wherein each of, X, Y, $L^1$, $L^{1'}$, $R^1$, $R^{1'}$, $R^3$, $R^4$, $R^{4'}$, $R^5$, $R^{5'}$, $R^7$, and m is as defined above and described in embodiments herein, both singly and in combination.

In certain embodiments, the present invention provides a compound of one of formulas I, II, III, or IV wherein Ring A is pyridin-2-yl, and $L^1$ is para to —N($R^4$)— or —N($R^{4'}$)—, thereby forming a compound of one of formulas I-f, II-f, III-f, and IV-f respectively:

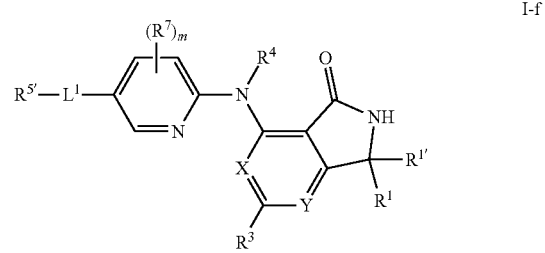

II-f

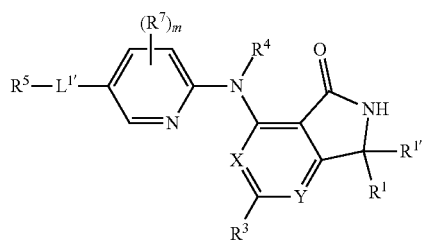

III-f

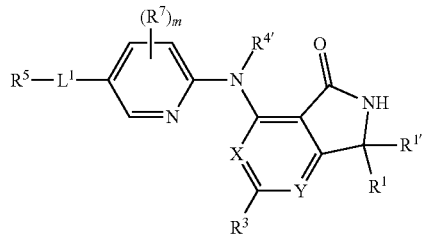

IV-f

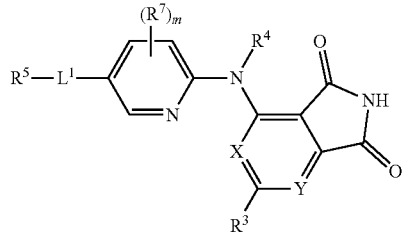

or a pharmaceutically acceptable salt thereof, wherein each of, X, Y, $L^1$, $L^{1'}$, $R^1$, $R^{1'}$, $R^3$, $R^4$, $R^{4'}$, $R^5$, $R^{5'}$, $R^7$, and m is as defined above and described in embodiments herein, both singly and in combination.

In certain embodiments, the present invention provides a compound of one of formulas I, II, III, or IV wherein Ring A is pyridine-3-yl, and $L^1$ is para to —N($R^4$)— or —N($R^{4'}$)—, thereby forming a compound of one of formulas I-g, II-g, III-g, and IV-g respectively:

I-g

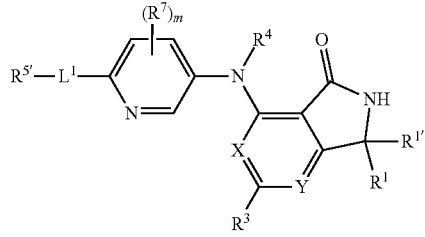

II-g

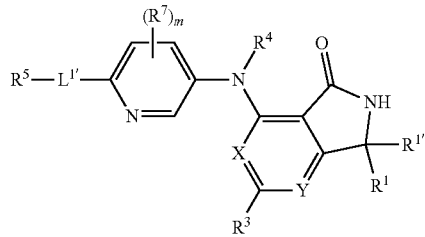

III-g

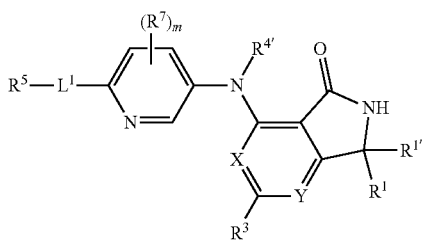

IV-g

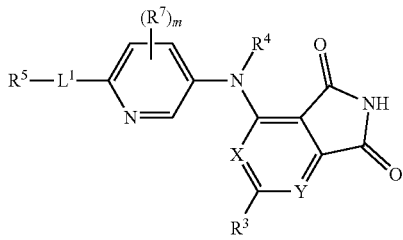

or a pharmaceutically acceptable salt thereof, wherein each of, X, Y, $L^1$, $L^{1'}$, $R^1$, $R^{1'}$, $R^3$, $R^4$, $R^{4'}$, $R^5$, $R^{5'}$, $R^7$, and m is as defined above and described in embodiments herein, both singly and in combination.

In certain embodiments, the present invention provides a compound of one of formulas I, II, III, or IV wherein Ring A is pyridazinyl, and $L^1$ is para to —N($R^4$)— or —N($R^{4'}$)—, thereby forming a compound of one of formulas I-h, II-h, III-h, and IV-h respectively:

I-h

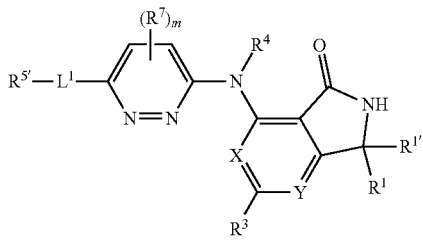

II-h

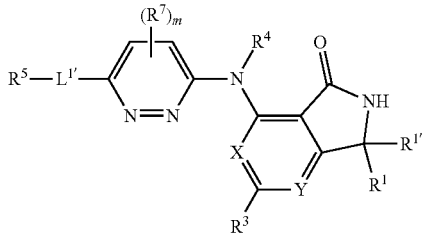

III-h

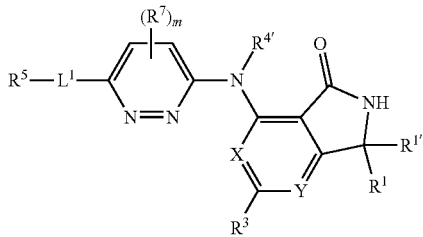

-continued

IV-h

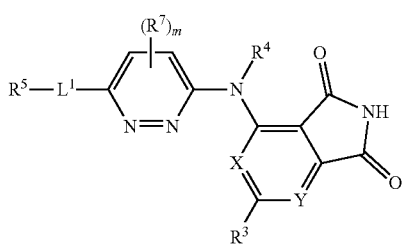

or a pharmaceutically acceptable salt thereof, wherein each of, X, Y, $L^1$, $L^{1'}$, $R^1$, $R^{1'}$, $R^3$, $R^4$, $R^{4'}$, $R^5$, $R^{5'}$, $R^7$, and m is as defined above and described in embodiments herein, both singly and in combination.

In certain embodiments, the present invention provides a compound of one of formulas I, II, III, or IV wherein Ring A is pyrazinyl, and $L^1$ is para to —N($R^4$)— or —N($R^{4'}$)—, thereby forming a compound of one of formulas I-i, II-i, III-i, and IV-i respectively:

I-i

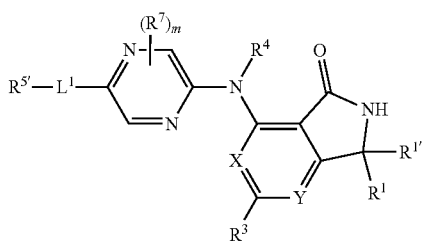

II-i

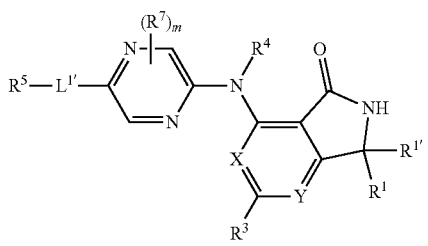

III-i

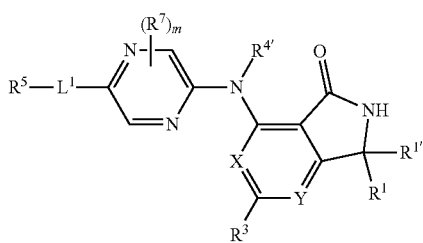

IV-i

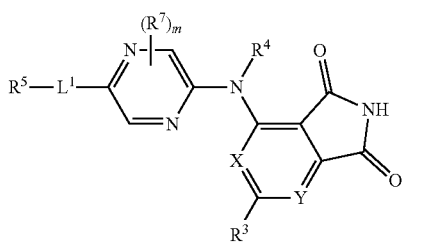

or a pharmaceutically acceptable salt thereof, wherein each of, X, Y, $L^1$, $L^{1'}$, $R^1$, $R^{1'}$, $R^3$, $R^4$, $R^{4'}$, $R^5$, $R^{5'}$, $R^7$, and m is as defined above and described in embodiments herein, both singly and in combination.

In certain embodiments, the present invention provides a compound of one of formulas I, II, III, or IV wherein Ring A is pyrazol-4-yl, and $L^1$ is para to —N($R^4$)— or —N($R^{4'}$)—, thereby forming a compound of one of formulas I-j, II-j, III-j, and IV-j respectively:

I-g

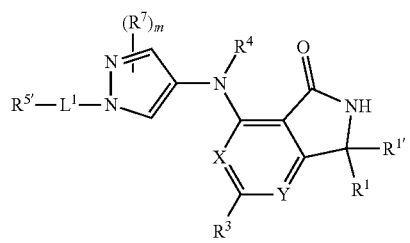

II-g

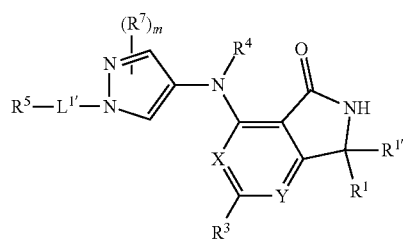

III-g

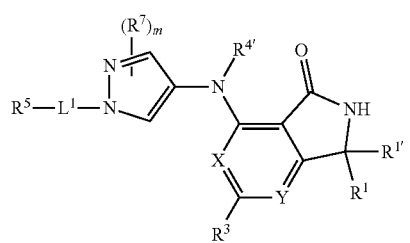

IV-g

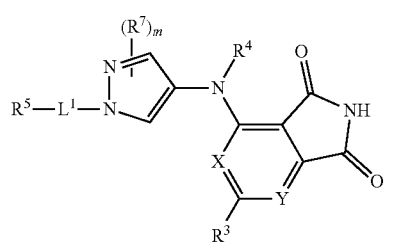

or a pharmaceutically acceptable salt thereof, wherein each of, X, Y, $L^1$, $L^{1'}$, $R^1$, $R^{1'}$, $R^3$, $R^4$, $R^{4'}$, $R^5$, $R^{5'}$, $R^7$, and m is as defined above and described in embodiments herein, both singly and in combination.

In certain embodiments, the present invention provides a compound of one of formulas I, II, III, or IV, wherein $R^3$ is phenyl, pyrrolidinyl, or piperidinyl. In certain embodiments, the present invention provides a compound of one of formulas I, II, III, or IV, wherein $R^3$ is phenyl, thereby forming a compound of formula I-k, II-k, III-k, or IV-k, respectively:

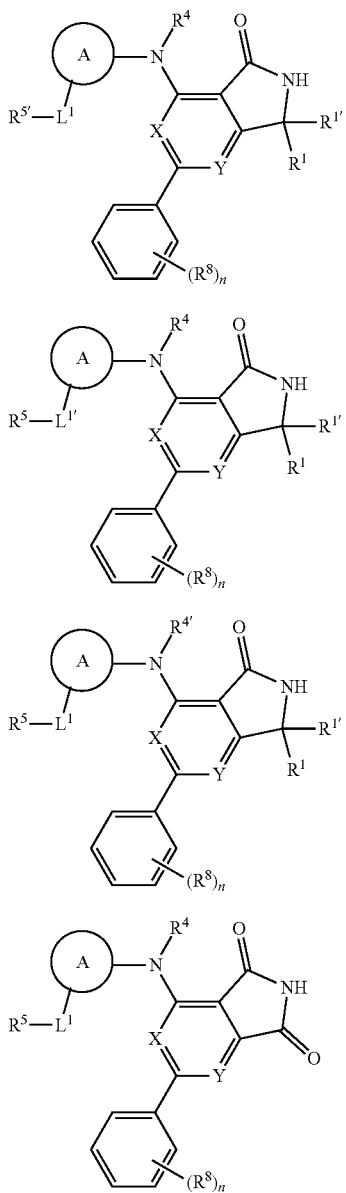

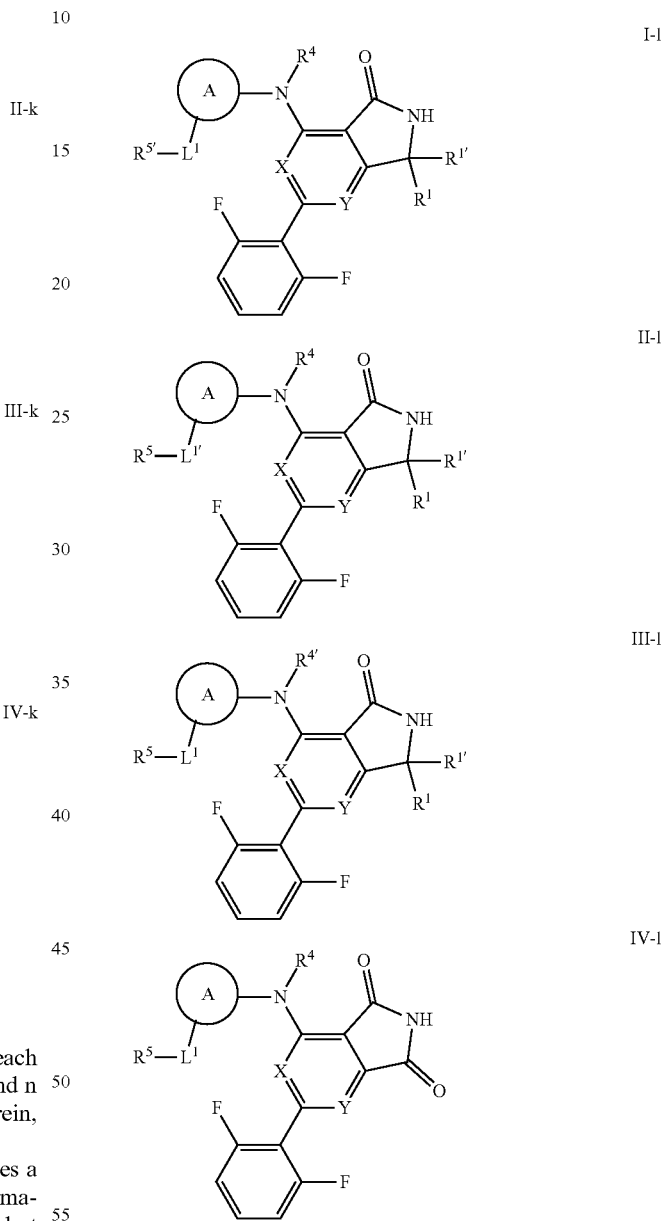

or a pharmaceutically acceptable salt thereof, wherein each of X, Y, Ring A, $L^1$, $L^{1'}$, $R^1$, $R^{1'}$, $R^4$, $R^{4'}$, $R^5$, $R^{5'}$, $R^8$, and n is as defined above and described in embodiments herein, both singly and in combination.

In certain embodiments, the present invention provides a compound of one of formulas I, II, III, or IV, or a pharmaceutically acceptable salt thereof, wherein n is 1-3, and at least one $R^8$ substituent is ortho to the point of attachment. In certain embodiments, the present invention provides a compound of one of formulas I, II, III, or IV, or a pharmaceutically acceptable salt thereof, wherein n is 1. In certain embodiments, the present invention provides a compound of one of formulas I, II, III, or IV, or a pharmaceutically acceptable salt thereof, wherein n is 2. In certain embodiments, the present invention provides a compound of one of formulas I, II, III, or IV, or a pharmaceutically acceptable salt thereof, wherein n is 2, and at least one $R^8$ is halogen. In certain embodiments, the present invention provides a compound of one of formulas I, II, III, or IV, or a pharmaceutically acceptable salt thereof, wherein n is 2, and at least one $R^8$ is fluoro.

In certain embodiments, the present invention provides a compound of one of formulas I-k, II-k, III-k, or IV-k, wherein n is 2 and each $R^8$ is fluoro, thereby forming a compound of formula I-1, II-1, III-1, or IV-1, respectively:

or a pharmaceutically acceptable salt thereof, wherein each of X, Y, Ring A, $L^1$, $L^{1'}$, $R^1$, $R^{1'}$, $R^4$, $R^{4'}$, $R^5$, and $R^{5'}$, is as defined above and described in embodiments herein, both singly and in combination.

In certain embodiments, the present invention provides a compound of one of formulas I, III, or IV, wherein $L^1$ is a covalent bond or —C(O)—, thereby forming a compound of formula I-m, III-m, or IV-m, respectively:

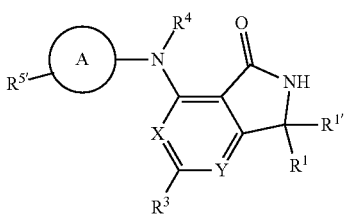

I-m

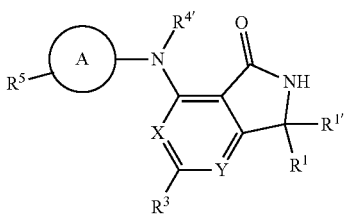

III-m

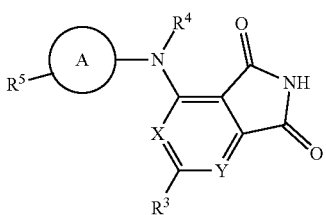

IV-m or a pharmaceutically acceptable salt thereof, wherein each of X, Y, Ring A, $R^1$, $R^{1'}$, $R^3$, $R^4$, $R^{4'}$, $R^5$, and $R^{5'}$ is as defined above and described in embodiments herein, both singly and in combination.

In certain embodiments, the present invention provides a compound of one of formulas I, III, or IV, wherein $L^1$ is —C(O)—, thereby forming a compound of formula I-n, III-n, or IV-n, respectively:

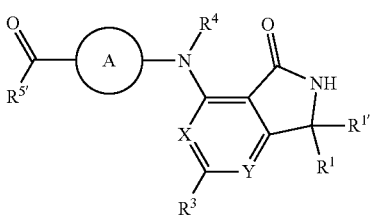

I-n

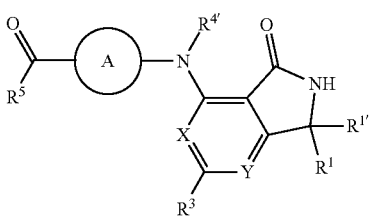

III-n

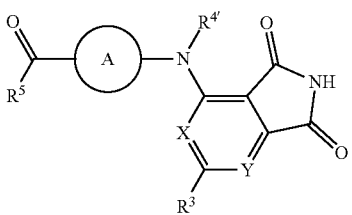

IV-n or a pharmaceutically acceptable salt thereof, wherein each of X, Y, Ring A, $R^1$, $R^{1'}$, $R^3$, $R^4$, $R^{4'}$, $R^5$, and $R^{5'}$ is as defined above and described in embodiments herein, both singly and in combination.

In certain embodiments, the present invention provides a compound of one of formulas I-n, III-n, or IV-n, wherein X is =C($R^6$)— and Y is =N—, thereby forming a compound of formula I-o, III-o, or IV-o, respectively:

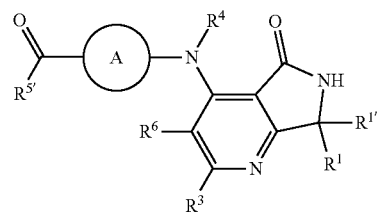

I-o

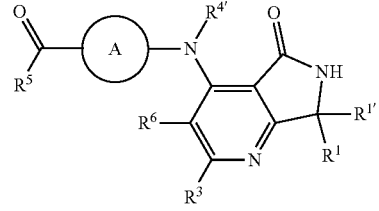

III-o

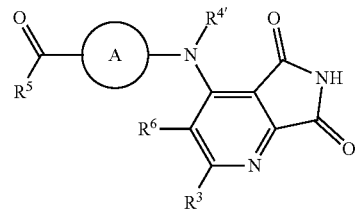

IV-o or a pharmaceutically acceptable salt thereof, wherein each of Ring A, $R^1$, $R^{1'}$, $R^3$, $R^4$, $R^{4'}$, $R^5$, $R^{5'}$, and $R^6$ is as defined above and described in embodiments herein, both singly and in combination.

In certain embodiments, the present invention provides a compound of one of formulas I-m, III-m, or IV-m, wherein X is =C($R^6$)— and Y is =N—, thereby forming a compound of formula I-p, III-p, or IV-p, respectively:

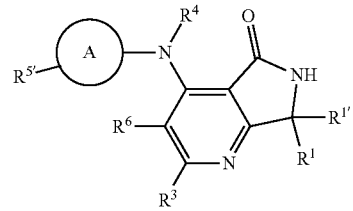

I-p

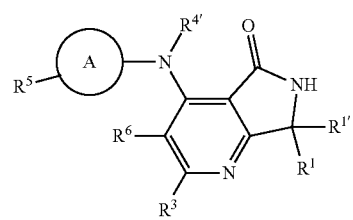

III-p

-continued
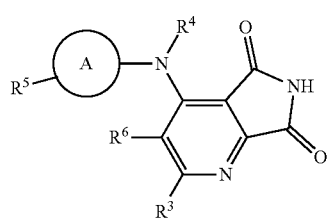
IV-p
or a pharmaceutically acceptable salt thereof, wherein each of Ring A, $R^1$, $R^{1'}$, $R^3$, $R^4$, $R^{4'}$, $R^5$, $R^{5'}$, and $R^6$ is as defined above and described in embodiments herein, both singly and in combination.
Exemplary compounds of the invention are set forth in Table 1, below.
TABLE 1
Exemplary Compounds
| Compound # | Structure |
|---|---|
| I-1 | |
| I-2 | |
| I-3 | |
| I-4 | 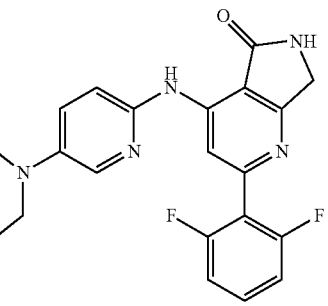 |
| I-5 | 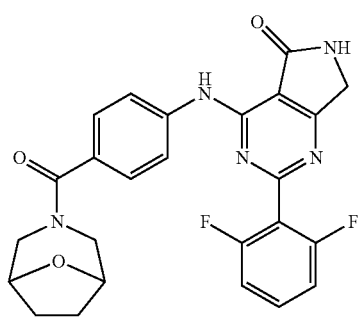 [SMILES: O=C1NCc2nc(-c3c(F)cccc3F)nc(Nc3ccc(C(=O)N4CC5CCC(C4)O5)cc3)c21] |
| I-6 | 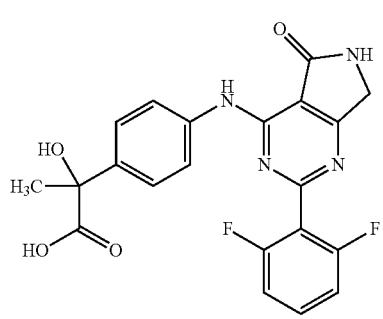 [SMILES: CC(O)(C(=O)O)c1ccc(Nc2nc(-c3c(F)cccc3F)nc3c2C(=O)NC3)cc1] |
| I-7 | 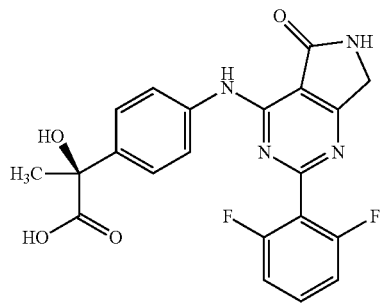 [SMILES: C[C@@](O)(C(=O)O)c1ccc(Nc2nc(-c3c(F)cccc3F)nc3c2C(=O)NC3)cc1] |

TABLE 1-continued

Exemplary Compounds

| Compound # | Structure |
|---|---|
| I-8 | 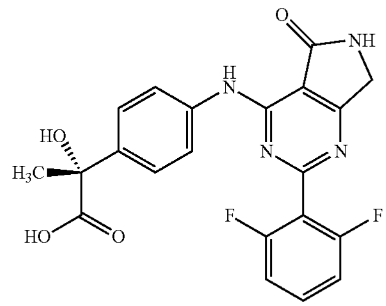 [SMILES: C[C@](O)(C(=O)O)c1ccc(Nc2nc(-c3c(F)cccc3F)nc3c2C(=O)NC3)cc1] |
| I-9 | 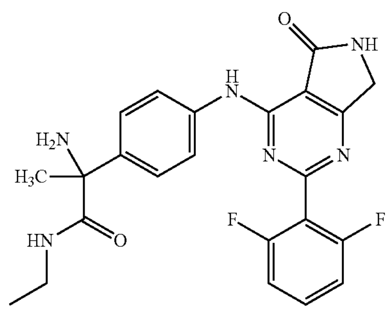 [SMILES: CCNC(=O)C(C)(N)c1ccc(Nc2nc(-c3c(F)cccc3F)nc3c2C(=O)NC3)cc1] |
| I-10 | 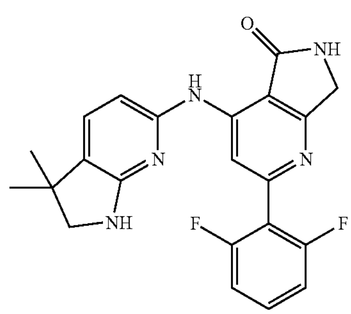 [SMILES: CC1(C)CNc2nc(Nc3cc(-c4c(F)cccc4F)nc4c3C(=O)NC4)ccc21] |
| I-12 | 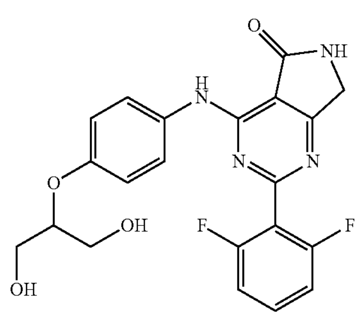 [SMILES: O=C1NCc2nc(-c3c(F)cccc3F)nc(Nc3ccc(OC(CO)CO)cc3)c21] |
| I-13 | |
| I-14 | |
| I-15 | |
| I-16 | |

TABLE 1-continued
Exemplary Compounds
| Compound # | Structure |
|---|---|
| I-17 | 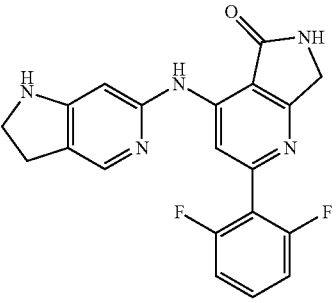 [SMILES: O=C1NCc2nc(-c3c(F)cccc3F)cc(Nc3cc4c(cn3)CCN4)c21] |
| I-18 | 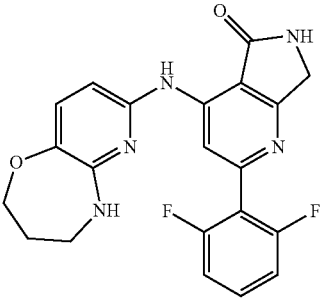 [SMILES: O=C1NCc2nc(-c3c(F)cccc3F)cc(Nc3ccc4c(n3)NCCCO4)c21] |
| I-19 | 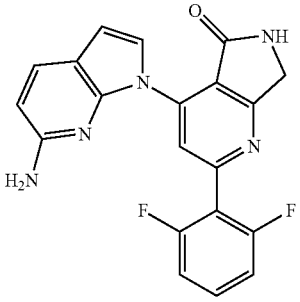 [SMILES: Nc1ccc2ccn(-c3cc(-c4c(F)cccc4F)nc4c3C(=O)NC4)c2n1] |
| I-20 | 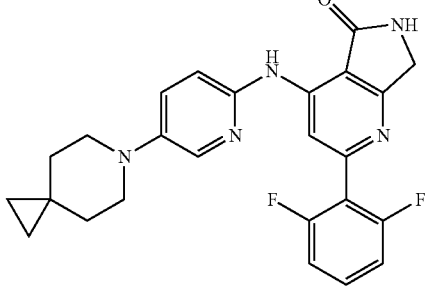 |
| I-21 | 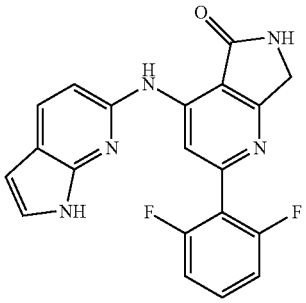 [SMILES: O=C1NCc2nc(-c3c(F)cccc3F)cc(Nc3ccc4cc[nH]c4n3)c21] |
| I-22 | 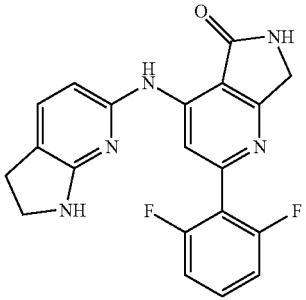 [SMILES: O=C1NCc2nc(-c3c(F)cccc3F)cc(Nc3ccc4c(n3)NCC4)c21] |
| I-23 | 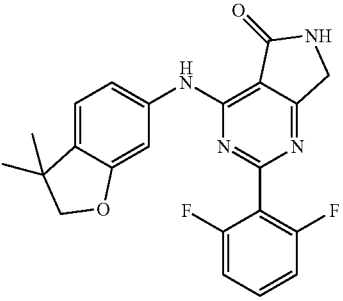 [SMILES: CC1(C)COc2cc(Nc3nc(-c4c(F)cccc4F)nc4c3C(=O)NC4)ccc21] |
| I-24 | 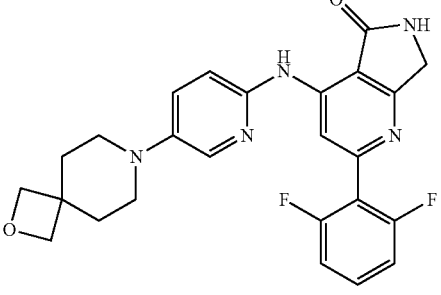 |

TABLE 1-continued

Exemplary Compounds

| Compound # | Structure |
|---|---|
| I-25 | 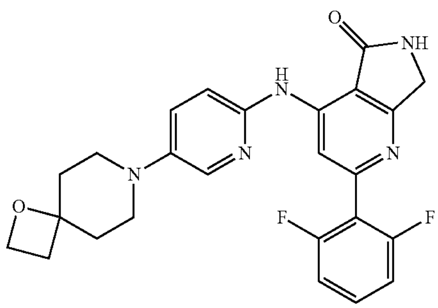 [SMILES: O=C1NCc2nc(-c3c(F)cccc3F)cc(Nc3ccc(N4CCC5(CCO5)CC4)cn3)c21] |
| I-26 | 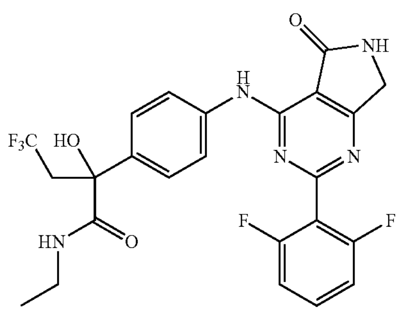 [SMILES: CCNC(=O)C(O)(CC(F)(F)F)c1ccc(Nc2nc(-c3c(F)cccc3F)nc3c2C(=O)NC3)cc1] |
| I-27 | 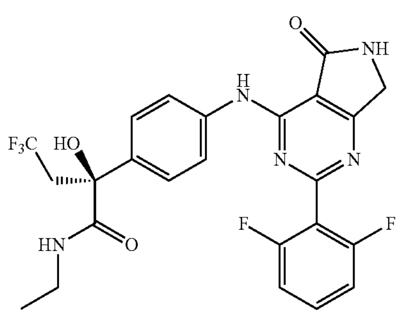 [SMILES: CCNC(=O)[C@](O)(CC(F)(F)F)c1ccc(Nc2nc(-c3c(F)cccc3F)nc3c2C(=O)NC3)cc1] |
| I-28 | 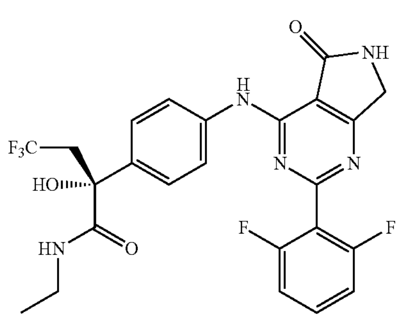 [SMILES: CCNC(=O)[C@@](O)(CC(F)(F)F)c1ccc(Nc2nc(-c3c(F)cccc3F)nc3c2C(=O)NC3)cc1] |
| I-29 | |
| I-30 | |
| I-31 | |
| I-32 | |

TABLE 1-continued
Exemplary Compounds
| Compound # | Structure |
|---|---|
| I-33 | 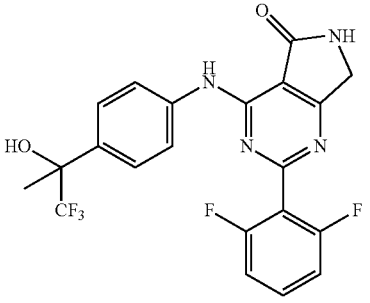 [SMILES: CC(O)(c1ccc(Nc2nc(-c3c(F)cccc3F)nc3c2C(=O)NC3)cc1)C(F)(F)F] |
| I-34 | 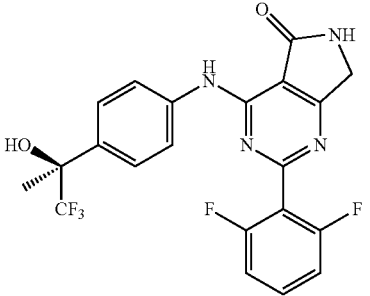 [SMILES: C[C@](O)(c1ccc(Nc2nc(-c3c(F)cccc3F)nc3c2C(=O)NC3)cc1)C(F)(F)F] |
| I-35 | 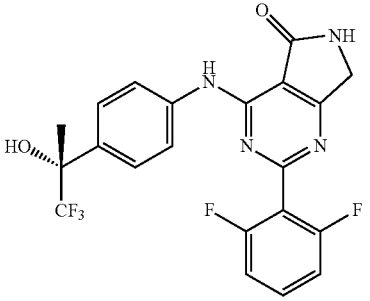 [SMILES: C[C@@](O)(c1ccc(Nc2nc(-c3c(F)cccc3F)nc3c2C(=O)NC3)cc1)C(F)(F)F] |
| I-36 | 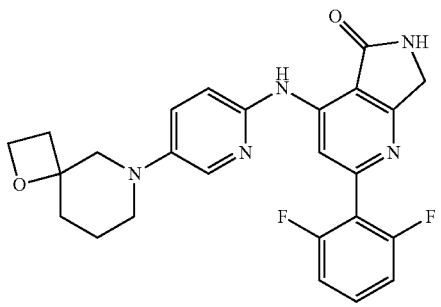 [SMILES: O=C1NCc2nc(-c3c(F)cccc3F)cc(Nc3ccc(N4CCCC5(CCO5)C4)cn3)c21] |
| I-37 | 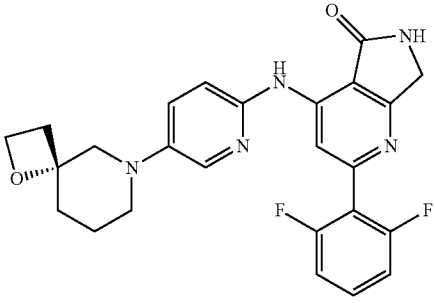 [SMILES: O=C1NCc2nc(-c3c(F)cccc3F)cc(Nc3ccc(N4CCC[C@@]5(CCO5)C4)cn3)c21] |
| I-38 | 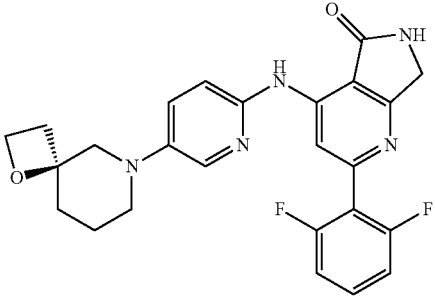 [SMILES: O=C1NCc2nc(-c3c(F)cccc3F)cc(Nc3ccc(N4CCC[C@]5(CCO5)C4)cn3)c21] |
| I-39 | 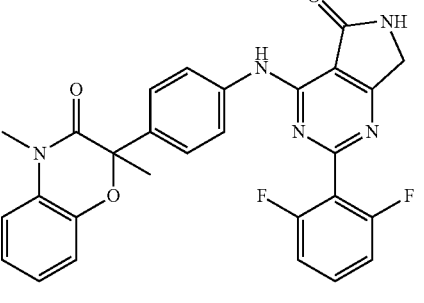 |
| I-40 | 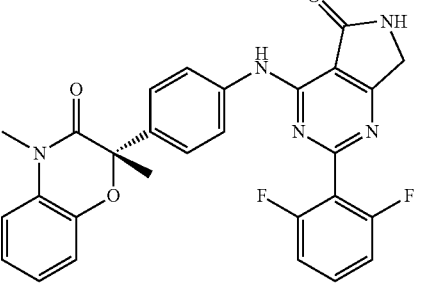 |

TABLE 1-continued
Exemplary Compounds
| Compound # | Structure |
|---|---|
| I-41 | 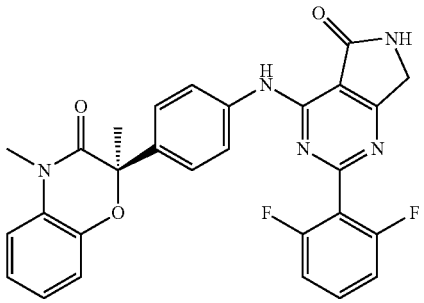 [SMILES: CN1C(=O)[C@@](C)(c2ccc(Nc3nc(-c4c(F)cccc4F)nc4c3C(=O)NC4)cc2)Oc2ccccc21] |
| I-42 | 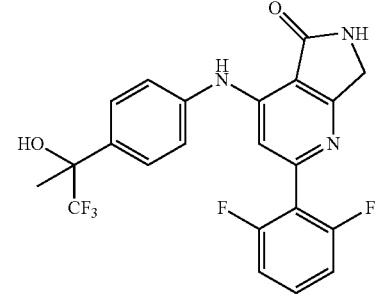 [SMILES: CC(O)(c1ccc(Nc2cc(-c3c(F)cccc3F)nc3c2C(=O)NC3)cc1)C(F)(F)F] |
| I-43 | 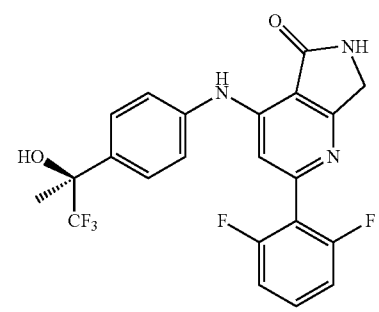 |
| I-44 | 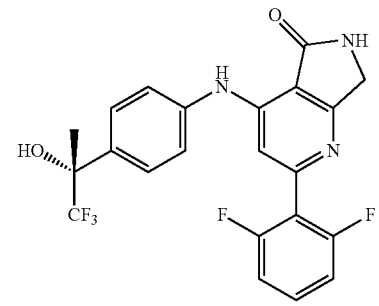 [SMILES: C[C@@](O)(c1ccc(Nc2cc(-c3c(F)cccc3F)nc3c2C(=O)NC3)cc1)C(F)(F)F] |
| I-45 | 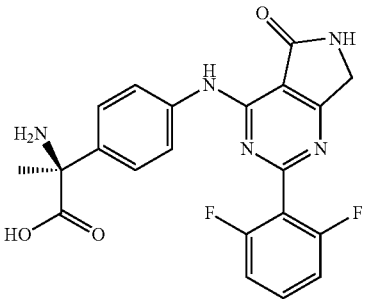 [SMILES: C[C@@](N)(C(=O)O)c1ccc(Nc2nc(-c3c(F)cccc3F)nc3c2C(=O)NC3)cc1] |
| I-46 | 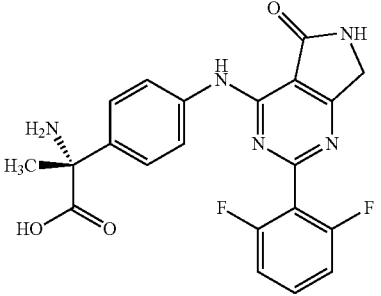 [SMILES: C[C@](N)(C(=O)O)c1ccc(Nc2nc(-c3c(F)cccc3F)nc3c2C(=O)NC3)cc1] |
| I-47 | 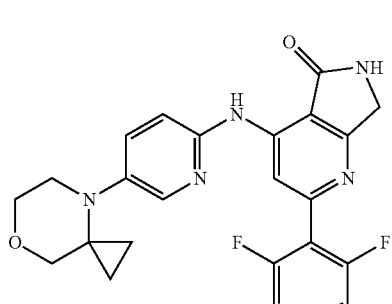 |
| I-48 | 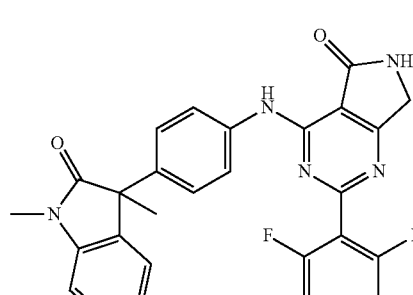 |

TABLE 1-continued

Exemplary Compounds

| Compound # | Structure |
|---|---|
| I-49 | 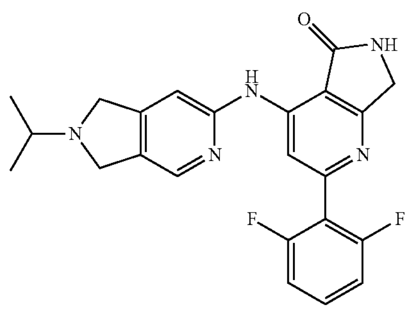 [SMILES: CC(C)N1Cc2cnc(Nc3cc(-c4c(F)cccc4F)nc4c3C(=O)NC4)cc2C1] |
| I-50 | 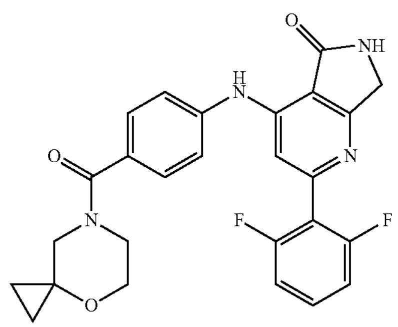 [SMILES: O=C1NCc2nc(-c3c(F)cccc3F)cc(Nc3ccc(C(=O)N4CCOC5(CC5)C4)cc3)c21] |
| I-51 | 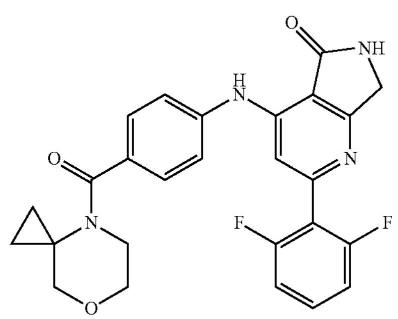 [SMILES: O=C1NCc2nc(-c3c(F)cccc3F)cc(Nc3ccc(C(=O)N4CCOCC45CC5)cc3)c21] |
| I-52 | 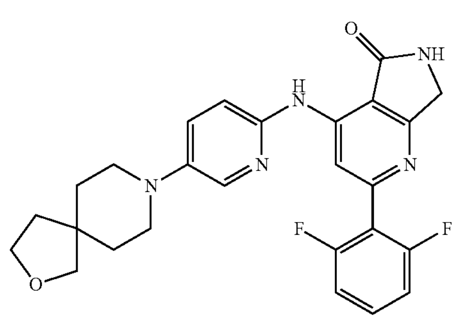 [SMILES: O=C1NCc2nc(-c3c(F)cccc3F)cc(Nc3ccc(N4CCC5(CCOC5)CC4)cn3)c21] |
| I-53 | |
| I-54 | |
| I-55 | |
| I-56 | |

TABLE 1-continued

Exemplary Compounds

| Compound # | Structure |
|---|---|
| I-57 | 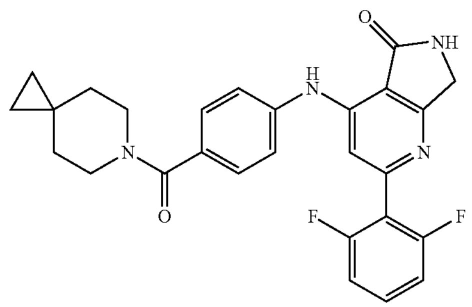 [SMILES: O=C1NCc2nc(-c3c(F)cccc3F)cc(Nc3ccc(C(=O)N4CCC5(CC4)CC5)cc3)c21] |
| I-58 | 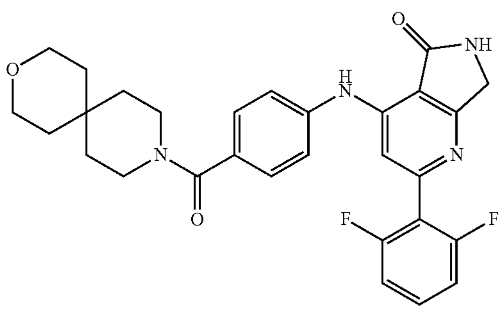 [SMILES: O=C1NCc2nc(-c3c(F)cccc3F)cc(Nc3ccc(C(=O)N4CCC5(CCOCC5)CC4)cc3)c21] |
| I-59 | 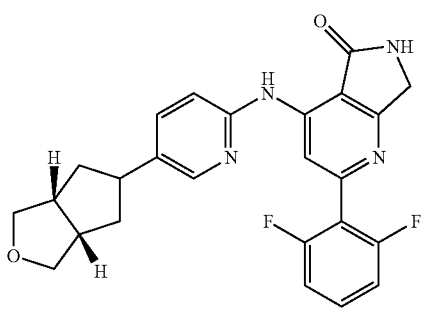 [SMILES: O=C1NCc2nc(-c3c(F)cccc3F)cc(Nc3ccc(C4C[C@H]5COC[C@H]5C4)cn3)c21] |
| I-60 | 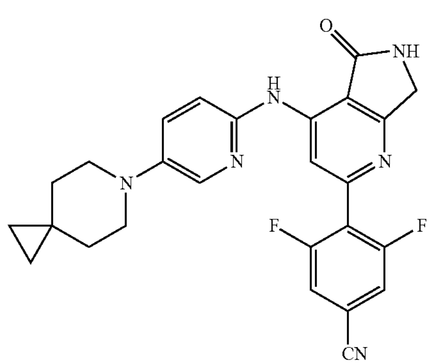 [SMILES: N#Cc1cc(F)c(-c2cc(Nc3ccc(N4CCC5(CC4)CC5)cn3)c3c(n2)CNC3=O)c(F)c1] |
| I-61 | |
| I-62 | |
| I-63 | |
| I-64 | |

TABLE 1-continued
Exemplary Compounds
| Compound # | Structure |
|---|---|
| I-65 | 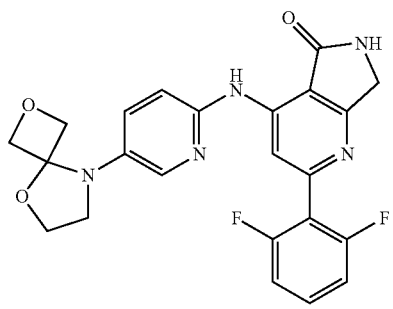 [SMILES: O=C1NCc2nc(-c3c(F)cccc3F)cc(Nc3ccc(N4CCOC45COC5)cn3)c21] |
| I-66 | 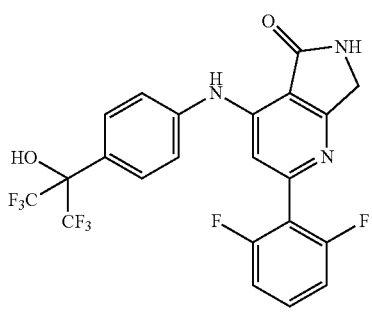 |
| I-67 | 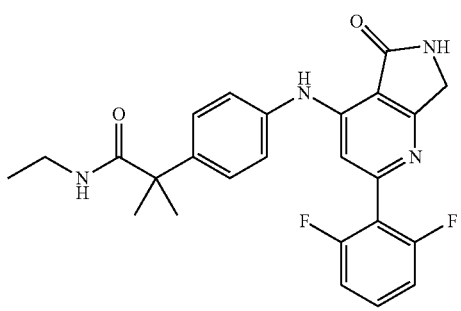 [SMILES: CCNC(=O)C(C)(C)c1ccc(Nc2cc(-c3c(F)cccc3F)nc3c2C(=O)NC3)cc1] |
| I-68 | 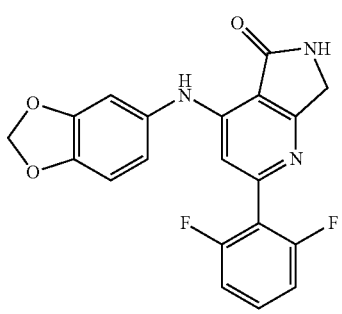 [SMILES: O=C1NCc2nc(-c3c(F)cccc3F)cc(Nc3ccc4c(c3)OCO4)c21] |
| I-69 | 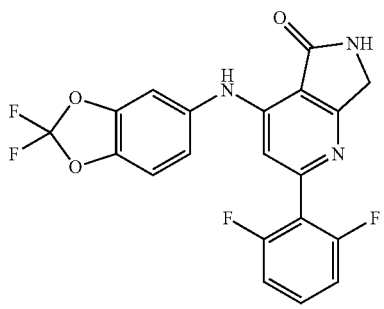 [SMILES: O=C1NCc2nc(-c3c(F)cccc3F)cc(Nc3ccc4c(c3)OC(F)(F)O4)c21] |
| I-70 | 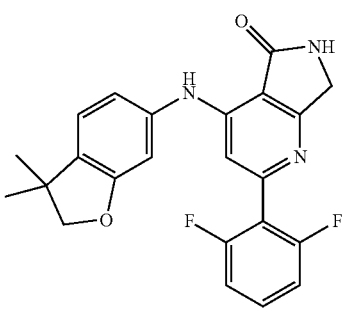 [SMILES: CC1(C)COc2cc(Nc3cc(-c4c(F)cccc4F)nc4c3C(=O)NC4)ccc21] |
| I-71 | 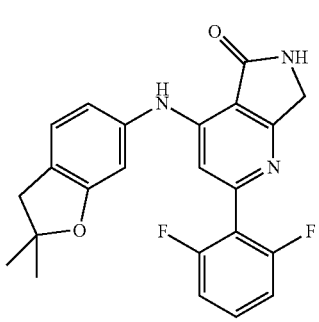 [SMILES: CC1(C)Cc2ccc(Nc3cc(-c4c(F)cccc4F)nc4c3C(=O)NC4)cc2O1] |
| I-72 | 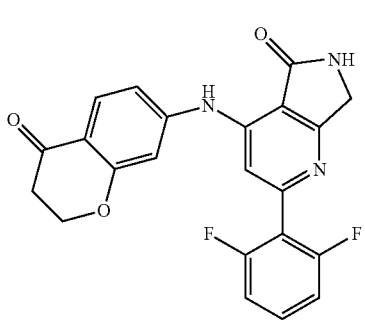 [SMILES: O=C1CCOc2cc(Nc3cc(-c4c(F)cccc4F)nc4c3C(=O)NC4)ccc21] |

TABLE 1-continued

Exemplary Compounds

| Compound # | Structure |
|---|---|
| I-73 | 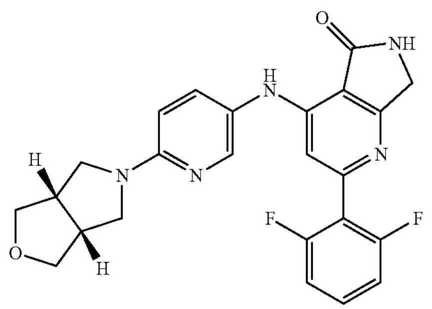 [SMILES: O=C1NCc2nc(-c3c(F)cccc3F)cc(Nc3ccc(N4C[C@H]5COC[C@H]5C4)nc3)c21] |
| I-74 | 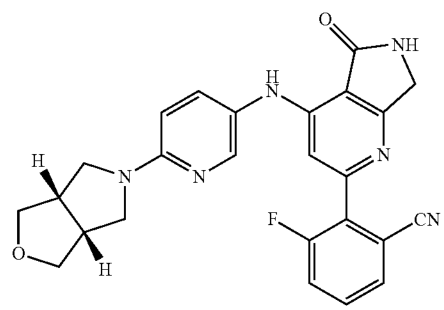 [SMILES: N#Cc1cccc(F)c1-c1cc(Nc2ccc(N3C[C@H]4COC[C@H]4C3)nc2)c2c(n1)CNC2=O] |
| I-75 | 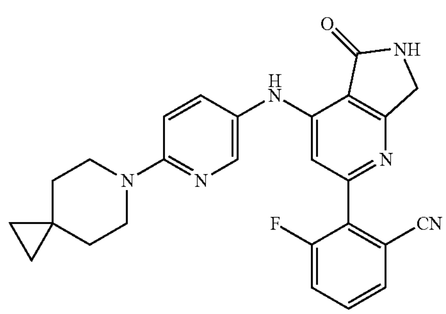 [SMILES: N#Cc1cccc(F)c1-c1cc(Nc2ccc(N3CCC4(CC3)CC4)nc2)c2c(n1)CNC2=O] |
| I-76 | 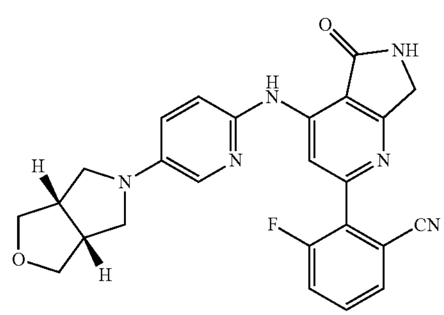 [SMILES: N#Cc1cccc(F)c1-c1cc(Nc2ccc(N3C[C@H]4COC[C@H]4C3)cn2)c2c(n1)CNC2=O] |
| I-77 | 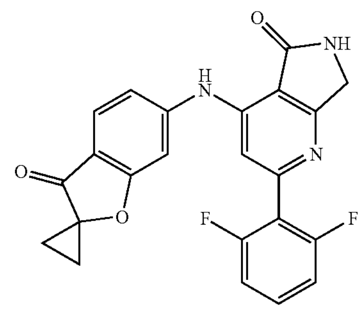 [SMILES: O=C1NCc2nc(-c3c(F)cccc3F)cc(Nc3ccc4c(c3)OC3(CC3)C4=O)c21] |
| I-78 | 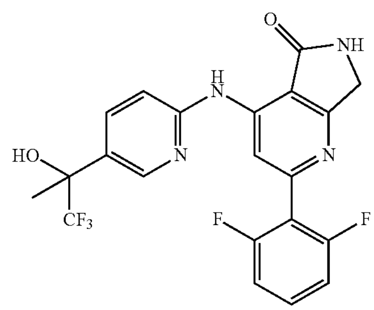 [SMILES: CC(O)(c1ccc(Nc2cc(-c3c(F)cccc3F)nc3c2C(=O)NC3)nc1)C(F)(F)F] |
| I-79 | 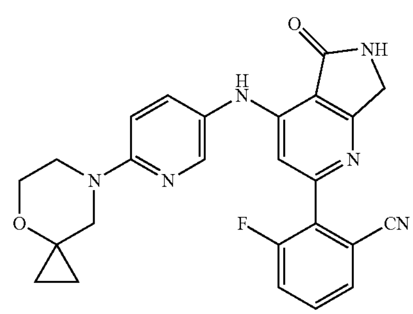 [SMILES: N#Cc1cccc(F)c1-c1cc(Nc2ccc(N3CCOC4(CC4)C3)nc2)c2c(n1)CNC2=O] |
| I-80 | 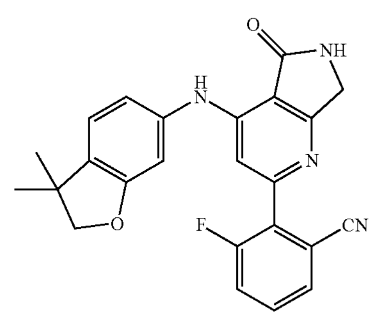 [SMILES: CC1(C)COc2cc(Nc3cc(-c4c(F)cccc4C#N)nc4c3C(=O)NC4)ccc21] |

TABLE 1-continued

Exemplary Compounds

| Compound # | Structure |
|---|---|
| I-81 | (structure) |
| I-82 | (structure) |
| I-83 | (structure) |
| I-84 | (structure) |
| I-85 | (structure) |
| I-86 | (structure) |
| I-87 | (structure) |
| I-88 | (structure) |

TABLE 1-continued

Exemplary Compounds

| Compound # | Structure |
|---|---|
| I-89 | (structure) |
| I-90 | (structure) |
| I-91 | (structure) |
| I-92 | (structure) |
| I-93 | (structure) |

In some embodiments, the method employs a compound set forth in Table 1, above, or a pharmaceutically acceptable salt thereof. In some embodiments, the present invention provides a compound set forth in Table 1, above, or a pharmaceutically acceptable salt thereof. In some embodiments, the present invention provides a pharmaceutical composition comprising a compound set forth in Table 1 above, or a pharmaceutically acceptable salt thereof, together with a pharmaceutically acceptable carrier, excipient, or diluent.

Without wishing to be bound by any particular theory, it is believed that proximity of an inhibitor compound, or pendant moiety of an inhibitor compound, to the water of interest facilitates displacement or disruption of that water by the inhibitor compound, or pendant moiety of an inhibitor compound. In some embodiments, a water molecule displaced or disrupted by an inhibitor compound, or pendant moiety of an inhibitor compound, is an unstable water molecule.

In certain embodiments, the method employs a complex comprising TYK2 and an inhibitor, wherein at least one unstable water of TYK2 is displaced or disrupted by the inhibitor. In some embodiments, at least two unstable waters selected are displaced or disrupted by the inhibitor.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit a TYK2 protein kinase, or a mutant thereof, in a biological sample or in a patient. In certain embodiments, the amount of compound in compositions of this invention is such that is effective to measurably inhibit a TYK2 protein kinase, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of a TYK2 protein kinase, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of kinase activity of one or more enzymes. In some embodiments the kinase inhibited by the compounds and methods of the invention is TYK2.

TYK2 is a non-receptor tyrosine kinase member of the Janus kinase (JAKs) family of protein kinases. The mammalian JAK family consists of four members, TYK2, JAK1, JAK2, and JAK3. JAK proteins, including TYK2, are integral to cytokine signaling. TYK2 associates with the cytoplasmic domain of type I and type II cytokine receptors, as well as interferon types I and III receptors, and is activated by those receptors upon cytokine binding. Cytokines implicated in TYK2 activation include interferons (e.g. IFN-α, IFN-β, IFN-κ, IFN-δ, IFN-ε, IFN-τ, IFN-ω, and IFN-ζ (also known as limitin), and interleukins (e.g. IL-4, IL-6, IL-10, IL-11, IL-12, IL-13, IL-22, IL-23, IL-27, IL-31, oncostatin M, ciliary neurotrophic factor, cardiotrophin 1, cardiotrophin-like cytokine, and LIF). Velasquez et al., "A protein kinase in the interferon α/β signaling pathway," Cell (1992) 70:313; Stahl et al., "Association and activation of Jak-Tyk kinases by CNTF-LIF-OSM-IL-6β receptor components," Science (1994) 263:92; Finbloom et al., "IL-10 induces the tyrosine phosphorylation of Tyk2 and Jak1 and the differential assembly of Stat1 and Stat3 complexes in human T cells and monocytes," J. Immunol. (1995) 155:1079; Bacon et al., "Interleukin 12 (IL-12) induces tyrosine phosphorylation of Jak2 and Tyk2: differential use of Janus family kinases by IL-2 and IL-12," J. Exp. Med. (1995) 181:399; Welham et al., "Interleukin-13 signal transduction in lymphohemopoietic cells: similarities and differences in signal transduction with interleukin-4 and insulin," J. Biol. Chem. (1995) 270:12286; Parham et al., "A receptor for the heterodimeric cytokine IL-23 is composed of IL-12Rβ1 and a novel cytokine receptor subunit, IL-23R," J. Immunol. (2002) 168:5699. The activated TYK2 then goes on to phosphorylate further signaling proteins such as members of the STAT family, including STAT1, STAT2, STAT4, and STAT6.

TYK2 activation by IL-23, has been linked to inflammatory bowel disease (IBD), Crohn's disease, and ulcerative colitis. Duerr et al., "A Genome-Wide Association Study Identifies IL23R as an Inflammatory Bowel Disease Gene," Science (2006) 314:1461-1463. As the downstream effector of IL-23, TYK2 also plays a role in psoriasis, ankylosing spondylitis, and Behcet's disease. Cho et al., "Genomics and the multifactorial nature of human auto-immune disease," N. Engl. J. Med (2011) 365:1612-1623; Cortes et al., "Identification of multiple risk variants for ankylosing spondylitis through high-density genotyping of immune-related loci," Nat. Genet. (2013) 45(7):730-738; Remmers et al., "Genome-wide association study identifies variants in the MEW class I, IL10, and IL23R-IL12RB2 regions associated with Behcet's disease," Nat. Genet. (2010) 42:698-702. A genome-wide association study of 2,622 individuals with psoriasis identified associations between disease susceptibility and TYK2. Strange et al., "A genome-wide association study identifies new psoriasis susceptibility loci and an interaction between HLA-C and ERAP1," Nat. Genet. (2010) 42:985-992. Knockout or tyrphostin inhibition of TYK2 significantly reduces both IL-23 and IL-22-induced dermatitis. Ishizaki et al., "Tyk2 is a therapeutic target for psoriasis-like skin inflammation," Intl. Immunol. (2013), doi: 10.1093/intimm/dxt062.

TYK2 also plays a role in respiratory diseases such as asthma, chronic obstructive pulmonary disease (COPD), lung cancer, and cystic fibrosis. Goblet cell hyperplasia (GCH) and mucous hypersecretion is mediated by IL-13-induced activation of TYK2, which in turn activates STAT6. Zhang et al., "Docking protein Gab2 regulates mucin expression and goblet cell hyperplasia through TYK2/STAT6 pathway," FASEB J. (2012) 26:1-11.

Decreased TYK2 activity leads to protection of joints from collagen antibody-induced arthritis, a model of human rheumatoid arthritis. Mechanistically, decreased Tyk2 activity reduced the production of $T_h1/T_h17$-related cytokines and matrix metalloproteases, and other key markers of inflammation. Ishizaki et al., "Tyk2 deficiency protects joints against destruction in anti-type II collagen antibody-induced arthritis in mice," Intl. Immunol. (2011) 23(9):575-582.

TYK2 knockout mice showed complete resistance in experimental autoimmune encephalomyelitis (EAE, an animal model of multiple sclerosis (MS)), with no infiltration of CD4 T cells in the spinal cord, as compared to controls, suggesting that TYK2 is essential to pathogenic CD4-mediated disease development in MS. Oyamada et al., "Tyrosine Kinase 2 Plays Critical Roles in the Pathogenic CD4 T Cell Responses for the Development of Experimental Autoimmune Encephalomyelitis," J. Immunol. (2009) 183: 7539-7546. This corroborates earlier studies linking increased TYK2 expression with MS susceptibility. Ban et al., "Replication analysis identifies TYK2 as a multiple sclerosis susceptibility factor," Eur J. Hum. Genet. (2009) 17:1309-1313. Loss of function mutation in TYK2, leads to decreased demyelination and increased remyelination of neurons, further suggesting a role for TYK2 inhibitors in the treatment of MS and other CNS demyelination disorders.

TYK2 is the sole signaling messenger common to both IL-12 and IL-23. TYK2 knockout reduced methylated BSA injection-induced footpad thickness, imiquimod-induced psoriasis-like skin inflammation, and dextran sulfate sodium or 2,4,6-trinitrobenzene sulfonic acid-induced colitis in mice.

Joint linkage and association studies of various type I IFN signaling genes with systemic lupus erythematosus (SLE, an autoimmune disorder), showed a strong, and significant correlation between loss of function mutations to TYK2 and decreased prevalence of SLE in families with affected members. Sigurdsson et al., "Polymorphisms in the Tyrosine Kinase 2 and Interferon Regulatory Factor 5 Genes Are Associated with Systemic Lupis Erythematosus," Am. J. Hum. Genet. (2005) 76:528-537. Genome-wide association studies of individuals with SLE versus an unaffected cohort showed highly significant correlation between the TYK2 locus and SLE. Graham et al., "Association of NCF2, IKZF1, IRF8, IFIH1, and TYK2 with Systemic Lupus Erythematosus," PLoS Genetics (2011) 7(10):e1002341.

TYK2 has been shown to play an important role in maintaining tumor surveillance and TYK2 knockout mice showed compromised cytotoxic T cell response, and accelerated tumor development. However, these effects were linked to the efficient suppression of natural killer (NK) and cytotoxic T lymphocytes, suggesting that TYK2 inhibitors would be highly suitable for the treatment of autoimmune disorders or transplant rejection. Although other JAK family members such as JAK3 have similar roles in the immune system, TYK2 has been suggested as a superior target because of its involvement in fewer and more closely related signaling pathways, leading to fewer off-target effects. Simma et al. "Identification of an Indispensable Role for Tyrosine Kinase 2 in CTL-Mediated Tumor Surveillance," Cancer Res. (2009) 69:203-211.

However, paradoxically to the decreased tumor surveillance observed by Simma et al., studies in T-cell acute lymphoblastic leukemia (T-ALL) indicate that T-ALL is highly dependent on IL-10 via TYK2 via STAT1-mediated signal transduction to maintain cancer cell survival through upregulation of anti-apoptotic protein BCL2. Knockdown of TYK2, but not other JAK family members, reduced cell growth. Specific activating mutations to TYK2 that promote cancer cell survival include those to the FERM domain (G36D, S47N, and R425H), the JH2 domain (V731I), and the kinase domain (E957D and R1027H). However, it was also identified that the kinase function of TYK2 is required for increased cancer cell survival, as TYK2 enzymes featuring kinase-dead mutations (M978Y or M978F) in addition to an activating mutation (E957D) resulted in failure to transform. Sanda et al. "TYK2-STAT1-BCL2 Pathway Dependence in T-Cell Acute Lymphoblastic Leukemia," Cancer Disc. (2013) 3(5):564-577.

Thus, selective inhibition of TYK2 has been suggested as a suitable target for patients with IL-10 and/or BCL2-addicted tumors, such as 70% of adult T-cell leukemia cases. Fontan et al. "Discovering What Makes STAT Signaling TYK in T-ALL," Cancer Disc. (2013) 3:494-496.

TYK2 mediated STAT3 signaling has also been shown to mediate neuronal cell death caused by amyloid-β (Aβ) peptide. Decreased TYK2 phosphorylation of STAT3 following Aβ administration lead to decreased neuronal cell death, and increased phosphorylation of STAT3 has been observed in postmorterm brains of Alzheimer's patients. Wan et al. "Tyk/STAT3 Signaling Mediates β-Amyloid-Induced Neuronal Cell Death: Implications in Alzheimer's Disease," J. Neurosci. (2010) 30(20):6873-6881.

Inhibition of JAK-STAT signaling pathways is also implicated in hair growth, and the reversal of the hair loss associated with alopecia areata. Xing et al., "Alopecia areata is driven by cytotoxic T lymphocytes and is reversed by JAK inhibition," Nat. Med. (2014) 20: 1043-1049; Harel et al., "Pharmacologic inhibition of JAK-STAT signaling promotes hair growth," Sci. Adv. (2015) 1(9):e1500973.

Accordingly, compounds that inhibit the activity of TYK2 are beneficial, especially those with selectivity over JAK2. Such compounds should deliver a pharmacological response that favorably treats one or more of the conditions described herein without the side-effects associated with the inhibition of JAK2.

Even though TYK2 inhibitors are known in the art, there is a continuing need to provide novel inhibitors having more effective or advantageous pharmaceutically relevant properties. For example, compounds with increased activity, selectivity over other JAK kinases (especially JAK2), and ADMET (absorption, distribution, metabolism, excretion, and/or toxicity) properties. Thus, in some embodiments, the present invention provides inhibitors of TYK2 which show selectivity over JAK2.

The activity of a compound utilized in this invention as an inhibitor of TYK2, or a mutant thereof, may be assayed in vitro, in vivo or in a cell line. In vitro assays include assays that determine inhibition of either the phosphorylation activity and/or the subsequent functional consequences, or ATPase activity of activated TYK2, or a mutant thereof. Alternate in vitro assays quantitate the ability of the inhibitor to bind to TYK2. Inhibitor binding may be measured by radiolabeling the inhibitor prior to binding, isolating the inhibitor/TYK2 complex and determining the amount of radiolabel bound. Alternatively, inhibitor binding may be determined by running a competition experiment where new inhibitors are incubated with TYK2 bound to known radioligands. Representative in vitro and in vivo assays useful in assaying a TYK2 inhibitor include those described and disclosed in, e.g., each of which is herein incorporated by reference in its entirety. Detailed conditions for assaying a compound utilized in this invention as an inhibitor of TYK2, or a mutant thereof, are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of TYK2 and are therefore useful for treating one or more disorders associated with activity of TYK2 or mutants thereof. Thus, in certain embodiments, the present invention provides a method for treating a TYK2-mediated disorder comprising the step of administering to a patient in need thereof a compound of the present invention, or pharmaceutically acceptable composition thereof.

As used herein, the term "TYK2-mediated" disorders, diseases, and/or conditions as used herein means any disease or other deleterious condition in which TYK2 or a mutant thereof is known to play a role. Accordingly, another embodiment of the present invention relates to treating or lessening the severity of one or more diseases in which TYK2, or a mutant thereof, is known to play a role. Such TYK2-mediated disorders include but are not limited to autoimmune disorders, inflammatory disorders, proliferative disorders, endocrine disorders, neurological disorders and disorders associated with transplantation.

In some embodiments, the present invention provides a method for treating one or more disorders, wherein the disorders are selected from autoimmune disorders, inflammatory disorders, proliferative disorders, endocrine disorders, neurological disorders, and disorders associated with transplantation, said method comprising administering to a patient in need thereof, a pharmaceutical composition comprising an effective amount of a compound of the present invention, or a pharmaceutically acceptable salt thereof.

In some embodiments, the disorder is an autoimmune disorder. In some embodiments the disorder is selected from type 1 diabetes, systemic lupus erythematosus, multiple sclerosis, psoriasis, Behcet's disease, POEMS syndrome, Crohn's disease, ulcerative colitis, and inflammatory bowel disease.

In some embodiments, the disorder is an inflammatory disorder. In some embodiments, the inflammatory disorder is rheumatoid arthritis, asthma, chronic obstructive pulmonary disease, psoriasis, hepatomegaly, Crohn's disease, ulcerative colitis, inflammatory bowel disease.

In some embodiments, the disorder is a proliferative disorder. In some embodiments, the proliferative disorder is a hematological cancer. In some embodiments the proliferative disorder is a leukemia. In some embodiments, the leukemia is a T-cell leukemia. In some embodiments the T-cell leukemia is T-cell acute lymphoblastic leukemia (T-ALL). In some embodiments the proliferative disorder is polycythemia vera, myelofibrosis, essential or thrombocytosis.

In some embodiments, the disorder is an endocrine disorder. In some embodiments, the endocrine disorder is polycystic ovary syndrome, Crouzon's syndrome, or type 1 diabetes.

In some embodiments, the disorder is a neurological disorder. In some embodiments, the neurological disorder is Alzheimer's disease.

In some embodiments the proliferative disorder is associated with one or more activating mutations in TYK2. In some embodiments, the activating mutation in TYK2 is a mutation to the FERM domain, the JH2 domain, or the kinase domain. In some embodiments the activating mutation in TYK2 is selected from G36D, S47N, R425H, V731I, E957D, and R1027H.

In some embodiments, the disorder is associated with transplantation. In some embodiments the disorder associated with transplantation is transplant rejection, or graft versus host disease.

In some embodiments the disorder is associated with type I interferon, IL-10, IL-12, or IL-23 signaling. In some embodiments the disorder is associated with type I interferon signaling. In some embodiments the disorder is associated with IL-10 signaling. In some embodiments the disorder is associated with IL-12 signaling. In some embodiments the disorder is associated with IL-23 signaling.

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In certain embodiments, the present invention provides a method of treating alopecia areata.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic jubenile idiopathic arthritis (SJIA), Cryopyrin Associated Periodic Syndrome (CAPS), and osteoarthritis.

In some embodiments the inflammatory disease which can be treated according to the methods of this invention is a $T_h1$ or $T_h17$ mediated disease. In some embodiments the $T_h17$ mediated disease is selected from Systemic lupus erythematosus, Multiple sclerosis, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

Furthermore, the invention provides the use of a compound according to the definitions herein, or a pharmaceutically acceptable salt, or a hydrate or solvate thereof for the preparation of a medicament for the treatment of an autoimmune disorder, an inflammatory disorder, or a proliferative disorder, or a disorder commonly occurring in connection with transplantation.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I and one or more additional therapeutic agents. The therapeutic agent may be administered together with a compound of formula I, or may be administered prior to or following administration of a compound of formula I. Suitable therapeutic agents are described in further detail below. In certain embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound of formula I and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating rheumatoid arthritis comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating systemic lupus erythematosus comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating Crohn's disesase, ulcerative colitis, or inflammatory bowel disease comprising administering to a patient in need thereof a compound of formula I and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In some embodiments, the present invention provides a method of treating COPD comprising administering to a patient in need thereof a compound of formula I and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In another embodiment, the present invention provides a method of treating a hematological malignancy comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a solid tumor comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a hematological malignancy comprising administering to a patient in need thereof a compound of formula I and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of formula I and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating or lessening the severity of a disease comprising administering to a patient in need thereof a compound of formula and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of formula I and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments the present invention provides a method of treating or lessening the severity of a disease comprising administering to a patient in need thereof a compound of formula I and a Bcl-2 inhibitor, wherein the disease is an inflammatory disorder, an autoimmune disorder, a proliferative disorder, an endocrine disorder, a neurological disorder, or a disorder associated with transplantation. In some embodiments, the disorder is a proliferative disorder, lupus, or lupus nephritis. In some embodiments, the proliferative disorder is chronic lymphocytic leukemia, diffuse large B-cell lymphoma, Hodgkin's disease, small-cell lung cancer, non-small-cell lung cancer, myelodysplastic syndrome, lymphoma, a hematological neoplasm, or solid tumor.

The compounds and compositions, according to the method of the present invention, may be administered using any amount and any route of administration effective for treating or lessening the severity of an autoimmune disorder, an inflammatory disorder, a proliferative disorder, an endocrine disorder, a neurological disorder, or a disorder associated with transplantation. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting TYK2, or a mutant thereof, activity in a biological sample comprising the step of contacting said biological sample with a compound of this invention, or a composition comprising said compound. In certain embodiments, the invention relates to a method of irreversibly inhibiting TYK2, or a mutant thereof, activity in a biological sample comprising the step of contacting said biological sample with a compound of this invention, or a composition comprising said compound.

In another embodiment, the invention provides a method of selectively inhibiting TYK2 over one or more of JAK1, JAK2, and JAK3. In some embodiments, a compound of the present invention is more than 2-fold selective over JAK1/2/3. In some embodiments, a compound of the present invention is more than 5-fold selective over JAK1/2/3. In some embodiments, a compound of the present invention is more than 10-fold selective over JAK1/2/3. In some embodiments, a compound of the present invention is more than 50-fold selective over JAK1/2/3. In some embodiments, a compound of the present invention is more than 100-fold selective over JAK1/2/3.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of TYK2 (or a mutant thereof) activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting activity of TYK2, or a mutant thereof, in a patient comprising the step of administering to said patient a compound of the present invention, or a composition comprising said compound. According to certain embodiments, the invention relates to a method of reversibly or irreversibly inhibiting one or more of TYK2, or a mutant thereof, activity in a patient comprising the step of administering to said patient a compound of the present invention, or a composition comprising said compound. In other embodiments, the present invention provides a method for treating a disorder mediated by TYK2, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other therapeutic compounds. In some embodiments, the other therapeutic compounds are antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j)

compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuranosylcytosine (ara-c) and bisulfan; ALK inhibitors, which are compounds which target, decrease or inhibit anaplastic lymphoma kinase, and Bcl-2 inhibitors.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412. In some embodiments, the present invention provides a method of treating AML associated with an ITD and/or D835Y mutation, comprising administering a compound of the present invention together with a one or more FLT3 inhibitors. In some embodiments, the FLT3 inhibitors are selected from quizartinib (AC220), a staurosporine derivative (e.g. midostaurin or lestaurtinib), sorafenib, tandutinib, LY-2401401, LS-104, EB-10, famitinib, NOV-110302, NMS-P948, AST-487, G-749, SB-1317, S-209, SC-110219, AKN-028, fedratinib, tozasertib, and sunitinib. In some embodiments, the FLT3 inhibitors are selected from quizartinib, midostaurin, lestaurtinib, sorafenib, and sunitinib.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BILL 284, ONO 4057, SB 209247; LTD4 antagonists such as montelukast and zafirlukast; PDE4 inhibitors such cilomilast (Ariflo® GlaxoSmithKline), Roflumilast (Byk Gulden),V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID(™) CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1

Synthesis of 2-(2,6-difluorophenyl)-4-(indolin-6-ylamino)-6,7-dihydro-5H-pyrrolo[3,4-d]pyrimidin-5-one, I-1

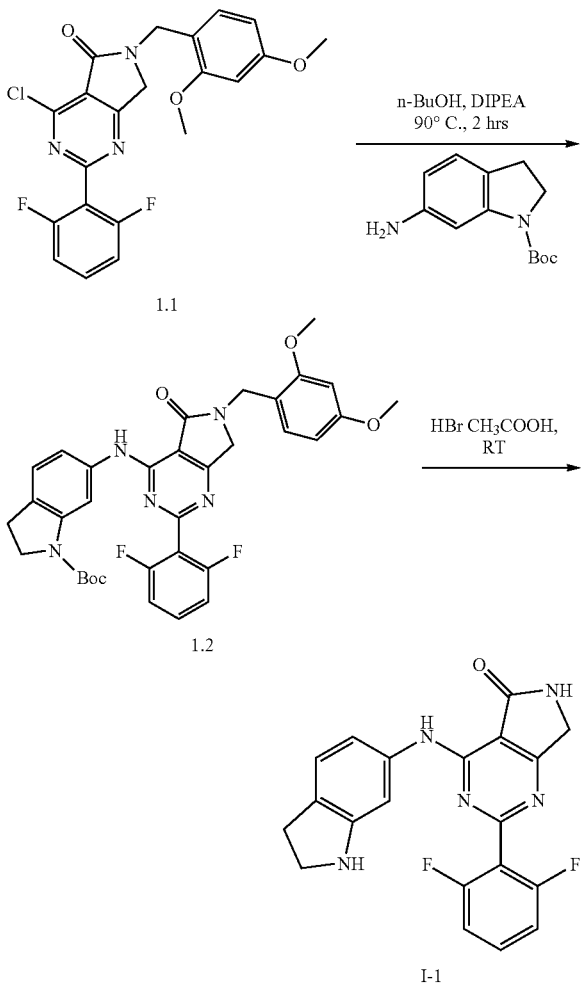

Synthesis of compound 1.2 To a solution of compound 1.1 (300 mg 0.69 mmol, 1.0 eq.) in 1-butanol (9.0 mL) were added tert-butyl 6-aminoindoline-1-carboxylate (162 mg, 0.69 mmol, 1.0 eq.) and DIPEA (224 mg, 1.74 mmol, 2.5 eq.) at room temperature. Reaction mixture was heated at 85-90° C. for 2 hours. After completion of the reaction, mixture was poured into the water and extracted using ethyl acetate. Organic layer was washed with by brine solution, dried over sodium sulfate and concentrated under reduced pressure. Crude was purified by column chromatography to provide compound 1.1 (302 mg, 69.04%), MS (ES): m/z 630.6 [M+H]$^+$.

Synthesis of compound I-1. A solution of compound 1.1 (302 mg, 0.48 mmol, 1.0 eq.) in HBr/HOAc solution (33%, 6.0 mL) was stirred at room temperature for 45 minutes.

After completion of the reaction, reaction mixture was poured into cold water, neutralized with NaHCO$_3$ and extracted with ethyl acetate (75 ml×2). Solvent was removed under reduced pressure and the crude was purified by column chromatography to afford pure compound I-1 (105 mg, 57.7%). MS (ES): m/z-380.3 [M+H]$^+$; $^1$H NMR (400 MHz, DMSO-d$_6$): δ 8.88 (s, 1H), 8.85 (s,1H), 7.61-7.57 (m,1H), 7.28-7.24 (t,2H), 6.97-6.93 (m,2H), 6.81-6.79 (dd, 1H), 5.62 (s, 1H), 4.45 (s,2H), 3.42-3.40 (t,2H), 2.87-2.83 (t, 2H).

Example 2

Synthesis of 2-(2,6-difluorophenyl)-4-((3,3-dimethylindolin-6-yl)amino)-6,7-dihydro-5H-pyrrolo[3,4-d]pyrimidin-5-one, I-2

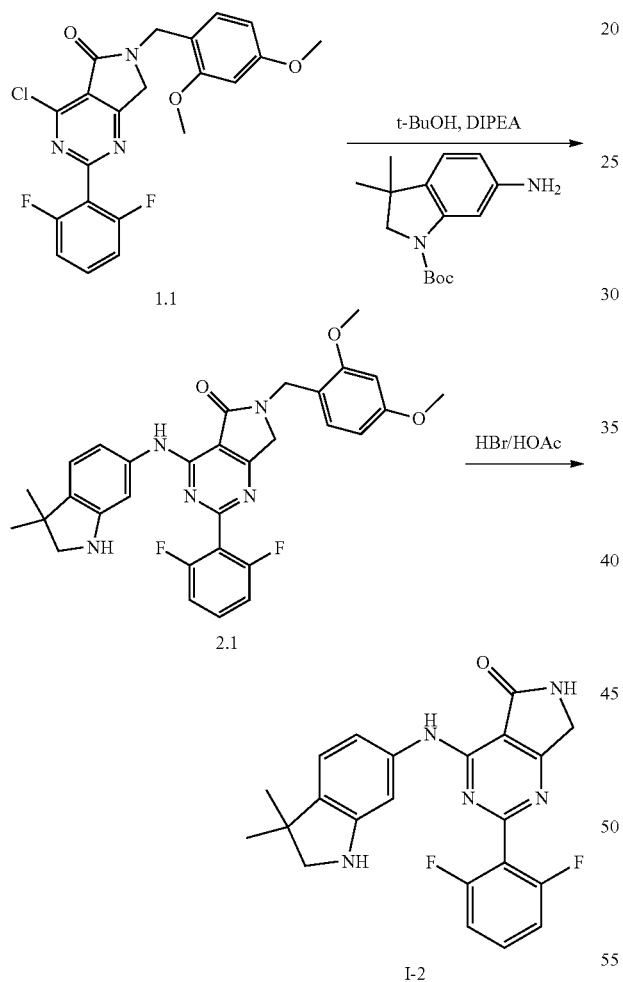

Synthesis of compound 2.1. To a solution of compound 1.1 (130 mg 0.3 mmol, 1.0 eq.) in 1-butanol (5.0 mL) was added tert-butyl 6-amino-3,3-dimethylindoline-1-carboxylate (79 mg, 0.3 mmol, 1.0 eq.) and diisopropylethylamine (97 mg, 0.75 mmol, 2.5 eq.) at room temperature. Reaction was heated at 85-90° C. for 2 hours. After completion of the reaction, reaction mixture was poured into water and extracted using ethyl acetate. Organic layer was washed with by brine solution, dried over sodium sulfate and concentrated under reduced pressure. Crude was purified by column chromatography to afford pure compound 2.1 (110 mg, 65.53%), MS (ES): m/z 558.6 [M+H]$^+$.

Synthesis of compound I-2. A solution of compound 2.1 (110 mg, 0.19 mmol, 1.0 eq.) in hydrogen bromide/CH$_3$COOH (33%, 4 ml) was stirred at room temperature for 45 minutes. After completion of the reaction, mixture was poured into cold water, neutralized with NaHCO$_3$. Product was extracted with ethyl acetate (75 mL×2). Solvent was removed under reduced pressure at 45° C. The crude was purified using column chromatography and preparative TLC to afford pure compound I-2 (20 mg, 24.9%). MS (ES): m/z-408.4 [M+H]$^+$;$^1$H NMR (400 MHz, DMSO-d$_6$): δ 8.88 (s,1H), 8.85 (s,1H), 7.62-7.57 (m,1H), 7.28-7.24 (t,2H), 6.94-6.92 (m,2H), 5.60 (s,1H), 4.45 (s,2H), 3.167-3.163 (d,2H), 1.23 (s,6H).

Example 3

Synthesis of compound 2-(2,6-difluorophenyl)-4-((2,2-dimethylindolin-6-yl)amino)-6,7-dihydro-5H-pyrrolo[3,4-d]pyrimidin-5-one, I-3

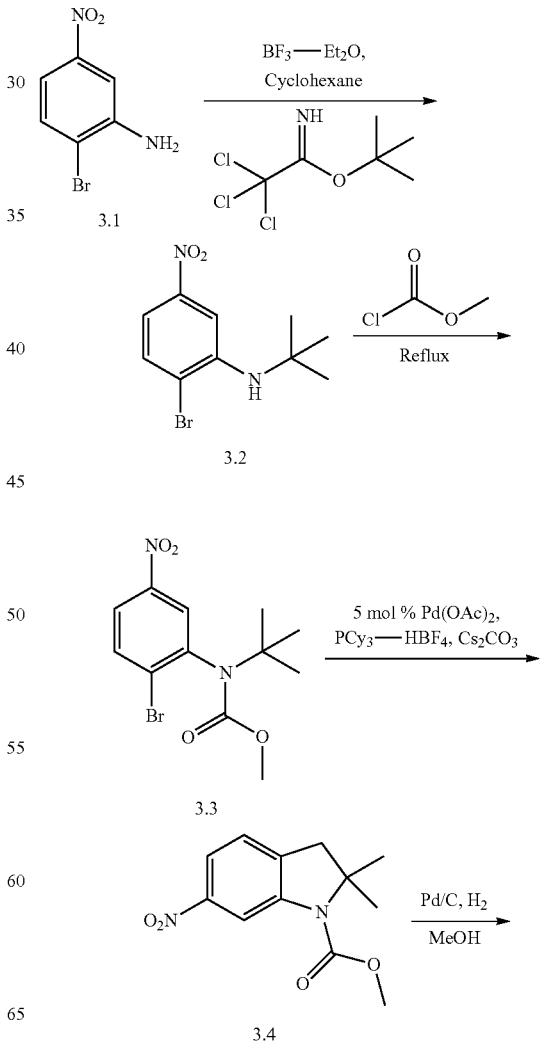

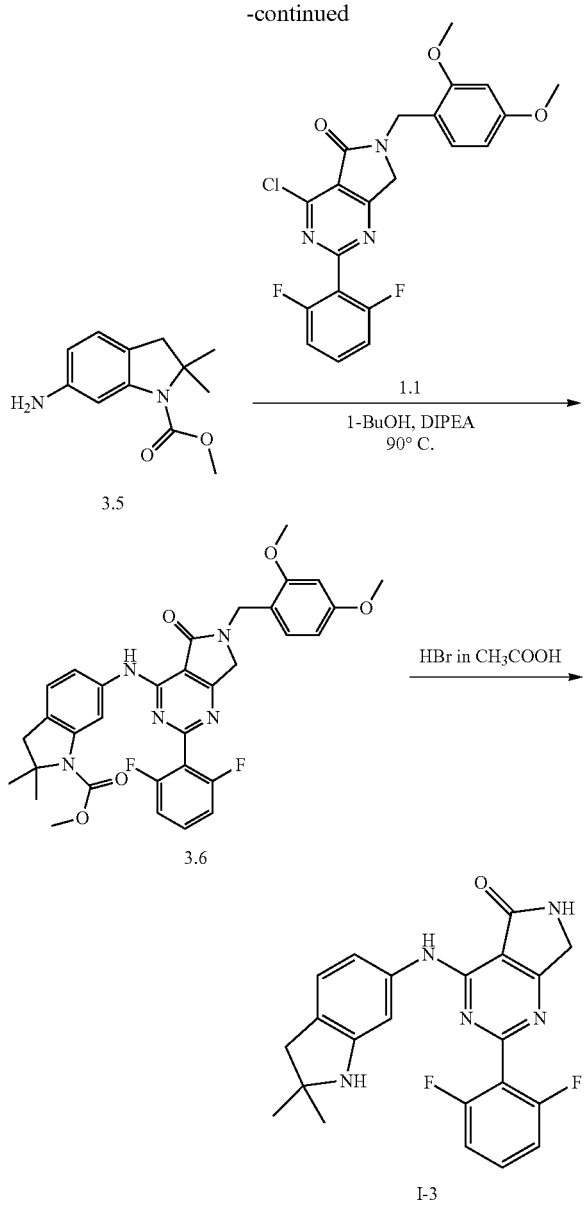

Synthesis of compound 3.2. To a solution of compound 3.1 (1 g 4.60 mmol, 1.0 eq.) in cyclohexane (8 mL) were added ter.-butyl 2,2,2-trichloroacetimidate (2.05 ml, 11.51 mmol, 2.5 eq.), BF₃-Et₂O (0.11 ml) at room temperature under argon atmosphere for 15 minutes. Reaction mixture was stirred at room temperature for 16 hours. After completion of reaction, mixture was poured into water and extracted using ethyl acetate. Organic layer was washed with by satd. NaHCO₃, dried over Na₂SO₄ and concentrated under reduced pressure. The crude was purified using column chromatography to provide compound 3.2 (0.27 g, 21.3%). MS (ES): No ionisation [M+H]⁺.

Synthesis of compound 3.3. Compound 3.2 (0.2 g, 0.73 mmol) was dissolved in methylchloroformate (2 mL). The reaction mixture was heated at 80° C. for 16 hrs. After completion of the reaction, water was added to the mixture and extracted using dichloromethane. Organic layer was dried over sodium sulfate and concentrated under reduced pressure. The crude reaction mixture was purified by column chromatography to afford compound 3.3 (0.12 g, 49.49%). MS (ES): m/z No ionisation [M+H]⁺.

Synthesis of compound 3.4. To a solution of compound 3.3 (0.050 g, 0.150 mmol, 1.0 eq.) in xylene were added cesium carbonate (0.068 g, 0.211 mmol), tricyclohexylphosphine tetrafluoroborate (0.004 g, 0.009 mmol, 0.06 eq.), pivalic acid (0.005 g, 0.0452 mmol, 0.3 eq), and palladium acetate (0.001 g,0.0045 mmol, 0.03 eq). Reaction mixture was degassed using argon atmosphere for 10 min. The reaction was stirred at 140° C. for 1 hour. After completion of the reaction, mixture was poured in water, and product was extracted with ethyl acetate (50 mL×2). Solvent was removed under reduced pressure at 45° C. to get crude, which was purified by column chromatography to afford pure compound 3.4 (0.035 g, 92.63%). MS (ES): m/z 251 [M+H]⁺.

Synthesis of compound 3.5. To a suspension of Pd/C (10 mg) in methanol (10 ml) was added compound 3.4 (0.085 g, 0.339 mmol, 1.0 eq.) under nitrogen atmosphere. The mixture was purged with H₂ (gas) at room temperature for 2 hours. After completion of the reaction, the mixture was filtered through celite. Solvent was removed under reduced pressure at 45° C. to afford compound 3.5 (0.070 g, 93.6%). MS (ES): m/z 221.3 [M+H]⁺.

Synthesis of compound 3.6. To a solution of compound 3.5 (130 mg 0.301 mmol, 1.0 eq.) in 1-butanol (2.0 mL) was added compound 3.5 (72 mg, 0.331 mmol, 1.1 eq.) and DIPEA (0.15 mL, 0.903 mmol, 3 eq.) at room temperature. Reaction was heated at 90° C. for 3 hours. After completion of the reaction, mixture was poured into water and extracted using ethyl acetate. Organic layer was washed with by brine solution. Organic layer was dried over sodium sulfate and concentrated under reduced pressure. Crude was purified by column chromatography to afford pure compound 3.6 (120 mg, 64.75%), MS (ES): m/z 616.7 [M+H]⁺.

Synthesis of compound I-3. A solution of compound 3.6 (0.120 g, 0.194 mmol, 1.0 eq.) in HBr/HOAc (33%, 3 ml) was stirred at room temperature for 45 minutes. After completion of the reaction, the mixture was poured into cold water, neutralized with NaHCO₃ and product was extracted with ethyl acetate (75 ml×2). Solvent was removed under reduced pressure at 45° C. to get crude which was purified to afford pure compound I-3 (10 mg, 12.59%). MS (ES): m/z-408.3 [M+H]⁺; ¹H NMR (400 MHz, DMSO-d₆): δ 8.87 (d,2H), 7.59 (m,1H), 7.25 (dd,2H), 6.91 (d,2H), 6.75 (dd, 1H), 5.64 (s,1H), 4.45 (s, 2H), 2.67 (s,2H), 1.20 (d,6H).

Example 4

Synthesis of 4-((5-((1R,5S)-8-oxa-3-azabicyclo[3.2.1]octan-3-yl)pyridin-2-yl)amino)-2-(2,6-difluorophenyl)-6,7-dihydro-5H-pyrrolo[3,4-b]pyridin-5-one, I-4

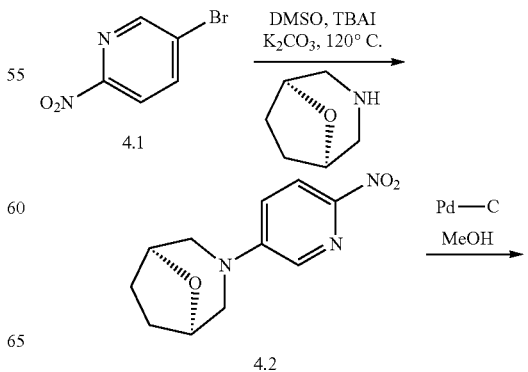

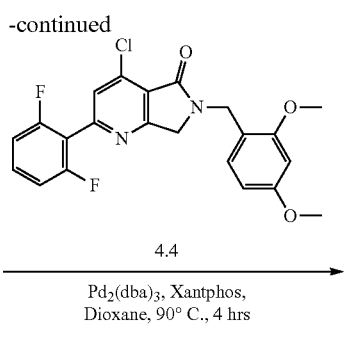

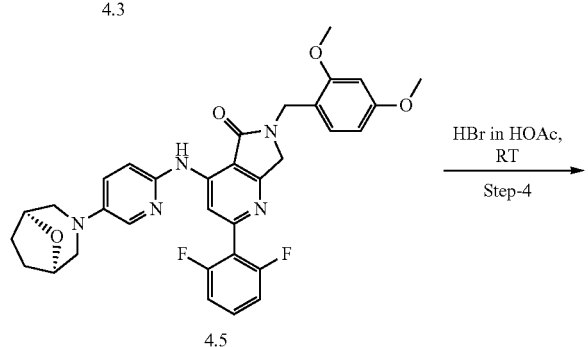

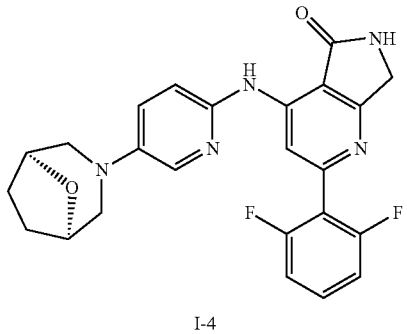

I-4

Synthesis of compound 4.2. To a solution of 4.1 (0.2 g, 0.9852 mmol, 1.0 equiv) in DMSO (3 ml) were added TBAI (0.036 g, 0.0985 mmol, 0.1 equiv), (1R,5S)-8-oxa-3-zabicyclo[3.2.1]octane (0.162 g, 1.083 mmol, 1.1 equiv.), and K₂CO₃ (0.544 g, 3.94 mmol, 4 equiv). Reaction mixture was heated at 120° C. for 2 hours. The reaction mixture was poured into water and product was extracted with ethyl acetate. Organic layers were combined and dried over sodium sulphate and concentrated under reduced pressure to obtain crude material which was purified using column chromatography to furnish 4.2 (0.120 g, 51.77%). MS (ES): m/z 236 [M+H]$^+$.

Synthesis of compound 4.3. To a solution of compound 4.2 (0.120 g, 0.5106 mmol, 1.0 equiv) in methanol (5 mL) was added with 10% Pd/C(0.012 mg) under nitrogen atmosphere. Suspension was purged with H₂ gas for 3 hours. Reaction mixture was filtered through celite and obtained filtrate was concentrated under reduced pressure to get crude compound 4.3 (0.105 g,) which was used as such for the next step, MS (ES): m/z 206.0 [M+H]$^+$.

Synthesis of compound 4.5. To a solution of compound 4.4 (0.2 g, 0.4645 mol, 1.0 equiv) in 1,4-dioxane (3 mL) were added compound 4.3 (0.104 g, 0.5109 mmol, 1.1 equiv) and potassium carbonate (0.160 g, 1.161 mmol, 2.5 equiv). The reaction mixture was degassed for 10 minutes using argon gas, then Pd₂(dba)₃ (0.042 g, 0.0464 mmol, 0.1 equiv) and Xantphos (0.053 g, 0.0929 mmol, 0.2 equiv) were added. Suspension was degassed for additional 5 minutes. The reaction was then heated at 110° C. for 2 h. After completion of reaction, reaction mixture was poured in water and product was extracted with ethyl acetate. Organic layers were combined and dried over sodium sulphate and concentrated under reduced pressure to obtain crude material which was purified using column chromatography to afford pure 4.5 (0.12 g, 43.1%). MS (ES): m/z 600.3 [M+H]$^+$.

Synthesis of compound I-4. The compound 4.5 was dissolved in HBr in acetic acid (2 ml) and stirred at room temperature for 1 h. After completion of the reaction, mixture was poured into water and basified with saturated bicarbonate solution and product was extracted with ethyl acetate. Organic layers were combined and dried over sodium sulphate and concentrated under reduced pressure to obtain crude material which was purified using column chromatography to get pure compound I-4 (0.052 g, 57.8%). MS (ES): m/z 450.21 [M+H]$^+$; $^1$H NMR(DMSO-d₆, 400 MHZ): 9.47(s, 1H), 8.80 (s, 1H), 8.34 (s,1H), 7.94 (d,1H), 7.60 (m,1H), 7.40 (dd,1H), 7.25(m,2H), 7.10 (d,1H), 4.40(s, 4H), 3.36 (t,2H), 2.80 (dd,2H), 1.83 (s,4H).

Example 5

Synthesis of 4-((4-(8-oxa-3-azabicyclo[3.2.1]octane-3-carbonyl)phenyl)-amino)-2-(2,6-difluorophenyl)-6,7-dihydro-5H-pyrrolo[3,4-d]pyrimidin-5-one, I-5

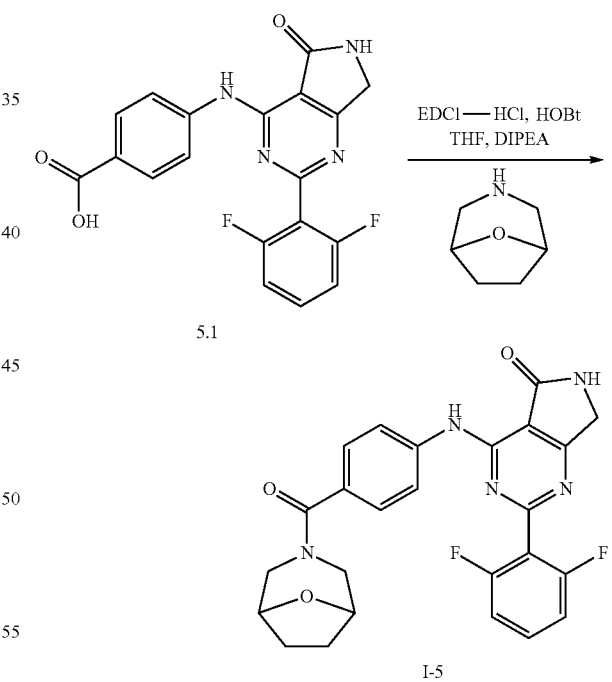

To a solution of 5.1 (0.1 g 0.26 mmol, 1.0 eq) in dry THF (5.0 mL) was added EDCl-HCl (0.1 g, 0.52 mmol, 2.0 eq) followed by HOBt (0.069 g, 0.39 mmol, 1.5 eq) at 0° C. Solution was allowed to stir at 0° C. for 1 hour. 8-oxa-3-azabicyclo[3.2.1]octane (0.035 g, 0.312 mmol, 1.2 eq) was added followed by DIPEA (0.1 g, 0.78 mmol, 3.0 eq). Reaction mixture was allowed to warm to room temperature and was stirred overnight. After completion of the reaction, mixture was poured into water and extracted using ethyl acetate (50 mL×2). Organic layer was washed with by brine solution, dried over sodium sulfate and concentrated under reduced pressure. Crude was purified by column chromatography to afford pure compound I-5 (65 mg, 52.1%). MS (ES): M/z 478.53 [M+H]$^+$, $^1$H NMR (400 MHz, DMSO-d$_6$): δ 9.226 (s, 1H), 8.963 (s, 1H), 7.828-7.849 (d,2H), 7.568-7.641 (m,1H), 7.373-7.394 (d,2H), 7.249-7.343 (m,2H), 4.505 (2H), 4.358 (m,2H), 7.193 (m,1H), 3.727-3.763 (m,1H), 2.950-2.976 (m,2H), 1.771 (m, 6H).

Example 6

Synthesis of 2-(4-((2-(2,6-difluorophenyl)-5-oxo-6,7-dihydro-5H-pyrrolo-[3,4-d]pyrimidin-4-yl)amino)phenyl)-2-hydroxypropanoic acid, I-6

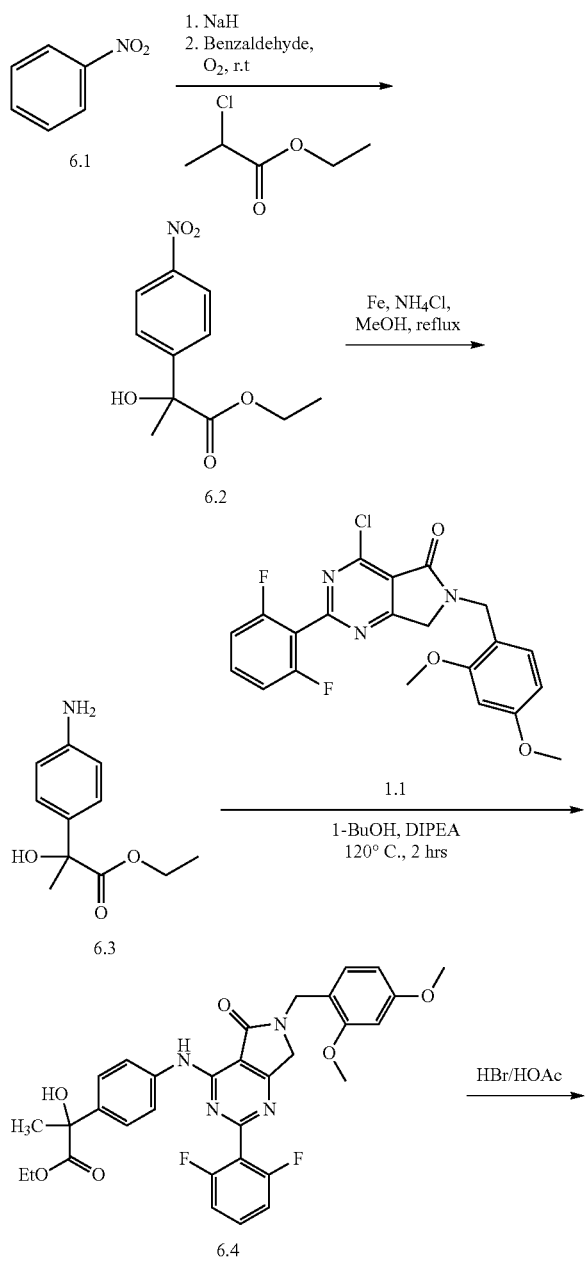

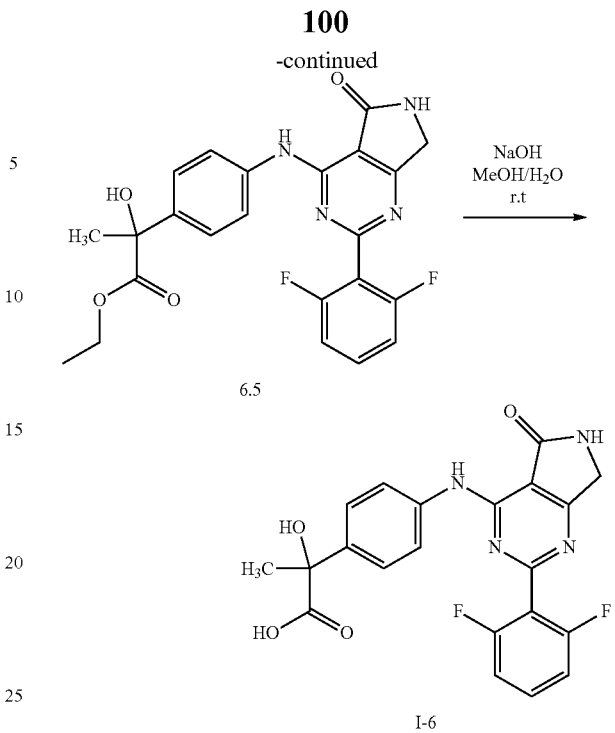

Synthesis of compound 6.2. To a suspension of NaH (0.740 g, 18.45 mmol, 1.5 eq) in DMF (10 mL) at 0° C. was added 6.1 (0.76 g, 6.15 mmol, 0.5 eq) followed by ethyl 2-chloropropionate (1.68 g, 12.3 mmol, 1 eq) dropwise via a syringe. The reaction was stirred at 0° C. for 1 hour then for 2 hours at room temperature. Benzaldehyde (0.98 g, 9.2 2 mmol, 0.75 eq) was added and reaction was purged with oxygen for 16 hours. The reaction mixture was quenched with ice; then dil. HCl was added. Product was extracted with ethyl acetate (20 mL×2). Organic layers were combined and dried over sodium sulphate and concentrated under reduced pressure. Crude was purified using column chromatography to frurnish 6.2 (0.466 g, 31.6%). MS (ES): m/z no ionisation [M+H]$^+$.

Synthesis of compound 6.3. To a solution of 6.2 (0.266 g, 1.112 mmol, 1.0 eq) in methanol (3 mL) and water (3 mL) was added NH$_4$Cl (0.350 g, 5.564 mmol, 5.0 eq) followed by iron powder (0.311 g, 5.564 mmol, 5.0 eq) for 1 h. Reaction mixture was heated at 80° C. for 2 hours. Reaction mixture was filtered through celite, washed with methanol and obtained filtrate was concentrated under reduced pressure to get crude 6.3 (0.2 g, 85.96%) which was used as such for the next step, MS (ES): m/z 210 [M+H]$^+$.

Synthesis of compound 6.4. To a solution of 1.1 (0.3 g, 0.69 mmol, 1.0 eq) in 1-butanol (5 mL) were added 6.3 (0.159 g, 0.764 mmol, 1.1 eq) and DIPEA (0.4 mL, 2.08 mmol, 3 eq). Reaction was stirred at 100° C. for 2 hours. After completion of the reaction, reaction mixture was poured into water and product was extracted with EtOAc (100 mL×2). Organic layer were combined, dried over sodium sulphate and concentrated under reduced pressure. Crude was purified purified by column chromatography to furnish 6.4 (0.3 g, 71.4%). MS (ES): m/z 605.3 [M+H]$^+$.

Synthesis of compound 6.5. Compound 6.4 (0.3 g, 0.496 mmol, 1.0 eq) was dissolved in HBr/HOAc mixture (3 mL) and stirred at room temperature for 1 hour. After completion, reaction mixture was poured into water and basified with saturated bicarbonate solution. Product was extracted with EtOAc (100 mL×2). Organic layers were combined, dried over sodium sulphate and concentrated under reduced pressure. The crude was purified using column chromatography to provide 6.5 (0.125 g, 55.44%). MS (ES): m/z 455.2 [M+H]⁺.

Synthesis of compound I-6. To a solution of 6.5 (0.125 g, 0.275 mmol, 1.0 eq) in MeOH (3 mL) and water (3 mL) was added NaOH (0.066 g, 1.65 mmol, 6.0 eq). Reaction was stirred at room temperature for 1 hour. Solvent was concentrated under reduced pressure and reaction mixture was acidified with diluted HCl and extracted with EtOAc (25 mL×2). Organic layers were combined, dried over sodium sulphate and concentrated under reduced pressure. The crude was triturated with diethyl ether and pentane to get pure compound I-6 (0.08 g, 68.2%). MS (ES): m/z 427.3 [M+H]⁺. ¹H NMR (DMSO-d₆, 400 MHz): 12.67 (s,1H), 9.081 (s,1H), 8.90 (s,1H), 7.70 (d,2H), 7.60 (m,1H), 7.47 (d,2H), 7.27 (t,2H), 5.76 (s,1H), 4.48 (s,2H), 1.6 (s,3H).

Example 7

Synthesis of (S)-2-(4-((2-(2,6-difluorophenyl)-5-oxo-6,7-dihydro-5H-pyrrolo[3,4-d]pyrimidin-4-yl)amino)phenyl)-2-hydroxypropanoic acid, I-7

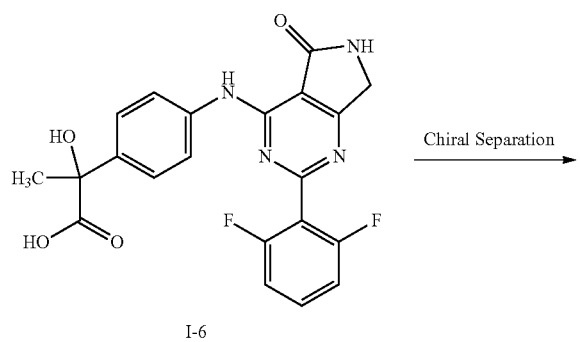

Compound I-7 was obtained by chiral separation of compound I-6. MS (ES): m/z [M+H]⁺, ¹H NMR (400 MHz, DMSO-d₆): δ 12.65 (s,1H), 9.079 (s,1H), 8.904 (s,1H), 7.70-7.72 (d,2H), 7.60 (m,1H), 7.58 (d,2H), 7.25-7.30 (m,2H), 4.48 (s,2H), 1.60 (s,3H).

Example 8

Synthesis of (R)-2-(4-((2-(2,6-difluorophenyl)-5-oxo-6,7-dihydro-5H-pyrrolo[3,4-d]pyrimidin-4-yl)amino)phenyl)-2-hydroxypropanoic acid, I-8

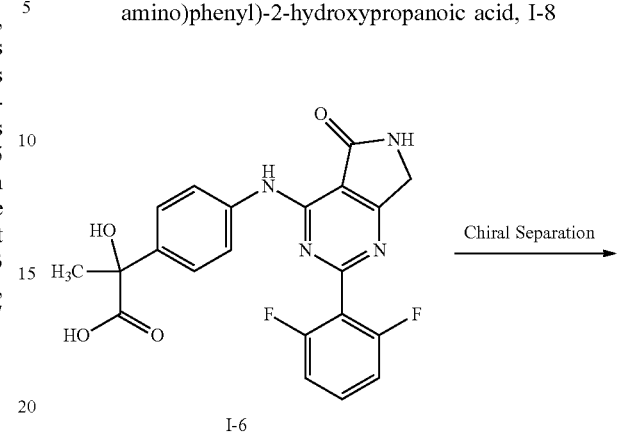

Compound I-8 was obtained by chiral separation of compound I-6. MS (ES): m/z [M+H]⁺, ¹H NMR (400 MHz, DMSO-d₆): δ 9.06 (s,1H), 8.88 (s,1H), 7.68-7.70 (d,2H), 7.58-7.62 (m,1H), 7.47-7.49 (d, 2H), 7.25-7.29 (m,2H), 4.47 (s,2H), 1.58-1.62 (d,3H).

Example 9

Synthesis of compound 2-amino-2-(4-((2-(2,6-difluorophenyl)-5-oxo-6,7-dihydro-5H-pyrrolo[3,4-d]pyrimidin-4-yl)amino)phenyl)-N-ethylpropanamide, I-9

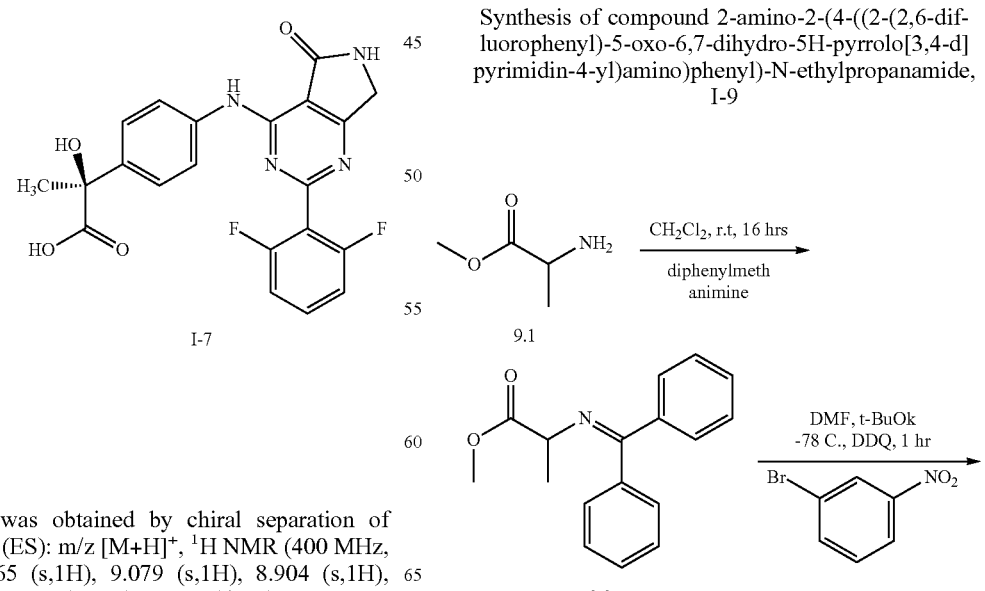

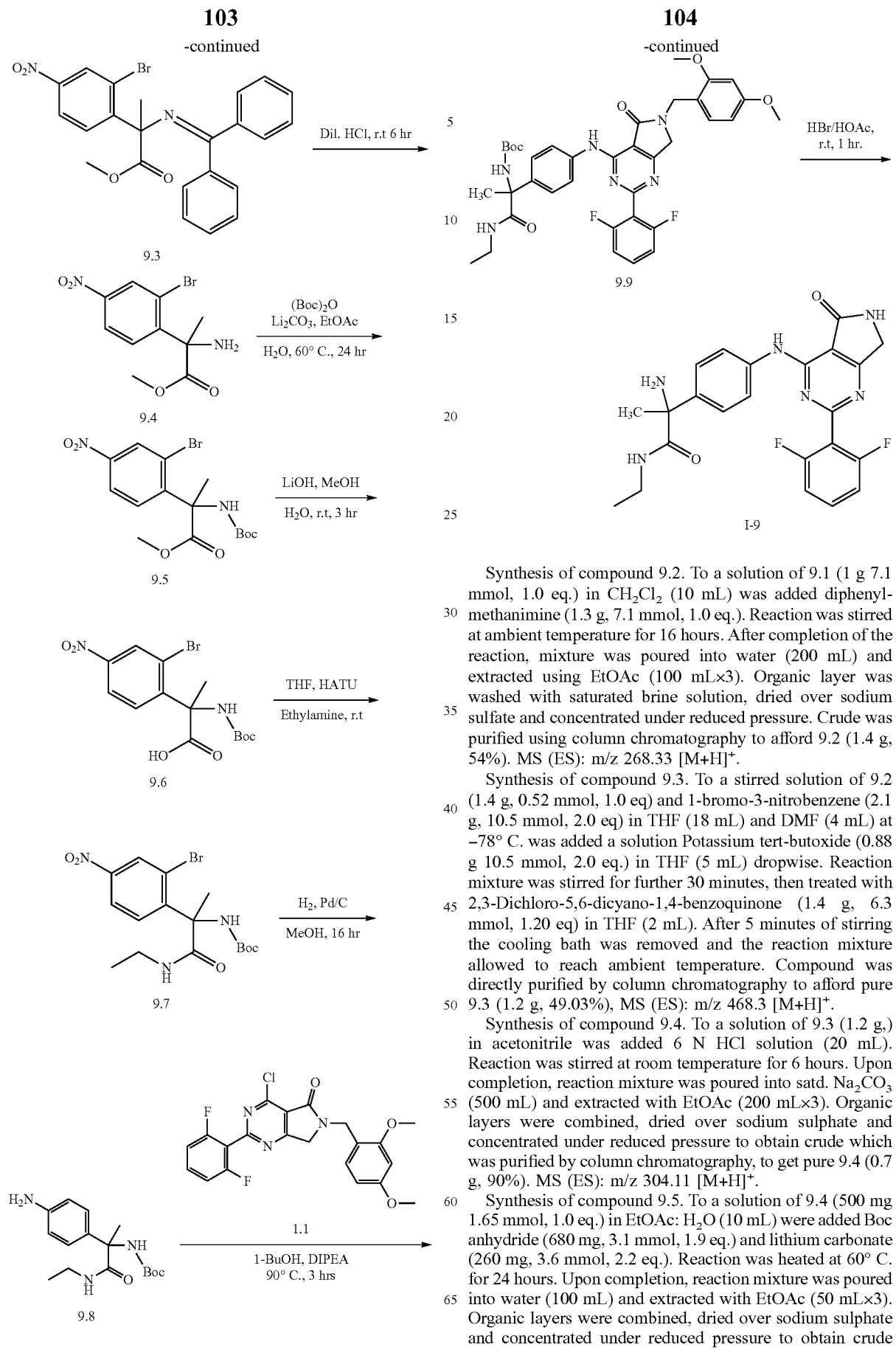

Synthesis of compound 9.2. To a solution of 9.1 (1 g 7.1 mmol, 1.0 eq.) in CH₂Cl₂ (10 mL) was added diphenylmethanimine (1.3 g, 7.1 mmol, 1.0 eq.). Reaction was stirred at ambient temperature for 16 hours. After completion of the reaction, mixture was poured into water (200 mL) and extracted using EtOAc (100 mL×3). Organic layer was washed with saturated brine solution, dried over sodium sulfate and concentrated under reduced pressure. Crude was purified using column chromatography to afford 9.2 (1.4 g, 54%). MS (ES): m/z 268.33 [M+H]⁺.

Synthesis of compound 9.3. To a stirred solution of 9.2 (1.4 g, 0.52 mmol, 1.0 eq) and 1-bromo-3-nitrobenzene (2.1 g, 10.5 mmol, 2.0 eq) in THF (18 mL) and DMF (4 mL) at −78° C. was added a solution Potassium tert-butoxide (0.88 g 10.5 mmol, 2.0 eq.) in THF (5 mL) dropwise. Reaction mixture was stirred for further 30 minutes, then treated with 2,3-Dichloro-5,6-dicyano-1,4-benzoquinone (1.4 g, 6.3 mmol, 1.20 eq) in THF (2 mL). After 5 minutes of stirring the cooling bath was removed and the reaction mixture allowed to reach ambient temperature. Compound was directly purified by column chromatography to afford pure 9.3 (1.2 g, 49.03%), MS (ES): m/z 468.3 [M+H]⁺.

Synthesis of compound 9.4. To a solution of 9.3 (1.2 g,) in acetonitrile was added 6 N HCl solution (20 mL). Reaction was stirred at room temperature for 6 hours. Upon completion, reaction mixture was poured into satd. Na₂CO₃ (500 mL) and extracted with EtOAc (200 mL×3). Organic layers were combined, dried over sodium sulphate and concentrated under reduced pressure to obtain crude which was purified by column chromatography, to get pure 9.4 (0.7 g, 90%). MS (ES): m/z 304.11 [M+H]⁺.

Synthesis of compound 9.5. To a solution of 9.4 (500 mg 1.65 mmol, 1.0 eq.) in EtOAc: H₂O (10 mL) were added Boc anhydride (680 mg, 3.1 mmol, 1.9 eq.) and lithium carbonate (260 mg, 3.6 mmol, 2.2 eq.). Reaction was heated at 60° C. for 24 hours. Upon completion, reaction mixture was poured into water (100 mL) and extracted with EtOAc (50 mL×3). Organic layers were combined, dried over sodium sulphate and concentrated under reduced pressure to obtain crude which was purified by column chromatography to furnish 9.5 (0.55 g, 59.1%). MS (ES): m/z 404.11 [M+H]⁺.

Synthesis of compound 9.6. A solution of 9.5 (500 mg 1.24 mmol, 1.0 eq.) in MeOH/H₂O water (10 mL) was charged with added LiOH (0.16 g, 3.7 mmol, 3 eq.) and stirred at ambient temeperature for 3 hours. Upon completion, reaction mixture was poured into water (100 mL) and extracted with ethyl acetate (50 mL×3). Organic layers were combined, dried over sodium sulphate and concentrated under reduced pressure to get 9.6 (0.5 g, 94%). MS (ES): m/z 390.2 [M+H]⁺.

Synthesis of compound 9.7. To a solution of 106.6 (500 mg 1.28 mmol, 1.0 eq.) in THF (2.0 mL) was added Ethylamine (1M solution in THF) (0.7 mL, 1.59 mmol, 1.2 eq.), HATU (720 mg 1.92 mmol, 1.5 eq.) and DIPEA (0.7 ml, 3.8 mmol, 3 eq.) at 0° C. The reaction was was stirred at room temperature for 16 hours. Upon completion, reaction mixture was poured into water (100 mL) and extracted using EtOAc (50 mL×3). Organic layers were combined, washed with saturated brine solution, dried over sodium sulfate and concentrated under reduced pressure. Resulting crude was purified by column chromatography to afford 9.7 (0.3 g, 56%). MS (ES): m/z 417.27 [M+H]⁺.

Synthesis of compound 9.8. To a suspension of Pd/C (100 mg) in MeOH (15 ml) was added 9.7 (0.3 g, 0.75 mmol, 1.0 eq.) under nitrogen atmosphere. Reaction mixture was purged with H₂ gas at room temperature for 12 hours. After completion of the reaction, reaction mixture was filter through celite. Solvent was removed under reduced pressure to afford 9.8 (0.12 g, 54%). MS (ES): m/z 308.7 [M+H]⁺

Synthesis of compound 9.9. To a solution of 1.1 (91 mg 0.21 mmol, 1.0 eq.) in 1-butanol (2.0 mL) was added 1.7 (65 mg, 0.2 1mmol, 1.0 eq.) and DIPEA (0.11 mL, 0.63 mmol, 3 eq.) at room temperature. Reaction was stirred at 90° C. for 3 hours. Upon completion mixture was poured into water (50 mL) and extracted using EtOAc (30 mL×3). Organic layers were combined, washed with saturated brine solution, dried over sodium sulfate and concentrated under reduced pressure. The crude was purified using column chromatography to afford 9.9 (0.08 g, 54%). MS (ES): m/z 703.2 [M+H]⁺

Synthesis of compound I-9. A solution of 9.9 (0.08 g, 0.13 mmol, 1.0 eq.) in HBr/HOAc solution (33%, 3 mL) was stirred at room temperature for 45 minutes. After completion of the reaction, mixture was poured into cold water, neutralized with NaHCO₃ and extracted with EtOAc (75 mL×2). Solvent was removed under reduced pressure, and crude purified by column chromatography to afford I-9 (35 mg, 68%). MS (ES): m/z-408.3 [M+H]⁺. ¹H NMR (400 MHz, DMSO-d₆): δ 9.04 (s, 1H), 8.89 (s,1H),7.90 (t,1H), 7.68 (d,2H), 7.60 (t,1H), 7.43 (d,2H), 7.27 (t,2H), 4.47 (s,2H), 3.07-3.02 (m,2H), 1.51 (d, 3H), 0.98(t,3H).

Example 10

Synthesis of 2-(2,6-difluorophenyl)-4-((3,3-dimethyl-2,3-dihydro-1H-pyrrolo[2,3-b]pyridin-6-yl)amino)-6,7-dihydro-5H-pyrrolo[3,4-b]pyridin-5-one, I-10

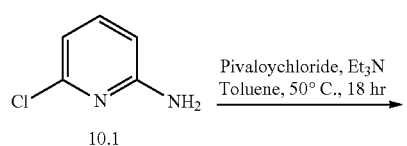
10.1

Pivaloychloride, Et₃N
Toluene, 50° C., 18 hr

-continued

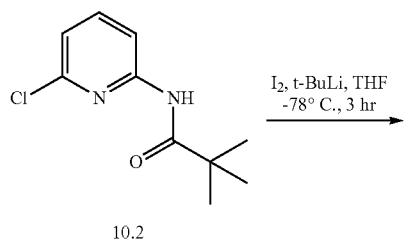
10.2

I₂, t-BuLi, THF
-78° C., 3 hr

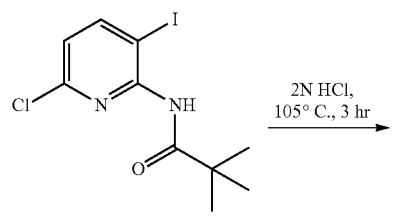
10.3

2N HCl,
105° C., 3 hr

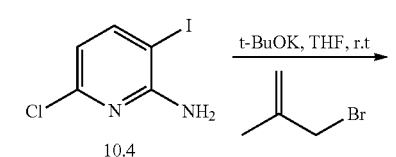
10.4 t-BuOK, THF, r.t

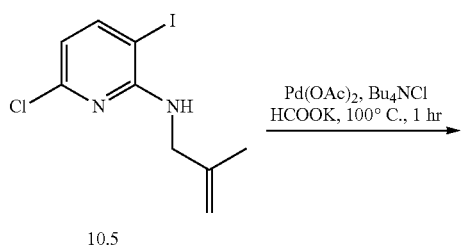
10.5

Pd(OAc)₂, Bu₄NCl
HCOOK, 100° C., 1 hr

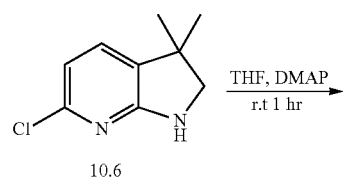
10.6

THF, DMAP
r.t 1 hr

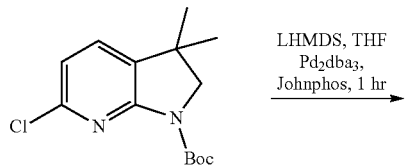
10.7

LHMDS, THF
Pd₂dba₃,
Johnphos, 1 hr

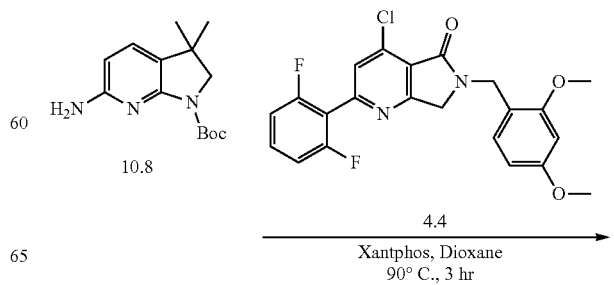
10.8          4.4

Xantphos, Dioxane
90° C., 3 hr

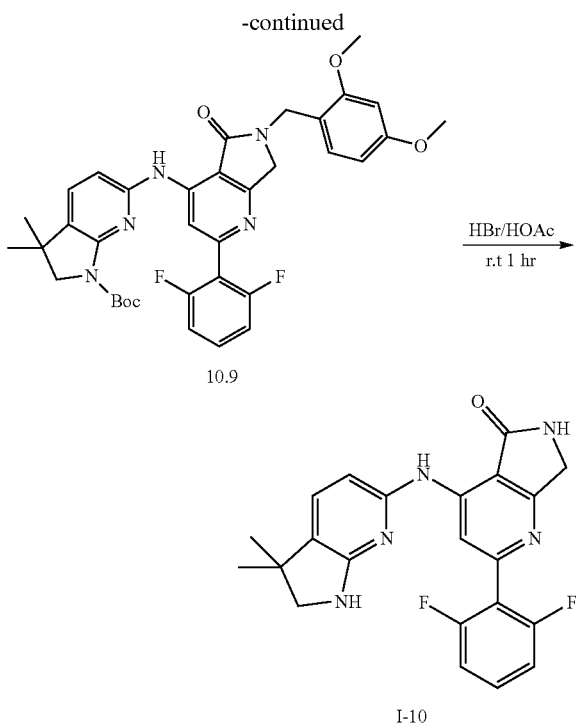

10.9

I-10

Synthesis of compound 10.2. To a solution of 10.1 (7.0 g, 54.54 mmol, 1.0 equiv) and pivaloyl chloride (6.7 mL, 57.0 mmol, 1.05 equiv) in toluene was added Et₃N (7.7 mL, 57.0 mmol, 2.5 equiv) and stirred at 60° C. for 16 hours. Upon completion, reaction mixture was poured into water (500 mL) and extracted with EtOAc (200 mL×3). Organic layers were combined, dried over sodium sulphate and concentrated under reduced pressure to obtain crude which was purified by column chromatography to provide pure 10.2 (9.0 g, 77.7%). MS (ES): m/z 213.3 [M+H]⁺.

Synthesis of compound 10.3. To a solution of 10.2 (9 g, 42 mmol, 1 eq) in THF (90 mL) was added tert-Butyllithium (1.6 M in pentane) (62 mL, 90.0 mmol, 2.2 eq) at −78° C. Reaction mixture was stirred at −78° C. for 3 hours. A solution of iodine (12.7 g, 50.0 mmol, 1.2 eq) in THF (40 mL) was added dropwise, at −78° C. Reaction was warmed to ambient temperature and stirred for 2 hours. Upon completion, reaction mixture was poured in diluted HCl (200 mL) and extracted with ethyl acetate (200 mL×3). Organic layers were combined, dried over sodium sulphate and concentrated under reduced pressure to obtain crude which was purified by column chromatography to get 10.3 (8.0 g, 55.84%), MS (ES): m/z 339.3 [M+H]⁺.

Synthesis of compound 10.4. To a solution of 10.3 (8.0 g, 23.63 mmol, 1.0 eq) in I-4 dioxane was added 2N HCl solution (20 mL). Reaction was stirred at 80° C. for 3 hours. Reaction mixture was poured in saturated solution of NaHCO₃ (500 mL) and extracted with EtOAc (200 mL×3). Organic layers were combined, dried over sodium sulphate and concentrated under reduced pressure to obtain crude which was purified by column chromatography, to provide 10.4 (4.2 g, 70%). MS (ES): m/z 255.46 [M+H]⁺.

Synthesis of compound 10.5. To a solution of 10.4 (1.5 g, 5.9 mmol, 1.0 eq) in THF was added 3-bromo-2-methyl-prop-1-ene (0.95 g, 7.08 mmol, 1.2 eq) and potassium tert-butoxide (0.8 g, 7.08 mmol, 1.2 eq). Reaction was and stirred at room temperature for 3 hours. Reaction mixture was poured in water (200 mL) and extracted with EtOAc (100 mL×3). Organic layers were combined and dried over sodium sulphate, concentrated under reduced pressure to obtain crude which was purified by column chromatography to provide 110.5 (1.5 g, 82%). MS (ES): m/z 309.55 [M+H]⁺.

Synthesis of compound 10.6. To a solution of 10.5 (1.5 g, 4.48 mmol, 1.0 eq) in toluene (15 mL) was added potassium formate (500 mg, 5.8 mmol, 1.2 eq), tetra-butyl ammonium chloride (1.6 g, 5.8 mmol, 1.2 eq) and Et₃N (2 mL, 1.4 mmol, 3 eq) at room temperature under argon bubbling for 15 minutes. To the above reaction mixture was added Pd(OAc)₂ (53 mg, 0.29 mmol, 0.1 eq) under argon bubbling for 10 minutes. Reaction mixture was heated at 100° C. for 1 hour. After completion of the reaction, reaction mixture was poured into water (100 mL) and extracted using ethyl acetate (50 mL×3). Organic layers were washed with by brine solution, combined and dried over sodium sulphate and concentrated under reduced pressure. Resulting crude was purified by column chromatography to provide 10.6 (0.8 g, 90%). MS (ES): m/z 183.5 [M+H]⁺.

Synthesis of compound 10.7. To a solution of 10.6 (0.6 g, 3.2 mmol, 1.0 eq) and Boc-anhydride (1.0 g, 4.86 mmol, 1.5 eq) in dichloromethane was added DMAP (39 mg, 0.32 mmol, 0.1 eq). Reaction was stirred at room temperature for 1 hour. Upon completion, mixture was poured into water (100 mL) and extracted with EtOAc (50 mL×3). Organic layers were combined, dried over sodium sulphate and concentrated under reduced pressure to obtain crude material. The crude was purified by column chromatography to provide 10.7 (0.8 g, 86%). MS (ES): m/z 283.2 [M+H]⁺.

Synthesis of compound 10.8. To a solution of 10.7 (0.2 g 0.70 mmol, 1.0 eq) in dry THF(5.0 mL) was added LHMDS (1.0 M in THF) (2.1 mL, 2.1 mmol, 3.0 eq) at room temperature under argon bubbling for 15 minutes. To the above reaction mixture was added Pd₂(dba)₃ (62 mg, 0.068 mmol, 0.1 eq) and 2-Biphenyl)di-tert-butylphosphine, (48 mg, 0.021 mmol, 0.2 eq) under argon bubbling for 10 minutes. Reaction mixture was heated at 60° C. temperature for 2 hours. After completion of the reaction, reaction mixture was poured into water (50 mL) and extracted using ethyl acetate (30 mL×3). Organic layers were combined, washed with brine, dried over Na₂SO₄ and concentrated under reduced pressure to obtain crude material. Crude was purified by column chromatography to provide 10.8 (0.08 g, 43.0%). MS (ES): m/z 264.2 [M+H]⁺.

Synthesis of compound 10.9. To a solution of 4.4 (0.10 g 0.23 mmol, 1.0 eq) in dry dioxane (5.0 mL) was added 10.8 (67 mg, 0.23 mmol, 1.0 eq), K₂CO₃ (0.095 g, 0.60 mmol, 3.0 eq.) at room temperature under argon bubbling for 15 minutes. To the above reaction mixture was added Pd₂(dba)₃ (21 mg, 0.023 mmol, 0.1 eq) and Xantphos (26 mg, 0.046 mmol, 0.2 eq) under argon bubbling for 10 minutes. Reaction mixture was heated at 105° C. temperature for 3-4 hours. After completion of the reaction, reaction mixture was poured into water and extracted using ethyl acetate. Organic layers were combined, washed with brine, then dried over sodium sulphate and concentrated under reduced pressure to obtain crude material. Crude was purified by column chromatography to furnish 10. 9 (0.08 g, 53.0%). MS (ES): m/z 658.20 [M+H]⁺.

Synthesis of compound I-10. A solution of 10.9 (80 mg) in HBr/HOAc solution (33%, 5 ml) was stirred at room temperature for 1 hour. After completion of the reaction, reaction mixture was poured into cold water, neutralized with NaHCO₃ and extracted with ethyl acetate (50 ml×2). Solvent was removed under reduced pressure and resulting crude was purified by column chromatography to furnish compound I-10 (30 mg, 60.0%). MS (ES): m/z 501.58 [M+H]⁺, ¹H NMR (400 MHz, DMSO-d₆): δ 9.48 (s,1H), 8.82 (s,1H), 8.38 (s,1H), 7.60-7.52 (m,1H), 7.27-7.23 (m,3H), 6.54 (s,1H), 6.15 (d,1H), 4.41 (s,2H), 3.20 (s,2H), 1.21 (s,6H).

Example 12

Synthesis of 2-(2,6-difluorophenyl)-4-((4-((1,3-di-hydroxypropan-2-yl)oxy)phenyl)amino)-6,7-di-hydro-5H-pyrrolo[3,4-d]pyrimidin-5-one, I-12

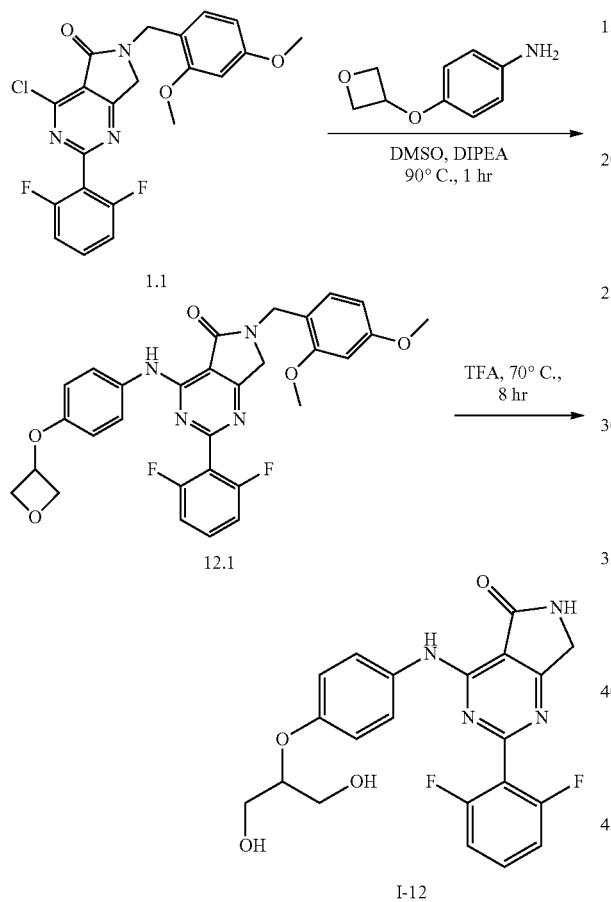

Synthesis of compound 12.1. To a solution of 1.1 (0.140 g, 0.324 mmol, 1.0 eq.) in DMSO (2 mL), 4-(oxetan-3-yloxy)aniline (0.051 g, 0.308 mmol, 0.95 eq) and DIPEA (0.16 mL, 0.974 mmol, 3.0 eq) were added at room temperature. Reaction mixture was heated at 90° C. for 1 hour. After completion of the reaction, mixture was poured into cold water and extracted using ethyl acetate (20 mL×2). Organic layers were combined and dried over sodium sulfate and concentrated under reduced pressure. Crude was purified by column chromatography to afford 12.1 (0.130 g, 71.53%). MS (ES): m/z 560.5 [M+H]⁺.

Synthesis of compound I-12. A solution of 12.1 (0.130 g, 0.232 mmol, 1 eq) in TFA (6 mL) was heated at 70° C. for 8 hours. After completion of the reaction, reaction mixture was poured in cold water, neutralized with saturated sodium bicarbonate solution and extracted with ethyl acetate (10 mL×2). Solvent was removed under reduced pressure and resulting crude was purified using column chromatography to provide I-12 (0.030 g, 30.2%). MS (ES): m/z 428.4 [M+H]⁺; ¹H NMR (400 MHz, DMSO-d₆): δ 8.96 (s,1H), 8.84 (s,1H), 7.61-7.51 (m,3H), 7.27-7.23 (t,2H), 6.97-6.94 (d,2H), 4.78-4.75 (t,2H), 4.46 (s,2H), 4.21-4.18 (q,1H), 3.60-3.50 (m,4H).

Example 13

Synthesis of compound 2-(2,6-difluorophenyl)-4-((4-methoxybenzyl)-amino)-6,7-dihydro-5H-pyrrolo[3,4-d]pyrimidin-5-one I-13

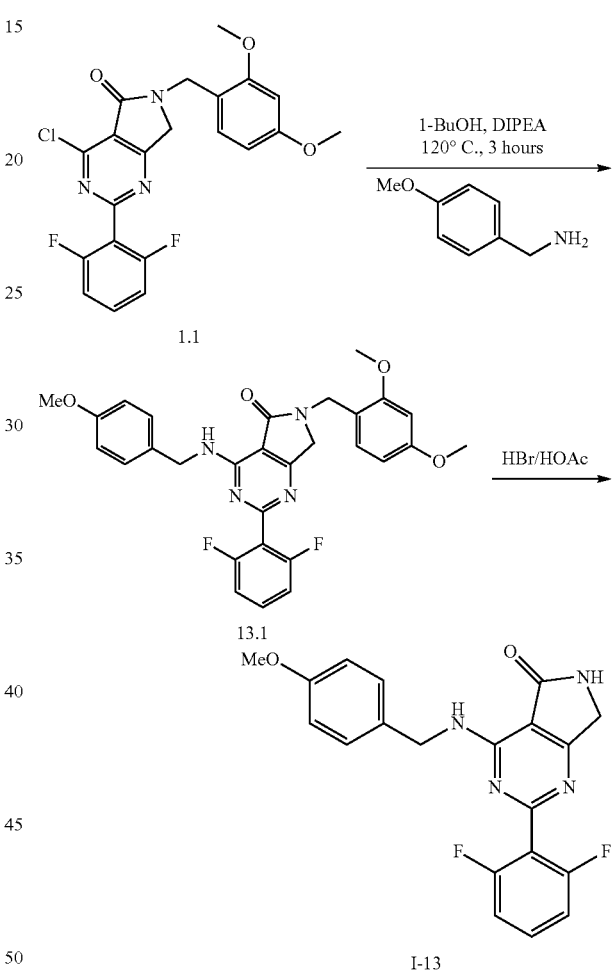

Synthesis of compound 13.1. To a solution of 1.1 (0.150 g 0.348 mmol, 1.0 eq) in 1-butanol (2.0 mL) was added 4-Methoxy benzyl amine (0.047 g, 0.348 mmol, 1.0 eq) and DIPEA (0.18 ml, 1.04 mmol, 3 eq) at room temperature. Reaction mixture was stirred at 120° C. for 3 hours. After completion of the reaction, mixture was poured into water and extracted using ethyl acetate. Organic layer was washed with brine, dried over sodium sulfate and concentrated under reduced pressure. Crude was purified by column chromatography to afford pure 13.1 (0.110 g, 59.5%), MS (ES): m/z 533.6 [M+H]⁺.

Synthesis of compound I-13. To a solution of 13.1 (0.11 g, 0.206 mmol, 1.0 eq.) in HBr/HOAc solution (33%, 3 ml) was stirred at room temperature for 1 hour. After completion of reaction, mixture was poured in cold water, neutralized with NaHCO₃ and extracted with ethyl acetate (25 mL×2). Solvent was removed under reduced pressure and resulting crude purified using column chromatography to provide I-13 (0.045 g, 56.9%). MS (ES): m/z-383.4 [M+H]⁺; ¹H NMR (400 MHz, DMSO-d₆): δ 8.59 (s,1H), 7.87 (m,1H), 7.56 (m,1H), 7.29-7.21 (m,4H), 6.86 (d,2H), 4.60 (d,2H), 4.36 (s,2H), 3.71 (s,3H).

Example 14

Synthesis of 2-(4-((2-(2,6-difluorophenyl)-5-oxo-6,7-dihydro-5H-pyrrolo[3,4-d]pyrimidin-4-yl)amino)phenyl)-N-ethyl-2-hydroxypropanamide, I-14

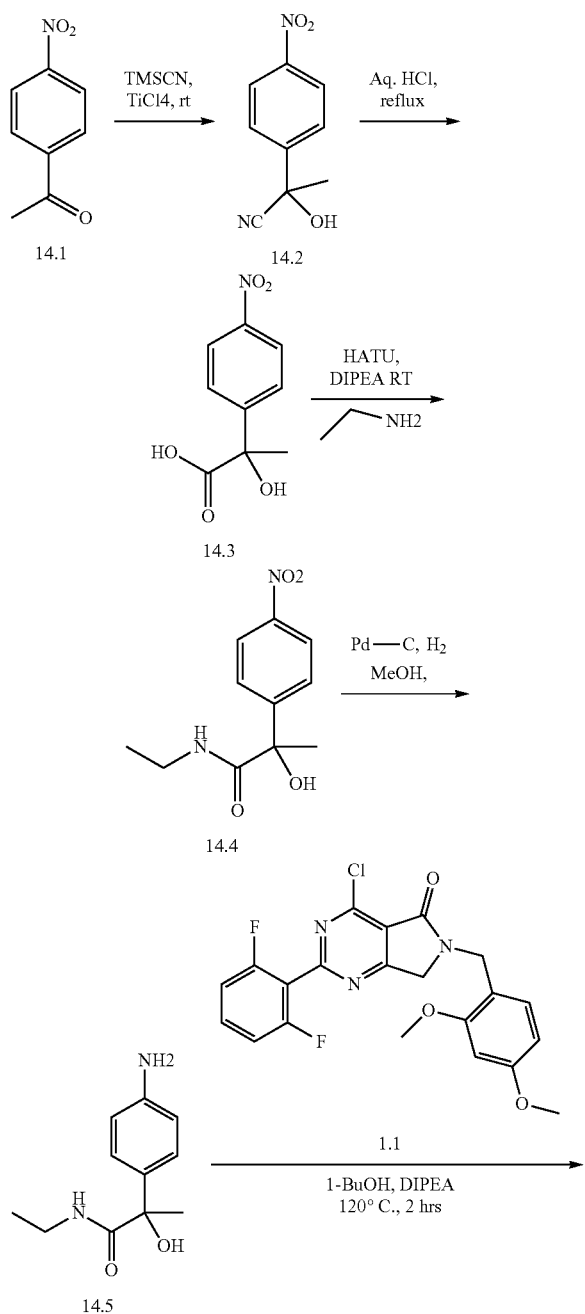

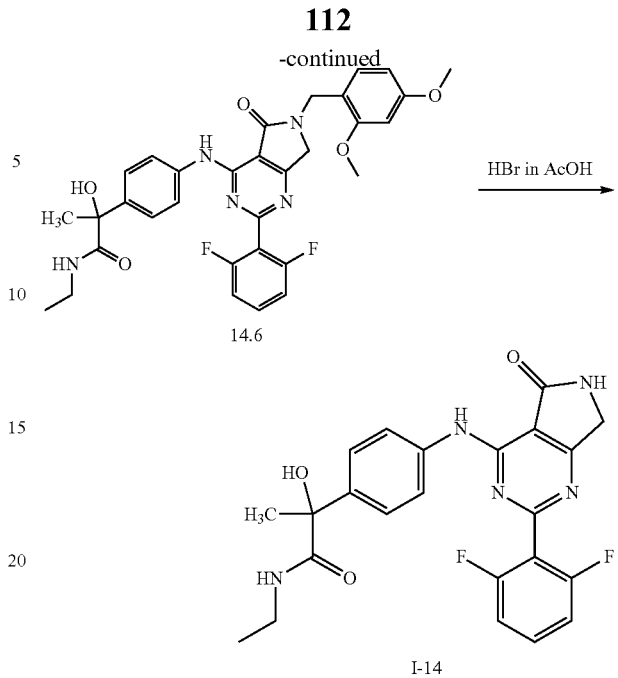

Synthesis of compound 14.2. To a solution of 14.1 (5.0 g, 30.3 mmol, 1.0 eq) in CH₂Cl₂ (50 mL) was added TMSCN (4.55 mL, 36.34 mmol, 1.2 eq) followed by TiCl₄ (1.14 g, 6.05 mmol, 0.2 eq) drop wise at room temperature. The reaction was stirred at room temperature for 18 hours. The reaction mixture was quenched with ice cold water and product was extracted with CH₂Cl₂ (50 mL×2). Organic layers were combined, dried over sodium sulphate and concentrated under reduced pressure to obtain 14.2 (5.8 g, 99.69%). MS (ES): m/z No ionisation [M+H]⁺.

Synthesis of compound 14.3. To a solution of 14.2 (5.8 g, 30.2 mmol, 1.0 eq) in 1,4-dioxane (10.0 mL) was added conc. HCl (50 mL, eq). Reaction mixture was heated at 120° C. for 5 hours. Reaction mixture was concentrated under reduced pressure. Residue was dissolved in ethyl acetate, washed with saturated sodium bicarbonate solution. Organic layer was separated, dried over sodium sulaphate and concentrated under reduced pressure to obtain 14.3 (4.7 g, 73.74%) which was used as such for the next step, MS (ES): m/z 210 [M+H]⁺.

Synthesis of compound 14.4. To a solution of 14.3 (4.7 g, 22.3 mmol, 1.0 eq) in DMF (50 mL) was added ethyl amine (13.4 mL, 26.7 mmol, 1.2 eq), DIPEA (7.62 mL, 44.5 mmol, 2 eq) and HATU (10.16 g, 26.7 mmol, 1.2 eq). The reaction mixture was stirred at room temperature for 1 hour. Upon completion mixture was diluted with EtOAc (100 mL) and washed with saturated NaHCO₃. Organic layer was dried over sodium sulphate and concentrated under reduced pressure to obtain 14.4 (3.6 g, 67.9%). MS (ES): m/z 239.3 [M+H]⁺.

Synthesis of compound 14.5. Compound 14.4 (3.6 g, 15.1 mmol, 1.0 eq) was dissolved in MeOH (3 mL) and added to 10% Pd/C. Hydrogen gas was bubbled though reaction mixture for 2 hours. After completion of the reaction, reaction mixture was filtered through celite. Filtrate was concentrated under reduced pressure to obtain 14.5 (3.12 g, 99.14%). MS (ES): m/z 209.2 [M+H]⁺.

Synthesis of compound 14.6. To a solution of 1.1 (0.3 g, 0.69 mmol, 1.0 eq) in 1-butanol (5 mL) was added 14.5 (0.16 g, 0.76 mmol, 1.1 eq) and DIPEA (0.4 mL, 2.08 mmol, 3.0 eq). The reaction was stirred at 120° C. for 2 hours. After completion of the reaction, mixture was poured into water and product was extracted with EtOAc (50 mL×2). Organic layers were combined and dried over sodium sulphate and concentrated under reduced pressure to obtain crude which was purified by column chromatography to furnish 14.6 (0.35 g, 83.46%). MS (ES): m/z 604.5 [M+H]+.

Synthesis of compound I-14. Mixture of 14.6 (0.3 g, 0.49 mmol, 1.0 eq) and HBr/HOAc (5 mL) was stirred at room temperature for 1 hour. Reaction mixture was neutralized using saturated NaHCO₃ and extracted with EtOAc (25 mL×2). Organic layers were combined, dried over Na₂SO₄ and concentrated under reduced pressure to obtain crude which was purified by column chromatography to furnish I-14 (0.17 g, 75.4%). MS (ES): m/z 454.7 [M+H]+; ¹H NMR (DMSO-d₆, 400 MHz): δ 9.05 (s, 1H), 8.89 (s, 1H), 7.83-7.86 (t, 1H), 7.66-7.68 (d,2H), 7.58-7.60 (m,1H), 7.46-7.48 (d,2H), 7.25-7.29 (m,2H), 6.01(s,1H), 4.47 (s,2H), 3.03-3.08 (m,2H),1.58(s,3H),0.94-0.98 (t,3H).

Example 15

Synthesis of (S)-2-(4-((2-(2,6-difluorophenyl)-5-oxo-6,7-dihydro-5H-pyrrolo[3,4-d]pyrimidin-4-yl)amino)phenyl)-N-ethyl-2-hydroxypropanamide, I-15

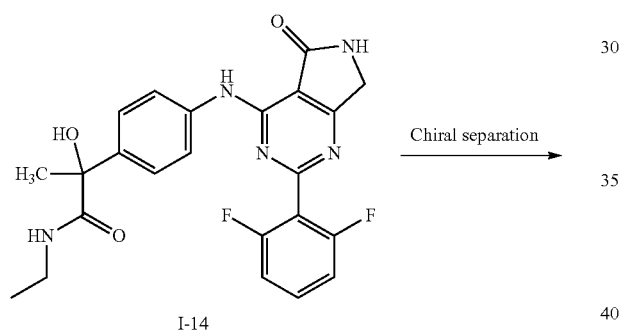

Compound I-15 was obtained by chiral separation of compound I-14. MS (ES): m/z 454.7 [M+H]³¹, ¹H NMR (400 MHz, DMSO): δ 9.05 (s, 1H), 8.89 (s, 1H), 7.84-7.87 (t, 1H), 7.66-7.68 (d,2H), 7.58-7.62 (m,1H), 7.46-7.48 (d,2H), 7.24-7.29 (t,2H), 6.01(s,1H), 4.47 (s,2H), 2.99-3.08 (m,2H), 1.58 (s,3H), 0.94-0.98 (t,3H)

Example 16

Synthesis of (R)-2-(4-((2-(2,6-difluorophenyl)-5-oxo-6,7-dihydro-5H-pyrrolo[3,4-d]pyrimidin-4-yl)amino)phenyl)-N-ethyl-2-hydroxypropanamide. I-16

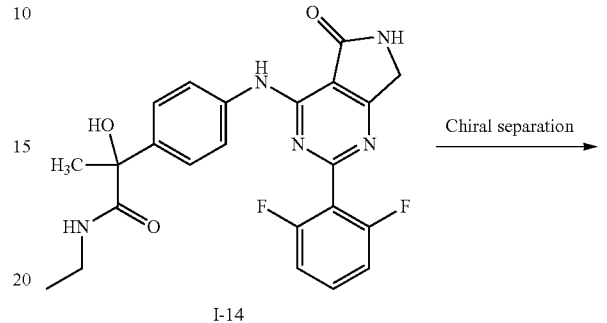

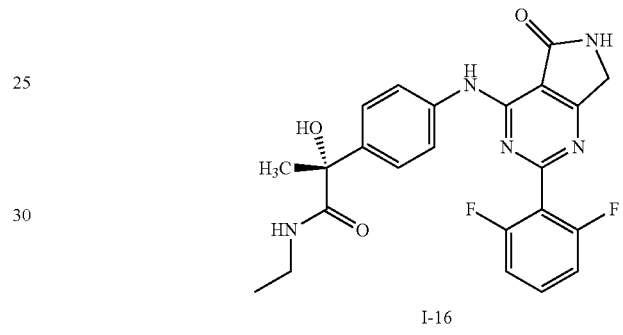

Compound I-16 was obtained by chiral separation of compound I-14. MS (ES): m/z 454.54 [M+H]+, ¹H NMR (400 MHz, DMSO): δ 9.05 (s,1H), 8.89 (s,1H), 7.84-7.87 (t, 1H), 7.66-7.68 (d,2H), 7.58-7.62 (m,1H), 7.46-7.48 (d,2H), 7.25-7.29 (t,2H), 6.01(s,1H), 4.47 (s,2H), 3.01-3.07 (m,2H), 1.58 (s,3H), 0.94-0.98 (t,3H).

Example 17

Synthesis of 2-(2,6-difluorophenyl)-4-((2,3-dihydro-1H-pyrrolo[3,2-c]pyridin-6-yl)amino)-6,7-dihydro-5H-pyrrolo[3,4-b]pyridin-5-one, I-17

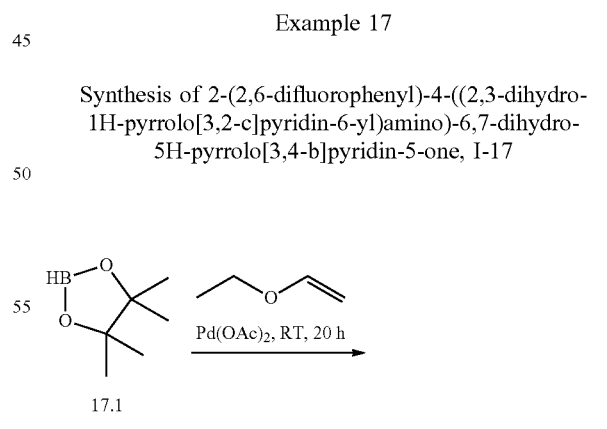

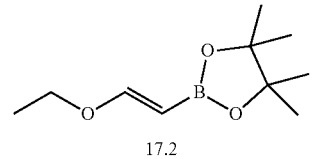

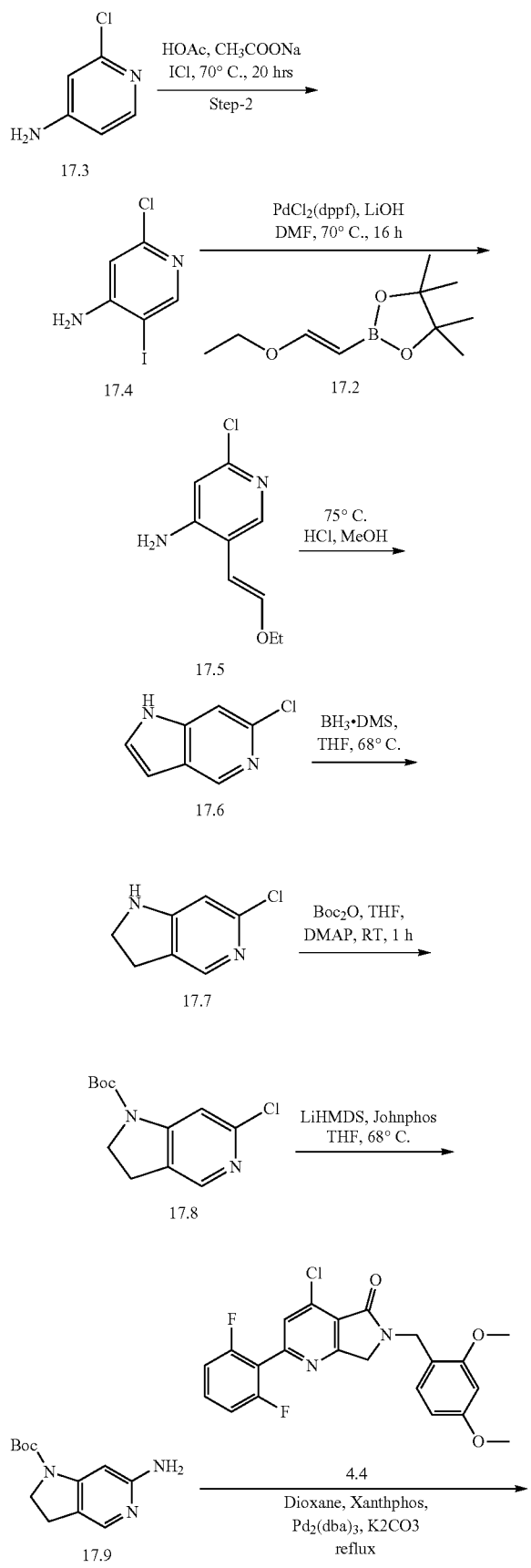

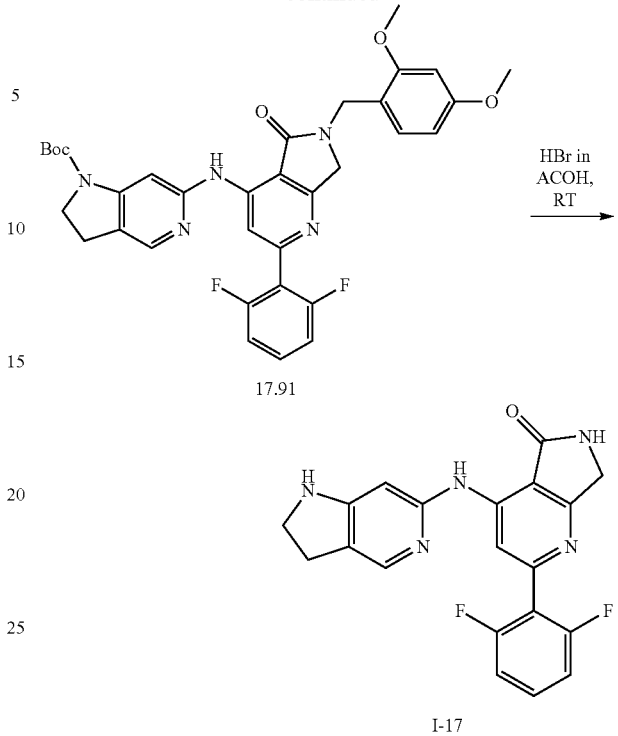

Synthesis of compound 17.2 To a solution of 17.1 (5.0 g, 39.0 mmol, 1.00 eq) in ethoxyethene (11.25 g, 156.0 mmol, 4.0 eq) was added palladium acetate slowly. Reaction was stirred at room temperature for 20 h. After completion of the reaction, the resulting solution was filtered through celite, washed with ethyl acetate and filtrate was distilled under reduced pressure to afford crude material which was purified by column chromatography to afford pure 17.2 (1.0 g, 12.92%). MS (ES): m/z 199.1 [M+H]$^+$.

Synthesis of compound 17.4. To a solution of 17.3 (5.0 g, 54.6 mmol,) in acetic acid (10 ml) was added sodium acetate (8.938 g, 109.0 mmol, 2.0 eq) and iodine monochloride (4.069 g, 65.5 mmol, 1.2 eq). Reaction mixture was heated at 70° C. for 20 hours. After completion of the reaction, mixture was concentrated under reduced pressure and residue was diluted with water and basified with sodium bicarbonate solution. Compound was extracted in EtOAc and washed with brine. Organic layer was separated, dried over sodium sulphate and concentrated under reduced pressure to afford crude material which was purified by chromatography using 12% to afford pure 17.4 (2.8 g, 28.2%), m/z=255.1 [M+H]$^+$.

Synthesis of compound 17.5. In a seal tube 17.4 (0.200 g, 0.78 mmol, 1 eq) and 17.2 (0.202 g, 1.02 mmol, 1.3 eq) was dissolved in DMF (5 mL). LiOH (0.095 g, 2.34 mmol, 3.0 eq) was added into the reaction mixture. Reaction mixture was degassed by argon gas for 10-15 mins. PdCl$_2$(dppf) (0.063 g, 0.078 mmole, 0.1 eq.) was then added. Reaction mixture was further degassed by argon gas for 10 min. Reaction mixture was heated with stirring at 70° C. for 16 hours, After completion of the reaction, water was added and product was extracted with EtOAc (2×50 ml), organic layer was separated, dried over sodium sulphate and concentrated under reduced pressure to afford crude material which was purified by column chromatography to afford pure compound 17.5 (0.04 g, 25.62%). MS (ES): m/z 199.2 [M+H]$^+$.

Synthesis of compound 17.6. A solution of 17.5 (0.04 g, 0.202 mmol, 1.00 eq) in MeOH(1 mL) and HCl (0.1 ml) was heated to reflux for overnight. After completion of the reaction, mixture was concentrated and residue was basifed with $K_2CO_3$ and extracted with EtOAc (2×50 ml). Organic layer was dried over sodium sulphate and concentrated under reduced pressure to afford crude material which was purified by column chromatography to afford pure compound 17.6 (0.025 g, 81.4%). MS (ES): m/z 153.5 [M+H]$^+$.

Synthesis of compound 17.7. A solution of 17.6 (0.25 g, 1.10 mmol, 1.00 eq) and a Borane dimethyl sulfide complex solution (2.0M in THF) (2 mL) in THF (1.0 mL) was heated at 68° C. for 3 h. Reaction mixture was cooled to room temperature and poured in water; product was extracted with EtOAc (50 mL×3). Combined organic layers were washed with brine, dried over sodium sulphate and concentrated under reduced pressure. The residue was purified using silica gel column to afford the compound 17.7 (0.08 g, 31.58, MS (ES): m/z 155.6 [M+H]$^+$.

Synthesis of compound 17.8. A solution of 17.7 (0.08 g, 0.519 mmol, 1.00 eq), Di-tert-butyl-dicarbonate (0.191 g, 0.876 mmol, 1.5 eq) and DMAP (0.01 g, 0.058 mmol, 0.1 eq) in THF (10 mL) was stirred at room temperature for 3 hours. After completion, the reaction was diluted with water and product was extracted with ethyl acetate (25 mL×3) and washed with brine. The combined organic layers were dried and concentrated under vacuum. Crude was purified by column chromatography to afford 17.8 (0.06 g, 45.52%). MS (ES): m/z 255.1 [M+H]$^+$.

Synthesis of compound 17.9. A solution of 17.8 (0.04 g 0.157 mmol, 1.0 eq) in dry THF (0.4 mL) was degassed at room temperature under argon for 15 minutes. To the above reaction mixture was added $Pd_2(dba)_3$ (0.014 g, 0.0157 mmol, 0.1 eq) and 2-Biphenyl-di-tert-butylphosphine (0.01 g, 0.031 mmol, 0.2 eq) under argon purge for 10 minutes followed by LHMDS (7.8 mg, 0.047 mmol, 3.0 eq). Reaction mixture was heated at 68° C. for 1 hour. After completion of the reaction, reaction mixture was poured into water and extracted using EtOAc (25 mL×2). Organic layer was washed with brine. Organic layer was dried over sodium sulfate and concentrated under reduced pressure. Crude was purified using column chromatography to afford pure 17.9 (0.028 g, 75.78%). MS (ES): m/z 254.1 [M+H]$^+$.

Synthesis of compound 17.91. To a solution of 4.4 (0.08 g, 0.18 mmol, 1.0 eq) and 17.9 (0.043 g, 0.186 mmol, 1.0 eq) in 1,4-dioxane (2 mL) was added $K_2CO_3$ (0.051 g, 0.580 mmol, 3.0 eq). Reaction mixture was degassed under argon gas for 5-10 min. and $Pd_2(dba)_3$ (0.016 g, 0.018 mmol, 0.1 eq) followed by Xantphos (0.01 g, 0.018 mmol, 0.2 eq) was added and again degassed under argon for 5 min. Reaction mixture was heated at 90° C. for 4 hours. After completion of the reaction, mixture was poured into water and product was extracted with EtOAc. Organic layers were combined and dried over sodium sulphate and concentrated under reduced pressure to obtain crude material. Crude was purified by column chromatography to get pure 133.91 (0.035 g, 29.94%). MS (ES): m/z 630.1 [M+H]$^+$.

Synthesis of compound I-17. A solution of 17.91 (0.035 g, 0.081 mmol, 1.0 eq.) in HBr/HOAc (33%, 1 ml) was stirred at room temperature for 1 hour. After completion of the reaction, mixture was poured into cold water, neutralized with $Na_2CO_3$ solution and product was extracted with ethyl acetate (25 mL×3). Solvent was removed under reduced pressure to get crude material which was purified by column chromatography to afford pure I-17 (0.012 g, 56.91%). MS (ES): m/z 468.1 [M+H]$^+$, $^1$H NMR (400 MHz, DMSO-d$^6$): δ 9.39(s, 1H), 8.81(s, 1H), 8.48 (s,1H), 7.71 (s,1H), 7.60- 7.55(m,1H), 7.27-7.23 (t,2H), 6.55 (s,1H), 6.02 (s,1H), 4.39 (s,2H), 3.78-3.67 (t,2H), 2.92-2.88 (t,2H).

Example 18

Synthesis of 2-(2,6-difluorophenyl)-4-((2,3,4,5-tetrahydropyrido[3,2-b][1,4]oxazepin-7-yl)amino)-6,7-dihydro-5H-pyrrolo[3,4-b]pyridin-5-one, I-18

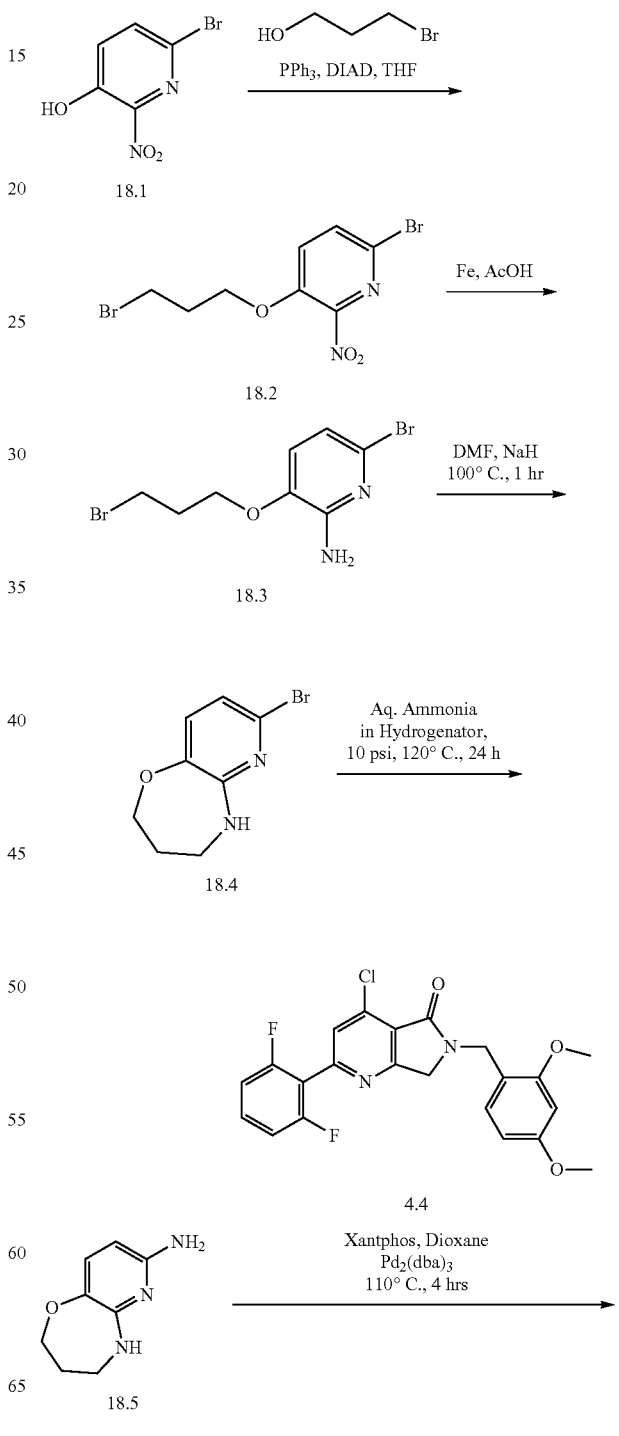

-continued

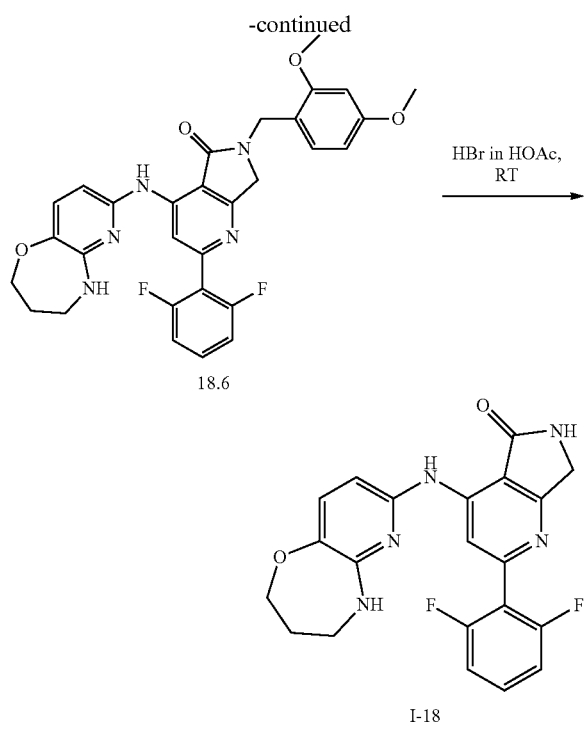

Synthesis of compound 18.2. Compound 18.1 (2.0 g, 9.1 mmol, 1.0 eq), 3-bromopropan-1-ol (1.9 g, 13.6 mmol, 1.5 eq) and PPh$_3$ (3.59 g, 13.6 mmol, 1.5 eq) were dissolved in dry THF (40 mL) at 0° C. and allowed to stir for 1 hour. Diisopropyl azodicarboxylate (2.76 g, 13.6 mmol, 1.5 eq) was added at 0° C. and reaction mixture was allowed to stir for 3 hours. After completion of reaction, water was added and product was extracted with EtOAc (100 mL×2). Organic layer was separated out, washed with brine, dried over sodium sulphate and concentrated under reduced pressure to give crude product, which was purified by column chromatography to afford compound 18.2 (1.8 g, 57.97%). MS (ES): m/z=339.1 [M−H]$^+$ Synthesis of compound 18.3. To a solution of 18.2 (1.8 g, 5.3 mmol, 1.0 eq) in HOAc (18 mL) was added iron powder (1.18 g, 21.0 mmol, 4.0 eq). Reaction mixture was then heated at 90° C. for 1 hour. After completion of the reaction, EtOAc was added to reaction mixture and reaction mixture was filtered through celite and filtrate was concentrated under reduced pressure to afford crude which was purified using column chromatography to afford 18.3. (1.2 g, 73.1%), MS (ES): m/z 311.1 [M+H]$^+$.

Synthesis of 18.4. To a cooled solution of NaH (60% in mineral oil, 0.31 g, 7.7 mmol, 2.0 eq) in DMF (6 mL) was added 18.3 (1.2 g, 3.8 mmol, 1.0 eq) at 0° C. and allowed to stir at room temperature for 30 minutes. After completion of the reaction saturated NH$_4$Cl solution was added to reaction mixture and product extracted with EtOAc (200 mL×2). Organic layer was washed with brine solution, dried over sodium sulfate and concentrated under reduced pressure to give crude product, which was purified by column chromatography to afford compound 18.3 (0.4 g, 45.11%). MS (ES): m/z 227 [M−H]$^+$ Synthesis of compound 18.5. A solution of 18.4 (0.24, 1.04 mmol, 1.0 eq) in ammonium hydroxide (10 mL) was heated in hydrogenator vessel at 10 psi for 24 h. After completion of the reaction, mixture was concentrated under reduced pressure to give crude product, which was triturated with diethyl ether to give pure 18.5 (0.09 g, 52.0%). MS (ES): m/z 166 [M−H]$^−$, Synthesis of compound 18.6. To a solution of 18.5 (0.042 g 0.25 mmol, 1.1 eq) in dry 1,4-dioxane (1.0 mL) was added 4.4 (0.1 g, 0.23 mmol, 1.0 eq), K$_2$CO$_3$ (0.080 g, 0.04 mmol, 0.2 eq) and Xantphos (0.026 g, 0.04 mmol, 0.2 eq) at room temperature and it was degassed with argon for 15 minutes. To the above reaction mixture was added Pd$_2$(dba)$_3$ (0.021 g, 0.02 mmol, 0.1 eq) and it was degassed again with argon for 15 minutes. Reaction mixture was heated at 110° C. for 4 hours. After completion of the reaction, reaction mixture was poured into water and extracted using ethyl acetate (50 mL×2). Organic layer was washed with brine solution. Organic layers were combined and dried over Na$_2$SO$_4$ and concentrated under reduced pressure to obtain crude, which was further purified by column chromatography to afford pure 18.6 (0.052 g, 40.0%). MS (ES): m/z 560.2 [M+H]$^+$ Synthesis of compound I-18. A solution of 18.6 (0.055 g, 0.09 mmol, 1 eq) in HBr/HOAc (33%, 1 mL) was stirred at room temperature for 1 hour. After completion of reaction, reaction mixture was poured in cold water, neutralized with sodium bicarbonate and product was extracted with EtOAc (25 mL×2). Solvent was removed under reduced pressure at to get crude product, which was purified by column chromatography to afford pure I-18 (0.022 g, 57.8%). MS (ES): m/z 410.20 [M+H]$^+$, $^1$H NMR (400 MHz, DMSO-d6): δ 9.48 (s,1H), 8.81 (s,1H), 8.35 (s,1H), 7.53-7.57 (t,1H), 7.21-7.25 (t,2H), 7.11-7.13 (d,1H), 6.29-6.31 (d,2H), 4.38 (s,2H), 4.03-4.05 (t,2H), 3.23-3.29 (m,2H), 1.89-1.92 (t, 2H), Example 19

Synthesis of 4-(6-amino-1H-pyrrolo[2,3-b]pyridin-1-yl)-2-(2,6-difluorophenyl)-6,7-dihydro-5H-pyrrolo[3,4-b]pyridin-5-one, I-19

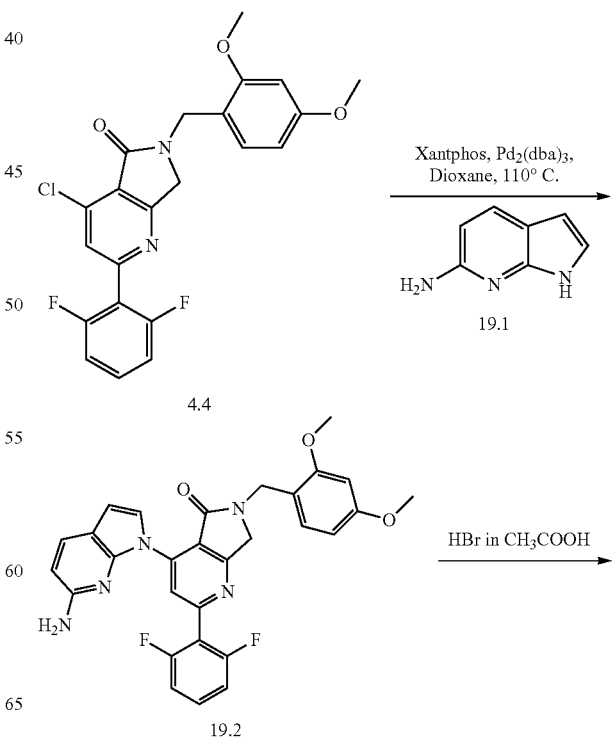

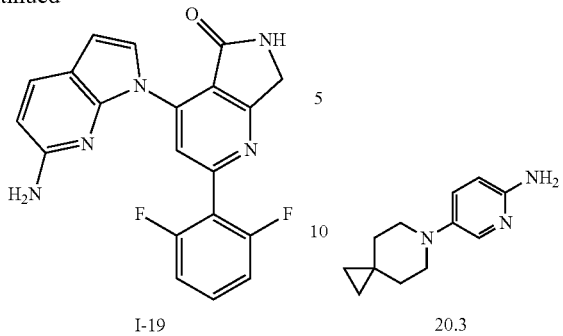

I-19

Synthesis of compound 19.2. To a solution of 4.4 (0.050 g, 0.116 mmol, 1.0 eq) in 1,4-dioxane (1 mL) was added 19.1 (0.023 g, 0.174 mmol, 1.5 eq) and $K_2CO_3$ (0.04 g, 0.29 mmol, 2.5 eq). The reaction mixture was degassed for 10 min. under argon atmosphere, then $Pd_2(dba)_3$ (0.011 g, 0.012 mmol, 0.1 eq) and Xantphos (0.013 g, 0.023 mmol, 0.2 eq) were added, again degassed for 5 min. The reaction was then heated at 110° C. for 2 hours. After completion of reaction, reaction mixture was poured in water and product was extracted with EtOAc. Organic layer was combined and dried over sodium sulphate and concentrated under reduced pressure to obtain crude which was purified using column chromatography to get pure 19.2 (0.040 g, 65.4%). MS (ES): m/z 528.5 [M+H]$^+$.

Synthesis of compound I-19. Compound 19.2 (0.025 g, 0.0473 mmol, 1.0 eq.) was dissolved in HBr/HOAc (1 mL) and stirred at room temperature for 1 hour. After completion of the reaction, mixture was poured into water and basified with saturated bicarbonate solution was extracted with ethyl acetate. Organic layers were combined and dried over sodium sulphate and concentrated under reduced pressure to obtain crude which was purified to get pure I-19 (0.012 g, 67.2%). MS (ES): m/z 378.3 [M+H]$^+$, $^1$H NMR (DMSO-$d_6$, 400 MHz): 8.95(s, 1H), 8.27 (s,1H), 6.49 (m,3H), 7.30 (t,2H), 6.43 (m, 2H), 5.86 (s,2H), 4.55 (s,2H).

Example 20

Synthesis of 4-((5-(6-azaspiro[2.5]octan-6-yl)pyridin-2-yl)amino)-2-(2,6-difluorophenyl)-6,7-dihydro-5H-pyrrolo[3,4-b]pyridin-5-one, I-20

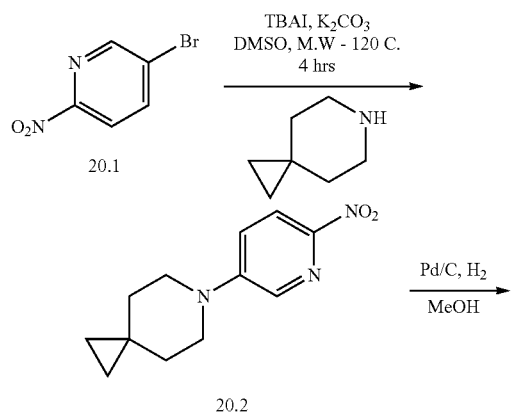

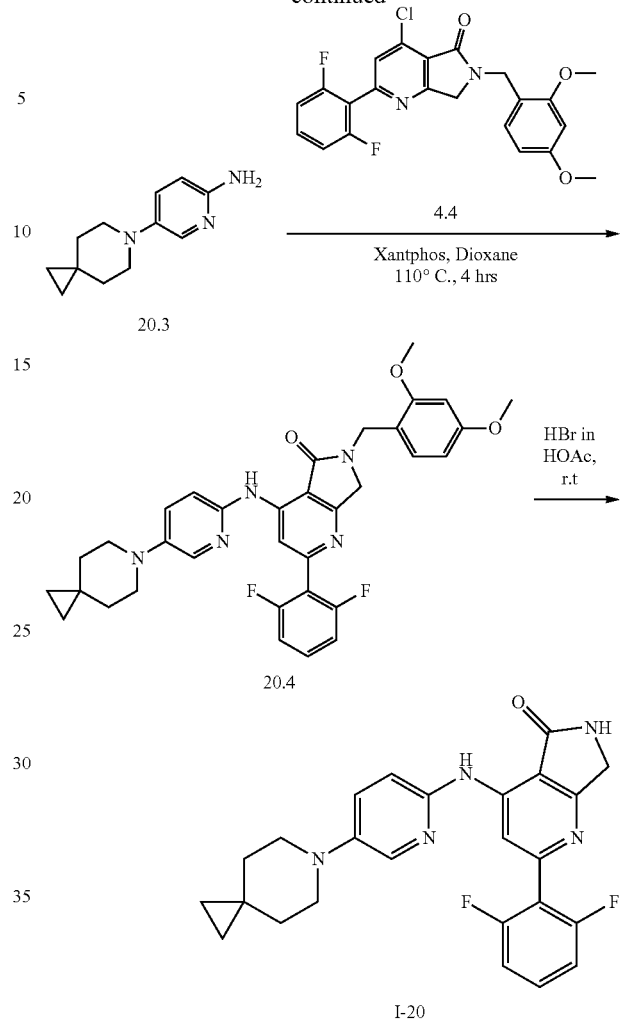

Synthesis of compound 20.2. To a solution of 20.1 (0.2 g, 0.985 mmol, 1.0 eq) in DMSO (3 ml) was added TBAI (0.036 g, 0.0985 mmol, 0.1 eq), 6-azaspiro [2.5] octane (0.131 g, 1.182 mmol, 1.2 eq), and $K_2CO_3$ (0.271 g, 1.97 mmol, 2 eq). Reaction mixture was heated in microwave at 120° C. for 4 hours. The reaction mixture was poured into water and extracted with EtOAc. Organic layers were combined and dried over sodium sulphate and concentrated under reduced pressure to obtain crude which was purified by column chromatography to get pure 20.2 (0.052 g, 22.70%). MS (ES): m/z 234.27 [M+H]$^+$.

Synthesis of compound 20.3. To a solution of 20.2 (0.052 g, 0.222 mmol, 1.0 eq) in MeOH (5 mL) was added with 10% Pd/C (0.0052 mg) under nitrogen atmosphere. It was purged with $H_2$ gas for 1 h. Reaction mixture was filtered through celite and obtained filtrate was concentrated under reduced pressure to get crude 20.3 (0.040 g,) which was used as such for the the next step, MS (ES): m/z 204.3 [M+H]$^+$.

Synthesis of compound 20.4. To a solution of 4.4 (0.08 g, 0.185 mmol, 1.0 eq) in 1,4-dioxane (3 mL) was added 20.3 (0.04 g, 0.204 mmol, 1.1 eq) and $K_2CO_3$ (0.064 g, 0.464 mmol, 2.5 eq). The reaction mixture was degassed for 10 min. under argon atmosphere, then $Pd_2(dba)_3$ (0.0169 g, 0.0185 mmol, 0.1 eq) and Xantphos (0.021 g, 0.0371 mmol, 0.2 eq) were added, again degassed for 5 min. The reaction was stirred 110° C. for 4 hours. After completion of the reaction, mixture was poured into water and product was extracted with EtOAC. Organic layere were combined, dried over sodium sulphate and concentrated under reduced pressure to obtain crude which was purified by column chromatography get pure 20.4 (0.070 g, 63.10%). MS (ES): m/z 598.7 [M+H]+.

Synthesis of compound I-20. Compound 20.4 (0.07 g, 0.117 mmol, 1.0 eq) was dissolved in HBr/HOAc (2 ml) and stirred at room temperature for 1 hour. After completion of the reaction, mixture was poured into water, basified with saturated bicarbonate solution and extracted with EtOAc. Organic layers were combined, dried over sodium sulphate and concentrated under reduced pressure to obtain crude which was purified get pure I-20 (0.025 g, 47.7%). MS (ES): m/z 448.5 [M+H]+; $^1$H NMR(DMSO-$d_6$, 400 MHz): 9.50(s, 1H), 8.80 (s, 1H), 8.36 (s, 1H), 8.04 (d, 1H),7.57 (m, 1H), 7.45(dd,1H), 7.25 (m,2H), 7.08 (d,1H), 4.40(s,2H), 3.18(t, 4H), 1.44 (t,4H), 0.32(s,4H)

Example 21

Synthesis of 4-((1H-pyrrolo[2,3-b]pyridin-6-yl)amino)-2-(2,6-difluoro-phenyl)-6,7-dihydro-5H-pyrrolo[3,4-b]pyridin-5-one, I-21

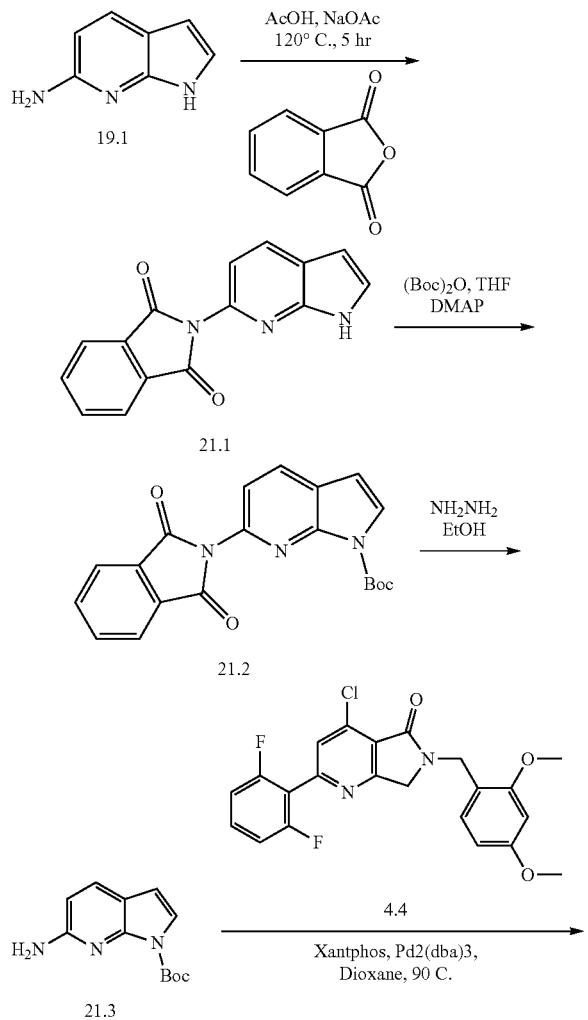

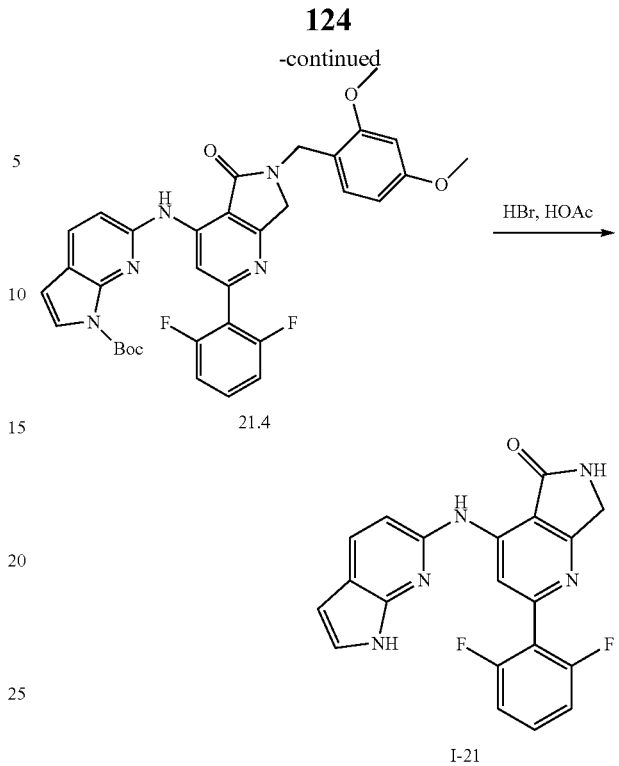

Synthesis of compound 21.1. To a solution of 19.1 (0.5 g, 3.75 mmol, 1.0 equiv) and NaOAc (0.49 g, 6.00 mmol, 1 equiv) in acetic acid (5 mL) was added phtalic anhydride (0.667 g, 4.5 mmol, 1.2 equiv) and stirred at 120° C. for 5 hours. Reaction mixture was poured into water (50 mL) and extracted with EtOAc (20 mL×3). Organic layers were combined, dried over $Na_2SO_4$ and concentrated under reduced pressure to obtain crude material. Crude was stirred in aqueous satd. $NaHCO_3$, filtered then dried to get pure 21.1 (0.400 g, 40.46%). MS (ES): m/z 264.3 [M+H]+.

Synthesis of compound 21.2. To a solution of 21.1 (0.450 g, 1.70 mmol, 1 eq) in THF (4.5 mL) was added DMAP (0.020 g, 0.17 mmol, 0.1 eq) followed by di-tert-butyl dicarbonate (0.447 g, 2.05 mmol, 1.2 eq) 0° C. Reaction mixture was stirred at room temperature for 1 hour. Reaction mixture was poured into water (50 mL) and extracted with EtOAc (20 mL×3). Organic layers were combined, dried over sodium sulphate and concentrated under reduced pressure to obtain crude which was purified by column chromatography to afford 21.2 (0.50 g, 80.5%). MS (ES): m/z 364.3 [M+H]+.

Synthesis of compound 21.3. To a solution of 21.2 (0.300 g, 0.825 mmol, 1.0 eq) in EtOH (3 mL) and $CH_2Cl_2$ (1 mL) was added $N_2H_4$—$H_2O$ (99%) (0.040 mL, 0.83 mmol, 1.0 eq) and stirred at room temperature for 1 hour. Reaction mixture was poured into ice cold saturated solution of $NaHCO_3$ (50 mL) and extracted with EtOAC (20 mL×3). Organic layers were combined, dried over sodium sulphate and concentrated under reduced pressure to obtain crude which was purified by column chromatography to furnish 21.3 (0.15 g, 77.9%). MS (ES): m/z 234.3 [M+H]+.

Synthesis of compound 21.4. To a solution of 4.4 (0.10 g 0.23 mmol, 1.0 eq) in dry Dioxane (5.0 mL) was added 21.3 (0.081 g, 0.35 mmol, 1.5 eq) and $K_2CO_3$ (0.095 g, 0.60 mmol, 3.0 eq.) at room temperature under argon purge for 15 minutes. To the above reaction mixture was added $Pd_2(dba)_3$ (0.021 g, 0.023 mmol, 0.1 eq) and Xantphos (0.026 g, 0.046 mmol, 0.2 eq) under argon purge for 10 minutes. Reaction mixture was stirred at 95° C. temperature for 3 to 4 hours. After completion of the reaction, mixture was poured into water and extracted using ethyl acetate. Organic layers were combined, washed with brine, dried over sodium sulphate and concentrated under reduced pressure to obtain crude. Crude was purified by column chromatography to get pure 21.4 (0.05 g, 34.32%). MS (ES): m/z 628.6 [M+H]⁺.

Synthesis of compound I-21. A solution of 21.4 (0.025 g) in HBr/HOAc solution (33%, 2 ml) was stirred at room temperature for 1 hour. After completion of the reaction, mixture was poured into cold water, neutralized with NaHCO₃ and extracted with ethyl acetate (50 ml×2). Solvent was removed under reduced pressure at 45° C. Resulting crude was purified by column chromatography to furnish I-21 (0.010 g, 66.58%). MS (ES): m/z 378.35 [M+H]⁺, ¹H NMR (400 MHz, DMSO-d₆): δ 11.51 (s,1H), 9.78 (s,1H), 8.87 (s,1H), 8.67 (s,1H), 7.94 (d,1H), 7.63-7.55 (m,1H), 7.30-7.26 (m,3H), 6.82 (d,1H), 6.39 (s,1H), 4.43 (s,2H).

Example 22

Synthesis of 2-(2,6-difluorophenyl)-4-((2,3-dihydro-1H-pyrrolo[2,3-b]pyridin-6-yl)amino)-6,7-dihydro-5H-pyrrolo[3,4-b]pyridin-5-one, I-22

Synthesis of compound 22.1. To a solution of 21.4 (0.10 g 0.159 mmol, 1.0 eq) in EtOH (10.0 mL) and 1,2-Dimethoxyethane (10.0 mL) was added 10% Pd/C (0.010 mg) under nitrogen atmosphere. Suspension was purged with hydrogen for 12 h. Reaction mixture was filtered through celite and obtained filtrate was concentrated under reduced pressure to get crude 22.1 (0.090 g, 89.72%) which was used as such for the next step, MS (ES): m/z 630.7 [M+H]⁺.

Synthesis of compound I-22. A solution of 22.1 (0.09 g) in HBr/HOAc solution (33%, 2 ml) was stirred at room temperature for 1 hour. After completion of the reaction, mixture was poured into cold water, neutralized with NaHCO3 and product was extracted with EtOAc (50 ml×2). Solvent was concentrated under reduced pressure to get crude which was triturated using Et₂O (2.0 mL) and MeOH (0.2 mL) to furnish I-22. (0.05 g, 92.2%). MS (ES): m/z 380.4 [M+H]⁺; ¹H NMR (400 MHz, DMSO-d₆): δ 9.46 (s,1H), 8.81 (s, 1H), 8.34 (s,1H), 7.56 (t,1H), 7.27-7.23 (m,3H), 6.52 (s,1H), 6.12 (d,1H), 4.39 (s,2H), 3.46 (t,2H), 2.91 (t,2H).

Example 23

Synthesis of 2-(2,6-difluorophenyl)-4-((3,3-dimethyl-2,3-dihydrobenzofuran-6-yl)amino)-6,7-dihydro-5H-pyrrolo[3,4-d]pyrimidin-5-one, I-23

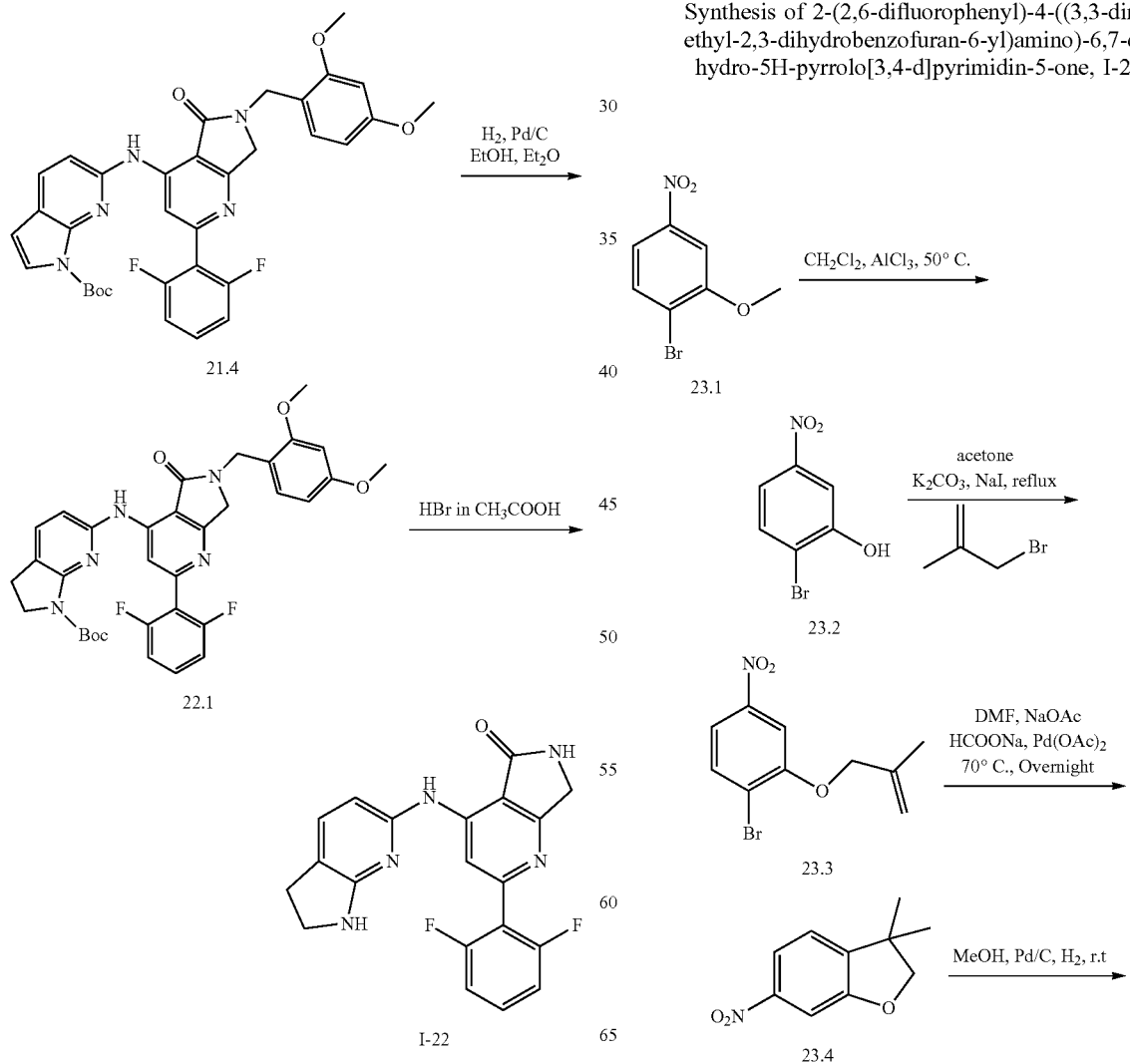

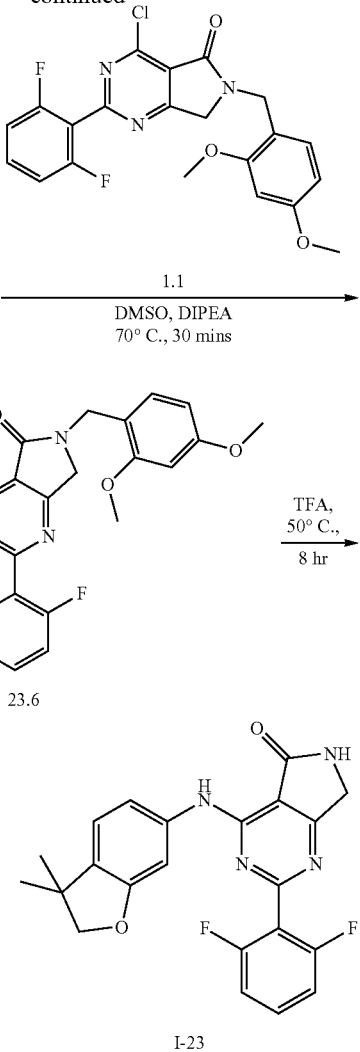

Synthesis of compound 23.2. To a solution of 23.1 (0.97 g 4.1 mmol, 1.0 eq.) in dry CH$_2$Cl$_2$ (6.0 mL) was added anhydrous AlCl$_3$ (1.66 g, 12.5 mmol, 3.0 eq) at 0° C. under argon atmosphere. The reaction mixture was stirred at 50° C. for 16 hours. After completion of the reaction, mixture was poured into diluted HCl to adjust pH to 4, and extracted using CH$_2$Cl$_2$. Organic layer was washed with brine and dried over sodium sulfate. Organic layer was concentrated under reduced pressure and crude was purified by column chromatography to afford pure 23.2 (0.76 g, 83.39%). MS (ES): m/z 219.1 [M+H]$^+$.

Synthesis of compound 23.3. To a solution of 23.2 (0.76 g, 3.57 mmol, 1.0 eq) in acetone (8 mL) were added K$_2$CO$_3$ (1.20 g, 8.71 mmol, 2.5 eq) and NaI (0.575 g, 3.83 mmol, 1.1 eq) at room temperature and stirred for 20 minutes. To the mixture 3-Bromo-2-methylpropane (0.611 g, 4.53 mmol, 1.3 eq) was added and reaction was heated at reflux temperature for 2 hours. After completion of the reaction, mixture was diluted with water and extracted with EtOAc. Organic layer was dried over sodium sulphate and concentrate under reduced pressure at 45° C. Crude was purified by column chromatography to afford 23.3 (0.60 g, 63.25%). MS (ES): m/z=273.1 [M+H]$^+$.

Synthesis of compound 23.4. To a solution of 23.3 (0.6 g, 2.20 mmol, 1.0 eq.) in dry DMF (15.0 ml) was added Et$_3$NI (0.38 g, 2.4 mmol, 1.09 eq), Sodium formate (0.156 g, 2.40 mmol, 1.09 eq) and NaOAc (0.44 g, 5.51 mmol, 2.5 eq). Reaction mixture was degassed for 10 min and Palladium acetate (0.048 g, 0.22 mmol, 0.1 eq) was added and again reaction mixture degassed for 10 min. Reaction mixture was heated at 70° C. overnight. After completion of the reaction, mixture was poured in cold water and product was extracted with EtOAc. Organic layer was washed with brine, dried over sodium sulphate. Solvent was removed under reduced pressure and crude was purified by column chromatography to afford pure 23.4 (0.34 g, 79.8%). MS (ES): m/z 194.3 [M+H]$^+$.

Synthesis of compound 23.5. To a suspension of Pd/C (0.034 g,) in MeOH (10 mL) was added 23.4 (0.340 g, 1.76 mmol, 1.0 eq) under nitrogen atmosphere. Above reaction mixture was purged with H$_2$ (gas) at room temperature for 1 hour. After completion of the reaction, reaction mixture was filter through celite. Solvent was removed under reduced pressure to afford 23.5 (0.250 g, 87.0%). MS (ES): m/z 164.4 [M+H]$^+$.

Synthesis of 23.6. To a solution of 1.1 in DMSO (5.0 mL) were added 24.5 (0.075 g, 0.46 mmol, 1.0 eq.) and DIPEA (0.149 mg, 1.16 mmol, 2.5 eq.) at room temperature. Reaction was heated at 70° C. for 30 minutes. After completion of the reaction, mixture was poured into water and extracted using EtOAc. Organic layer was washed with by brine, dried over sodium sulfate and concentrated under reduced pressure. Crude was purified by column chromatography to afford pure 23.6 (0.151 g, 58.37%). MS (ES): m/z 559.6 [M+H]$^+$ Synthesis of compound I-23. A solution of 23.6 (0.151 g,) in TFA (6 mL) was heated at 70° C. for 8 hrs. After completion of the reaction, mixture was concentrated under reduced pressure at 45° C. Obtained residue was poured in cold water, neutralized with NaHCO$_3$ and product was extracted with EtOAc. Solvent was removed under reduced pressure to get crude which was purified by preparative TLC to afford pure I-23 (34 mg, 30.8%). MS (ES): m/z 409.4 [M+H]$^+$, $^1$H NMR (400 MHz, DMSO-d$_6$): δ 8.99 (s,1H), 8.89 (s,1H), 7.62-7.58 (m,1H), 7.40 (s,1H), 7.30-7.26 (t,2H), 7.17-7.15 (d,1H), 7.10-7.08 (s,1H), 4.47 (s,2H), 4.21 (s,2H), 1.27 (s,6H).

Example 24

Synthesis of compound 4-((5-(2-oxa-7-azaspiro[3.5]nonan-7-yl)pyridin-2-yl)amino)-2-(2,6-difluorophenyl)-6,7-dihydro-5H-pyrrolo[3,4-b]pyridin-5-one, I-24

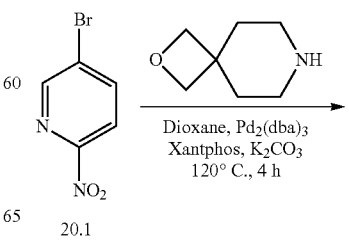

-continued

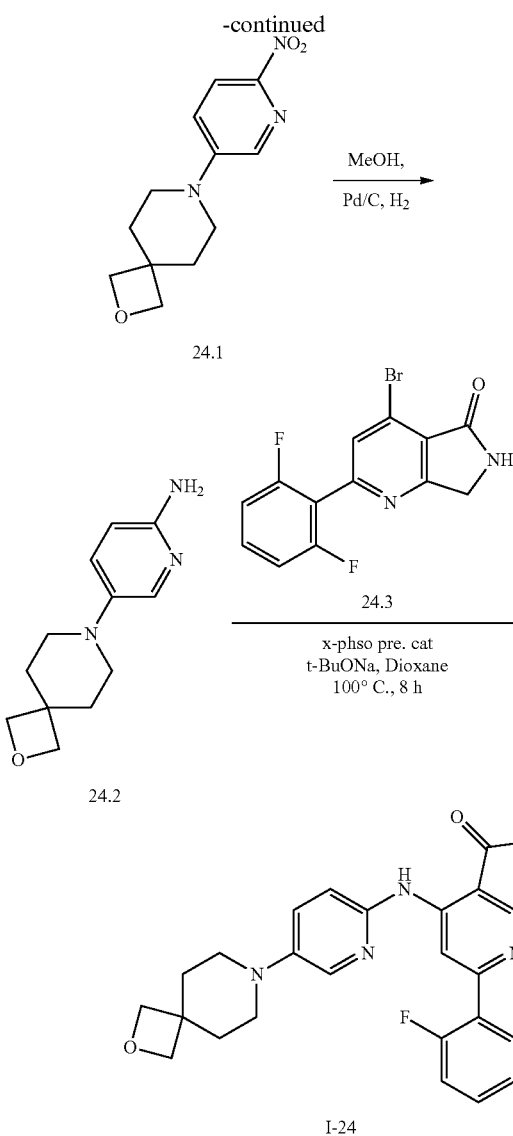

Synthesis of compound 24.1. To a solution of 20.1 (0.6 g, 2.95 mmol, 1.0 eq) in 1,4-dioxane (10 ml) was added 2-oxa-7-azaspiro[3.5]nonane (0.641 g, 2.95 mmol, 1.0 eq) and $K_2CO_3$ (1.2 g, 8.86 mmol, 3.0 eq). The reaction mixture was degassed for 10 min. using argon, then $Pd_2(dba)_3$ 0.063 g, 0.29 mmol, 0.1 eq) and Xantphos (0.341 g, 0.59 mmol, 0.2 eq) were added, again degassed for 5 minutes. Reaction was stirred at 120° C. for 4 hours. After completion of the reaction, reaction mixture was poured into water and product was extracted with EtOAc. Organic layers were combined, dried over sodium sulphate and concentrated under reduced pressure to obtain crude which was purified to get pure 24.1 (0.210 g, 28.5%). MS (ES): m/z 250.2 [M+H]$^+$.

Synthesis of compound 24.2. A solution of 24.1 (0.210 g, 0.84 mmol, 1.0 eq) in MeOH (5 mL) was added 10% Pd/C (0.050 g) under nitrogen atmosphere. It was purged with $H_2$ gas for 1 hour. Reaction mixture was filtered through celite and obtained filtrate was concentrated under reduced pressure to get crude 24.2 (0.130 g, 70.37%) which was used as such for the next step, MS (ES): m/z 220.2 [M+H]$^+$.

Synthesis of compound I-24. To a solution of 24.3 (0.050 g, 0.15 mmol, 1.0 eq) in 1,4-dioxane (3 mL) was added 1.2 (0.027 g, 0.12 mmol, 0.8 eq) and Sodium t-butoxide (0.029 g, 0.30 mmol, 2.0 eq). The reaction mixture was degassed for 10 minutes under argon atmosphere, then Chloro(2-dicyclohexylphosphino-2',4',6'-triisopropyl-1,1'-biphenyl) [2-(2'-amino-1,1'-biphenyl)]palladium(II) (0.022 g, 0.030 mmol, 0.2 eq) was added, again degassed for 5 min. The reaction was stirred at 100° C. for 8 hours. After completion of the reaction, mixture was poured into water and product was extracted with EtOAC. Organic layers were combined, dried over sodium sulphate and concentrated under reduced pressure to obtain crude which was purified by column chromatography to get pure I-24 (0.011 g, 10.4%). MS (ES): m/z 464.4 [M+H]$^-$. 1H NMR (CDCl$_3$, 400 MHz): 9.41 (s,1H), 8.54 (s,1H), 8.04 (s,1H), 7.43-7.30 (m,2H), 7.06-7.01 (m,2H), 6.92-6.90 (d,1H), 4.54 (s,2H), 4.49 (s,4H), 3.09-3.06 (t,4H), 2.05-2.03 (t, 4H).

Example 25

Synthesis of 4-((5-(1-oxa-7-azaspiro[3.5]nonan-7-yl)pyridin-2-yl)amino)-2-(2,6-difluorophenyl)-6,7-dihydro-5H-pyrrolo[3,4-b]pyridin-5-one, I-25

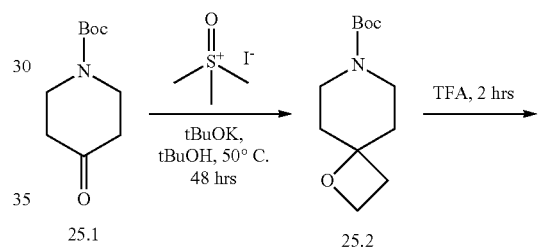

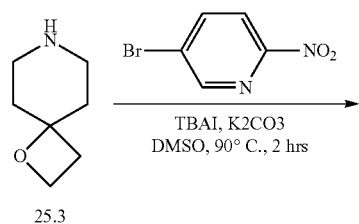

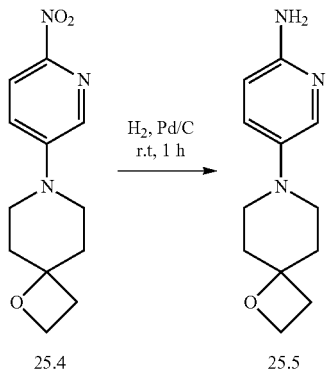

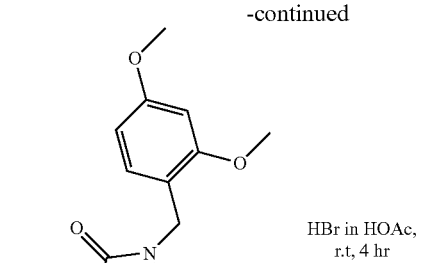

4.4

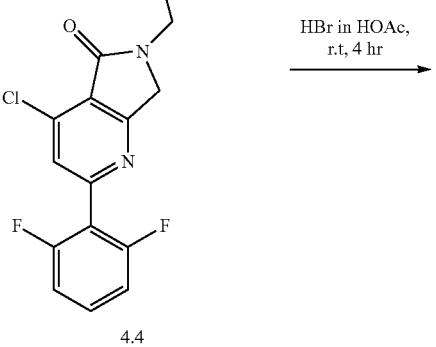

24.3

25.5 x-phos pre. cat
K₃PO₄, Dioxane
100° C., 20 mins

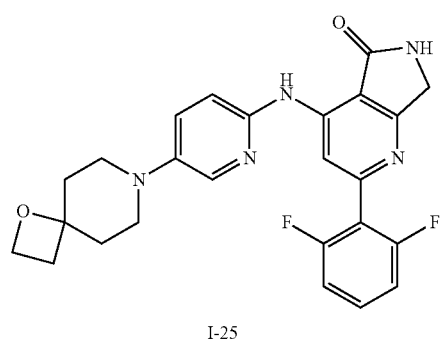

I-25

Synthesis of compound 25.2. To a solution of Trimethyl sulphoxonium iodide (22.09 g, 100.4 mmol, 4.0 eq) in t-butanol (150 mL) was added potassium tert-butoxide (11.24 g, 100.4 mmol, 4.0 eq). Reaction was stirred at 50° C. for 1 h. Then 25.1 (5 g, 25 mmol, 1 eq) was added at 50° C. and allowed to stir for 2 days. After completion of the reaction, mixture was concentrated under reduced pressure. Water was added to reaction mixture and product was extracted with Et₂O. Organic layer was combined and dried over Na₂SO₄ and concentrated under reduced pressure to obtain crude which was purified by tituration in hexane to give pure 25.2 (3.6 g, 63.11%). MS (ES): m/z 227.30 [M+H]⁺.

Synthesis of compound 25.3. To compound 25.2 (3.6 g, 15.78 mmol, 1.0 eq) TFA was added. The reaction was stirred for 2 h. After completion of the reaction, mixture was concentrated under reduced pressure. The reaction mixture was neutralized using amberlyst resin in methanol. Reaction mixture was concentrated under reduced pressure to get crude 25.3 (2.0 g, 99.3%) which was used as such for the next step, MS (ES): m/z 127.19 [M+H]⁺.

Synthesis of compound 25.4. To a solution of 20.1 (2.0 g, 9.85 mmol, 1 eq.) in DMSO (18 ml) was added compound 25.3 (1.87 g, 14.77 mmol, 1.5 eq), tetra butyl ammonium iodide (0.363 g, 0.98 mmol, 0.1 eq), and K₂CO₃ (4.078 g, 29.55 mmol, 3.0 eq). Reaction mixture was heated at 90° C. for 2 h. After completion of the reaction, mixture was poured into water to give solid product. The product was extracted with EtOAC. Organic layers were combined and dried over sodium sulphate and concentrated under reduced pressure to obtain crude which was purified by column chromatography to furnish 25.4 (0.37 g, 10.1%). MS (ES): m/z 249.27 [M+H]⁻.

Synthesis of compound 199.5. To a solution of 199.4 (0.370 g, 1.48 mmol, 1.0 eq) in MeOH (15 mL) was added 10% Pd/C (0.060 g) under nitrogen atmosphere. It was purged with hydrogen for 1 hours. Reaction mixture was filtered through celite and obtained filtrate was concentrated under reduced pressure to get crude 199.5 (0.263 g, 98.88%) which was used as such for the next step. MS (ES): m/z 219.29 [M+H]⁺.

Synthesis of compound 24.3. Compound 4.4 (1.0 g, 2.32 mmol, 1.0 eq) was dissolved in H Br/HOAc (10 ml) and stirred at room temperature for 4 h. After completion of the reaction, mixture was poured into water and basified with saturated bicarbonate solution and extracted with EtOAc. Organic layers were combined, dried over sodium sulphate and concentrated under reduced pressure to obtain crude which was purified by column chromatography to get pure 24.3 (0.630 g, 83.49%). MS (ES): m/z 325.11 [M+H]⁺.

Synthesis of compound I-25. To a solution of compound 24.3 (0.250 g, 0.768 mmol, 1.0 eq.) in 1,4-dioxane were added compound 25.5 (0.168 g, 0.768 mmol, 1.0 eq) and K₃PO₄ (0.326 g, 1.53 mmol, 2.0 eq). The reaction mixture was degassed for 15 minutes. Pre-catalyst Xantphos (0.111 g, 0.153 mmol, 0.2 eq) was added to the reaction mixture and reaction was further degassed for 10 minutes. The reaction mixture was heated at 100° C. for 20 minutes. After completion of the reaction, mixture was poured into water and product was extracted with EtOAC. Organic layers were combined, dried over sodium sulphate and concentrated under reduced pressure to obtain crude which was purified by column chromatography and preparative HPLC to furnish I-25 (0.007 g, 2.92%). MS (ES): m/z 463.49 [M+H]⁺, $^1$H NMR (DMSO-d6, 400 MHz): 9.48 (s, 1H), 8.80 (s,1H), 8.36 (s,1H), 8.02-8.01 (d,2H), 7.59-7.54 (m,1H), 7.46-7.43 (dd,1H), 7.27-7.23 (t,3H), 7.10-7.08(d,1H), 5.50 (s,1H), 4.48-4.46 (t,1H), 4.40 (s,2H), 3.60 (s,2H), 3.52-3.44 (m, 2H), 3.31-3.28 (m,2H), 2.16 (s,4H).

Example 26

Synthesis of 2-(4-((2-(2,6-difluorophenyl)-5-oxo-6,7-dihydro-5H-pyrrolo[3,4-d]pyrimidin-4-yl)amino)phenyl)-N-ethyl-4,4,4-trifluoro-2-hydroxybutanamide, I-26

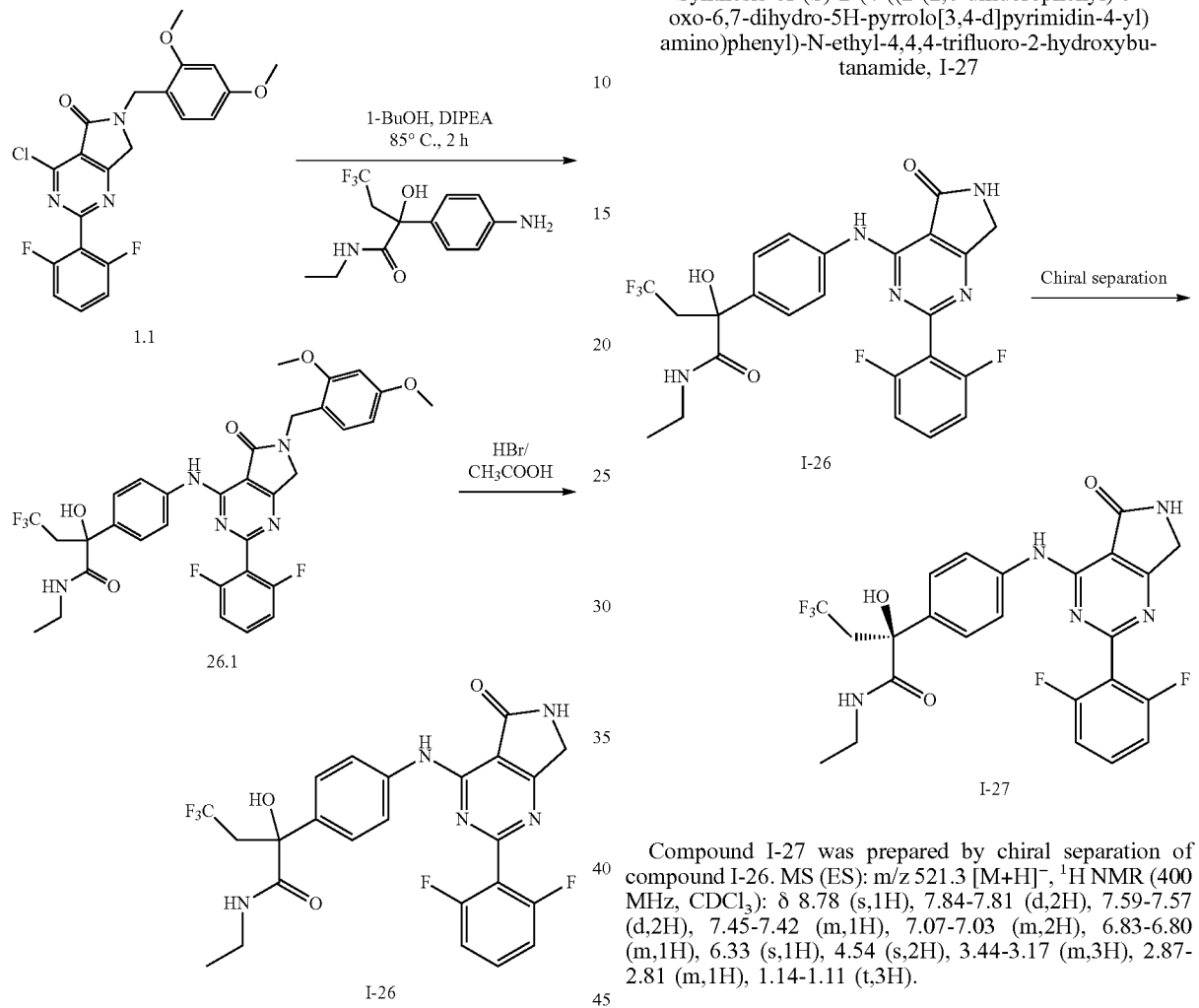

Synthesis of compound 26.1. To a solution of 1.1 (0.06 g, 0.137 mmol, 1.0 eq) in Butanol (3 mL) was added 2-(4-aminophenyl)-N-ethyl-3-fluoro-2-hydroxypropanamide compound with 113,311-prop-1-yne (1:1) (0.038 g, 0.137 mmol, 1.0 eq) and DIPEA (0.07 ml, 0.411 mmol, 3.0 eq). The reaction was then heated at 85° C. for 2 h. After completion of the reaction, mixture was poured in water and product was extracted with ethyl acetate. Organic layers were combined, dried over sodium sulphate and concentrated under reduced pressure to obtain crude 26.1 which was used in next step without further purification. 1.1 (0.07 g, 64.3%). MS (ES): m/z 671.6 [M+H]$^+$.

Synthesis of compound I-26. A solution of 26.1 (0.12 g, 0.214 mmol, 1.0 eq) in HBr/HOAc (3 mL) was stirred at room temperature for 2 h. Upon completion reaction was quenched with water and extracted with EtOAc. Organic layer was washed with satd. NaHCO$_3$ solution. Combined organic layers were washed with brine, dried over sodium sulphate and concentrated under reduced pressure to afford crude, which was purified by column chromatography to furnish I-26 (0.053 g, 97.5%). MS (ES): m/z 521.6 [M+H]$^+$. $^1$H NMR (400 MHz, CDCl$_3$): δ 8.82 (s,1H), 7.83-7.81 (d,2H), 7.60-7.57 (d,2H), 7.48-7.41 (m,1H), 7.08-7.02 (m,2H), 6.82-6.79 (m,1H), 6.25 (s,1H), 4.56 (s,2H), 3.51-3.16 (m, 4H), 1.14-1.11 (t,3H).

Example 27

Synthesis of (S)-2-(4-((2-(2,6-difluorophenyl)-5-oxo-6,7-dihydro-5H-pyrrolo[3,4-d]pyrimidin-4-yl)amino)phenyl)-N-ethyl-4,4,4-trifluoro-2-hydroxybutanamide, I-27

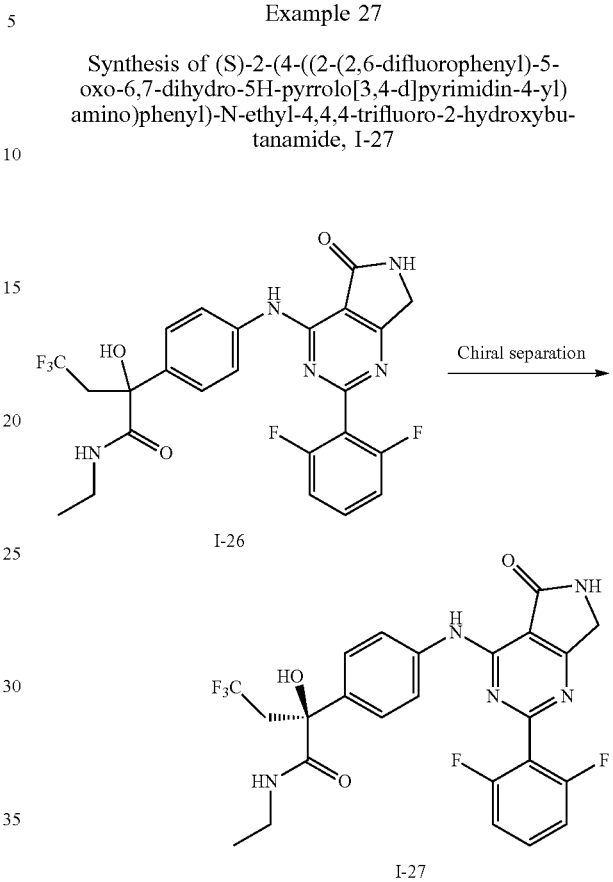

Compound I-27 was prepared by chiral separation of compound I-26. MS (ES): m/z 521.3 [M+H]$^-$, $^1$H NMR (400 MHz, CDCl$_3$): δ 8.78 (s,1H), 7.84-7.81 (d,2H), 7.59-7.57 (d,2H), 7.45-7.42 (m,1H), 7.07-7.03 (m,2H), 6.83-6.80 (m,1H), 6.33 (s,1H), 4.54 (s,2H), 3.44-3.17 (m,3H), 2.87-2.81 (m,1H), 1.14-1.11 (t,3H).

Example 28

Synthesis of (R)-2-(4-((2-(2,6-difluorophenyl)-5-oxo-6,7-dihydro-5H-pyrrolo[3,4-d]pyrimidin-4-yl)amino)phenyl)-N-ethyl-4,4,4-trifluoro-2-hydroxybutanamide, I-28

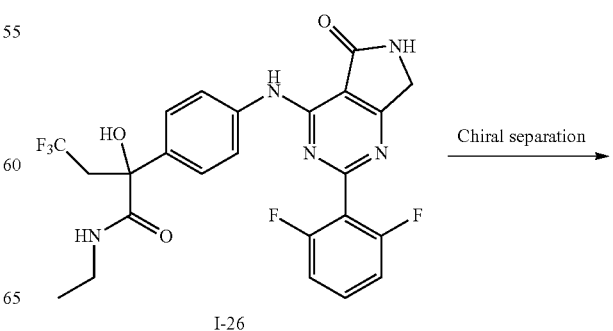

-continued

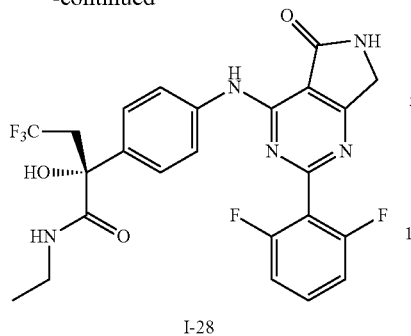

I-28

Compound I-28 was prepared by chiral separation of compound I-26. MS (ES): m/z 521.3 [M+H]⁻, ¹H NMR (400 MHz, CDCl₃): δ 8.78 (s,1H), 7.84-7.81 (d,2H), 7.59-7.57 (d,2H), 7.45-7.42 (m,1H), 7.07-7.03 (m,2H), 6.83-6.80 (m,1H), 6.33 (s,1H), 4.54 (s,2H), 3.44-3.17 (m,3H), 2.87-2.81 (m,1H), 1.14-1.11 (t, H).

Example 29

Synthesis of 2-(2,6-difluorophenyl)-4-((4-(2,2,2-trifluoro-1-hydroxy-ethyl)phenyl)amino)-6,7-dihydro-5H-pyrrolo[3,4-d]pyrimidin-5-one, I-29

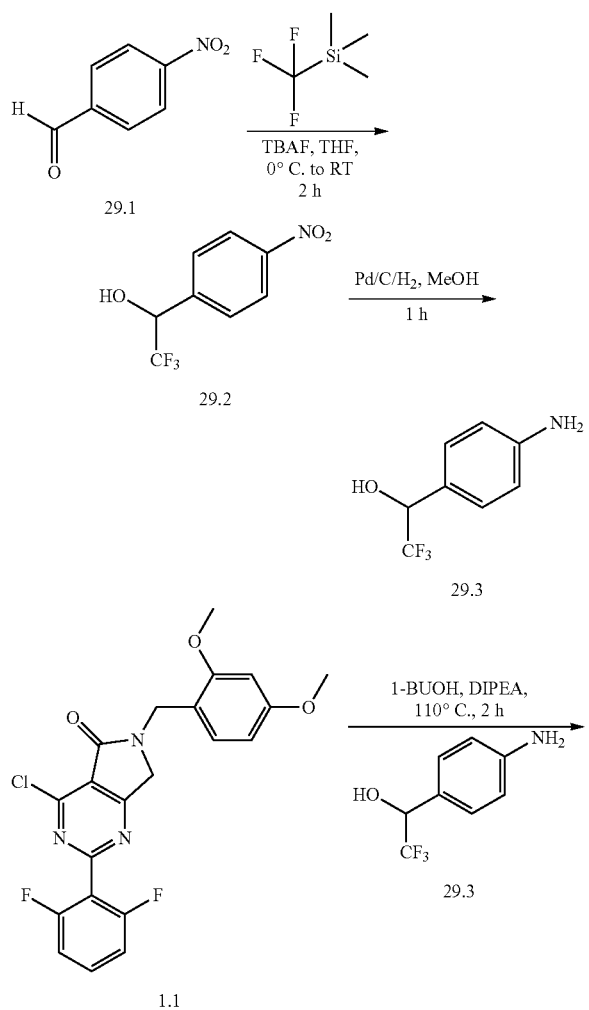

-continued

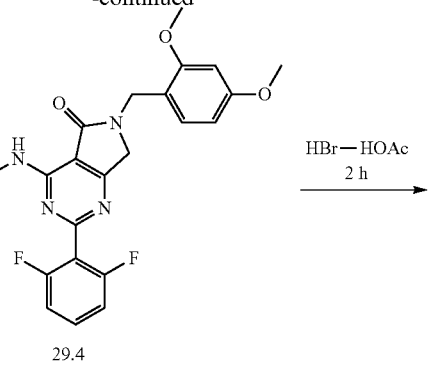

Synthesis of compound 29.2. To a solution of 29.1 (1 g, 6.6 mmol, 1.0 eq) in THF (3 ml) was added trimethyl (trifluoromethyl) silane (1.41 g, 9.9 mmol, 1.5 eq) at 0° C. Tetrabutyl ammonium fluoride (0.132 ml, 0.13 mmol, 0.02 eq) was added at 0° C. and allowed to stir for 10 minutes and then at room temperature for 2 hours. Reaction mixture was poured into 3 N HCl and product was extracted with CH₂Cl₂. Organic layers were combined, dried over sodium sulphate and concentrated under reduced pressure to obtain crude which was purified by column chromatography to get pure 29.2 (1.1 g, 75.17%). MS (ES): m/z 221.14 [M+H]⁺.

Synthesis of compound 29.3. To a solution of 29.2 (1.1 g, 5.0 mmol, 1.0 eq) in MeOH (10 ml) was added 10% Pd/C (0.2 g) under nitrogen atmosphere. It was purged with hydrogen for 1 hour. Reaction mixture was filtered through celite and obtained filtrate was concentrated under reduced pressure to get crude 29.3 (0.820 g, 86.2%) which was used as such for the next step, MS (ES): m/z 191.15 [M+H]⁺.

Synthesis of compound 29.4. To a solution of 1.1 (0.300 g, 0.697 mmol, 1.0 eq) in n-Butanol (4 ml) was added 29.3 (0.146 g, 0.767 mmol, 1.1 eq) and DIPEA (0.27 g, 2.093 mmol, 3.0 eq). Reaction was stirred at 110° C. for 2 hours. After completion of the reaction, mixture was poured into water and product was extracted with EtOAc. Organic layers were combined, dried over sodium sulphate and concentrated under reduced pressure to obtain crude which was purified by column chromatography to furnish 29.4 (0.320 g, 78.53%). MS (ES): m/z 586.52 [M+H]⁻.

Synthesis of compound I-29. Compound 29.4 (0.320 g, 0.545 mmol, 1.0 eq) was dissolved in HBr/HOAc (5 ml) and stirred at room temperature for 2 hours. After completion of the reaction, mixture was poured into water, basified with satd. NaHCO₃ solution and extracted with EtOAc. Organic layers were combined, dried over sodium sulphate and concentrated under reduced pressure to obtain crude which was purified by column chromatography to furnish I-26 (0.125 g, 52.52%). MS (ES): m/z 436.34 [M+H]⁺, ¹H NMR (MeOD, 400 MHz): 7.87-7.85 (d,2H), 7.60-7.52 (m,1H), 7.50-7.48 (d,2H), 7.18-7.14 (m,2H), 5.05-4.99 (s,2H), 4.52 (s,1H).

Example 30

Synthesis of (S)-2-(2,6-difluorophenyl)-4-((4-(2,2,2-trifluoro-1-hydroxyethyl)phenyl)amino)-6,7-dihydro-5H-pyrrolo[3,4-d]pyrimidin-5-one, I-30

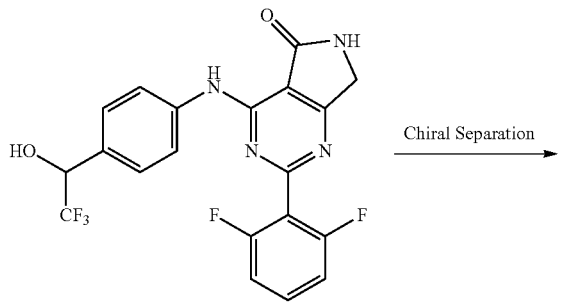

I-29

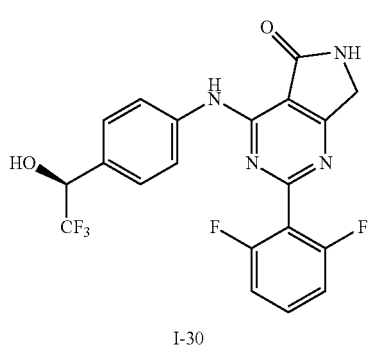

I-30

Compound I-30 was prepared by chiral separation of compound I-29. MS (ES): m/z 436.34 [M+H]⁺, ¹H NMR (400 MHz, MeOD): δ 7.87-7.85 (d,2H), 7.58-7.53 (m,3H), 7.50-7.48 (d,2H), 7.18-7.14 (m,2H), 4.52 (s,1H).

Example 31

Synthesis of (R)-2-(2,6-difluorophenyl)-4-((4-(2,2,2-trifluoro-1-hydro-xyethyl)phenyl)amino)-6,7-dihydro-5H-pyrrolo[3,4-d]pyrimidin-5-one, I-31

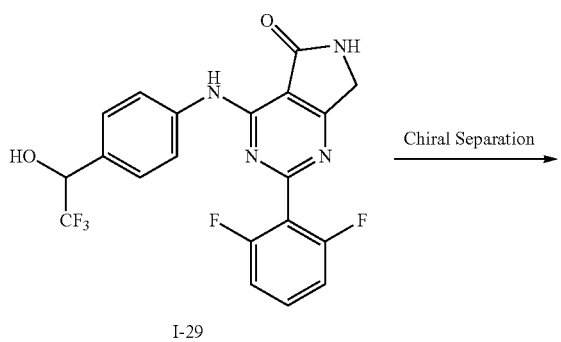

I-29

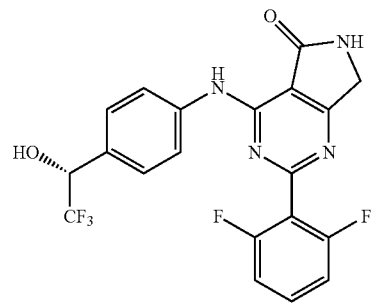

I-31

Compound I-31 was prepared by chiral separation of compound I-29. MS (ES): m/z 436.34 [M+H]⁺, ¹H NMR (400 MHz, MeOD): δ 7.87-7.85 (d,2H), 7.60-7.53 (m,1H), 7.50-7.48(d,2H), 7.18-7.14 (m,2H), 4.64(s,2H), 4.52 (s,1H).

Example 32

Synthesis of 2-amino-2-(4-((2-(2,6-difluorophenyl)-5-oxo-6,7-dihydro-5H-pyrrolo[3,4-d]pyrimidin-4-yl)amino)phenyl)propanoic acid, I-32

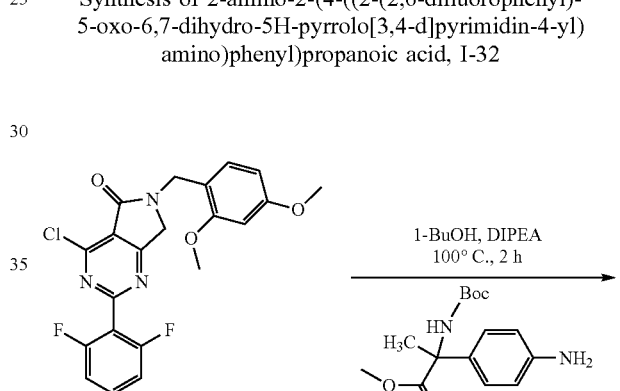

32.1

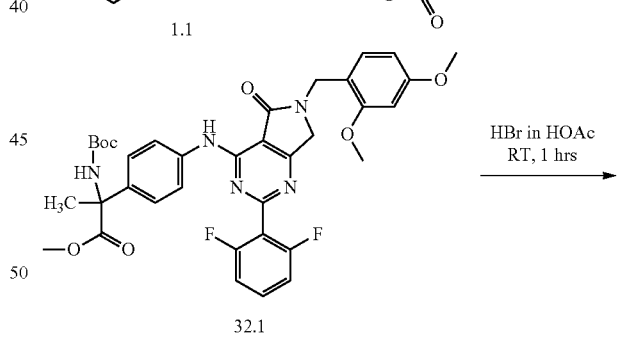

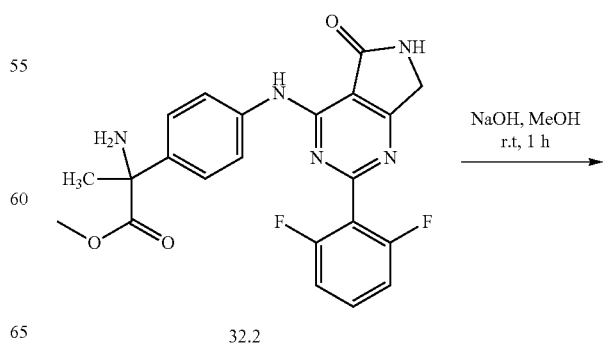

32.2

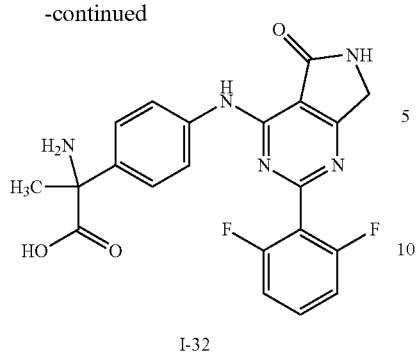

I-32

Synthesis of compound 32.1. To a solution of 1.1 (0.073 g, 0.170 mmol, 1.0 eq) in Butanol (5 mL) were added methyl 2-(4-aminophenyl)-2-((tert-butoxycarbonyl)-amino)propionate (0.050 g, 0.170 mmol, 1.0 eq) and DIPEA (0.09 ml, 0.510 mmol, 3.0 eq). The reaction was stirred at 100° C. for 2 hours. After completion of the reaction, mixture was poured into water and product was extracted with EtOAc. Organic layers were combined, dried over sodium sulphate and concentrated under reduced pressure to obtain crude 32.1 (0.070 g, 60.04%) which was used in next step without further purification. MS (ES): m/z 690.72 [M+H]$^+$.

Synthesis of compound 32.2. Solution of 32.1 (0.070 g, 0.106 mmol, 1.0 eq) in HBr/HOAc (3 mL) was stirred at room temperature for 2 hr. Upon completion, water was added and product was extracted with EtOAc. Organic layers were washed with satd. NaHCO$_3$ solution. Combined organic layers were washed with brine, dried over sodium sulphate and concentrated under reduced pressure afford crude, which was purified by column chromatography to furnish 32.2 (0.030 g, 67.27%). MS (ES): m/z 440.42 [M+H]$^+$.

Synthesis of compound I-32. Compound 32.2 (0.030 g, 0.068 mmol, 1.0 eq) was dissolved in MeOH (2 ml). 2N NaOH (0.090 ml, 0.204 mmol, 3.0 eq) was added and stirred at room temperature for 1 hr. After completion of reaction, mixture was concentrated under reduced pressure. Crude compound was purifide by prep HPLC to get pure I-32 (0.008 g, 24.4%). MS (ES): m/z 425.40 [M+H]$^+$, $^1$H NMR (MeOD, 400 MHz): 7.88-7.85 (m, 2H), 7.58-7.53 (m,3H), 7.16-7.12 (m,2H), 4.51 (s,2H), 1.88 (s,3H).

Example 33

Synthesis of 2-(2,6-difluorophenyl)-4-((4-(1,1,1-trifluoro-2-hydroxy-propan-2-yl)phenyl)amino)-6,7-dihydro-5H-pyrrolo[3,4-d]pyrimidin-5-one, I-33

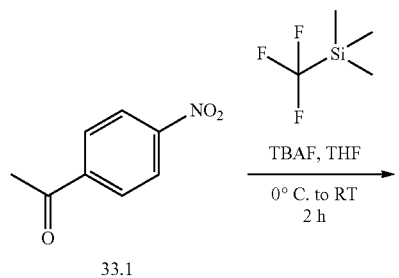

33.1

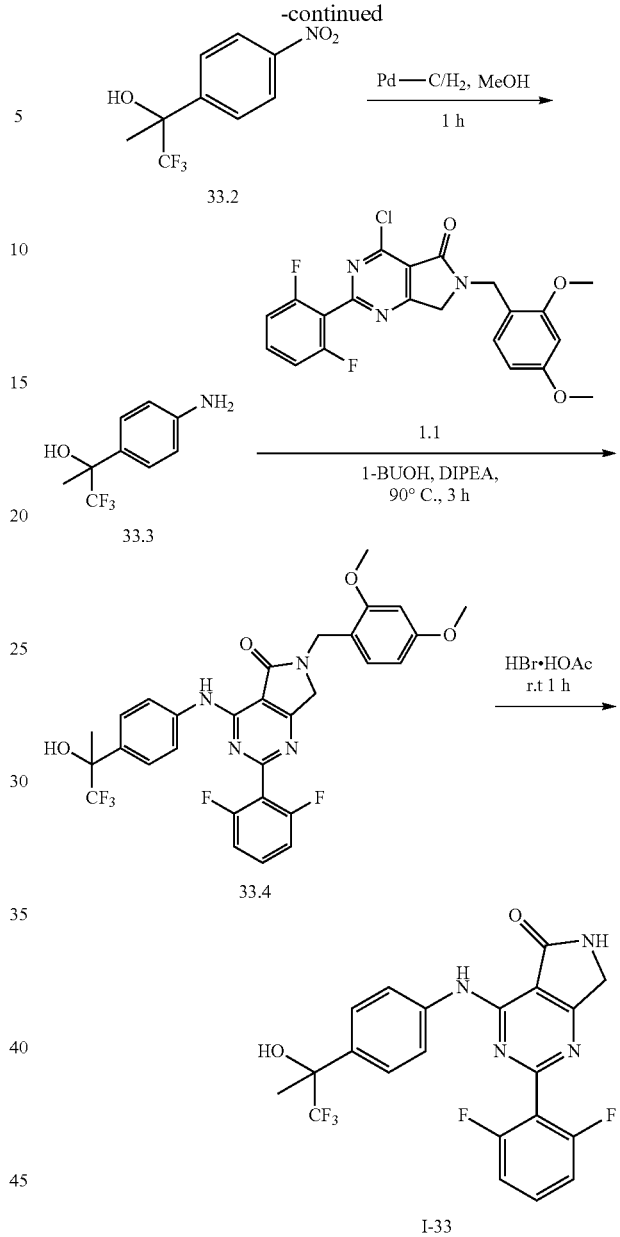

Synthesis of compound 33.2. To a solution of 33.1 (1 g, 6 mmol, 1.0 eq) in THF (15 ml) was added trimethyl (trifluoromethyl) silane (1.3 g, 9 mmol, 1.5 eq) and cooled at 0° C. Tetrabutyl ammonium fluoride (0.132 ml, 0.13 mmol, 0.02 eq) was added at 0° C. and allowed to stir for 10 minutes and then at room temperature for 2 hours. Reaction mixture was poured in 3 N HCl and product was extracted with EtOAc. Organic layers were combined, dried over sodium sulphate and concentrated under reduced pressure to obtain crude which was purified by column chromatography to get pure 33.2 (1 g, 70.2%). MS (ES): m/z 235.16 [M+H]$^+$.

Synthesis of compound 33.3. To a solution of 33.2 (0.3 g, 1.2 mmol, 1.0 eq) in MeOH (10 ml) was added 10% Pd/C (0.2 g) under nitrogen atmosphere. It was purged with hydrogen for 1 hour. Reaction mixture was filtered through celite and obtained filtrate was concentrated under reduced pressure to get crude 33.3 (0.250 g, 95.51%) which was used as such for the next step, MS (ES): m/z 205.18 [M+H]$^+$.

Synthesis of compound 33.4. To a solution of 1.1 (0.100 g, 0.23 mmol, 1.0 eq) in n-Butanol (5 ml) was added 33.3 (0.047 g, 0.23 mmol, 1.0 eq) and DIPEA (0.089 g, 0.69 mmol, 3.0 eq). Reaction mixture was stirred at 90° C. for 3 hours. After completion of the reaction, n-butanol was removed under high vaccum to obtain crude material 33.4 (0.100 g, 71.99%). MS (ES): m/z 600.18 [M+H]$^+$.

Synthesis of compound I-33. Compound 33.4 (0.100 g, 0.166 mmol, 1.0 eq) was dissolved in HBr/HOAc (3 ml) and stirred at room temperature for 1 hour. After completion of the reaction, mixture was poured into water and basified with satd. NaHCO$_3$ and product was extracted with EtOAc. Organic layers were combined, dried over sodium sulphate and concentrated under reduced pressure to obtain crude which was purified by column chromatography to get pure I-33 (0.050 g, 66.7%). MS (ES): m/z 450.37 [M+H]$^+$, $^1$H NMR (DMSO-d$_6$, 400 MHz): 9.13 (s,1H), 8.92 (s,1H), 7.80-7.78 (d,2H), 7.56-7.54 (m,3H), 7.29-7.27(m,2H), 6.55 (d,1H), 4.49 (s, 2H), 1.67 (s,3H).

Example 34

Synthesis of (S)-2-(2,6-difluorophenyl)-4-((4-(1,1,1-trifluoro-2-hydroxy-propan-2-yl)phenyl)amino)-6,7-dihydro-5H-pyrrolo[3,4-d]pyrimidin-5-one, I-34

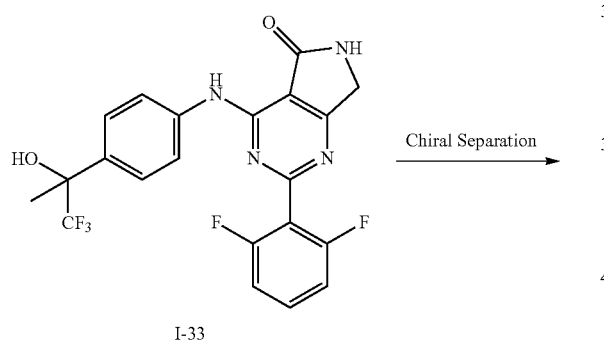

Compound I-34 was prepared by chiral separation of compound I-33 MS (ES): m/z 450.37 [M+H]$^+$, $^1$H NMR (400 MHz, MeOD): δ 7.85-7.80 (m,2H), 7.63-7.52 (m,3H), 7.18-7.13 (m,2H), 4.52 (s,2H), 1.73 (s,3H).

Example 35

Synthesis of (R)-2-(2,6-difluorophenyl)-4-((4-(1,1,1-trifluoro-2-hydroxy-propan-2-yl)phenyl)amino)-6,7-dihydro-5H-pyrrolo[3,4-d]pyrimidin-5-one I-35

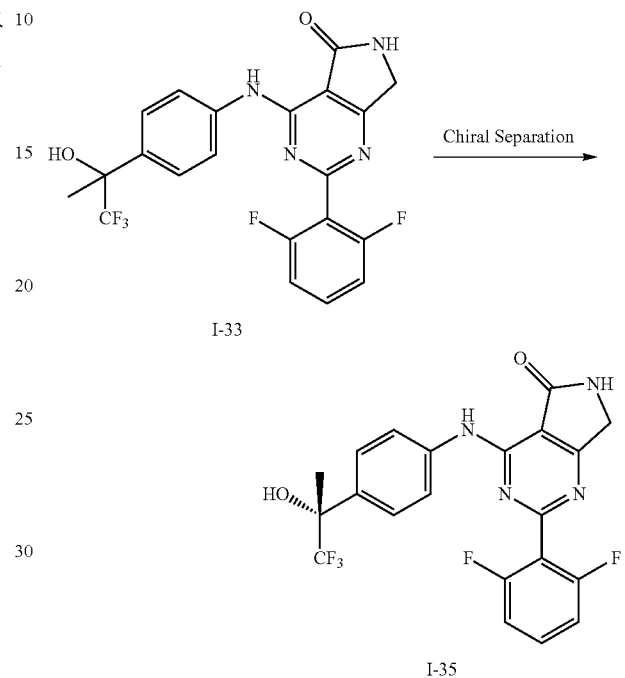

Compound I-35 was prepared by chiral separation of compound I-33 MS (ES): m/z 450.37 [M+H]$^+$, $^1$H NMR (400 MHz, MeOD): δ 7.85-7.83 (m,2H), 7.61-7.54 (m,3H), 7.18-7.14(m, 2H), 4.52 (s,2H), 1.73 (s,3H).

Example 36

Synthesis of 4-((5-(1-oxa-6-azaspiro[3.5]nonan-6-yl)pyridin-2-yl)amino)-2-(2,6-difluorophenyl)-6,7-dihydro-5H-pyrrolo[3,4-b]pyridin-5-one, I-36

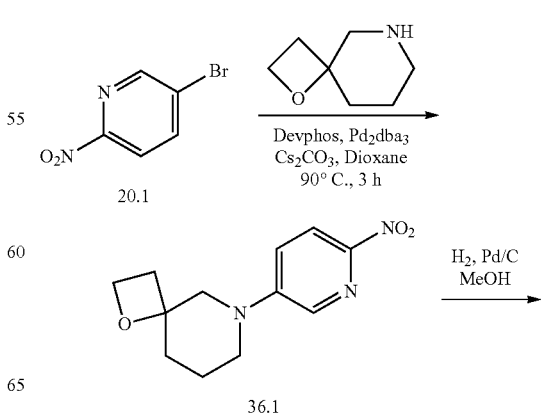

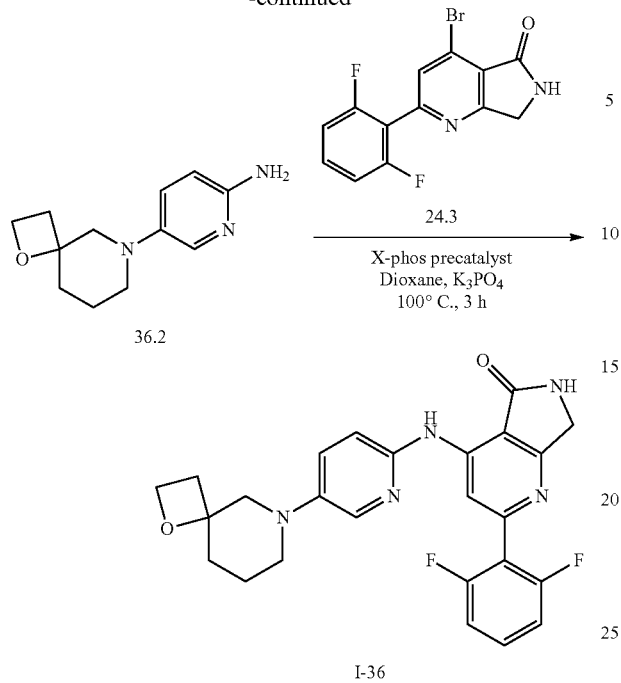

Synthesis of compound 36.1. To a solution of 20.1 (0.400 g, 1.97 mmol, 1.0 eq) in 1,4-dioxane (10 mL) were added 1-oxa-6-azaspiro[3.5]nonane (0.406 g, 2.36 mmol, 1.2 eq) and Cs$_2$CO$_3$ (1.92 g, 5.91 mmol, 3.0 eq). The reaction mixture was degassed for 10 min. using argon, then Pd$_2$(dba)$_3$ (0.180 g, 0.197 mmol, 0.1 eq) and 2-Dicyclohexylphosphino-2'-(N,N-dimethylamino)biphenyl (0.154 g, 0.394 mmol, 0.2 eq) were added, and again degassed for 5 min. Reaction was stirred at 110° C. for 4 h. After completion of the reaction, mixture was poured into water and product was extracted with EtOAc. Organic layers were combined and dried over sodium sulphate and concentrated under reduced pressure to obtain crude which was purified by column chromatography to furnish 36.1 (0.36 g, 73.3%). MS (ES): m/z 250.6 [M+H]$^+$.

Synthesis of compound 36.2. To a solution of 36.1 (0.360 g, 1.44 mmol, 1.0 eq) in MeOH (5 mL) was added 10% Pd/C (0.350 g) under nitrogen atmosphere. It was purged with hydrogen for 1 hour. Reaction mixture was filtered through celite and obtained filtrate was concentrated under reduced pressure to get crude 36.2 (0.300 g, 94.73%) which was used as such for the next step, MS (ES): m/z 220.23 [M+H]$^+$.

Synthesis of compound I-36. To a solution of 24.3 (0.400 g, 1.23 mmol, 1.0 eq) in 1,4-dioxane (3 mL) was added 36.2 (0.269 g, 1.23 mmol, 1.0 eq) and K$_3$PO$_4$ (0.52 g, 2.46 mmol, 2.0 eq). The reaction mixture was degassed for 10 min. using argon, then chloro(2-dicyclohexylphosphino-2',4',6'-triisopropyl-1,1'-biphenyl)[2-(2-aminoethyl)phenyl)]palladium (II) (0.182 g, 0.25 mmol, 0.2 eq) was added, again degassed for 5 minutes. Reaction was then stirred at 100° C. for 1 hour. After completion of the reaction, mixture was poured into water and product was extracted with EtOAc. Organic layers were combined, dried over Na$_2$SO$_4$ and concentrated under reduced pressure to obtain crude which was purified by column chromatography to furnish I-36 (0.163 g, 28.6%). MS (ES): m/z 463.6 [M+H]$^+$. $^1$H NMR (400 MHz, DMSO-d$_6$): δ 9.51 (s,1H), 8.81 (s,1H), 8.39 (s,1H), 8.09 (s,1H), 7.64-7.49 (m,2H), 7.34-7.23 (m,2H), 7.10-7.08 (d,1H), 4.48-4.39 (m,1H), 4.38 (s,2H), 3.43-3.40 (m,1H), 3.12-3.01 (m, 2H), 2.90-2.86 (m,1H), 2.43-2.28 (m,3H), 1.87-1.83 (m,1H), 1.73-1.62 (m,2H), 1.56-1.50 (m, 1H).

Example 37

Synthesis of (R)-4-((5-(1-oxa-6-azaspiro[3.5]nonan-6-yl)pyridin-2-yl)amino)-2-(2,6-difluorophenyl)-6,7-dihydro-5H-pyrrolo[3,4-b]pyridin-5-one, I-37

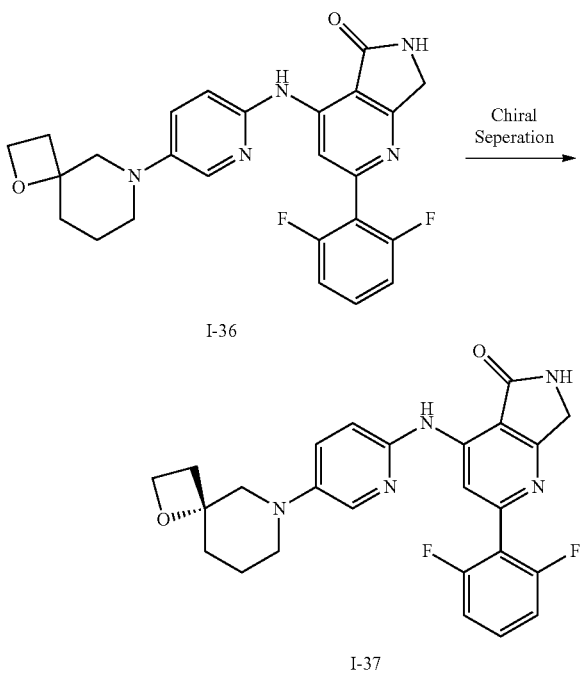

Compound I-37 was prepared by chiral separation of compound I-36. MS (ES): m/z 463.3 [M+H]$^+$, $^1$H NMR (400 MHz, MeOD): δ 8.45 (s,1H), 8.10 (s,1H), 7.56-7.50 (m,2H), 7.16-7.12 (m,2H), 7.06-7.04 (d,1H), 4.65-4.55 (m,2H), 4.47 (s,2H), 3.33-3.31 (m,2H), 3.09-3.07 (m,2H), 2.55-2.45 (m,2H), 1.91-1.86 (m,2H), 1.70-1.66 (m,2H).

Example 38

Synthesis of (S)-4-((5-(1-oxa-6-azaspiro[3.5]nonan-6-yl)pyridin-2-yl)amino)-2-(2,6-difluorophenyl)-6,7-dihydro-5H-pyrrolo[3,4-b]pyridin-5-one, I-38

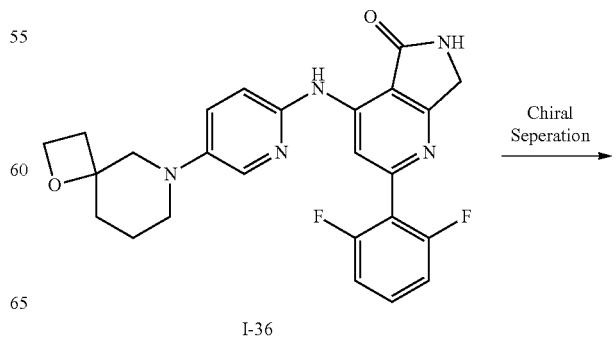

-continued

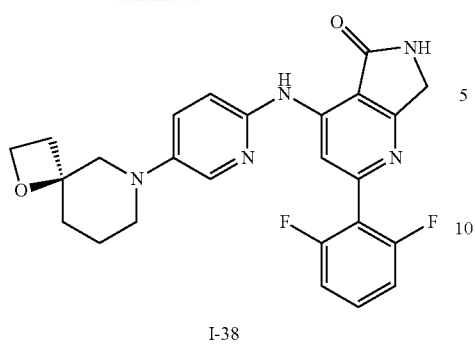

I-38

Compound I-38 was prepared by chiral separation of compound I-36. MS (ES): m/z 463.3 [M+H]⁺, ¹H NMR (400 MHz, MeOD): δ 8.45 (s,1H), 8.10 (s,1H), 7.56-7.50 (m,2H), 7.16-7.12 (m,2H), 7.06-7.04 (d,1H), 4.65-4.55 (m,2H), 4.47 (s,2H), 3.33-3.31 (m,2H), 3.09-3.07 (m,2H), 2.55-2.45 (m,2H), 1.91-1.86 (m,2H), 1.70-1.66 (m,2H).

Example 39

Synthesis of 2-(4-((2-(2,6-difluorophenyl)-5-oxo-6,7-dihydro-5H-pyrrolo[3,4-d]pyrimidin-4-yl)amino)phenyl)-2,4-dimethyl-2H-benzo[b][1,4]oxazin-3(4H)-one, I-39

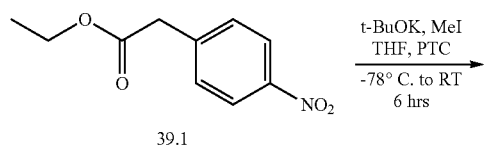

39.1

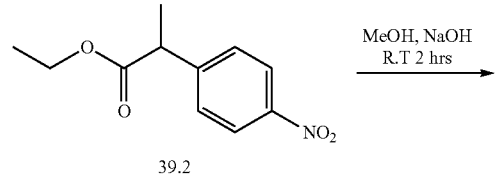

39.2

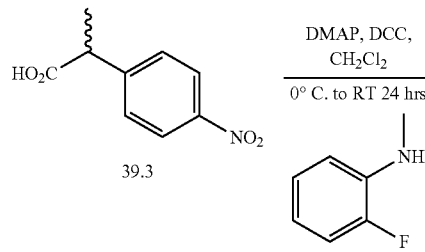

39.3

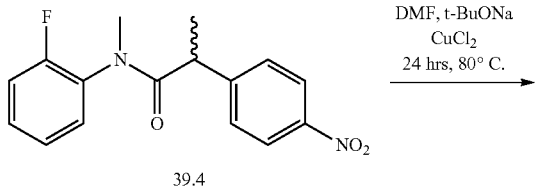

39.4

-continued

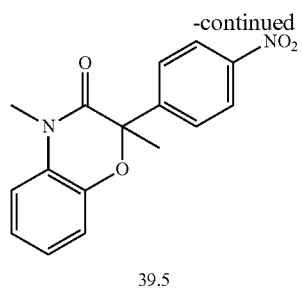

39.5

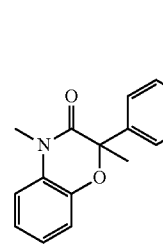

39.6

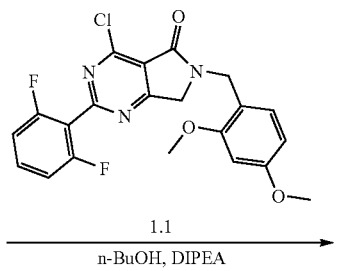

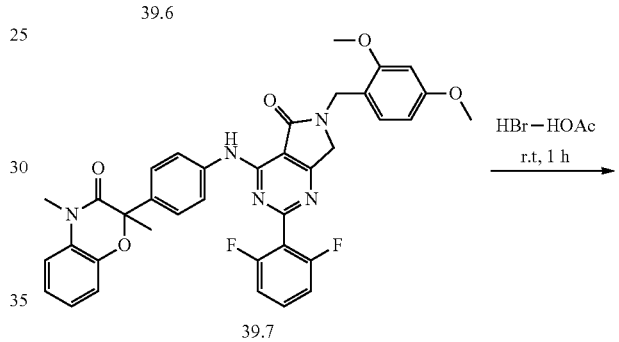

39.7

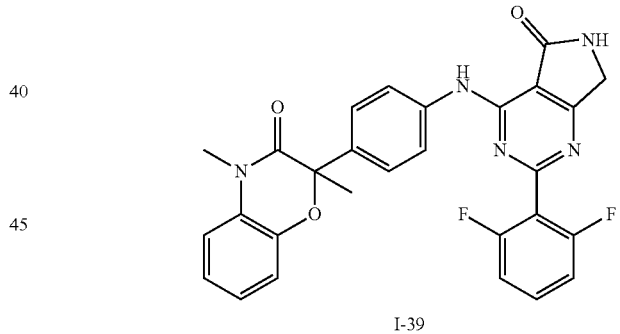

I-39

Synthesis of compound 39.2. To a solution of 39.1 (5.0 g, 23.92 mmol, 1.0 eq) in THF (50 ml) was added MeI (3.73 g, 26.31 mmol, 1.1 eq.) and 18-crown-6 (1.57 g, 59.80 mmol, 0.25 eq.). The reaction mixture was cooled to −78° C. and potassium t-butoxide (2.94 g, 26.31 mmol, 1.1 eq) was added. Reaction was stirred at room temperature for 6 hours. After completion of reaction, NH₄Cl was added at −78° C. Product was extracted with EtOAc. Organic layers were combined and dried over Na₂SO₄ and concentrated under reduced pressure to obtain crude which was purified by column chromatography to furnish 39.2 (4.5 g, 84.34%). MS (ES): m/z 223.23 [M+H]⁺.

Synthesis of compound 39.3. To a solution of compound 39.2 (4.5 g, 20.17 mmol, 1.0 eq) in ethanol (40 ml) was added NaOH (1.614 g, 40.35 mmol, 2 eq.) and water (10 ml). Reaction was stirred at room temperature for 2 hours. After completion of the reaction, solvent was evaporated under reduced pressure and water was added. Dilute HCl was added to acidify the reaction mixture. The product was extracted with ethyl acetate. Organic layers were combined and dried over $Na_2SO_4$ and concentrated under reduced pressure to obtain crude which was purified by column chromatography to furnish 39.3 (3.1 g, 78.8%). MS (ES): m/z 195.17 $[M+H]^+$.

Synthesis of compound 39.4. To a solution of 2-fluoro-N-methylaniline (1.98 g, 15.89 mmol, 1 eq.) in $CH_2Cl_2$ (50 ml) was added compound 39.3 (3.1 g, 15.8 mmol, 1 eq). Further DMAP (0.386 g, 3.168 mmol, 0.2 eq) was added and the reaction was cooled at 0° C. Dicyclohexyl carbodiimide (3.91 g, 19.00 mmol, 1.2 eq) was added at 0° C. and the reaction was stirred at room temeperature for 24 hours. After completion of the reaction, mixture was filtered through celite and the filtrate was concentrated under reduced pressure to obtain crude which was purified by column chromatography to furnish 39.4 (0.330 g, 10.76%). MS (ES): m/z 302.31 $[M+H]^+$.

Synthesis of compound 39.5. To a solution of compound 39.4 (0.280 g, 0.927 mmol, 1 eq.) in DMF (10 ml) was added copper (II) chloride (0.273 g, 2.039 mmol, 2.2 eq.) and sodium t-butoxide (0.45 g, 4.64 mmol, 5.0 eq.) Reaction was stirred at 80° C. for 24 hours. After completion of the reaction, mixture was poured into water and brine solution was added to it. Product was extracted with EtOAc. Organic layers were combined, dried over sodium sulphate and concentrated under reduced pressure to obtain crude which was further purified by column chromatography to get pure 39.5 (0.069 g, 24.9%). MS (ES): m/z 298.30 $[M+H]^+$.

Synthesis of compound 39.6. To a Pd/C (20 mg) suspension in methanol (2 ml) was added 39.5 (0.069 mg, 0.231 mmol, 1.0 eq). Hydrogen gas was purged into the reaction mixture for 2 hours at ambient temperature. After completion of the reaction, mixture was filtered through celite and washed with methanol. The filtrate was evaporated under reduced pressure to obtain crude which was purified by column chromatography to get pure 9.5 (0.059 g, 95.06%). MS (ES): m/z 268.32 $[M+H]^+$.

Synthesis of compound 39.7. To a solution of 1.1 (0.100 g, 0.234 mmol, 1.0 eq.) in n-butanol (1 mL) were added compound 39.6 (0.059 g, 0.234 mmol, 1.0 eq.) and DIPEA (0.075 g, 0.58 mmol, 2.5 eq.). Reaction was stirred at 80° C. for 3 hours. After completion of the reaction, mixture was poured into water. The product was extracted with EtOAc. Organic layers were combined, dried over $Na_2SO_4$ and concentrated under reduced pressure to obtain crude which was purified by column chromatography to get pure 221.6 (0.130 g, 84.58%). MS (ES): m/z 663.68 $[M+H]^+$.

Synthesis of compound I-39. Compound 39.7 (0.130 g, 0.195 mmol, 1.0 eq) was dissolved in HBr/HOAc (2 mL) and stirred at room temperature for 1 hour. After completion of the reaction, mixture was poured into water and basified with satd. $NaHCO_3$ and extracted with EtOAc Organic layers were combined, dried over $Na_2SO_4$ and concentrated under reduced pressure to obtain crude which was purified by column and preparative HPLC to furnish I-39 (0.060 g, 59.65%). MS (ES): m/z 513.50 $[M+H]^+$, $^1H$ NMR (DMSO-$d_6$, 400 MHz): δ 9.05 (s, 1H), 8.91 (s,1H), 7.71-7.69 (d,2H), 7.63-7.59 (m,1H), 7.30-7.25 (m,4H), 7.13-7.11 (m,1H), 7.05-7.03 (m,1H), 6.99-6.95 (m,2H), 4.46 (s, 2H) 1.77 (s,3H).

Example 40

Synthesis of (S)-2-(4-((2-(2,6-difluorophenyl)-5-oxo-6,7-dihydro-5H-pyrrolo[3,4-d]pyrimidin-4-yl)amino)phenyl)-2,4-dimethyl-2H-benzo[b][1,4]oxazin-3(4H)-one. I-40

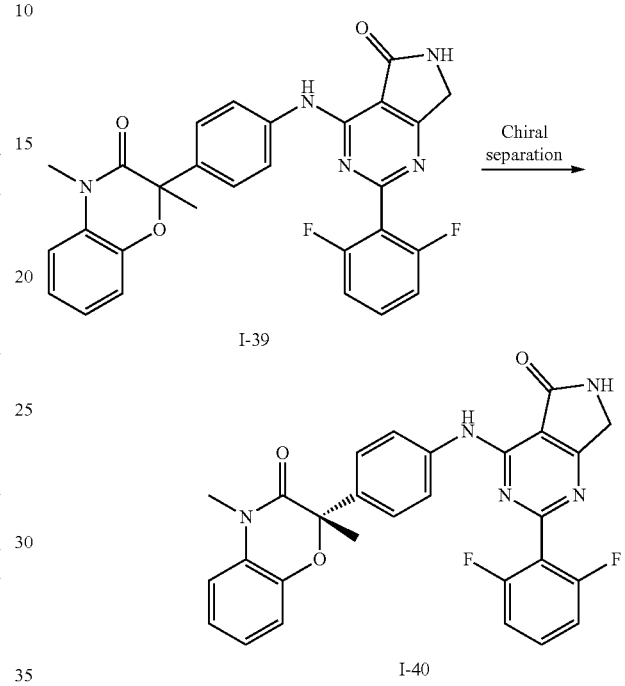

Compound I-40 was prepared by chiral separation of compound I-39. MS (ES): m/z 513.50 $[M+H]^+$, $^1H$ NMR (DMSO-$d_6$, 400 MHz): δ 9.05 (s,1H), 8.90 (s,1H), 7.71-7.69 (d,2H), 7.63-7.59 (m,1H), 7.30-7.25 (m,4H), 7.13-7.11 (m,1H), 7.05-7.03 (m,1H), 6.99-6.95 (m,2H), 4.45 (s,2H) 1.77 (s, 3H).

Example 41

Synthesis of (R)-2-(4-((2-(2,6-difluorophenyl)-5-oxo-6,7-dihydro-5H-pyrrolo[3,4-d]pyrimidin-4-yl)amino)phenyl)-2,4-dimethyl-2H-benzo[b][1,4]oxazin-3(4H)-one, I-41

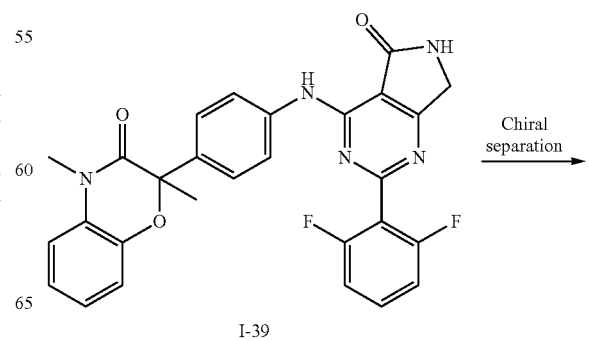

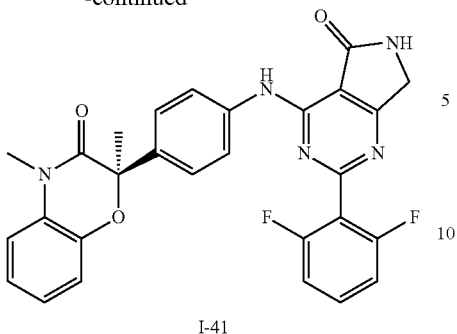

I-41

Compound I-41 was prepared by chiral separation of compound I-39. MS (ES): m/z 513.50 [M+H]+, $^1$H NMR (DMSO-d$_6$, 400 MHz): 9.05 (s,1H), 8.90 (s,1H), 7.71-7.69 (d,2H), 7.62-7.59 (m,1H), 7.30-7.25 (m,4H), 7.13-7.03 (m,2H), 6.99-6.95 (m,2H), 4.46 (s,2H) 1.77 (s,3H).

Example 42

Synthesis of 2-(2,6-difluorophenyl)-4-((4-(1,1,1-trifluoro-2-hydroxypropan-2-yl)phenyl)amino)-6,7-dihydro-5H-pyrrolo[3,4-b]pyridin-5-one, I-42

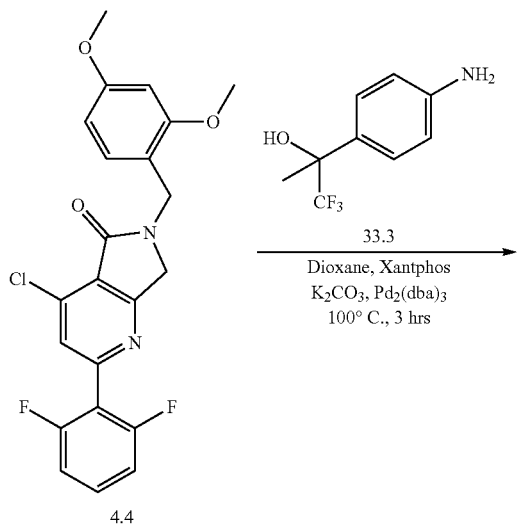

4.4

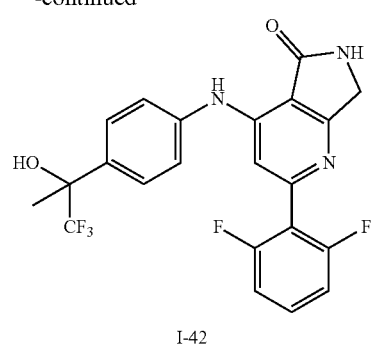

I-42

Synthesis of compound 42.1. To a solution of 4.4 (0.150 g, 0.348 mmol, 1.0 eq) in 1,4-dioxane (8 mL) was added 33.3 (0.071 g, 0.348 mmol, 1.0 eq) and K$_2$CO$_3$ (0.144 g, 1.04 mmol, 3 eq). The reaction mixture was degassed for 10 min. using argon, then Pd$_2$(dba)$_3$ (0.031 g, 0.034 mmol, 0.1 eq) and Xantphos (0.040 g, 0.069 mmol, 0.2 eq) were added, and again degassed for 5 minutes. Reaction was stirred at 90° C. for 3 hours. After completion of the reaction, mixture was poured into water and product was extracted with EtOAc. Organic layers were combined, dried over Na$_2$SO$_4$ and concentrated under reduced pressure to obtain crude which was purified by column chromatography to furnish 42.1 (0.120 g, 57.5%). MS (ES): m/z 599.46 [M+H]+.

Synthesis of compound I-42. Solution of 42.1 (0.120 g, 0.200 mmol, 1.0 eq) in HBr/HOAc (3 mL) was stirred at ambient temperature for 1 h. After completion of reaction pH was adjusted to 7 by addition of NaHCO$_3$ solution. The product was extracted with EtOAc. Combined organic layers were washed with brine, dried over sodium sulphate and concentrated under reduced pressure to afford crude, which was purified by column chromatography to furnish I-42 (0.065 g, 72.3%). MS (ES): m/z 449.38 [M+H]+. $^1$H NMR (DMSO-d$_6$, 400 MHz): δ 9.07 (s, 1H), 8.75 (s,1H), 7.61-7.59 (d,2H), 7.57-7.49 (m,1H), 7.40-7.38 (d,2H), 7.23-7.18 (m,2H), 7.11 (s,1H), 6.59 (s,1H), 4.40(s,2H), 1.68 (s,3H).

Example 43

Synthesis of (S)-2-(2,6-difluorophenyl)-4-((4-(1,1,1-trifluoro-2-hydroxypropan-2-yl)phenyl)amino)-6,7-dihydro-5H-pyrrolo[3,4-b]pyridin-5-one, I-43

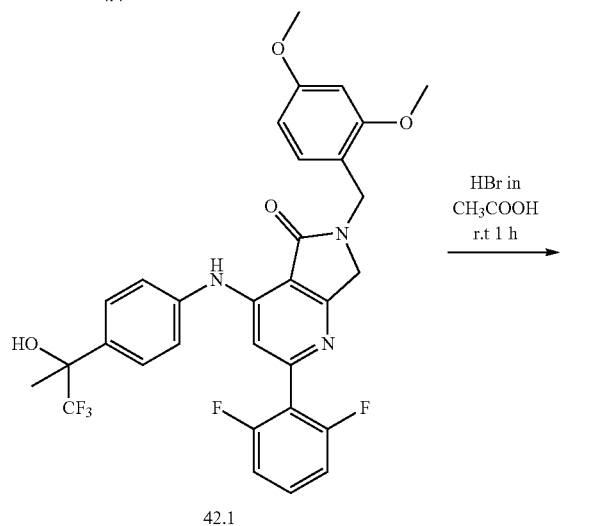

42.1

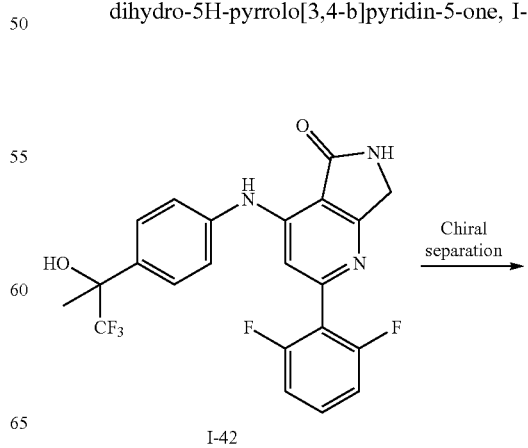

I-42

151

-continued

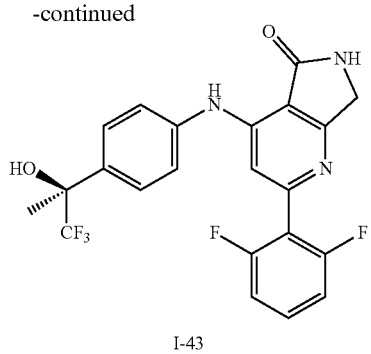

I-43 compound I-43 was prepared by chiral separation of I-42. MS (ES): m/z 449.38 [M+H]+, 1H NMR (400 MHz, DMSO-d6): δ 9.15 (s,1H), 8.78 (s,1H), 7.62-7.60 (d,2H), 7.56-7.51 (m,1H), 7.41-7.39 (d,2H), 7.24-7.20 (m,2H), 7.12 (s,1H), 6.60 (s,1H), 4.24 (s,2H), 1.68 (s,3H).

Example 44

Synthesis of (R)-2-(2,6-difluorophenyl)-4-((4-(1,1,1-trifluoro-2-hydroxy-nronan-2-yl)phenyl)amino)-6,7-dihydro-5H-pyrrolo[3,4-b]pyridin-5-one, I-44

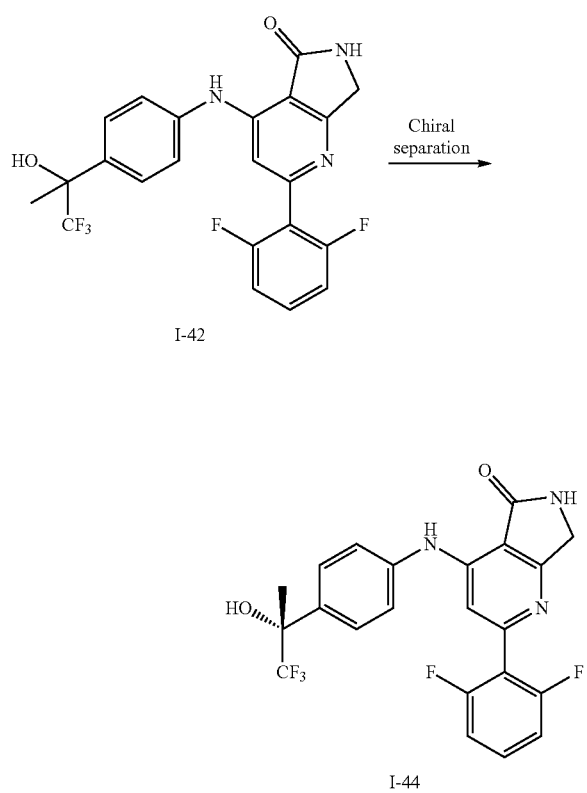

Compound I-44 was prepared by chiral separation of I-42. MS (ES): m/z 449.38 [M+H]+, 1H NMR (400 MHz, DMSO-d6): δ 9.15 (s,1H), 8.77 (s,1H), 7.62-7.59 (d,2H), 7.56-7.51 (m,1H), 7.41-7.38 (d,2H), 7.24-7.19 (m,2H), 7.12 (s,1H), 6.59 (s,1H), 4.42 (s,2H), 1.68 (s,3H).

152

Example 45

Synthesis of (S)-2-amino-2-(4-((2-(2,6-difluorophenyl)-5-oxo-6,7-dihydro-5H-pyrrolo[3,4-d]pyrimidin-4-yl)amino)phenyl)propanoic acid hydrochloride, I-45

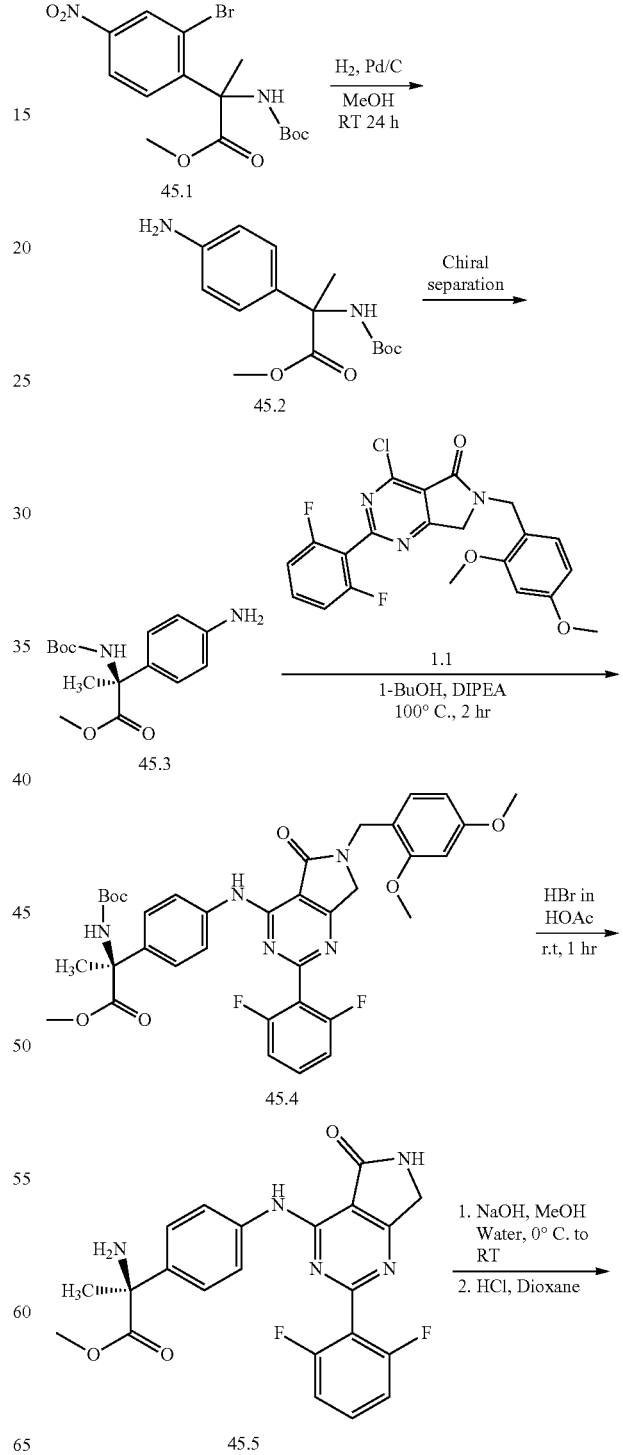

153

-continued

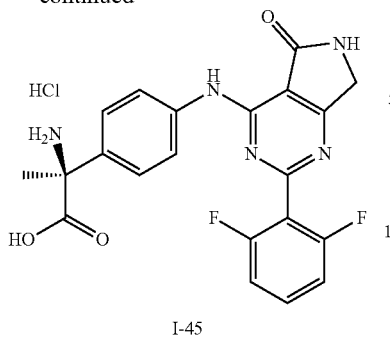

I-45

Synthesis of compound 45.2. To a solution of 45.1 (0.500 g, 1.23 mmol, 1.0 eq) in MeOH (10 ml) was added 10% Pd/C (0.2 g) under nitrogen. It was purged with $H_2$ gas at ambient temperature for 24 h. Reaction mixture was filtered through celite, washed with methanol and obtained filtrate was concentrated under reduced pressure to get crude which was purified by column chromatography to furnish 232.1 (0.26 g, 71.2%) MS (ES): m/z 294.35 [M+H]$^+$.

Synthesis of compound 45.3. Compound 45.2 was prepared by chiral separation of 232.1 (0.085 g), MS (ES): m/z 294.35 [M+H]$^+$, $^1$H NMR (400 MHz, DMSO-d$_6$): δ 7.07-7.04 (d,2H), 6.50-6.48 (d,2H), 5.10 (s,2H), 3.55 (s,3H), 1.67 (s,3H), 1.36 (s,9H).

Synthesis of compound 45.4. To a solution of 1.1 (0.120 g, 0.278 mmol, 1.0 eq) in n-butanol (5 ml) were added 45.3 (0.081 g, 0.278 mmol, 1.0 eq) and DIPEA (0.107 g, 0.835 mmol, 3.0 eq). Reaction was stirred at 100° C. for 2 h. After completion of the reaction, solvents were removed under reduced pressure to obtain crude 45.4 0.120 g, 62.61%). MS (ES): m/z 689.72 [M+H]$^+$.

Synthesis of compound 45.5. Compound 45.4 (0.120 g, 0.173 mmol, 1.0 eq) was dissolved in HBr/HOAc (2 mL) and stirred at room temperature for 1 hour. After completion of the reaction, mixture was poured into water and basified with satd. NaHCO$_3$ solution and extracted with EtOAc. Organic layers were combined, dried over Na$_2$SO$_4$ and concentrated under reduced pressure to obtain crude which was purified by column chromatography to get pure 45.5 (0.055 g, 71.9%). MS (ES): m/z 439.42 [M+H]$^+$.

Synthesis of compound I-45. Compound 45.5 (0.055 g, 0.125 mmol, 1.0 eq) was dissolved in MeOH (2 mL) at 0° C. 2N NaOH solution (0.165 ml, 0.375 mmol, 3.0 eq.) was added at same temperature. Reaction mixture was stirred at room temperature for 1 h. After completion of the reaction, mixture was acidified by using solution of HCl in dioxane. The solvent was removed under reduced pressure to obtain crude which was purified by preparative HPLC to furnish I-45 (0.025 g, 46.9%). MS (ES): m/z 425.40 [M+H]$^+$; $^1$H NMR (400 MHz, MeOD): δ 8.18 (s, 1H), 7.89-7.86 (d,2H), 7.60-7.54 (m,3H), 7.17-7.11 (m,2H), 4.51 (s, 2H), 1.89 (s, H).

154

Example 46

Synthesis of (R)-2-amino-2-(4-((2-(2,6-difluorophenyl)-5-oxo-6,7-dihydro-5H-pyrrolo[3,4-d]pyrimidin-4-yl)amino)phenyl)propanoic acid hydro-chloride, I-46

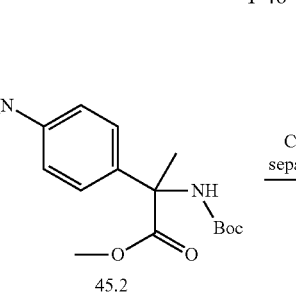

45.2

↓ Chiral separation

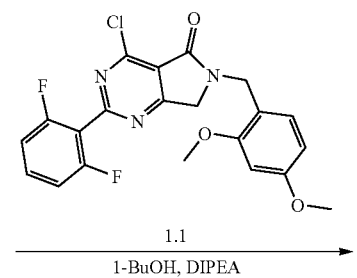

1.1
1-BuOH, DIPEA
100° C., 2 hr

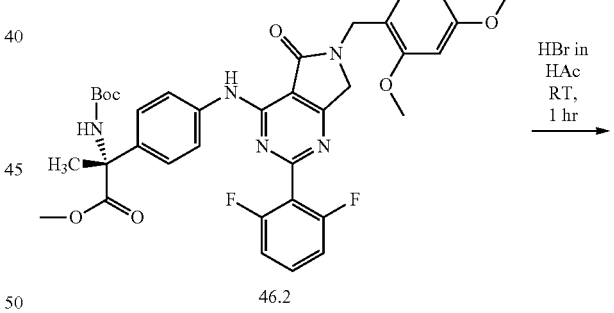

46.2

HBr in HAc
RT, 1 hr

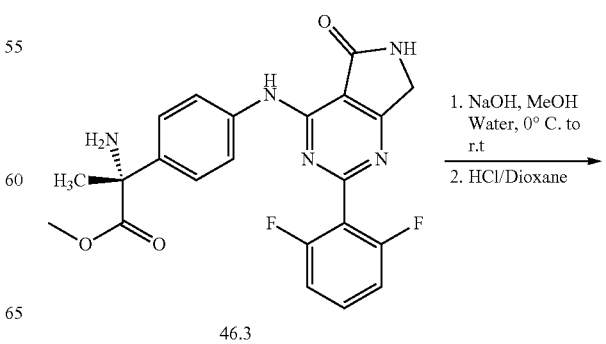

46.3

1. NaOH, MeOH Water, 0° C. to r.t
2. HCl/Dioxane

155

-continued

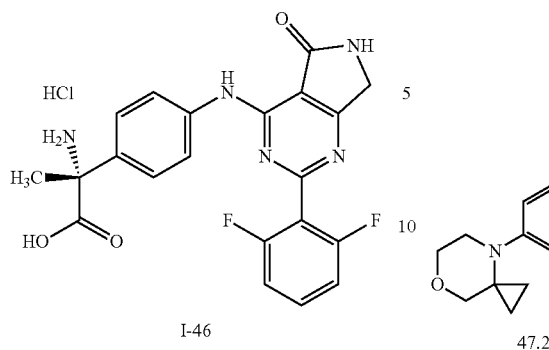

I-46

Synthesis of compound 46.1. Compound 46.1 was prepared by chiral separation of 45.2. MS (ES): m/z 294.35 [M+H]+, 1H NMR (400 MHz, DMSO-$d_6$): δ 7.06-7.04 (d,2H), 6.50-6.48 (d, 2H), 5.10 (s,2H), 3.55 (s,3H), 1.67 (s,3H), 1.36 (s,9H).

Synthesis of compound 46.2. Compound 46.2 was prepared using equivalent procedure as described for synthesis of compound 45.4. MS (ES): m/z 689.72 [M+H]+.

Synthesis of compound 46.3. Compound 46.3 was prepared using the same procedure as described for preparation of 45.5. MS (ES): m/z 439.42 [M+H]+.

Synthesis of compound I-46. Compound I-46 was prepared using the same procedure as described for preparation of compound I-45. MS (ES): m/z 425.40 [M+H]+, 1H NMR (400 MHz, MeOD): δ 8.30 (s,1H), 7.88-7.86 (d,2H), 7.58-7.52 (m,3H), 7.16-7.12 (m,2H), 4.51 (s, 2H), 1.89 (s,3H).

Example 47

Synthesis of 4-((5-(7-oxa-4-azaspiro[2.5]octan-4-yl)pyridin-2-yl)amino)-2-(2,6-difluorophenyl)-6,7-dihydro-5H-pyrrolo[3,4-b]pyridin-5-one, I-47

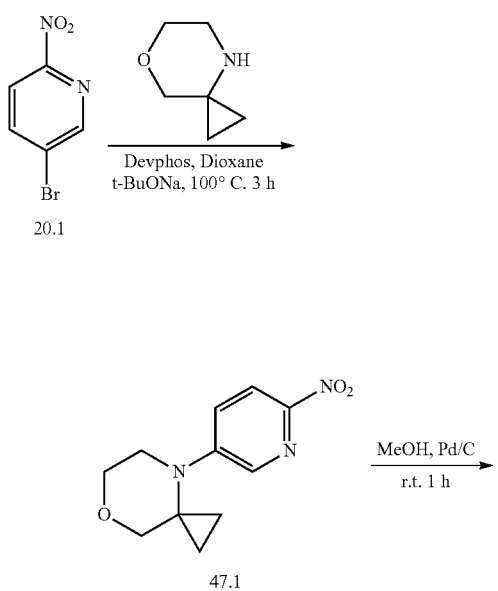

156

-continued

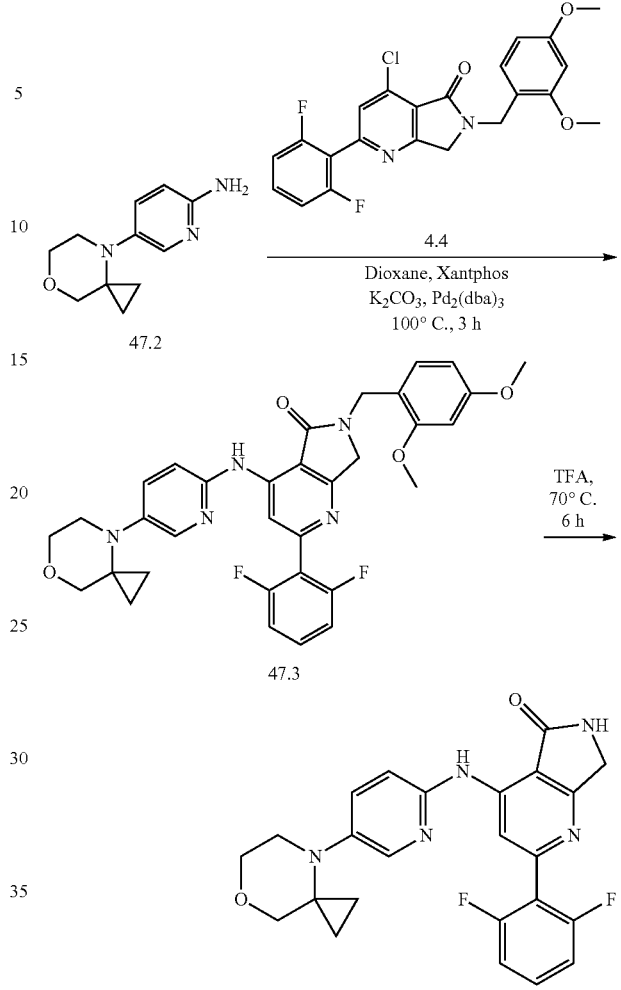

I-47

Synthesis of compound 47.1. To a solution of 20.1 (0.120 g, 0.591 mmol, 1.0 eq) in 1,4-dioxane (3 ml) were added 7-oxa-4-azaspiro[2.5]octane (0.088 g, 0.591 mmol, 1.0 eq) and sodium tert-butoxide (0.17 g, 1.77 mmol, 3.0 eq). The reaction mixture was degassed for 10 min. under argon atmosphere, then Pd$_2$(dba)$_3$ (0.054 g, 0.059 mmol, 0.1 eq) and 2-Dicylcohexylphosphino-2'-(N,N-dimethylamino)-biphenyl(0.046 g, 0.118 mmol, 0.2 eq) were added, and again degassed for 5 minutes. The reaction was stirred at 100° C. for 3 h. After completion of the reaction, mixture was poured into water and product was extracted with EtOAc. Organic layers were combined, dried over Na$_2$SO$_4$ and concentrated under reduced pressure to obtain crude which was purified by column chromatography to furnish 47.1 (0.059 g, 42.43%). MS (ES): m/z 235.24 [M+H]+.

Synthesis of compound 47.2. To a solution of 47.1 (0.059 g, 0.25 mmol, 1.0 eq) in MeOH (8 mL) was added 10% Pd/C (0.06 g) under nitrogen atmosphere. It was purged with H$_2$ gas for 1 hour. Reaction mixture was filtered through celite and obtained filtrate was concentrated under reduced pressure to get crude 47.2 (0.045 g, 87.41%) which was used as such for the next step, MS (ES): m/z 205.26 [M+H]+.

Synthesis of compound 47.3. To a solution of 4.4 (0.100 g, 0.232 mmol, 1.0 eq) in 1,4-dioxane (3 ml) was added 47.2 (0.045 g, 0.232 mmol, 1.0 eq) and K$_2$CO$_3$ (0.080 g, 0.581 mmol, 2.5 eq). The reaction mixture was degassed for 10 min. under argon atmosphere, then Pd₂(dba)₃ (0.021 g, 0.023 mmol, 0.1 eq) and Xantphos (0.026 g, 0.046 mmol, 0.2 eq) were added, and again degassed for 5 min. Reaction was stirred at 100° C. for 3 hours. After completion of the reaction, mixture was poured into water and product was extracted with EtOAc. Organic layers were combined, dried over Na₂SO₄ and concentrated under reduced pressure to obtain crude which was purified by column chromatography to furnish 47.3 (0.075 g, 53.89%). MS(ES): m/z 599.64 [M+H]⁺.

Synthesis of compound I-47. Compound 47.3 (0.075 g, 0.125 mmol, 1.0 eq) was dissolved in TFA (5 mL) and heated at 70° C. for 6 hours. After completion of the reaction, trifluoroacetic acid was removed under reduced pressure. Water was added to reaction mixture, basified with satd. NaHCO₃ and extracted with EtOAc. Organic layers were combined, dried over sodium sulphate and concentrated under reduced pressure to obtain crude which was purified by column chromatography to furnish I-47 (0.032 g, 56.9%). MS (ES): m/z 449.46 [M+H]⁺, ¹H NMR (DMSO-d₆, 400 MHz): δ 9.53 (s,1H), 8.82 (s,1H), 8.40 (s,1H), 8.12 (s,1H), 7.59-7.47 (m,2H), 7.28-7.24 (t,2H), 7.10-7.08 (d,1H), 4.41 (s,2H), 3.63-3.53 (m,2H), 3.50-3.40 (m,4H), 0.90-0.84 (t,2H), 0.72 (s,2H).

Example 48

Synthesis of 2-(2,6-difluorophenyl)-4-((4-(1,3-dimethyl-2-oxoindolin-3-yl)phenyl)amino)-6,7-dihydro-5H-pyrrolo[3,4-d]pyrimidin-5-one, I-298

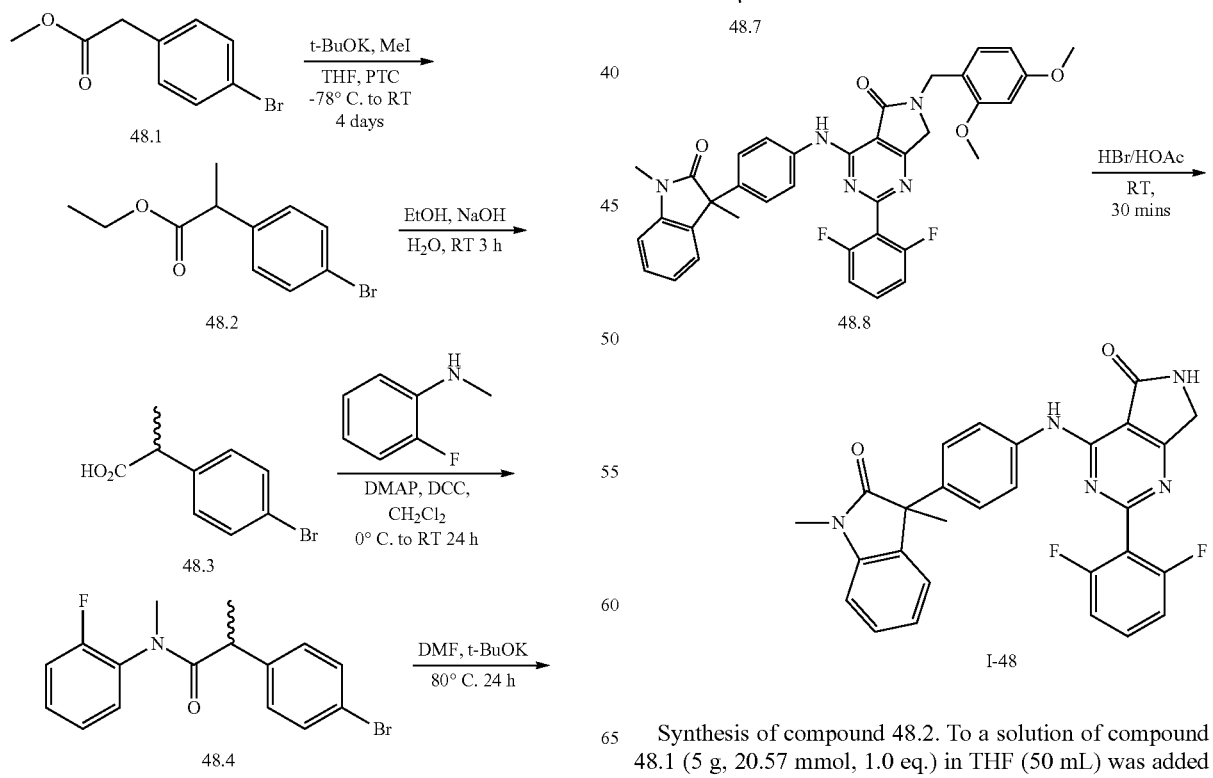

Synthesis of compound 48.2. To a solution of compound 48.1 (5 g, 20.57 mmol, 1.0 eq.) in THF (50 mL) was added MeI (3.21 g, 22.6 mmol, 1.1 eq.) and 18-crown-6 (1.35 g, 5.14 mmol, 0.25 eq.). The reaction was cooled to −78° C. Potassium tert-butoxide (2.53 g, 22.63 mmol, 1.1 eq.) was added to the reaction mixture and it was stirred at room temperature for 4 days. After completion of the reaction, mixture was poured into water, NH₄Cl solution was added and product was extracted with EtOAc. Organic layers were combined, dried over Na₂SO₄ and concentrated under reduced pressure to obtain crude which was purified by column chromatography to get pure 48.2 (5 g, 89.09%). MS (ES): m/z 257.13 [M+H]⁺.

Synthesis of compound 48.3. To a solution of compound 48.2 (5.0 g, 19.45 mmol, 1.0 eq) in EtOH (100 mL), a solution of NaOH (3.9 g, 97.2 mmol, 5.0 eq.) in water (20 mL) was added. Reaction was stirred at room temperature for 3 hours. After completion of the reaction, solvent was evaporated under reduced pressure and reaction mixture was poured into water. Aqueous leyer was acidified with HCl and product was extracted with EtOAc. Organic layers were combined and dried over Na₂SO₄ and concentrated under reduced pressure to obtain crude which was purified by column chromatography to get pure 48.3 (3.73 g, 83.7%). MS (ES): m/z 229.07 [M+H]⁺.

Synthesis of compound 48.4. To a solution of 48.3 (3.7 g, 16.3 mmol, 1.0 eq) in CH₂Cl₂ (60 ml) was added 2-fluoro-N-methylaniline (2.03 g, 16.28 mmol, 1.0 eq.) at room temperature. The reaction mixture was cooled to 0° C. and DMAP (0.397 g, 3.25 mmol, 0.2 eq.) was added. Further dicyclohexyl carbodiimide (4.0 g, 19.5 mmol, 1.2 eq.) was added to the reaction mixture at 0° C. The reaction mixture was stirred at room temperature for 24 h. After completion of the reaction, mixture was poured into water and extracted with CH₂Cl₂. Organic layers were combined, dried over Na₂SO₄ and concentrated under reduced pressure to obtain crude which was purified by column chromatography to furnish pure 48.4 (4 g, 73.1%). MS (ES): m/z 336.20 [M+H]⁺.

Synthesis of compound 48.5. To a solution of compound 48.4 (1 g, 2.97 mmol, 1.0 eq.) in DMF (10 mL) was added potassium tert-butoxide (0.66 g, 5.95 mmol, 2.0 eq.). The reaction mixture was stirred at 80° C. for 24 h. After completion of the reaction, mixture was poured into water and product was extracted with EtOAc. Organic layers were combined, dried over Na₂SO₄ and concentrated under reduced pressure to obtain crude which was purified by column chromatography to furnish 48.5 (0.28 g, 29.8%). MS (ES): m/z 316.20 [M+H]⁺.

Synthesis of compound 48.6. To a solution of 48.5 (0.28 g, 0.88 mmol, 1.0 eq) in 1,4-dioxane (20 mL) was added benzyl amine (0.19 g, 1.77 mmol, 2.0 eq.) and Cs₂CO₃ (0.86 g, 2.65 mmol, 3.0 eq.). The reaction mixture was degassed for 30 minutes using argon, then Pd₂(dba)₃ (0.081 g, 0.09 mmol, 0.1 eq) and 2-Dicylcohexylphosphino-2'-(N,N-dimethylamino)-biphenyl (0.069 g, 0.18 mmol, 0.2 eq) were added, and suspension was again degassed for 5 min. Reaction was stirred at 100° C. for 3 h. After completion of the reaction, mixture was poured into water and product was extracted with EtOAc. Organic layers were combined, dried over Na₂SO₄ and concentrated under reduced pressure to obtain crude which was purified by column chromatography to furnish 48.6 (0.15 g, 49.46%). MS (ES): m/z 342.44 [M+H]⁺.

Synthesis of compound 48.7. To a suspension of Pd(OH)₂ (0.02 g) in MeOH (5 ml) was added 48.6 (0.15 g, 0.44 mmol, 1.0 eq) under nitrogen. It was purged with H₂ gas for 1 h. Reaction mixture was filtered through celite and obtained filtrate was concentrated under reduced pressure to get crude 48.7 (0.1 g, 90.5%) which was used as such for the next step, MS (ES): m/z 252.32 [M+H]⁺.

Synthesis of compound 48.8. To a solution of 1.1 (0.08 g, 0.185 mmol, 1.0 eq) in n-butanol (2 mL) was added 48.7 (0.046 g, 0.185 mmol, 1.0 eq) and DIPEA (0.071 g, 0.556 mmol, 3.0 eq). The reaction mixture was stirred at 90° C. for 3 h. After completion of the reaction, mixture was poured into water and product was extracted with EtOAc. Organic layers were combined, dried over Na₂SO₄ and concentrated under reduced pressure to obtain crude which was purified by column chromatography to furnish 48.8 (0.08 g, 66.7%). MS(ES): m/z 647.68 [M+H]⁺.

Synthesis of compound I-48. Compound 48.8 (0.08 g, 0.123 mmol, 1.0 eq) was dissolved in HBr/HOAc (1 ml). Reaction was stirred at room temperature for 30 minutes. After completion of the reaction, water was added to reaction mixture and basified with satd. NaHCO₃ and extracted with EtOAc. Organic layers were combined, dried over Na₂SO₄ and concentrated under reduced pressure to obtain crude which was purified by column chromatography to furnish I-48 (0.05 g, 81.4%). MS (ES): m/z 497.51 [M+H]⁺; ¹H NMR (DMSO-d₆, 400 MHz): δ 9.06 (s,1H), 8.90 (s,1H), 7.71-7.04 (m,11H), 4.47 (s,2H), 3.18 (s,3H) 1.66 (s,3H).

Example 49

Synthesis of 2-(2,6-difluorophenyl)-4-((2-isopropyl-2,3-dihydro-1H-pyrrolo[3,4-c]pyridin-6-yl)amino)-6,7-dihydro-5H-pyrrolo[3,4-b]pyridin-5-one, I-49

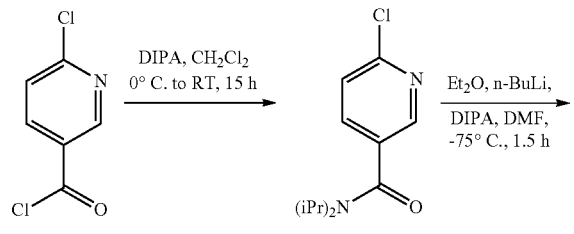

49.1     49.2

-continued
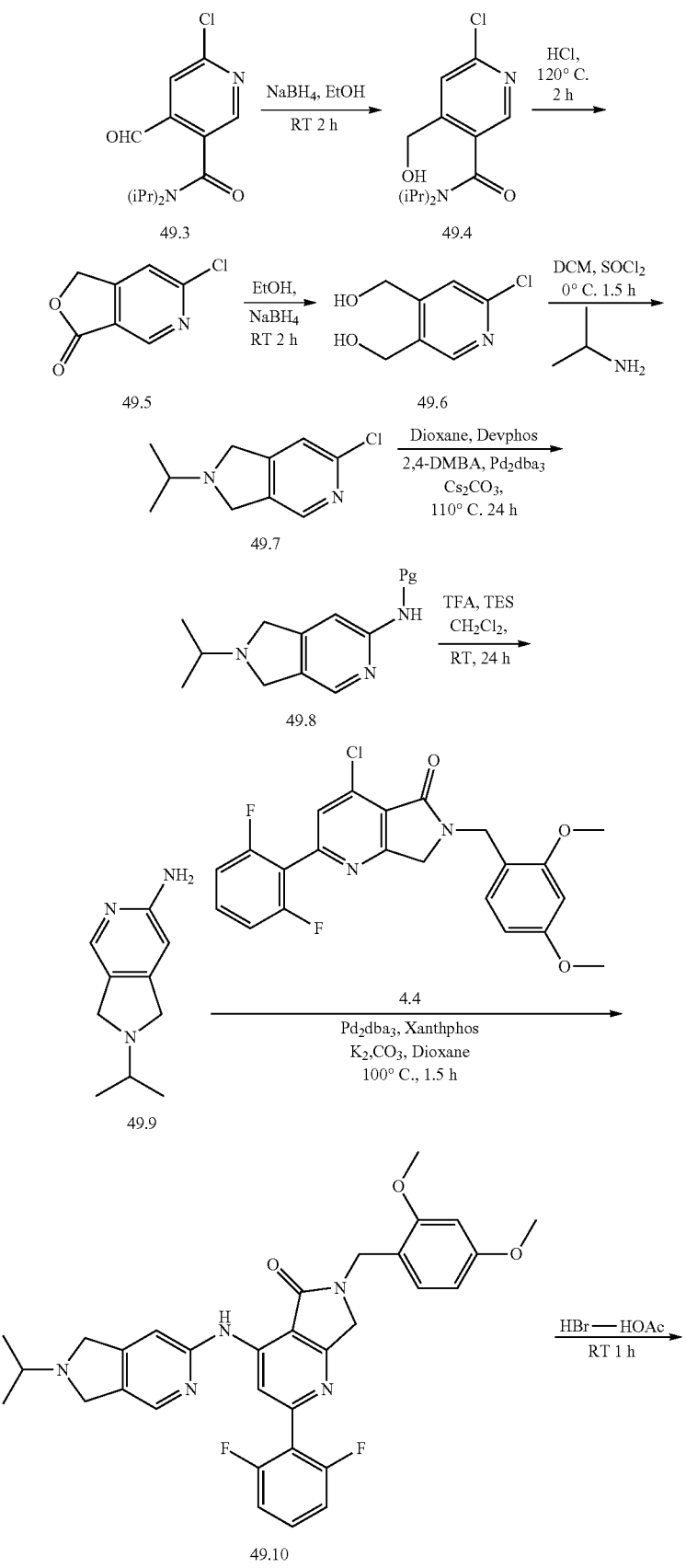

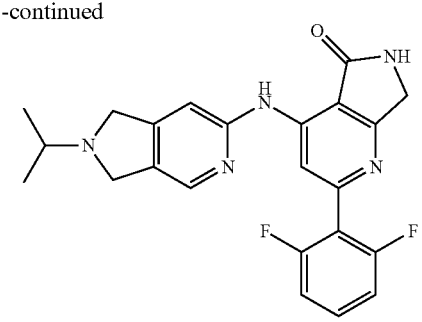

I-49

Synthesis of compound 49.2. Compound 49.1 (19 g, 107.9 mmol, 1.0 eq.) was dissolved in CH$_2$Cl$_2$ (200 mL) and cooled at 0° C. N,N-Diisopropyl amine (53.5 ml, 0.375 mmol, 3.48 eq.) was added and mixture was stirred at room temperature for 15 h. After completion of rthe eaction, reaction mixture was poured into water and product was extracted with CH$_2$Cl$_2$. Organic layer was combined and dried over Na$_2$SO$_4$ and concentrated under reduced pressure to obtain crude which was purified by column chromatography to furnish 49.2 (24 g, 92.35%). MS (ES): m/z 240.73 [M+H]$^+$.

Synthesis of compound 49.3. The compound 49.2 (24.0 g, 100 mmol, 1.0 eq) was dissolved in diethyl ether (200 mL) and cooled to −75° C. N,N-Diisopropyl amine (72 mL, 500 mmol, 5 eq.) and n-BuLi (200 ml, 500 mmol, 5.0 eq.) were added dropwise to the reaction mixture at −78° C. Reaction was stirred for 15 minutes at −78° C., then DMF (12 ml, 150 mmol, 1.5 eq.) was added at −78° C. and reaction was stirred for 1 h. After completion of the reaction, mixture was poured into water, quenched with 10% citric acid and extracted with diethyl ether. Organic layers were combined, dried over Na$_2$SO$_4$ and concentrated under reduced pressure to obtain crude which is purified by column chromatography to furnish 49.3 (23.3 g, 86.8%). MS (ES): m/z 268.74 [M+H]$^+$.

Synthesis of compound 49.4. To a solution of 49.3 (23.25 g, 86.51 mmol, 1.0 eq) in ethanol (500 ml) was added NaBH$_4$ (23.34 g, 614 mmol, 7.1 eq.). Reaction stirred at room temperature for 2 h. After completion of the reaction, reaction mixture was poured into water, quenched with 1N HCl and extracted with EtOAc. Organic layers were combined, dried over Na$_2$SO$_4$ and concentrated under reduced pressure to obtain crude which was purified by column chromatography to provide 49.4 (20 g, 85.4%). MS (ES): m/z 270.76 [M+H]$^+$.

Synthesis of compound 49.5. Compound 49.4 (20 g, 74.1 mmol, 1.0 eq.) was added in 6N HCl solution. Reaction was heated at 120° C. for 2 h. After completion of the reaction, mixture was cooled, basified with sodium carbonate and the product was extracted with EtOAc. Organic layers were combined, dried over Na$_2$SO$_4$ and concentrated under reduced pressure to obtain crude which was purified by column chromatography to furnish 49.5 (5.69 g, 45.43%). MS(ES): m/z 169.56 [M+H]$^+$.

Synthesis of compound 49.6. To a solution of 49.5 (5.69 g, 33.55 mmol, 1.0 eq) in ethanol (100 ml) was added NaBH$_4$ (8.92 g, 234.9 mmol, 7.0 eq.). Reaction was stirred at room temperature for 2 h. After completion of the reaction, mixture was poured into water, quenched with 1N HCl solution and extracted with EtOAc. Organic layers were combined, dried over Na$_2$SO$_4$ and concentrated under reduced pressure to obtain crude which was purified by column chromatography to furnish 49.6 (2.1 g, 36.05%). MS (ES): m/z 173.60 [M+H]$^+$.

Synthesis of compound 49.7. To a solution of 49.6 (2.1 g, 12.1 mmol, 1.0 eq) in CH$_2$Cl$_2$ (30 mL) was added SOCl$_2$ (7.22 g, 60.7 mmol, 5.0 eq.). Reaction was heated at 50° C. till it becomes clear. Thionyl chloride was removed by distillation. Dry CH$_2$Cl$_2$ was added and the reaction mixture was cooled to 0° C. Isopropyl amine (3.58 g, 60.7 mmol, 5.0 eq.) was added under nitrogen atmosphere and the reaction mixture was stirred for 1.5 h at same temperature. After completion of the reaction, mixture was poured into water and product was extracted with CH$_2$Cl$_2$. Organic layers were combined, dried over Na$_2$SO$_4$ and concentrated under reduced pressure to obtain crude which was purified by column chromatography to furnish 49.7 (0.6 g, 25.22%). MS (ES): m/z 196.68 [M+H]$^+$.

Synthesis of compound 49.8. Compound 49.7 (0.55 g, 28.06 mmol, 1.0 eq) was dissolved in 1,4-dioxane (20 ml) and was degassed using argon for 10 minutes. 2,4-Dimethoxy benzyl amine (0.703 g, 42.09 mmol, 1.5 eq.) and cesium carbonate (1.828 g, 5.612 mmol, 2.0 eq.) were added to the reaction mixture. The reaction mixture was degassed for further 10 minutes. Dicylcohexylphosphino-2'-(N,N-dimethylamino)-biphenyl (0.220 g, 0.561 mmol, 0.5 eq.) and Pd$_2$(dba)$_3$ (0.256 g, 0.280 mmol, 0.1 eq) were added to the reaction mixture and it was heated at 110° C. for 24 h. After completion of the reaction, mixture was poured into water and product was extracted with CH$_2$Cl$_2$. Organic layers were combined, dried over Na$_2$SO$_4$ and concentrated under reduced pressure to obtain crude which was purified by column chromatography to get pure 49.8 (0.35 g, 71.0%). MS (ES): m/z 176.24 [M+H]$^-$.

Synthesis of compound 49.9. Compound 49.8 (0.25 g, 0.764 mmol, 1.0 eq) was dissolved in CH$_2$Cl$_2$ (5 mL). Triethyl silane (0.27 g, 2.29 mmol, 3.0 eq.) and TFA (3 mL) were added to the reaction mixture. The reaction mixture was stirred at room temperature for 24 h. After completion of reaction, mixture was concentrated under reduced pressure, basified by NaHCO$_3$ solution and extracted with EtOAc. Organic layers were combined, dried over Na$_2$SO$_4$ and concentrated under reduced pressure to obtain crude which was purified by column to yield 49.9 (0.075 g, 29.8%). MS (ES): m/z 177.25 [M+H]$^+$.

Synthesis of compound 49.10. To a solution of 4.4 (0.150 g, 0.348 mmol, 1.0 eq) in 1,4-dioxane (3 ml) was added 49.9 (0.067 g, 0.383 mmol, 1.1 eq) and K$_2$CO$_3$ (0.120 g, 0.871 mmol, 2.5 eq). The reaction mixture was degassed for 10 min. using argon, then Pd$_2$(dba)$_3$ (0.031 g, 0.034 mmol, 0.1 eq) and Xantphos (0.040 g, 0.069 mmol, 0.2 eq) were added, and suspension was again degassed for 5 min. The reaction was stirred at 100° C. for 1.5 h. After completion of the reaction, mixture was poured into water and product was extracted with EtOAc. Organic layers were combined, dried over $Na_2SO_4$ and concentrated under reduced pressure to obtain crude which was purified by column chromatography to furnish 49.10 (0.035 g, 17.6%). MS(ES): m/z 571.63 $[M+H]^+$.

Synthesis of compound I-49. Compound 49.10 (0.030 g, 0.052 mmol, 1.0 eq) was dissolved in HBr/HOAc (0.5 ml) and the reaction was stirred at room temperature for 1 h. After completion of the reaction, water was added. Mixture was basified with saturated bicarbonate solution and product was extracted with EtOAc. Organic layers were combined and dried over $Na_2SO_4$ and concentrated under reduced pressure to obtain dehydrated crude which was purified by column chromatography to furnish I-49 (0.002 g, 9.0%). MS (ES): m/z 421.45 $[M+H]^+$; $^1$H NMR ($CD_3OD$, 400 MHz): δ 8.70 (s,1H), 8.24 (s,1H), 7.56-7.52 (m,1H), 7.17-7.13 (t,2H), 7.05 (s, 1H), 4.48 (s,2H), 4.04-4.01 (s,4H), 2.88-2.85 (m,1H), 1.25-1.23 (d,3H).

Example 50

Synthesis of 4-((4-(4-oxa-7-azaspiro[2.5]octane-7-carbonyl)phenyl)amino)-2-(2,6-difluorophenyl)-6,7-dihydro-5H-pyrrolo[3,4-b]pyridin-5-one, I-50

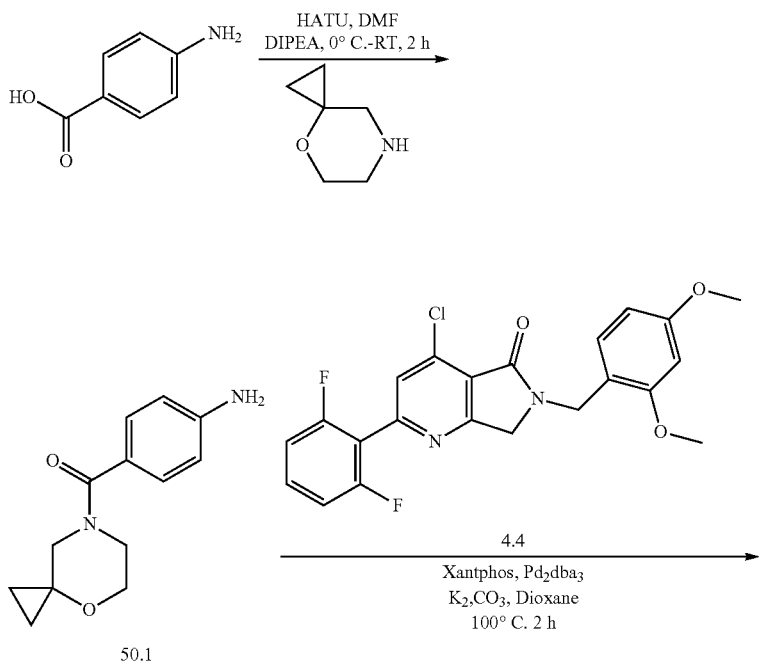

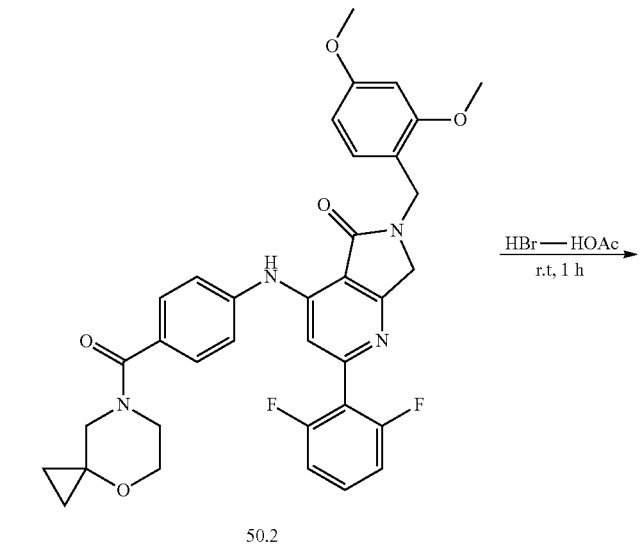

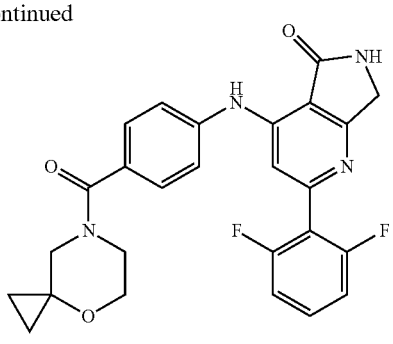

I-50

Synthesis of compound 50.1. To a solution of p-aminobenzoic acid (0.080 g, 0.583 mmol, 1.0 eq) in DMF (2 mL) was added HATU (0.33 g, 0.88 mmol, 1.5 eq) at 0° C. The reaction was stirred at 0° C. for 45 minutes. The reaction was warmed to ambient temperature and stirred for additional ten minutes. Further 4-oxa-7-azaspiro[2.5]octane (0.104 g, 0.700 mmol, 1.2 eq) and DIPEA (0.150 g, 1.17 mmol, 2.0 eq) were added at 0° C. and the reaction was allowed to stir at room temperature for 2 hours. After completion of the reaction, mixture was poured into water and product was extracted with EtOAc. Organic layers were combined, washed with brine, dried over Na$_2$SO$_4$ and concentrated under reduced pressure to obtain crude material. Crude was purified by column chromatography to furnish 50.1 (0.070 g, 51.66%). MS (ES): m/z 232.28 [M+H]$^+$.

Synthesis of compound 50.2. To a solution of 4.4 (0.100 g, 0.232 mmol, 1.0 eq) in 1,4-dioxane (3 mL) was added 50.1 (0.054 g, 0.23 mmol, 1.0 eq) and K$_2$CO$_3$ (0.064 g, 0.47 mmol, 2.0 eq). Reaction mixture was degassed for 10 minutes under argon atmosphere, then Pd$_2$(dba)$_3$ (0.021 g, 0.023 mmol, 0.1 eq) and Xantphos (0.026 g, 0.046 mmol, 0.2 eq) were added, and again degassed for 5 minutes. Reaction was stirred at 100° C. for 2 h. After completion of the reaction, reaction mixture was poured in water and product was extracted with EtOAc. Organic layers were combined, washed with brine, dried over Na$_2$SO$_4$ and concentrated under reduced pressure to obtain crude which was purified by column chromatography to furnish 50.2 (0.098, 67.4%). MS(ES): m/z 626.66 [M+H]$^+$.

Synthesis of compound I-50. The compound 50.2 (0.098 g, 0.156 mmol, 1.0 eq) was dissolved in HBr/HOAc (33% solution, 3 mL) and stirred at room temperature for 1 hour. After completion of the reaction, mixture was poured into ice-water and basified with satd. NaHCO$_3$ and with EtOAc. Organic layers were combined, washed with brine, dried over Na$_2$SO$_4$ and concentrated under reduced pressure to obtain crude which was purified by column chromatography to furnish I-50 (0.041 g, 55.0%). MS(ES): m/z 476.48 [M+H]$^+$; $^1$HNMIR (DMSO-d$_6$, 400 MHz): 9.17 (s, 1H), 8.77 (s,1H), 7.56-7.50 (m,1H), 7.43 (s,4H), 7.24-7.20 (m,3H), 4.40 (s,2H), 3.64-3.43 (m, 6H), 0.85-0.52 (m,4H).

Example 51

Synthesis of 4-((4-(7-oxa-4-azaspiro[2.5]octane-4-carbonyl)phenyl)amino)-2-(2,6-difluorophenyl)-6,7-dihydro-5H-pyrrolo[3,4-b]pyridin-5-one, I-51

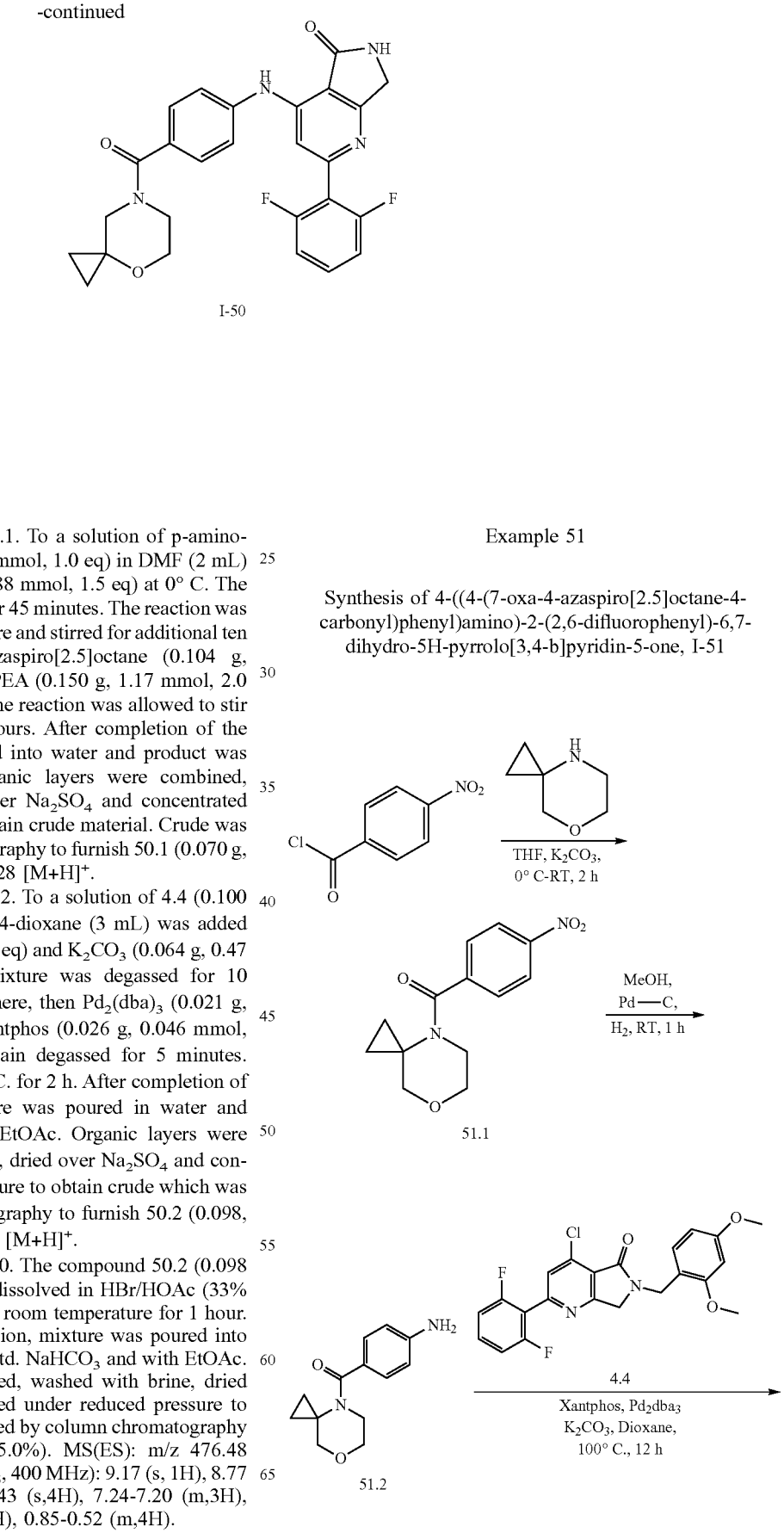

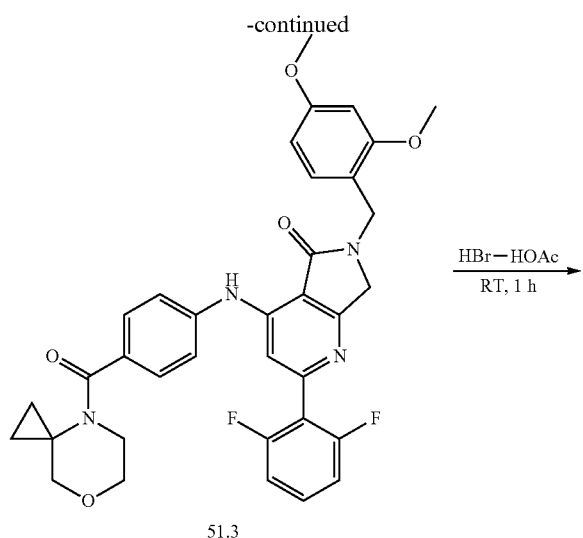

51.3

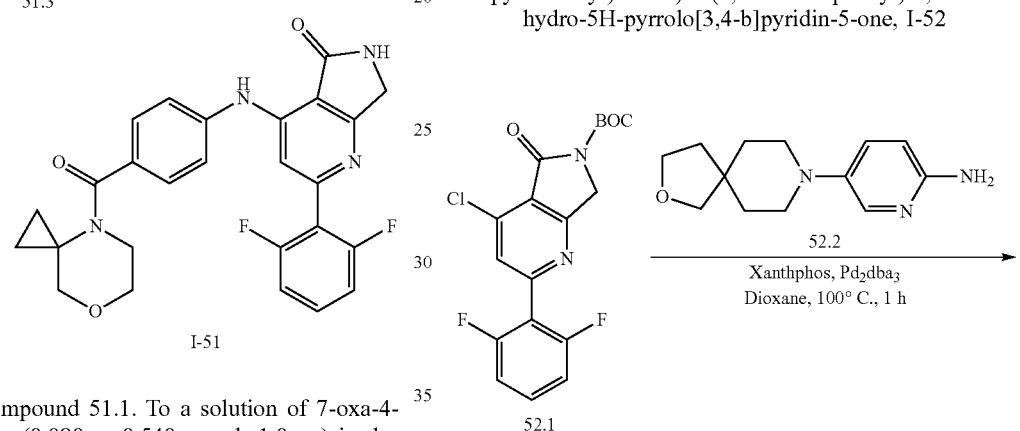

I-51

Synthesis of compound 51.1. To a solution of 7-oxa-4-azaspiro[2.5]octane (0.080 g, 0.540 mmol, 1.0 eq) in dry THF were added K$_2$CO$_3$ (0.149 g, 1.081 mmol, 2.0 eq) and p-nitrobenzoyl chloride (0.1 g, 0.54 mmol, 1.0 eq) at 0° C. The reaction mixture was stirred at room temperature for 2 h. After completion of the reaction, mixture was poured into crushed ice, neutralized by satd. NaHCO$_3$ and extracted with EtOAc. Organic layers were combined, washed with brine, dried over sodium sulphate and concentrated under reduced pressure to obtain crudewhich was purified by column chromatography to furnsih 51.1 (0.12 g, 84.9%). MS(ES): m/z 262.27 [M+H]$^+$.

Synthesis of compound 51.2. To a suspension of Pd/C (0.025 g) in methanol (3 mL) was added 51.1 (0.12 g, 0.46 mmol, 1.0 eq) in MeOH (2 mL). Suspension was purged with H$_2$ gas for 1.5 hr. After completion of the reaction, mixture was filtered through celite, washed with methanol and the filtrate was concentrated under reduced pressure to obtain crude material. The crude was purified by column chromatography to get pure 51.2 (0.06 g, 56.5%). MS(ES): m/z 232.28 [M+H]$^+$.

Synthesis of compound 51.3. To a mixture of 4.4 (0.10 g, 0.23 mmol, 1.0 eq) in 1,4-dioxane (3 mL) was added 51.2 (0.053 g, 0.232 mmol, 1.0 eq) and K$_2$CO$_3$ (0.064 g, 0.47 mmol, 2.0 eq). The reaction mixture was degassed for 10 minutes under argon atmosphere, then Pd$_2$(dba)$_3$ (0.021 g, 0.023 mmol, 0.1 eq) and Xantphos (0.026 g, 0.046 mmol, 0.2 eq) were added, again degassed for 5 min. The reaction was stirred at 100° C. for 12 h. After completion of the reaction, mixture was poured into water and product was extracted with EtOAC. Organic layers were combined, washed with brine, dried over Na$_2$SO$_4$ and concentrated under reduced pressure to obtain crude which was purified by column chromatography to furnish 51.3 (0.093 g, 63.94%). MS(ES): m/z 626.66 [M+H]$^+$.

Synthesis of compound I-51. Compound 51.3 (0.093 g, 0.148 mmol, 1.0 eq) was dissolved in HBr/HOAc (2 mL) and reaction was stirred at room temperature for 1 h. After completion of reaction, reaction mixture was poured in water, basified with satd. NaHCO$_3$ and extracted with EtOAc. Organic layers were combined, dried over Na$_2$SO$_4$ and concentrated under reduced pressure to obtain crude which was purified by column chromatography to furnish I-51 (0.041 g, 57.9%). MS(ES): m/z 476.48 [M+H]$^+$; $^1$H NMR (DMSO-d$_6$, 400 MHz): 9.17 (s,1H), 8.78 (s,1H), 7.56-7.39 (m,5H), 7.24-7.20 (m,3H), 4.41 (s,2H), 3.63 (s,4H), 3.54 (s,2H), 0.78 (s,4H).

Example 52

Synthesis of 4-((5-(2-oxa-8-azaspiro[4.5]decan-8-yl)pyridin-2-yl)amino)-2-(2,6-difluorophenyl)-6,7-dihydro-5H-pyrrolo[3,4-b]pyridin-5-one, I-52

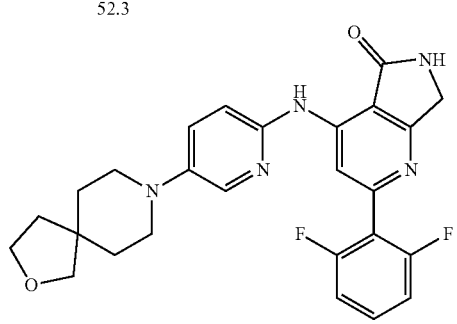

I-52

Synthesis of 52.3. To a mixture of 52.1 (0.045 g, 0.118 mmol, 1.0 eq) in 1,4-dioxane (1.0 mL) was added 52.2 (0.023 g, 0.118 mmol, 1.0 eq) and K$_2$CO$_3$ (0.048 g, 0.354 mmol, 3.0 eq). The reaction mixture was degassed for 10 minutes using argon, then Pd₂(dba)₃ (0.010 g, 0.011 mmol, 0.1 eq) and Xantphos (0.013 g, 0.023 mmol, 0.2 eq) were added and mixture was degassed for additional five minutes. The reaction was stirred at 100° C. for 1 hour. After completion of the reaction, mixture was poured into water and product was extracted with EtOAc. Organic layers were combined, washed with brine, dried over Na₂SO₄ and concentrated under reduced pressure to obtain crude material. The crude was purified by column chromatography to furnish 52.3 (0.045 g, 61.8%). MS(ES): m/z 577.63 [M+H]⁺.

Synthesis of I-52. Compound 52.3 (0.045 g, 0.077 mmol, 1.0 eq) was dissolved in CH₂Cl₂ (1 mL) and TFA (0.5 mL) was added to the reaction. The reaction was stirred at room temperature for 1 hour. After completion of the reaction, mixture was poured into water, basified with NaHCO₃ solution and extracted with CH₂Cl₂. Organic layers were combined and dried over Na₂SO₄ and concentrated under reduced pressure to obtain crude which was purified by column chromatography to furnish I-52 (0.025 g, 59.9%). MS(ES): m/z 477.52 [M+H]⁺; ¹H NMR (DMSO-d₆, 400 MHz): δ 9.50 (s,1H), 8.80 (s,1H), 8.36 (s,1H), 8.03 (d,1H), 7.60-7.53 (m,1H), 7.47-7.44 (dd,1H), 7.27-7.23 (t,2H), 7.09-7.07 (d,1H), 4.40 (s,2H), 3.76-3.73 (t,2H), 3.46 (s,2H), 3.19-3.07 (m,4H), 1.74-1.70 (t,2H), 1.61-1.53 (m,4H).

Example 53

Synthesis of 4-((5-(1-oxa-9-azaspiro[5.5]undecan-9-yl)pyridin-2-yl)amino)-2-(2,6-difluorophenyl)-6,7-dihydro-5H-pyrrolo[3,4-b]pyridin-5-one, I-53

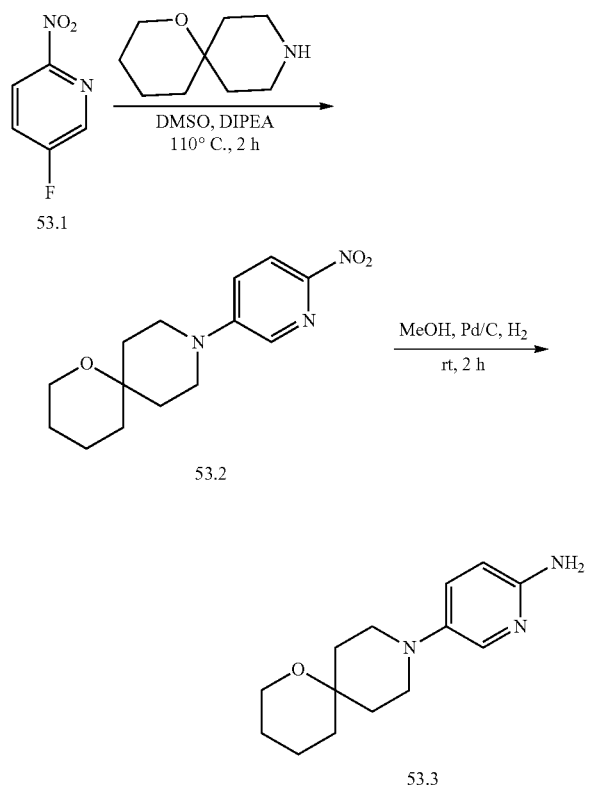

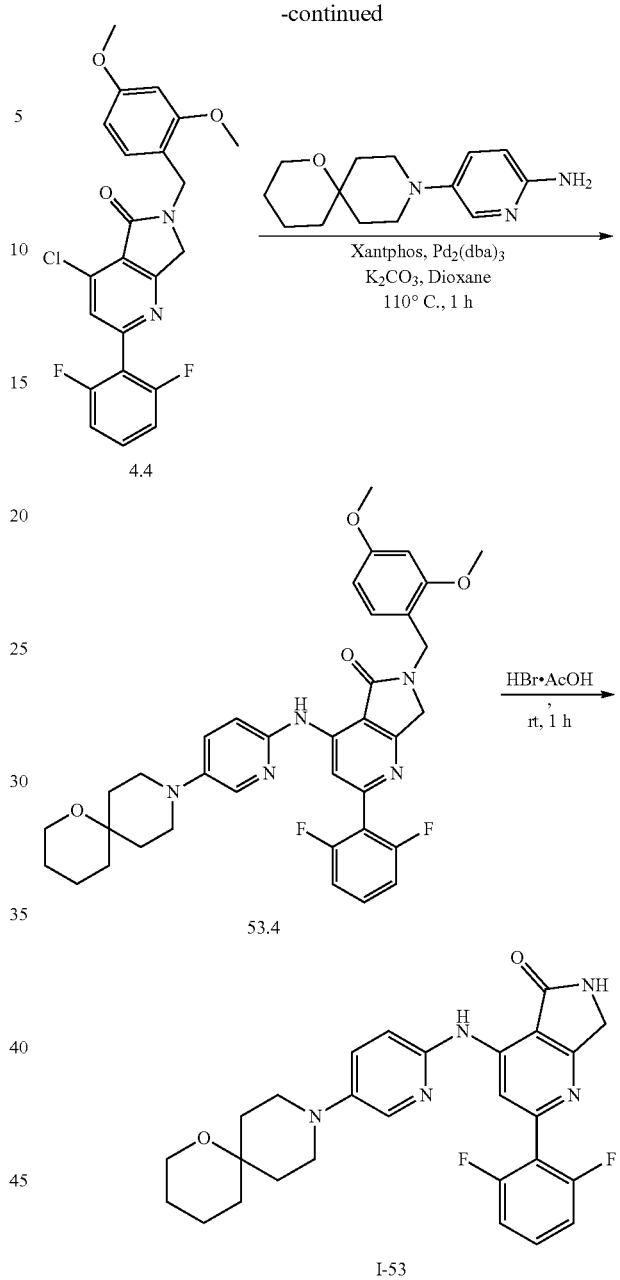

Synthesis of compound 53.2. To a solution of 53.1 (0.17 g, 1.19 mmol, 1.0 eq) in DMSO (3 mL) was added 1-oxa-9-azaspiro[5.5]undecane (0.229 g, 0.119 mmol, 1.0 eq.) and DIPEA (1.54 g, 11.9 mmol, 10.0 eq.). The reaction was stirred at 110° C. for 2 hours. After completion of the reaction, mixture was poured into water and extracted with EtOAc. Organic layers were combined, washed with brine, dried over Na₂SO₄ and concentrated under reduced pressure to obtain crude material. This was purified by tituration with hexane to provide 53.2 (0.2 g, 60.3%). MS(ES): m/z 277.32 [M+H]⁺.

Synthesis of compound 53.3. To a suspension of 10% Pd/C (0.05 g) in MeOH (2 mL) was added a solution of 53.2 (0.2 g, 0.72 mmol, 1.0 eq) in MeOH (3.0 mL) under nitrogen atmosphere. Reaction was purged with H₂ gas for 2 hours. After completion of the reaction, mixture was filtered through celite, washed with MeOH and concentrated under reduced pressure. The crude material was purified by column chromatography to furnish 53.3 (0.14 g, 78.5%) MS (ES): m/z 247.34 [M+H]+.

Synthesis of compound 53.4. To a mixture of 4.4 (0.1 g, 0.23 mmol, 1.0 eq) in 1,4-dioxane (3 mL) was added 53.3 (0.063 g, 0.255 mmol, 1.1 eq) and K$_2$CO$_3$ (0.064 g, 0.465 mmol, 2.0 eq). The reaction mixture was degassed for 10 minutes using argon gas, then Pd$_2$(dba)$_3$ (0.021 g, 0.023 mmol, 0.1 eq) and Xantphos (0.026 g, 0.046 mmol, 0.2 eq) were added and suspension was degassed for additional 5 minutes. The reaction was stirred at 110° C. for 1 hour. After completion of the reaction, mixture was poured into water and extracted with EtOAc. Organic layers were combined, washed with brine, dried over Na$_2$SO$_4$ and concentrated under reduced pressure to obtain crude material. The crude was purified by column chromatography to provide 53.4 (0.09 g, 60.4%). MS(ES): m/z 641.72 [M+H]+.

Synthesis of compound I-53. Compound 53.4 (0.09 g, 0.14 mmol, 1.0 eq) was dissolved in HBr/HOAc (3 mL) and reaction was stirred at room temperature for 1 hour. After completion of the reaction, mixture was poured into water, basified with NaHCO$_3$ solution and extracted with EtOAc. Organic layers were combined, dried over Na$_2$SO$_4$ and concentrated under reduced pressure to obtain crude. The crude was purified by column chromatography to provide I-53 (0.038 g, 55.1%). MS(ES): m/z 491.54 [M+H]+; $^1$H NMR (DMSO-d$_6$, 400 MHz): δ 9.49 (s,1H), 8.79 (s,1H), 8.35 (s,1H), 8.02 (d,2H), 7.59-7.54 (m,1H), 7.46-7.43 (dd, 1H), 7.27-7.23 (t,2H), 7.08-7.06 (d,1H), 4.40 (s,2H), 3.58-3.55 (t,2H), 3.33-3.28 (t,2H), 2.98-2.93 (t,2H), 1.89-1.86 (d, 2H), 1.59-1.39 (m,8H).

Example 54

Synthesis of 4-((4-(1-oxa-9-azaspiro[5.5]undecane-9-carbonyl)phenyl)amino)-2-(2,6-difluorophenyl)-6,7-dihydro-5H-pyrrolo[3,4-b]pyridin-5-one, I-54

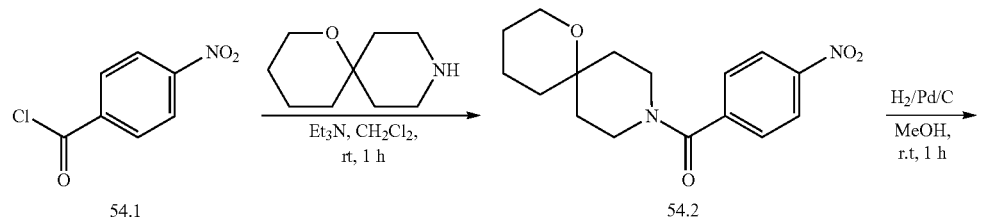

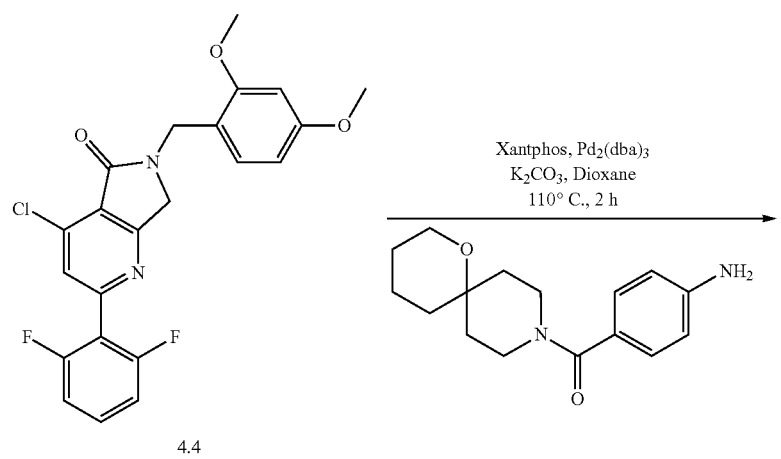

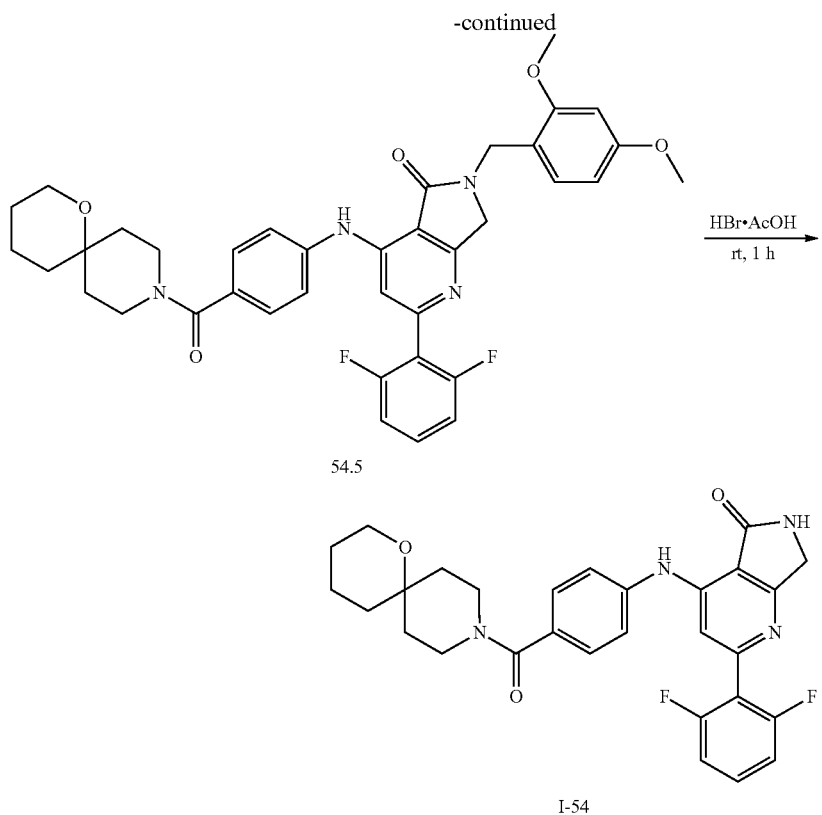

Synthesis of compound 54.2. To a solution of 54.1 (0.2 g, 1.08 mmol, 1.0 eq) in $CH_2Cl_2$ (2 mL) was added 1-oxa-9-azaspiro[5.5]undecane (0.21 g, 1.08 mmol, 1.0 eq) and DIPEA (0.33 g, 3.24 mmol, 3.0 eq). The reaction was stirred at room temperature for 1 hour. After completion of the reaction, mixture was poured into water and extracted with EtOAc. Organic layers were combined, washed with brine, dried over $Na_2SO_4$ and concentrated under reduced pressure to obtain pure 54.2 (0.16 g, 48.8%). MS(ES): m/z 304.35 $[M+H]^+$.

Synthesis of compound 54.3. To a suspension of 10% Pd/C (0.05 g) in MeOH (2 mL) was added a solution of 54.2 (0.16 g, 0.53 mmol, 1.0 eq) in MeOH (3 mL) under nitrogen. Reaction mixture was purged with $H_2$ gas for 1 hour. After completion of the reaction, mixture was filtered through celite and washed with MeOH. Obtained filtrate was concentrated under reduced pressure to furnish 54.3 (0.05 g, 34.7%) MS (ES): m/z 274.36 $[M+H]^+$.

Synthesis of compound 54.4. To a mixture of 4.4 (0.075 g, 0.174 mmol, 1.0 eq) in 1,4-dioxane (3 mL) was added 54.3 (0.047 g, 0.174 mmol, 1.0 eq) and $K_2CO_3$ (0.048 g, 0.348 mmol, 2.0 eq). Reaction mixture was degassed for 10 minutes using argon, then $Pd_2(dba)_3$ (0.015 g, 0.017 mmol, 0.1 eq) and Xantphos (0.02 g, 0.034 mmol, 0.2 eq) were added. Suspension was degassed for additional 5 minutes. The reaction was stirred at 110° C. for 2 hours. After completion of the reaction, mixture was poured into water and extracted with EtOAc. Organic layers were combined, washed with brine, dried over $Na_2SO_4$ and concentrated under reduced pressure to obtain crude material. This crude was purified by column chromatography to provide 54.4 (0.07 g, 60.1%). MS(ES): m/z 668.74 $[M+H]^+$.

Synthesis of compound I-54. Compound 54.4 (0.07 g, 0.104 mmol, 1.0 eq) was dissolved in HBr/HOAc (3 mL, 33% HBr in AcOH) and reaction was stirred at room temperature for 1 hour. After completion of the reaction, mixture was poured into water, basified with satd. $NaHCO_3$ solution and product was extracted with EtOAc. Organic layers were combined, dried over $Na_2SO_4$ and concentrated under reduced pressure to obtain crude material which was purified by column chromatography to furnish I-54 (0.029 g, 53.4%). MS(ES): m/z 518.56 $[M+H]^+$; $^1H$ NMR (DMSO-$d_6$, 400 MHz): δ 9.15 (s,1H), 8.77 (s,1H), 7.57-7.50 (m,1H), 7.41 (s,4H), 7.23-7.18 (m,3H), 4.41 (s,2H), 4.09 (m,2H), 3.56 (m,2H), 3.16 (m,2H), 1.84-1.82 (m,4H), 1.56 (m, 2H), 1.43-1.40 (m,6H).

Example 55

Synthesis of 2-(2,6-difluorophenyl)-4-((5-(1-(3,6-dihydro-2H-pyran-4-yl)-3,5,5-trimethyl-2-oxopyrrolidin-3-yl)pyridin-2-yl)amino)-6,7-dihydro-5H-pyrrolo[3,4-b]pyridin-5-one. I-55

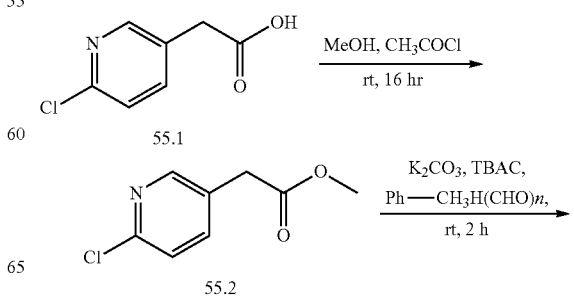

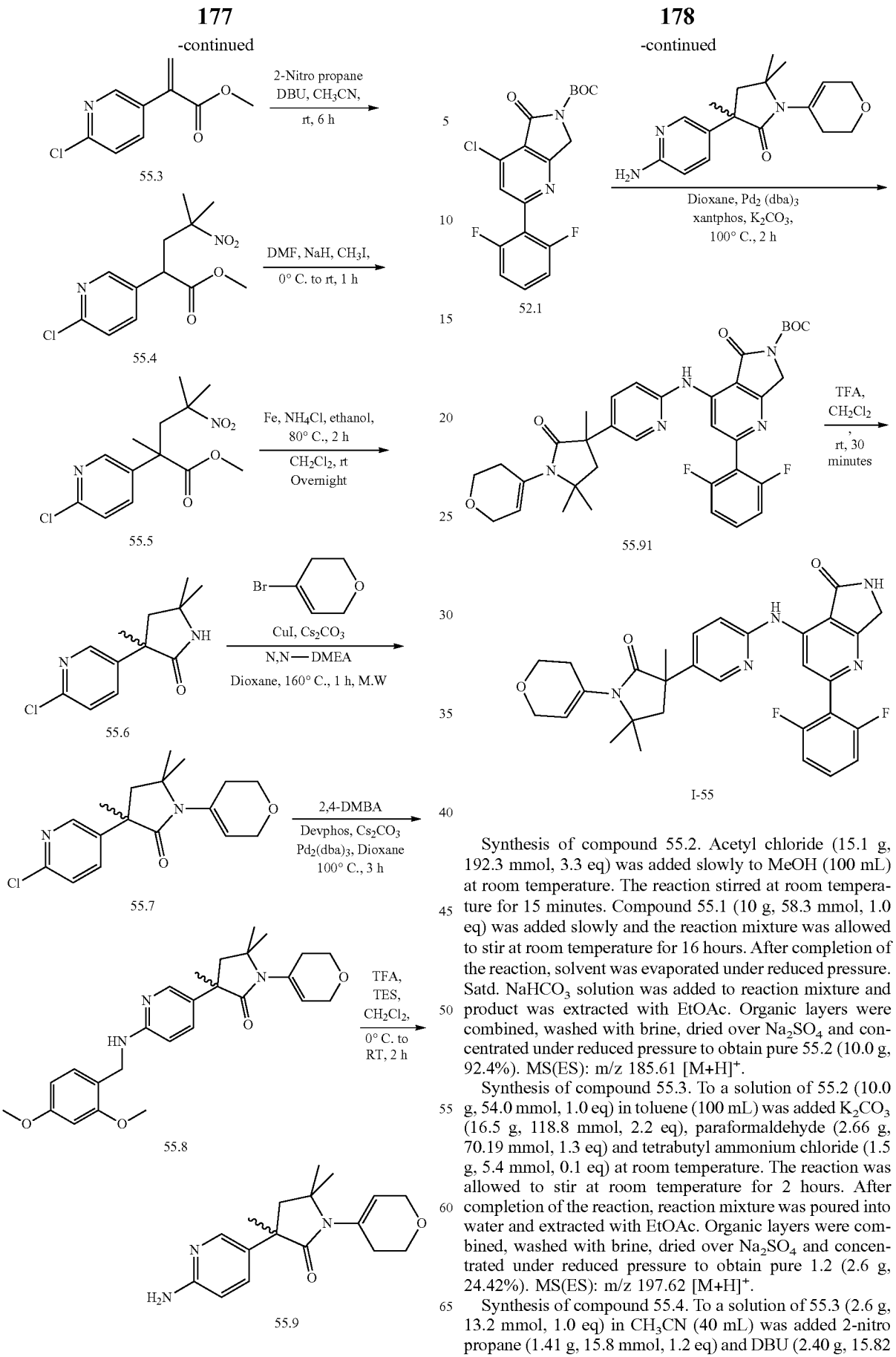

Synthesis of compound 55.2. Acetyl chloride (15.1 g, 192.3 mmol, 3.3 eq) was added slowly to MeOH (100 mL) at room temperature. The reaction stirred at room temperature for 15 minutes. Compound 55.1 (10 g, 58.3 mmol, 1.0 eq) was added slowly and the reaction mixture was allowed to stir at room temperature for 16 hours. After completion of the reaction, solvent was evaporated under reduced pressure. Satd. NaHCO$_3$ solution was added to reaction mixture and product was extracted with EtOAc. Organic layers were combined, washed with brine, dried over Na$_2$SO$_4$ and concentrated under reduced pressure to obtain pure 55.2 (10.0 g, 92.4%). MS(ES): m/z 185.61 [M+H]$^+$.

Synthesis of compound 55.3. To a solution of 55.2 (10.0 g, 54.0 mmol, 1.0 eq) in toluene (100 mL) was added K$_2$CO$_3$ (16.5 g, 118.8 mmol, 2.2 eq), paraformaldehyde (2.66 g, 70.19 mmol, 1.3 eq) and tetrabutyl ammonium chloride (1.5 g, 5.4 mmol, 0.1 eq) at room temperature. The reaction was allowed to stir at room temperature for 2 hours. After completion of the reaction, reaction mixture was poured into water and extracted with EtOAc. Organic layers were combined, washed with brine, dried over Na$_2$SO$_4$ and concentrated under reduced pressure to obtain pure 1.2 (2.6 g, 24.42%). MS(ES): m/z 197.62 [M+H]$^+$.

Synthesis of compound 55.4. To a solution of 55.3 (2.6 g, 13.2 mmol, 1.0 eq) in CH$_3$CN (40 mL) was added 2-nitro propane (1.41 g, 15.8 mmol, 1.2 eq) and DBU (2.40 g, 15.82 mmol, 1.2 eq) at room temperature. The reaction was stirred at room temperature for 6 hours. After completion of the reaction, CH₃CN was evaporated under reduced pressure, water was added to the reaction mixture and product was extracted with EtOAc. Organic layers were combined, washed with brine, dried over Na$_2$SO$_4$ and concentrated under reduced pressure to obtain crude material. The crude was purified by column chromatography to provide 55.3 (2.2 g, 58.3%). MS(ES): m/z 286.71 [M+H]$^+$.

Synthesis of compound 55.5. To a solution of NaH (0.40 g, 16.9 mmol, 2.2 eq) in DMF (20 mL) at 0° C. was added 55.4 (2.2 g, 7.68 mmol, 1.0 eq) and the reaction was stirred at 0° C. for 5 minutes. Methyl iodide (2.73 g, 19.2 mmol, 2.5 eq) was added dropwise to the reaction mixture at 0° C. The reaction mixture was stirred at room temperature for 1 hour. After completion of the reaction, water was added to the reaction mixture and product was extracted with EtOAc. Organic layers were combined, washed with brine solution, dried over Na$_2$SO$_4$ and concentrated under reduced pressure to obtain crude which was purified by column chromatography to provide pure 55.5 (1.5 g, 65.0%). MS(ES): m/z 300.74 [M+H]$^+$.

Synthesis of compound 55.6. To a solution of 55.5 (1.5 g, 5.0 mmol, 1.0 eq) in EtOH (15.0 mL) was added iron powder (2.8 g, 50.0 mmol, 10.0 eq) and NH$_4$Cl (2.65 g, 50.0 mmol, 10.0 eq). The reaction mixture was stirred at 80° C. for 2 hours. After completion of the reaction, water was added to the reaction mixture and product was extracted with EtOAc. Organic layers were combined, washed with brine, dried over Na$_2$SO$_4$ and concentrated under reduced pressure to obtain pure product. Dichloromethane was added to the pure product and the reaction was stirred at room temperature overnight to get pure cyclized product 55.6 (0.8 g, 67.2%). MS(ES): m/z 238.72 [M+H]$^+$.

Syntheiss of compound 55.7. To a solution of 55.7 (0.8 g, 3.36 mmol, 1.0 eq) in 1,4-dioxane (5.0 mL) was added Cs$_2$CO$_3$ (3.27 g, 10.1 mmol, 3.0 eq) and CuI (0.063 g, 0.336 mmol, 0.1 eq). The reaction mixture was degassed using argon for 15 minutes at room temperature. 4-Bromo-3,6-dihydro-2H-pyran (1.64 g, 10.1 mmol, 3.0 eq) and N,N-dimethyl ethylene diamine (0.029 g, 0.34 mmol, 0.1 eq) were added to the reaction mixture. The reaction was stirred at 160° C. for 1 hour in a microwave reactor. After completion of the reaction, water was added to the reaction mixture and product was extracted with EtOAc. Organic layers were combined, washed with brine, dried over Na$_2$SO$_4$ and concentrated under reduced pressure to obtain crude which was purified by column chromatography to provide 55.7 (0.3 g, 27.9%). MS(ES): m/z 320.82 [M+H]$^+$.

Synthesis of compound 55.8. To a solution of 55.7 (0.16 g, 0.5 mmol, 1.0 eq) in 1,4-dioxane (5 mL) was added 2,4-dimethoxy benzyl amine (0.11 g, 0.65 mmol, 1.3 eq) and Cs$_2$CO$_3$ (0.325 g, 10.0 mmol, 2.0 eq). The reaction mixture was degassed using argon for 30 minutes at room temperature. Devphos ligand (0.039 g, 0.1 mmol, 0.2 eq) and Pd$_2$(dba)$_3$ (0.045 g, 0.05 mmol, 0.1 eq) were added to the reaction mixture. The reaction was stirred at 100° C. for 3 hours. After completion of the reaction, water was added to the mixture and product was extracted with EtOAc. Organic layers were combined, washed with brine, dried over Na$_2$SO$_4$ and concentrated under reduced pressure to obtain crude material. The crude was purified by column chromatography to furnish 55.8 (0.09 g, 40.1%). MS(ES): m/z 451.57 [M+H]$^+$.

Synthesis of compound 55.9. To a solution of 55.8 (0.06 g, 0.132 mmol, 1.0 eq) in CH$_2$Cl$_2$ (2 mL) was added TFA (0.1 mL) and triethyl silane (0.1 mL) at 0° C. under nitrogen atmosphere. The reaction was allowed to stir at room temperature for 2 hours. After completion of the reaction, solvent was removed under reduced pressure to furnish 55.9 (0.05 g, 99.0%) MS (ES): m/z 301.39 [M+H]$^+$.

Synthesis of compound 55.91. To a mixture of 52.1 (0.02 g, 0.052 mmol, 1.0 eq) in 1,4-dioxane (2 mL) was added 55.9 (0.015 g, 0.52 mmol, 1.0 eq) and K$_2$CO$_3$ (0.021 g, 0.157 mmol, 3.0 eq). The reaction mixture was degassed for 10 minutes using argon then Pd$_2$(dba)$_3$ (0.004 g, 0.005 mmol, 0.1 eq) and Xantphos (0.006 g, 0.01 mmol, 0.2 eq) were added. Suspension was degassed for additional 5 minutes. The reaction was stirred at 100° C. for 2 hours. After completion of the reaction, mixture was poured into water and product was extracted with EtOAc. Organic layers were combined, washed with brine, dried over Na$_2$SO$_4$ and concentrated under reduced pressure to obtain crude which was purified by column chromatography to provide pure 55.91 (0.015 g, 40.9%). MS(ES): m/z 583.40 [M+H]$^+$.

Synthesis of compound I-55. Compound 55.91 (0.015 g, 0.025 mmol, 1.0 eq) was dissolved in CH$_2$Cl$_2$ (1 mL) and TFA (0.1 mL) was added to the reaction mixture. The reaction was stirred at room temperature for 30 minutes. After completion of the reaction, reaction mixture was poured into water, basified with satd. NaHCO$_3$ and extracted with EtOAc. Organic layers were combined, dried over Na$_2$SO$_4$ and concentrated under reduced pressure to obtain crude which was purified by column chromatography to provide I-55 (0.009 g, 64.2%). MS(ES): m/z 545.59 [M+H]$^+$; $^1$H NMR (DMSO-d$_6$, 400 MHz): δ 9.74 (s,1H), 8.90 (s,1H), 8.58 (s,1H), 8.37-8.36 (d, 1H), 7.81-7.78 (dd, 1H), 7.62-7.54 (m,1H), 7.28-7.24 (t,2H), 7.17-7.14 (d,1H), 5.70 (s,1H), 4.43 (s,2H), 4.17-4.16 (d,2H), 3.76-3.73 (t,2H), 2.19-2.13 (s,2H), 1.67 (s,1H), 1.45 (s,3H), 1.28 (s, 3H), 1.03 (s,3H).

Example 56

Synthesis of 2-(6-fluoro-2-oxopyridin-1(2H)-yl)-4-((5-morpholinopyridin-2-yl)amino)-6,7-dihydro-5H-pyrrolo[3,4-b]pyridin-5-one, I-56

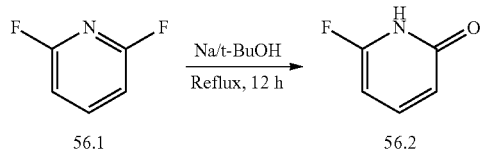

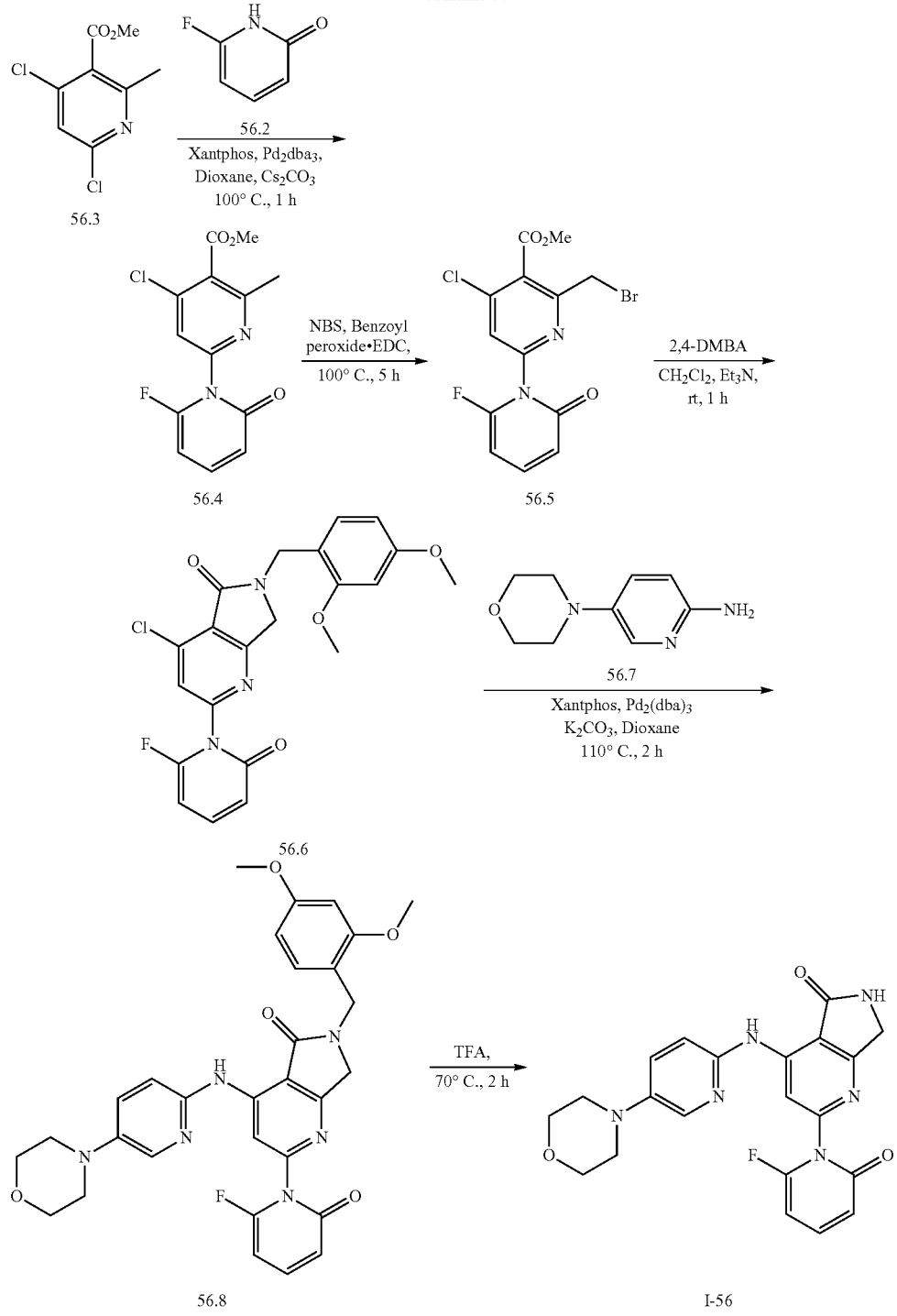

Synthesis of compound 56.2. Sodium metal (2.0 g) was dissolved in t-butanol (50 mL) and refluxed for 1 hour. The reaction mixture was cooled to room temperature and 56.1 (5.0 g, 43.85 mmol, 1.0 eq) was added. The reaction was stirred at reflux temperature for 12 hours. After completion of the reaction, solvent was removed under reduced pressure. Ice cold water was added and the pH was adjusted to 3.0 by addition of dilute HCl. The product was extracted with EtOAc. Organic layers were combined, washed with brine, dried over $Na_2SO_4$ and concentrated under reduced pressure to obtain crude which was purified by column chromatography to provide 56.2 (2.0 g, 40.1%). MS(ES): m/z 113.09 [M+H]$^+$.

Synthesis of compound 56.4. To a solution of 56.3 (1.0 g, 4.55 mmol, 1.0 eq) in 1,4-dioxane (10 mL) was added 56.2 (0.51 g, 4.55 mmol, 1.0 eq) and $Cs_2CO_3$ (4.43 g, 13.63 mmol, 3.0 eq). The Reaction mixture was degassed for 10 minutes using argon, then $Pd_2(dba)_3$ (0.415 g, 0.454 mmol, 0.1 eq) and Xantphos (0.525 g, 0.91 mmol, 0.2 eq) were added. Suspension was degassed for additional 5 minutes.

The reaction was stirred at 100° C. for 1 hour. After completion of the reaction, reaction mixture was poured into water and product was extracted with EtOAc. Organic layers were combined, washed with brine solution, dried over $Na_2SO_4$ and concentrated under reduced pressure to obtain crude which was purified by column chromatography to furnish 56.4 (0.40 g, 29.7%). MS(ES): m/z 296.68 [M+H]$^+$.

Synthesis of compound 56.5. To a solution of 56.4 (0.3 g, 1.013 mmol, 1.0 eq) in ethylene dichloride (10 mL) was added N-bromo succinimide (0.902 g, 5.067 mmol, 5.0 eq) and benzyl peroxide (0.061 g, 0.255 mmol, 0.25 eq). The reaction was stirred at 100° C. for 5 hours. After completion of the reaction, mixture was poured into water and product was extracted with EtOAc. Organic layers were combined, washed with brine, dried over $Na_2SO_4$ and concentrated under reduced pressure to obtain crude which was purified by column chromatography to provide 56.5 (0.175 g, 46.1%). MS(ES): m/z 375.58 [M+H]$^+$.

Synthesis of compound 56.6. To a solution of 56.5 (0.175 g, 0.466 mmol, 1.0 eq) in $CH_2Cl_2$ (3 mL) was added 2,4-dimethoxy benzyl amine (0.077 g, 0.466 mmol, 1.0 eq) and $Et_3N$ (0.094, 0.933 mmol, 2.0 eq). The reaction was stirred at room temperature for 1 hour. After completion of the reaction, mixture was poured into water and product was extracted with $CH_2Cl_2$. Organic layers were combined, washed with brine, dried over $Na_2SO_4$ and concentrated under reduced pressure to obtain crude material. The crude was purified by column chromatography to furnsih 56.6 (0.09 g, 44.9%). MS(ES): m/z 429.83 [M+H]$^+$.

Synthesis of compound 56.8. To a mixture of 56.6 (0.090 g, 0.209 mmol, 1.0 eq) in 1,4-dioxane (2 mL) was added 56.7 (0.037 g, 0.209 mmol, 1.0 eq) and $K_2CO_3$ (0.086 g, 0.627 mmol, 3.0 eq). The reaction mixture was degassed for 10 minutes using argon, then $Pd_2(dba)_4$ (0.018 g, 0.020 mmol, 0.1 eq) and xantphos (0.023 g, 0.041 mmol, 0.2 eq) were added. Suspension was degassed for additional five minutes. The reaction was stirred at 110° C. for 2 hours. After completion of the reaction, mixture was poured into water and product was extracted with EtOAc. Organic layers were combined, washed with brine, dried over $Na_2SO_4$ and concentrated under reduced pressure to obtain crude material. The crude was purified by column chromatography to furnish 56.8 (0.08 g, 66.7%). MS(ES): m/z 572.60 [M+H]$^-$.

Synthesis of compound I-56. Compound 56.8 (0.08 g, 0.139 mmol, 1.0 eq) was dissolved in TFA (2.0 mL). The reaction was stirred at 70° C. for 2 hours. After completion of the reaction, mixture was poured into water, basified with satd. $NaHCO_3$ and extracted with EtOAc. Organic layers were combined and dried over $Na_2SO_4$ and concentrated under reduced pressure to obtain crude material. The crude was purified by column chromatography to provide I-56 (0.040 g, 77.5%). MS (ES): m/z 422.42 [M+H]$^+$; $^1$H NMR (DMSO-d$_6$, 400 MHz): δ 9.51 (s,1H), 8.68 (s, 1H), 8.13-7.97 (m,3H), 7.49-7.46 (dd,1H), 7.14-7.03 (m,3H), 4.25 (s,2H), 3.76-3.73 (t,4H), 3.12-3.10 (t,4H).

Example 57

Synthesis of 4-((4-(6-azaspiro[2.5]octane-6-carbonyl)phenyl)amino)-2-(2,6-difluorophenyl)-6,7-dihydro-5H-pyrrolo[3,4-b]pyridin-5-one, I-57

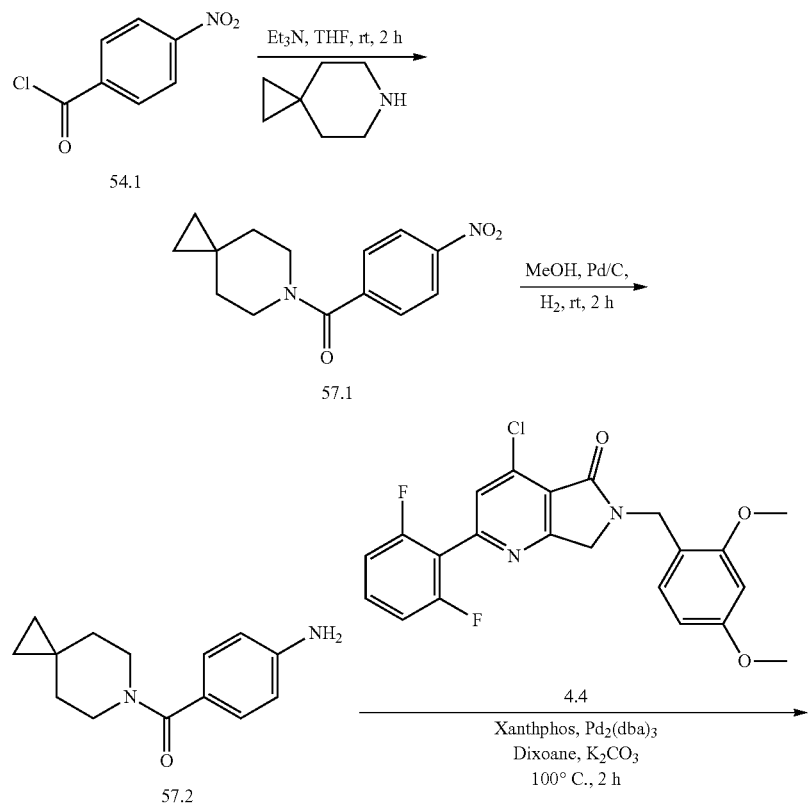

-continued

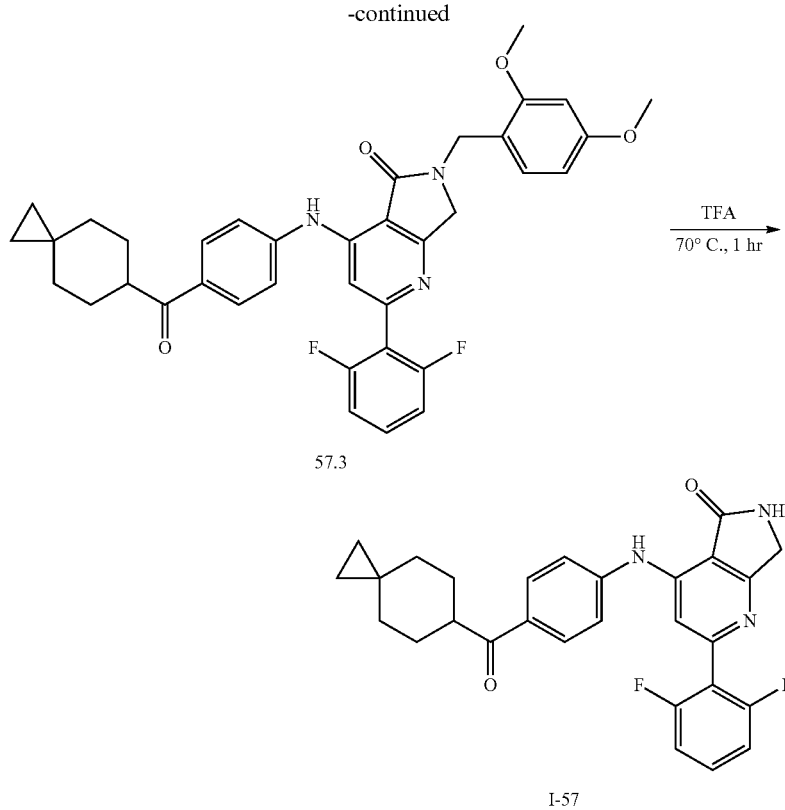

57.3

I-57

Synthesis of compound 57.1. To a solution of 6-azaspiro [2.5]octane (0.119 g, 0.808 mmol, 1.0 eq) in THF (3.0 mL) was added 54.1 (0.15 g, 0.81 mmol, 1.0 eq) and Et$_3$N (0.245 g, 2.425 mmol, 3.0 eq) dropwise at 0° C. The reaction was stirred at room temperature for 2 hours. After completion of the reaction, water was added to the mixture and product was extracted with EtOAc. Organic layers were combined, washed with brine, dried over Na$_2$SO$_4$ and concentrated under reduced pressure to obtain crude material. The crude was purified by titration with hexanes to provide pure 57.1 (0.16 g, 76.0%). MS(ES): m/z 260.29 [M+H]$^+$.

Synthesis of compound 57.2. To a suspension of 10% Pd/C (0.050 g) in MeOH (5 mL) was added a solution of 57.1 (0.16 g, 0.614 mmol, 1.0 eq) in MeOH (1 mL) under nitrogen. Reaction mixture was purged with hydrogen gas for 2 hours. After completion of the reaction, mixture was filtered through celite, washed with MeOH. Obtained filtrate was concentrated under reduced pressure to get pure 57.2 (0.1 g, 70.6%) MS (ES): m/z 230.31 [M+H]$^+$.

Synthesis of compound 57.3. To a mixture of 4.4 (0.1 g, 0.23 mmol, 1.0 eq) in 1,4-dioxane (2.0 mL) was added 57.2 (0.058 g, 0.254 mmol, 1.1 eq) and K$_2$CO$_3$ (0.063 g, 0.462 mmol, 2.0 eq). The reaction mixture was degassed for 10 minutes using argon, then Pd$_2$(dba)$_3$ (0.021 g, 0.023 mmol, 0.1 eq) and Xantphos (0.026 g, 0.046 mmol, 0.2 eq) were added. Suspension was degassed for additional 5 minutes. The reaction was stirred at 100° C. for 2 hours. After completion of reaction, mixture was poured into water and product was extracted with EtOAc. Organic layer was combined, washed with brine, dried over Na$_2$SO$_4$ and concentrated under reduced pressure to obtain crude material. The crude was purified by column chromatography to furnish 57.3 (0.088 g, 60.7%). MS(ES): m/z 624.69 [M+H]$^+$.

Syntheis of compound I-57. The compound 57.3 (0.088 g, 0.14 mmol, 1.0 eq) was dissolved in TFA (2.0 mL). The reaction mixture was stirred at 70° C. for 1 hour. After completion of the reaction, mixture was poured into water, basified with satd. NaHCO$_3$ solution and extracted with EtOAc. Organic layers were combined, dried over Na$_2$SO$_4$ and concentrated under reduced pressure to obtain crude material. The crude was purified by column chromatography to furnish I-57 (0.035 g, 52.4%). MS(ES): m/z 474.51 [M+H]$^+$; $^1$H NMR (DMSO-d$_6$, 400 MHz): δ 9.16 (s, 1H), 8.76 (s, 1H), 7.57-7.50 (m, 1H), 7.45-7.39 (m, 4H), 7.24-7.19 (m, 3H), 4.41 (s, 2H), 3.67-3.31 (m, 4H), 1.34-1.17 (m, 4H), 0.34 (m, 4H).

Example 58

Synthesis of 4-((4-(3-oxa-9-azaspiro[5.5]undecane-9-carbonyl)phenyl)amino)-2-(2,6-difluorophenyl)-6,7-dihydro-5H-pyrrolo[3,4-b]pyridin-5-one, I-58

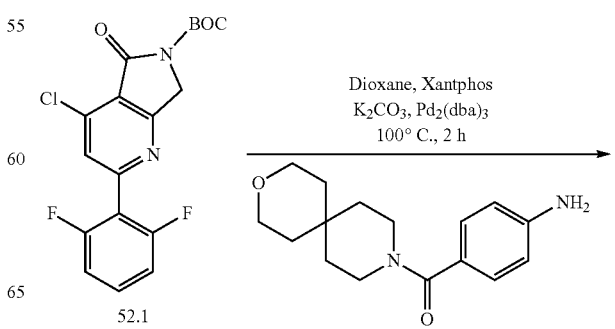

52.1

187

-continued

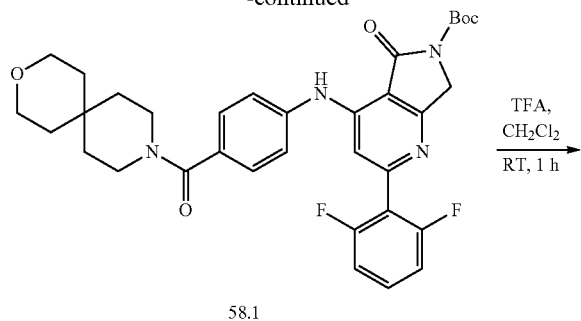

58.1

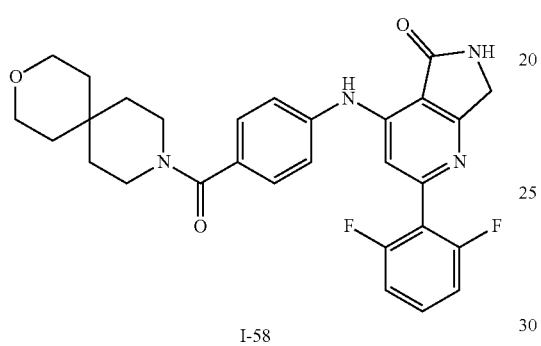

I-58

Synthesis of compound 58.1. To a mixture of 52.1 (0.06 g, 0.157 mmol, 1.0 eq) in 1,4-dioxane (2.0 mL) was added (4-aminophenyl)(3-oxa-9-azaspiro[5.5]undecan-9-yl)methanone (0.043 g, 0.157 mmol, 1.0 eq) and K₂CO₃ (0.065 g, 0.473 mmol, 3.0 eq). Suspension was degassed for 10 minutes using argon, then Pd₂(dba)₃ (0.014 g, 0.015 mmol, 0.1 eq) and Xantphos (0.018 g, 0.031 mmol, 0.2 eq) were added. The reaction was stitted at 100° C. for 2 hours. After completion of the reaction, mixture was poured into water and extracted with EtOAc. Organic layers were combined, washed with brine, dried over Na₂SO₄ and concentrated under reduced pressure to obtain crude material. The crude was purified by column chromatography to furnish 58.1 (0.055 g, 56.4%). MS(ES): m/z 618.68 [M+H]⁺.

Synthesis of compound I-58. Compound 58.1 (0.055 g, 0.088 mmol, 1.0 eq) was dissolved in CH₂Cl₂ (1.0 mL) and TFA (0.5 mL) was added to the reaction. The reaction was stirred at room temperature for 1 hour. After completion of the reaction, mixture was poured into water, basified with NaHCO₃ solution and extracted with CH₂Cl₂. Organic layers were combined, dried over Na₂SO₄ and concentrated under reduced pressure to obtain crude which was purified by column chromatography to furnish I-58 (0.042 g, 91.1%). MS(ES): m/z 518.56 [M+H]⁺; ¹H NMR (DMSO-d₆, 400 MHz): 9.21 (s,1H), 8.78 (s,1H), 7.57-7.53 (m,1H), 7.42 (s,4H), 7.24-7.19 (m, 3H), 4.42 (s,2H), 3.55-3.46 (m,8H), 1.46 (m,8H).

188

Example 59

Synthesis of 2-(2,6-difluorophenyl)-4-((5-((3aR,6aS)-tetrahydro-1H-furo[3,4-c]pyrrol-5(3H)-yl)pyridin-2-yl)amino)-6,7-dihydro-5H-pyrrolo[3,4-b]pyridin-5-one, I-59

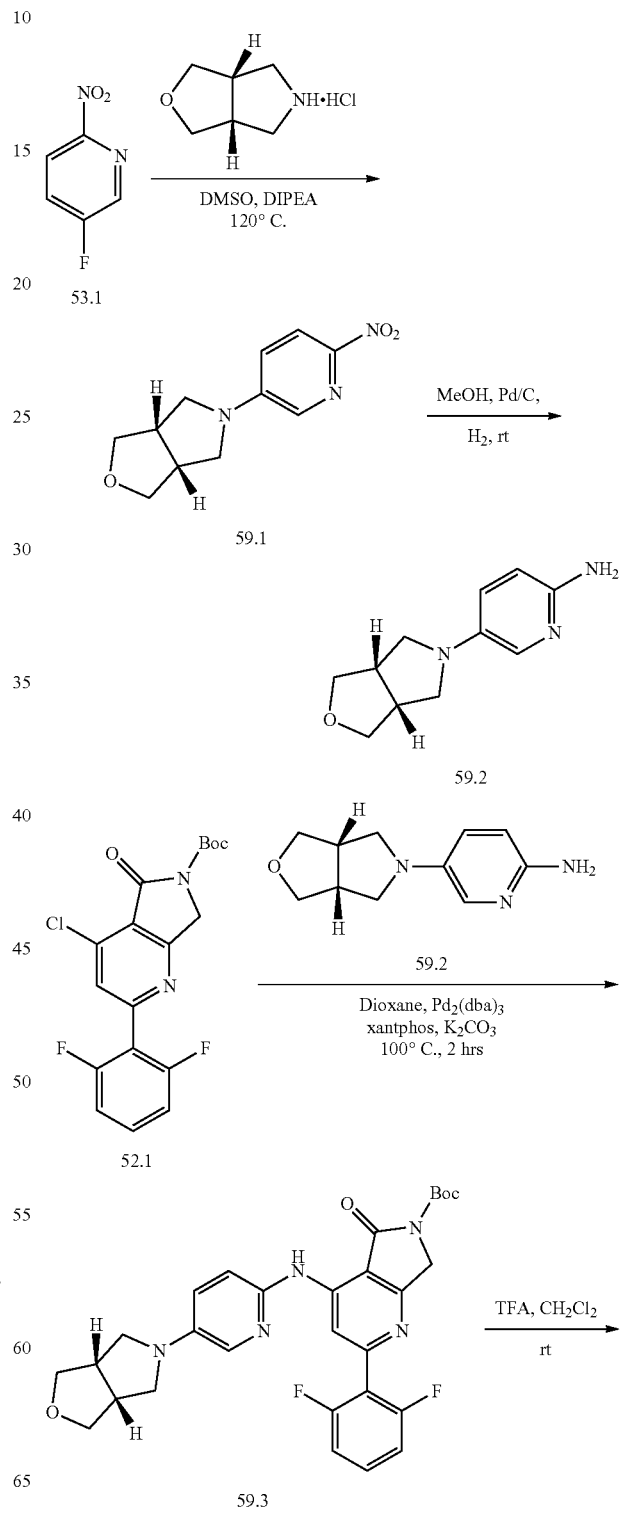

189

-continued

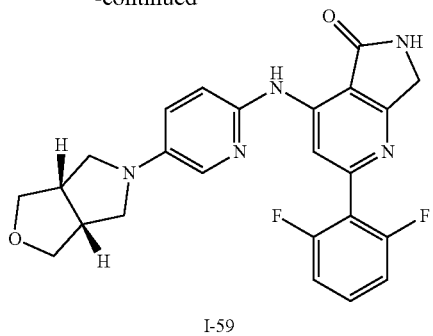

I-59

Synthesis of compound 59.1. To a solution of 53.1 (0.2 g, 1.40 mmol, 1.0 eq) in DMSO (2.0 mL) was added (3aR, 6aS)-hexahydro-1H-furo[3,4-c]pyrrole hydrochloride (0.21 g, 1.40 mmol, 1.0 eq.) and DIPEA (2.45 mL, 14.07 mmol, 10.0 eq.). The reaction mixture was stirred at 120° C. for 1 hour. After completion of the reaction, mixture was poured into water and product was extracted with EtOAc. Organic layers were combined, washed with brine, dried over $Na_2SO_4$ and concentrated under reduced pressure to obtain crude which was purified by column chromatography to provide 59.1 (0.23 g, 69.5%). MS(ES): m/z 236.17 [M+H]$^+$.

Synthesis of compound 59.2. To a suspension of 10% Pd/C (0.025 g) in MeOH (5.0 mL) was added a solution of 59.1 (0.225 g, 0.957 mmol, 1.0 eq) in MeOH (5.0 mL) under nitrogen atmosphere. Suspension was purged for 2 hours with $H_2$ gas. After completion of the reaction, mixture was filtered through celite, washed with MeOH and obtained filtrate was concentrated under reduced pressure to obtain crude 59.2 (0.18 g) MS (ES): m/z 206.26 [M+H]$^+$.

Synthesis of compound 59.3. To a solution of 52.1 (0.065 g, 0.17 mmol, 1.0 eq) in 1,4-dioxane (2.0 mL) was added 59.2 (0.038 g, 0.187 mmol, 1.1 eq) and $K_2CO_3$ (0.058 g, 0.426 mmol, 2.5 eq). The reaction mixture was degassed for 10 minutes under argon atmosphere, then $Pd_2(dba)_3$ (0.015 g, 0.017 mmol, 0.1 eq) and xantphos (0.019 g, 0.034 mmol, 0.2 eq) were added, and suspension was degassed for additional 5 min. The reaction was stirred at 100° C. for 2 hours. After completion of the reaction, mixture was poured into water and product was extracted with EtOAc. Organic layers were combined, washed with brine solution, dried over $Na_2SO_4$ and concentrated under reduced pressure to obtain crude material. The crude was purified by column chromatography to provide 59.3 (0.065 g, 69.7%). MS(ES): m/z 551.5 [M+H]$^+$.

Synthesis of compound I-59. Compound 59.3 (0.065 g, 0.118 mmol, 1.0 eq) was dissolved in $CH_2Cl_2$ (1.5 mL) and TFA (0.3 mL) was added to the reaction mixture. The reaction was stirred at room temperature for 1 hour After completion of reaction, mixture was poured into water, basified with $NaHCO_3$ solution and extracted with EtOAc. Organic layers were combined, dried over $Na_2SO_4$ and concentrated under reduced pressure to obtain crude which was purified by trituration with $Et_2O$ get pure I-59 (0.030 g, 84.7%). MS(ES): m/z 450.37 [M+H]$^+$; $^1$H NMR (DMSO-d$_6$, 400 MHz): δ 9.48 (s,1H), 8.81 (s,1H), 8.28 (s 1H), 7.79-7.78 (d,1H), 7.54-7.61 (m, 1H), 7.28-7.24 (t,2H), 7.18-7.15 (m,1H), 7.11-7.09 (d,1H), 4.41 (s,2H), 3.86-3.83 (t,2H), 3.52-3.50 (t,2H), 3.32-3.28 (t,2H), 3.19-3.17 (d, 2H), 2.98 (bs,2H).

190

Example 60

Synthesis of 4-(4-((5-(6-azaspiro[2.5]octan-6-yl) pyridin-2-yl)amino)-5-oxo-6,7-dihydro-5H-pyrrolo [3,4-b]pyridin-2-yl)-3,5-difluorobenzonitrile, I-60

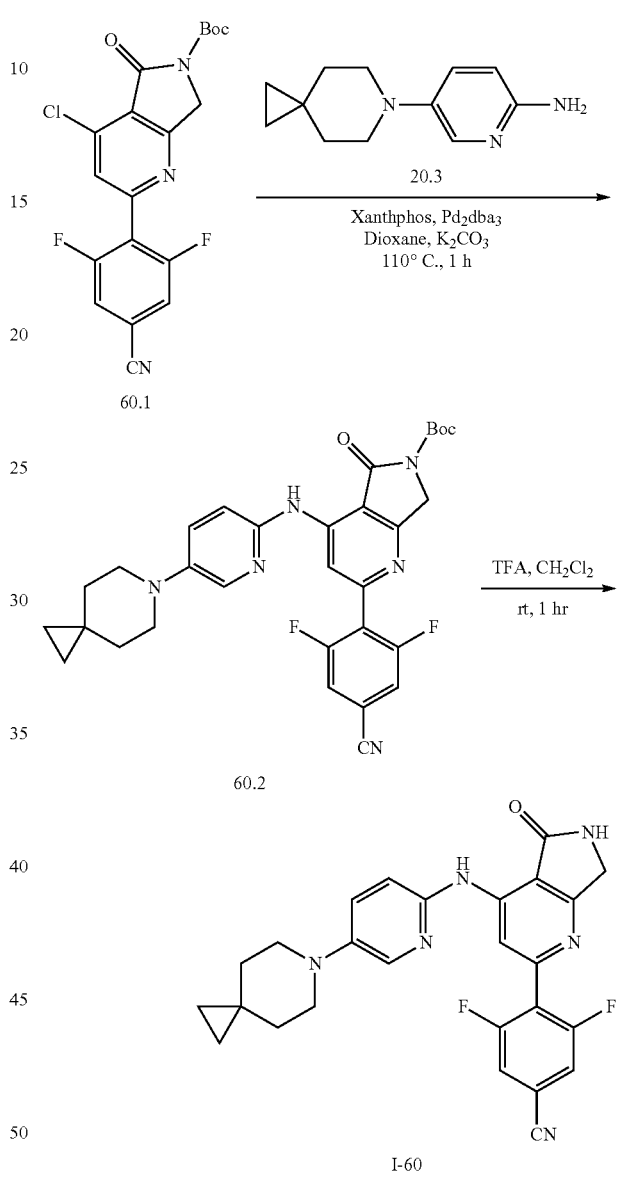

Synthesis of compound 60.2. To a solution of 60.1 (0.070 g, 0.155 mmol, 1.0 eq) in 1,4-dioxane (2.0 mL) was added 20.3 (0.032 g, 0.155 mmol, 1.0 eq) and $K_2CO_3$ (0.043 g, 0.31 mmol, 2.0 eq). The reaction mixture was degassed for 10 minutes under argon atmosphere, then $Pd_2(dba)_3$ (0.014 g, 0.0155 mmol, 0.1 eq) and Xantphos (0.018 g, 0.031 mmol, 0.2 eq) were added. Suspension was degassed again for 5 minutes. The reaction was stirred at 110° C. for 1 hour. After completion of the reaction, mixture was poured into water and product was extracted with EtOAc. Organic layers were combined, washed with brine, dried over $Na_2SO_4$ and concentrated under reduced pressure to obtain crude material. The crude was purified by column chromatography to provide 60.2 (0.070 g, 70.9%). MS(ES): m/z 572.62 [M+H]$^+$.

Synthesis of compound I-60. Compound 60.2 (0.070 g, 0.122 mmol, 1.0 eq) was dissolved in CH₂Cl₂ (3.0 mL) and TFA (0.4 mL) was added to the reaction mixture. The reaction mixture was stirred at room temperature for 1 hour. After completion of the reaction, mixture was poured into water, basified with satd. NaHCO₃ solution and extracted with EtOAc. Organic layers were combined, dried over Na₂SO₄ and concentrated under reduced pressure to obtain crude which was purified by trituration with n-pentane and diethyl ether toprovide pure I-60 (0.047 g, 81.4%). MS(ES): m/z 472.50 [M+H]$^+$; $^1$H NMR (DMSO-d$_6$, 400 MHz): δ 9.55 (s,1H), 8.85 (s,1H), 8.39 (s,1H), 8.03 (d,1H), 7.99-7.97 (d,2H), 7.49-7.46 (dd,1H), 7.11-7.09 (d,1H), 4.41 (s,2H), 3.20-3.17 (t,4H), 1.46-1.40 (t,4H), 0.329 (s,4H).

Example 61

Synthesis of 2-(2,6-difluorophenyl)-4-((1-hydroxy-1,3-dihydro-benzo-[c][1,2]oxaborol-5-yl)amino)-6,7-dihydro-5H-pyrrolo[3,4-b]pyridin-5-one, I-61

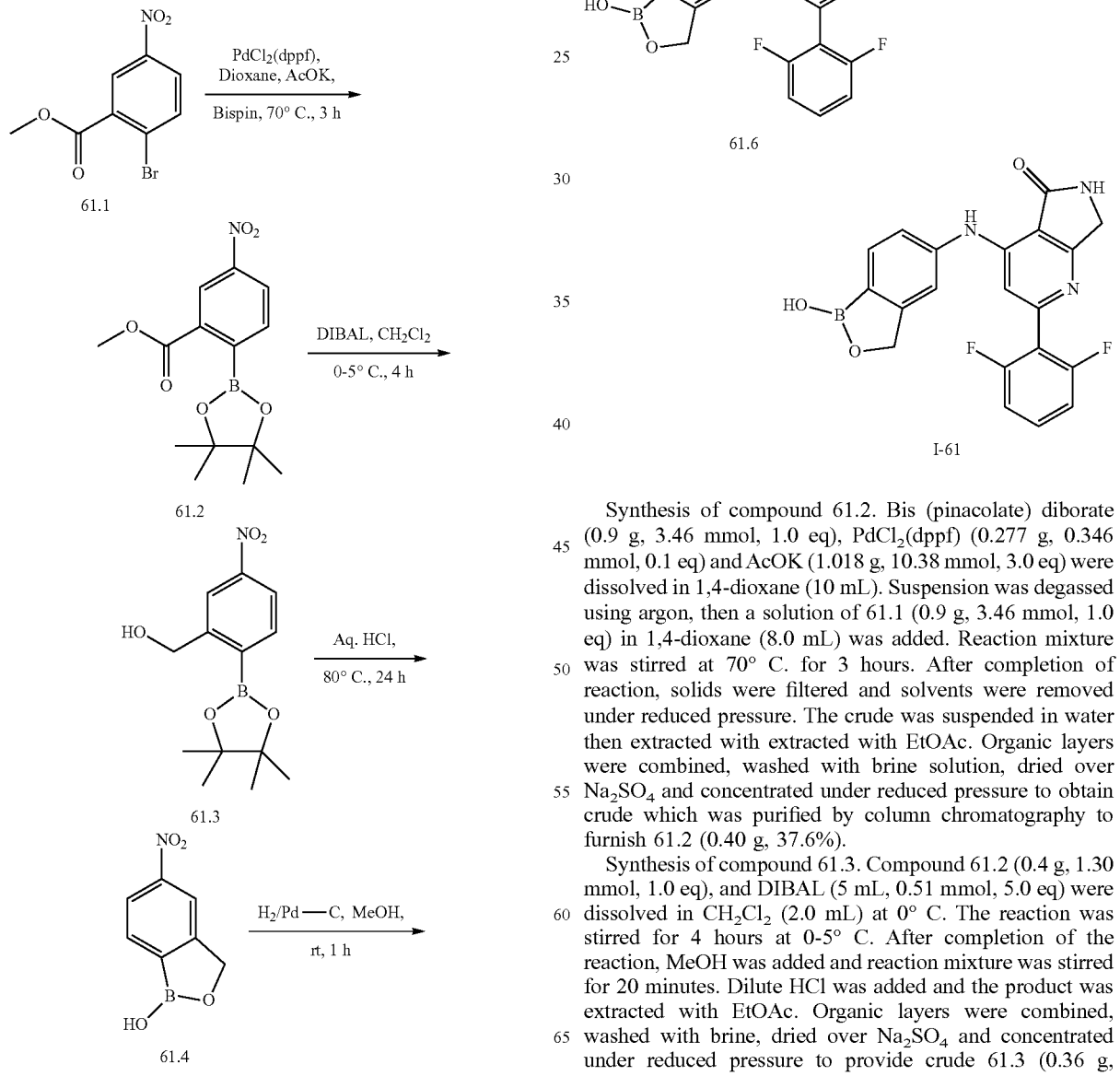

Synthesis of compound 61.2. Bis (pinacolate) diborate (0.9 g, 3.46 mmol, 1.0 eq), PdCl₂(dppf) (0.277 g, 0.346 mmol, 0.1 eq) and AcOK (1.018 g, 10.38 mmol, 3.0 eq) were dissolved in 1,4-dioxane (10 mL). Suspension was degassed using argon, then a solution of 61.1 (0.9 g, 3.46 mmol, 1.0 eq) in 1,4-dioxane (8.0 mL) was added. Reaction mixture was stirred at 70° C. for 3 hours. After completion of reaction, solids were filtered and solvents were removed under reduced pressure. The crude was suspended in water then extracted with extracted with EtOAc. Organic layers were combined, washed with brine solution, dried over Na₂SO₄ and concentrated under reduced pressure to obtain crude which was purified by column chromatography to furnish 61.2 (0.40 g, 37.6%).

Synthesis of compound 61.3. Compound 61.2 (0.4 g, 1.30 mmol, 1.0 eq), and DIBAL (5 mL, 0.51 mmol, 5.0 eq) were dissolved in CH₂Cl₂ (2.0 mL) at 0° C. The reaction was stirred for 4 hours at 0-5° C. After completion of the reaction, MeOH was added and reaction mixture was stirred for 20 minutes. Dilute HCl was added and the product was extracted with EtOAc. Organic layers were combined, washed with brine, dried over Na₂SO₄ and concentrated under reduced pressure to provide crude 61.3 (0.36 g, 99.0%), which was used in the next step without purification Synthesis of compound 61.4. Compound 61.3 (0.36 g, 1.43 mmol, 1.0 eq) was dissolved in 6 M HCl (30 mL) and the reaction was stirred at 80° C. for 24 hours. After completion of the reaction, water was added to the reaction mixture and the product was extracted with EtOAc. Organic layers were combined, washed with brine, dried over Na$_2$SO$_4$ and concentrated under reduced pressure to furnish 1.3 (0.1 g, 43.3%).

Synthesis of compound 61.5. To a suspension of 10% Pd/C (0.25 g) in MeOH (5.0 mL) was added a solution of 61.4 (0.1 g, 0.3 mmol, 1.0 eq) in MeOH (3.0 mL) under nitrogen. Suspension was purged with H$_2$ gas for 1 hour. After completion of the reaction, mixture was filtered through celite, washed with MeOH and obtained filtrate was concentrated under reduced pressure to get crude material. The crude was purified by trituration with n-hexane and Et$_2$O to provide 61.5 (0.060 g, 72.1%).

Synthesis of compound 61.6. To a mixture of 52.1 (0.06 g, 0.157 mmol, 1.0 eq) in 1,4-dioxane (2.5 mL) was added 61.5 (0.025 g, 0.157 mmol, 1.0 eq) and K$_2$CO$_3$ (0.067 g, 0.471 mmol, 3.0 eq). Mixture was degassed for 10 minutes using argon, then Pd$_2$(dba)$_3$ (0.014 g, 0.015 mmol, 0.1 eq) and Xantphos (0.016 g, 0.031 mmol, 0.2 eq) were added. Suspension was degassed for additional 5 minutes. The reaction was stirred at 100° C. for 2 hours. After completion of the reaction, mixture was poured into water and product was extracted with EtOAc. Organic layers were combined, washed with brine, dried over Na$_2$SO$_4$ and concentrated under reduced pressure to obtain crude material. The crude was purified using column chromatography to furnish 61.6 (0.027 g, 34.7%).

Synthesis of compound I-61. Compound 61.6 (0.027 g, 0.054 mmol, 1.0 eq) was dissolved in CH$_2$Cl$_2$ (2.0 mL) and TFA (0.5 mL) was added to the reaction mixture. The reaction was stirred at room temperature for 1 hour. After completion of the reaction, mixture was poured into water, basified with saturated NaHCO3 solution and extracted with EtOAc. Organic layers were combined, washed with brine, dried over Na$_2$SO$_4$ and concentrated under reduced pressure to obtain crude material. The crude was purified by column chromatography to provide I-61 (0.006 g, 27.9%). $^1$H NMR (DMSO-d$_6$, 400 MHz): δ 9.12 (s,1H), 8.61 (s,1H), 7.48-7.37 (m,4H), 7.08-7.03 (m,3H), 4.26 (s,2H), 4.12 (s,2H).

Example 62

Synthesis of 4-((5-(1,4-dioxa-8-azaspiro[4.5]decan-8-yl)pyridin-2-yl)amino)-2-(2,6-difluorophenyl)-6,7-dihydro-5H-pyrrolo[3,4-b]pyridin-5-one, I-62

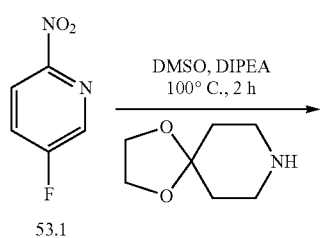

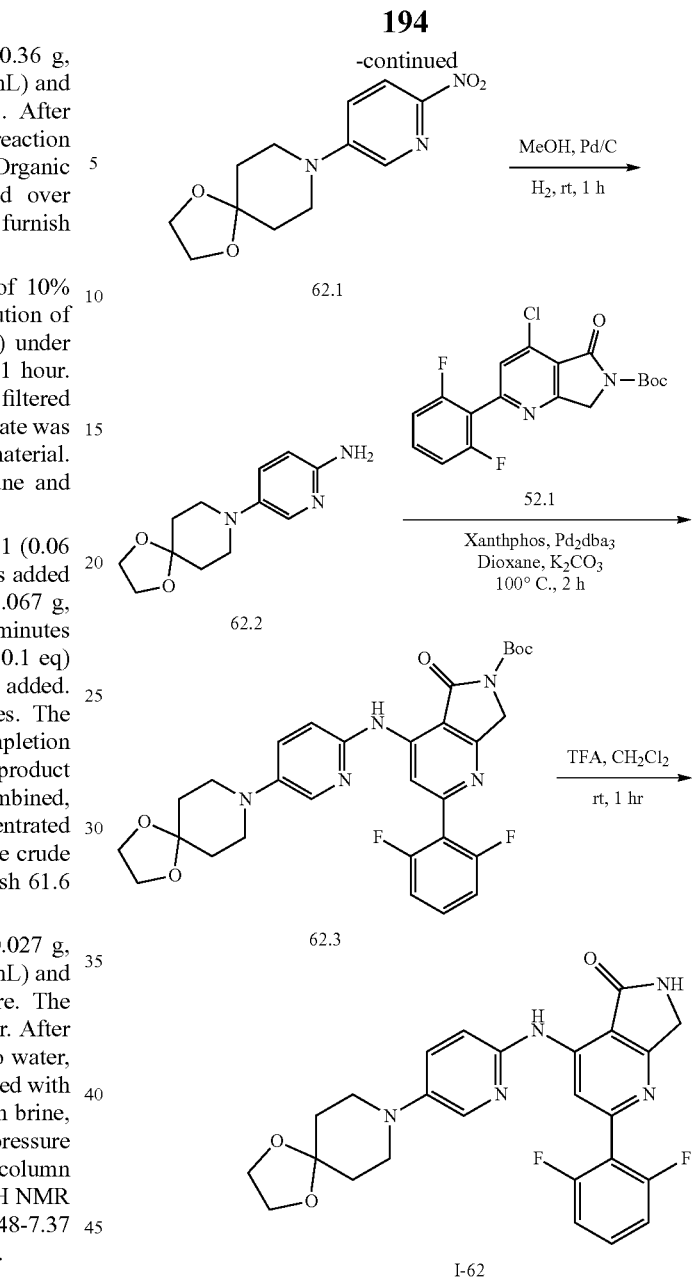

Synthesis of compound 62.1. To a solution of 53.1 (0.3 g, 2.11 mmol, 1.0 eq) in DMSO (10 mL) was added 1,4-dioxa-8-azaspiro[4.5]decane (0.30 g, 2.11 mmol, 1.0 eq) followed by DIPEA (3.63 mL, 21.1 mmol, 10.0 eq). The reaction mixture was stirred at 100° C. for 2 hours. After completion, reaction was quenched with water and product was extracted with EtOAc. Organic layers were combined, washed with brine, dried over Na$_2$SO$_4$ and concentrated under reduced pressure to obtain pure 62.1 (0.50 g, 89.3%). MS(ES): m/z 265.27 [M+H]$^+$.

Synthesis of compound 62.2. To a suspension of 10% Pd/C (0.150 g) in MeOH (3.5 mL) was added a solution of 62.1 (0.5 g, 1.88 mmol, 1.0 eq) in MeOH (3.5 mL) under nitrogen. Suspension was purged using H$_2$ gas for 2 hours. After completion of reaction, mixture was filtered through celite and washed with MeOH. Solvents were removed under reduced pressure and the crude was purified by trituration with n-pentane to provide 62.2 (0.41 g, 92.5%). MS(ES): m/z 235.29 [M+H]$^+$.

Synthesis of compound 62.3. To a solution of 52.1 (0.07 g, 0.184 mmol, 1.0 eq) in 1,4-dioxane (3.0 mL) was added 62.2 (0.043 g, 0.184 mmol, 1.1 eq) and K$_2$CO$_3$ (0.05 g, 0.368 mmol, 2.0 eq). Suspension was degassed for 10 minutes using argon then Pd$_2$(dba)$_3$ (0.016 g, 0.018 mmol, 0.1 eq) and Xantphos (0.021 g, 0.036 mmol, 0.2 eq) were added. After additional aron purge (5 min), the reaction was stirred at 100° C. for 2 hours. After completion of the reaction, mixture was poured into water and mixture was extracted with EtOAc. Organic layers were combined, washed with brine, dried over Na$_2$SO$_4$ and concentrated under reduced pressure to obtain crude material. The crude was purified using column chromatography to furnish 62.3 (0.068 g, 63.8%). MS(ES): m/z 579.60 [M+H]$^+$.

Synthesis of compound I-62. Compound 62.3 (0.068 g, 0.117 mmol, 1.0 eq) was dissolved in CH$_2$Cl$_2$ (2.0 mL) and TFA (0.3 mL) was added to the reaction mixture. The reaction was stirred at room temperature for 1 hour. After completion of the reaction, mixture was poured in water, basified with satd. NaHCO$_3$ solution and extracted with EtOAc. Organic layers were combined, dried over Na$_2$SO$_4$ and concentrated under reduced pressure to obtain crude. The crude was purified by column chromatography to furnish I-62 (0.039 g, 69.3%). MS(ES): m/z 479.49 [M+H]$^+$; $^1$H NMR (DMSO-d$_6$, 400 MHz): δ 9.51 (s,1H), 8.80 (s,1H), 8.37 (s,1H), 8.05-8.04 (d, 1H), 7.60-7.53 (m,1H), 7.49-7.46 (dd,1H), 7.28-7.22 (m,2H), 7.15-7.07 (m,1H), 4.40 (s,2H), 3.90 (m,4H), 3.24-3.18 (m,4H), 1.71-1.69 (t,4H).

Example 63

Synthesis of 2-(2,6-difluorophenyl)-4-((4-((3aR,6aS)-hexahydro-1H-furo[3,4-c]pyrrole-5-carbonyl)phenyl)amino)-6,7-dihydro-5H-pyrrolo[3,4-b]pyridin-5-one, I-63

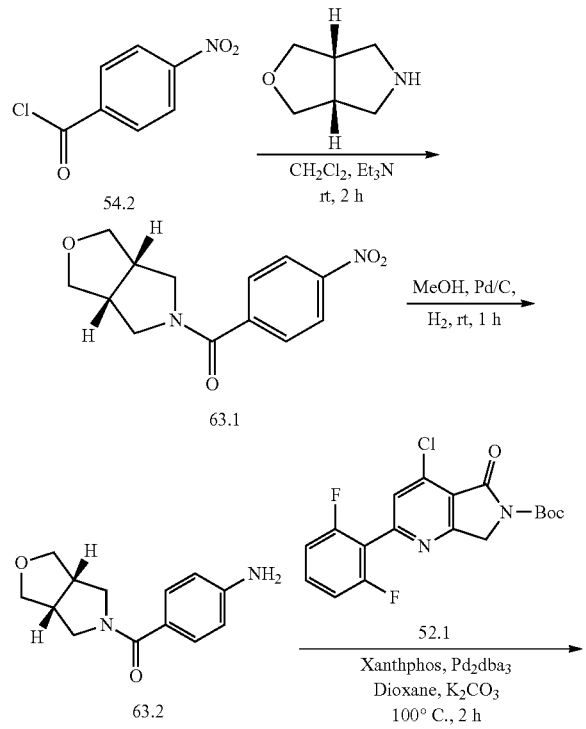

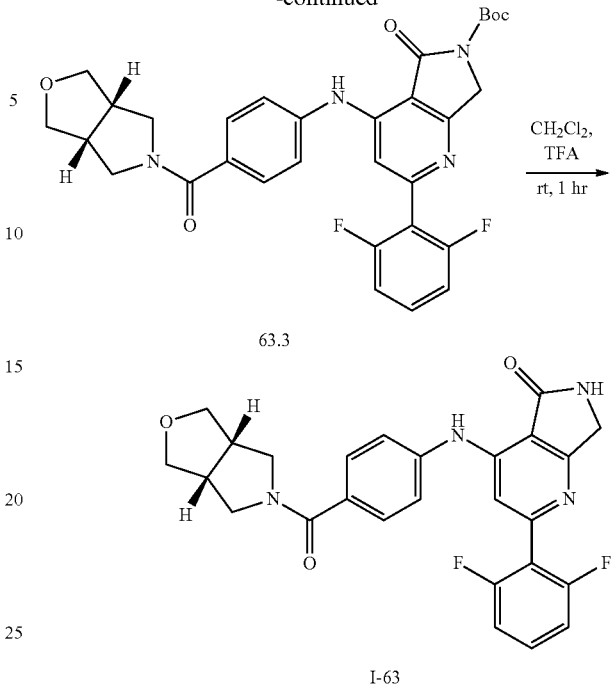

Synthesis of compound 63.1. To a solution of 54.2 (0.124 g, 0.668 mmol, 1.0 eq) in THF (3.0 mL) was added Et$_3$N (0.202 g, 2.0 mmol, 3.0 eq) and (3aR,6aS)-hexahydro-1H-furo[3,4-c]pyrrole (0.1 g, 0.668 mmol, 1.0 eq) dropwise. The reaction was stirred at room temperature for 2 hours. After completion of the reaction, mixture was quenched with satd. NaHCO$_3$ solution and product was extracted with EtOAc. Organic layers were combined, washed with brine, dried over Na$_2$SO$_4$ and concentrated under reduced pressure to obtain pure 63.1 (0.09 g, 53.1%). MS(ES): m/z 262.27 [M+H]$^+$.

Synthesis of compound 63.2. To a suspension of 10% Pd/C (0.050 g) in MeOH (3.5 mL) was added a solution of 63.1 (0.09 g, 0.343 mmol, 1.0 eq) in MeOH (2.5 mL) under N$_2$. Suspension was purged with H$_2$ gas for 1 hour After completion of the reaction, mixture was filtered through celite, washed with MeOH. Obtained filtrate was concentrated under reduced pressure to get pure 63.2 (0.06 g, 75.3%). MS(ES): m/z 232.28 [M+H]$^+$.

Synthesis of compound 63.3. To a solution of 52.1 (0.065 g, 0.17 mmol, 1.0 eq) in 1,4-dioxane (2.0 mL) was added 63.2 (0.040 g, 0.171 mmol, 1.0 eq) and K$_2$CO$_3$ (0.047 g, 0.342 mmol, 2.0 eq). The reaction mixture was degassed for 10 minutes using argon, then Pd$_2$(dba)$_3$ (0.015 g, 0.017 mmol, 0.1 eq) and Xantphos (0.020 g, 0.034 mmol, 0.2 eq) were added. The reaction was stirred at 100° C. for 2 hours. After completion of the reaction, mixture was poured into water and product was extracted with EtOAc. Organic layers were combined, washed with brine, dried over Na$_2$SO$_4$ and concentrated under reduced pressure to obtain crude material. The crude was purified by column chromatography to furnish 63.3 (0.065 g, 66.0%). MS(ES): m/z 576.60 [M+H]$^+$.

Synthesis of compound I-63. Compound 63.3 (0.065 g, 0.112 mmol, 1.0 eq) was dissolved in CH$_2$Cl$_2$ (3.0 mL) and TFA (0.3 mL) was added to the reaction mixture. The reaction was stirred at room temperature for 1 hour. After completion of the reaction, mixture was poured into water, basified with satd. NaHCO$_3$ and extracted with EtOAc.

Organic layers were combined, dried over Na₂SO₄ and concentrated under reduced pressure to obtain crude material. The crude was purified by trituration with n-pentane and Et₂O to get pure I-63 (0.040 g, 74.5%). MS(ES): m/z 476.48 [M+H]⁺; ¹H NMR (DMSO-d₆, 400 MHz): δ 9.17 (s,1H), 8.78 (s,1H), 7.56-7.50 (m,3H), 7.42-7.40 (d,2H), 7.24-7.20 (t,3H), 4.41 (s,2H), 3.71 (m,4H), 3.46 (m,4H), 2.89 (m,2H).

Example 64

Synthesis of 6-((2-(2,6-difluorophenyl)-5-oxo-6,7-dihydro-5H-pyrrolo[3,4-b]pyridin-4-yl)amino)-2-methyl-3,4-dihydroisoquinolin-1 (2H)-one, I-64

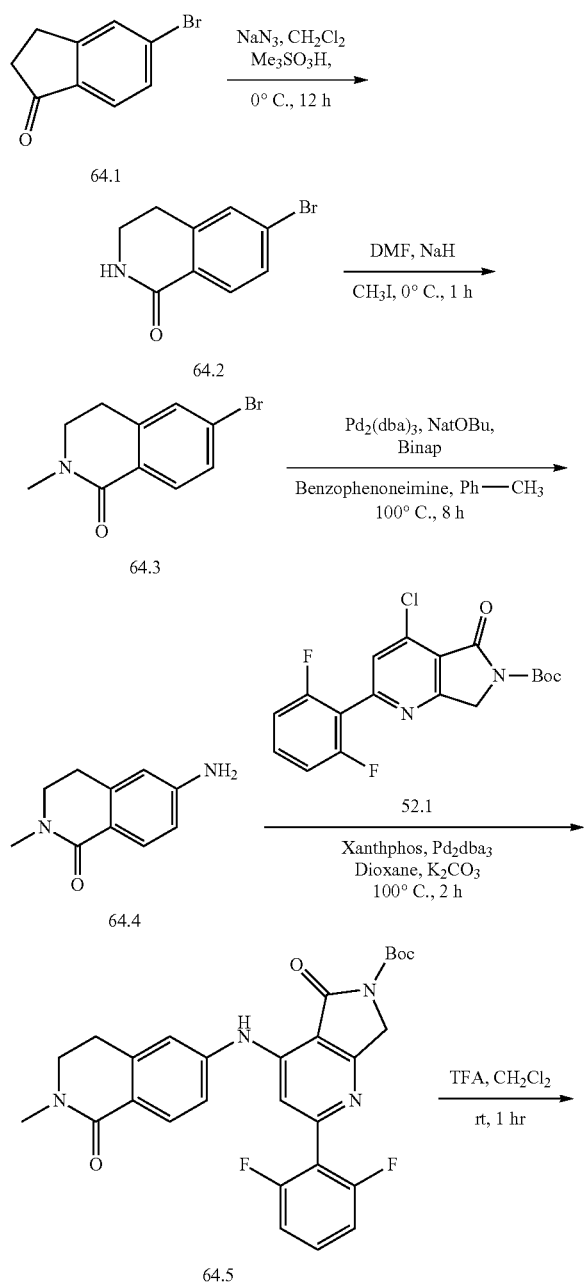

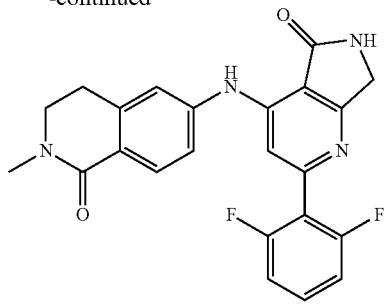

I-64

Synthesis of compound 64.2. 2-Methane sulphonic acid (3.1 mL, 47.39 mmol, 10.0 eq) was added to a mixture of 64.1 (1.0 g, 4.74 mmol, 1.0 eq) in CH₂Cl₂ (10.0 mL) at 0° C. Sodium azide (0.62 g, 9.48 mmol, 2.0 eq) was added slowly in portions. After completion of the addition, mixture was stirred for additional 12 hours. After completion of reaction, aqueous mixture of NaOH (20%) was added until the mixture was slightly basic. The mixture was extracted with CH₂Cl₂. Organic layers were combined and solvents evaporated under reduced pressure. The crude material was purified by column chromatography to provide 64.2 (0.5 g, 46.7%). MS(ES): m/z 226.07 [M+H]⁺.

Synthesis of compound 64.3. Compound 64.2 (0.5 g, 2.21 mmol, 1.0 eq) was dissolved in DMF (3.5 mL) and NaH (0.076 g, 3.32 mmol, 1.5 eq) was added to the reaction mixture at 0° C. Methyl iodide (0.47 g, 3.32 mmol, 1.5 eq) was added to the reaction mixture dropwise at 0° C. The reaction was stirred at 0° C. for 1 hour. After completion of the reaction, the mixture was quenched with 2N HCl solution and the product was extracted with EtOAc. Organic layers were combined, washed with brine, dried over Na₂SO₄ and concentrated under reduced pressure to obtain crude material. The crude was purified by column chromatography to furnish 64.3 (0.25 g, 47.1%). MS(ES): m/z 240.10 [M+H]⁺.

Synthesis of compound 64.4. To a solution of compound 64.3 (0.25 g, 1.04 mmol, 1.0 eq) in toluene (1.0 mL) was added benzophenonimine (0.21 g, 1.14 mmol, 1.1 eq) and NaOBuᵗ (0.15 g, 1.56 mmol, 1.5 eq). The mixture was degassed for 10 minutes using argon, then Pd₂(dba)₃ (0.009 g, 0.01 mmol, 0.01 eq) and BINAP (0.029 g, 0.052 mmol, 0.05 eq) were added. The reaction was then heated at 100° C. for 8 hours. After completion, reaction mixture was poured into water and product was extracted with EtOAc. Organic layers were combined, washed with brine, dried over Na₂SO₄ and concentrated under reduced pressure to obtain crude material. The crude was purified by column chromatography to provide 64.4 (0.04 g, 21.8%). MS(ES): m/z 176.22 [M+H]⁺.

Synthesis of compound 64.5. To a mixture of 52.1 (0.060 g, 0.157 mmol, 1.0 eq) in 1,4-dioxane (1.5 mL) was added 64.4 (0.027 g, 0.157 mmol, 1.0 eq) and K₂CO₃ (0.065 g, 0.47 mmol, 3.0 eq). The reaction mixture was degassed with argon for 10 minutes then Pd₂(dba)₃ (0.014 g, 0.015 mmol, 0.1 eq) and Xantphos (0.018 g, 0.031 mmol, 0.2 eq) were added. Suspension was degassed again for 5 minutes. The reaction was stirred at 100° C. for 2 hours. After completion of the reaction, mixture was poured into water and product was extracted with EtOAc. Organic layers were combined, washed with brine, dried over Na₂SO₄ and concentrated under reduced pressure to obtain crude material. The crude was purified by column chromatography to provide 64.5 (0.038 g, 46.3%). MS(ES): m/z 520.54 [M+H]⁺.

Synthesis of compound I-64. The compound 64.5 (0.038 g, 0.073 mmol, 1.0 eq) was dissolved in CH$_2$Cl$_2$ (1.0 mL) and TFA (0.5 mL) was added to the reaction mixture. The reaction was stirred at room temperature for 1 hour. After completion of reaction, mixture was poured into water, basified with satd. NaHCO$_3$ solution and product was extracted with EtOAc. Organic layers were combined, washed with brine, dried over Na$_2$SO$_4$ and concentrated under reduced pressure to obtain crude material. The crude was purified by column chromatography to furnish I-64 (0.023 g, 74.9%). MS(ES): m/z 420.42 [M+H]⁺; ¹H NMR (DMSO-d$_6$, 400 MHz): δ 9.23 (s,1H), 8.80 (s,1H), 7.86-7.84 (d,1H), 7.56-7.52 (m,1H), 7.33-7.20 (m,5H), 4.41 (s,2H), 3.55-3.51 (t,2H), 3.00 (s,3H), 2.99-2.95 (t,2H).

Example 65

Synthesis of 4-((5-(2,5-dioxa-8-azaspiro[3.4]octan-8-yl)pyridin-2-yl)amino)-2-(2,6-difluorophenyl)-6,7-dihydro-5H-pyrrolo[3,4-b]pyridin-5-one, I-65

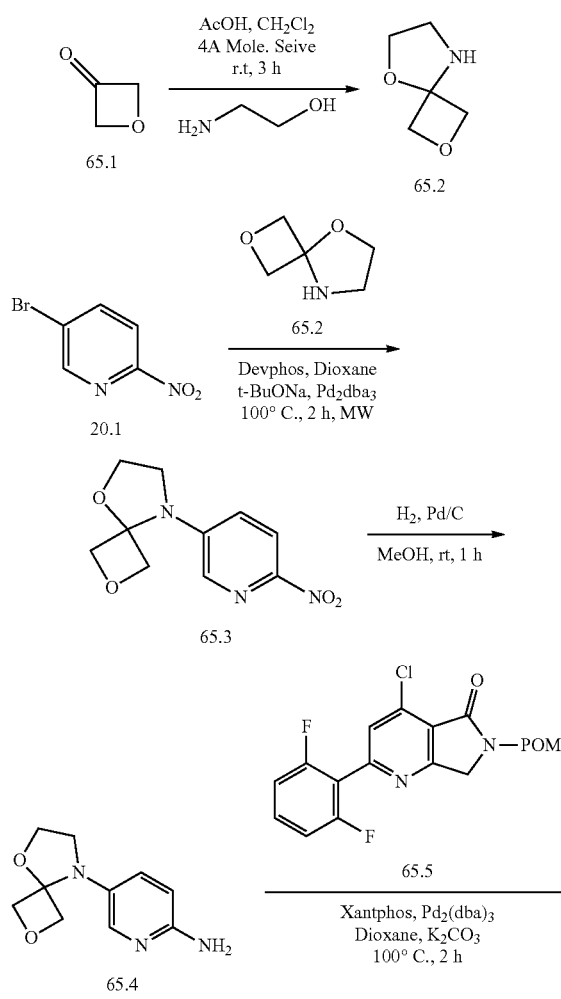

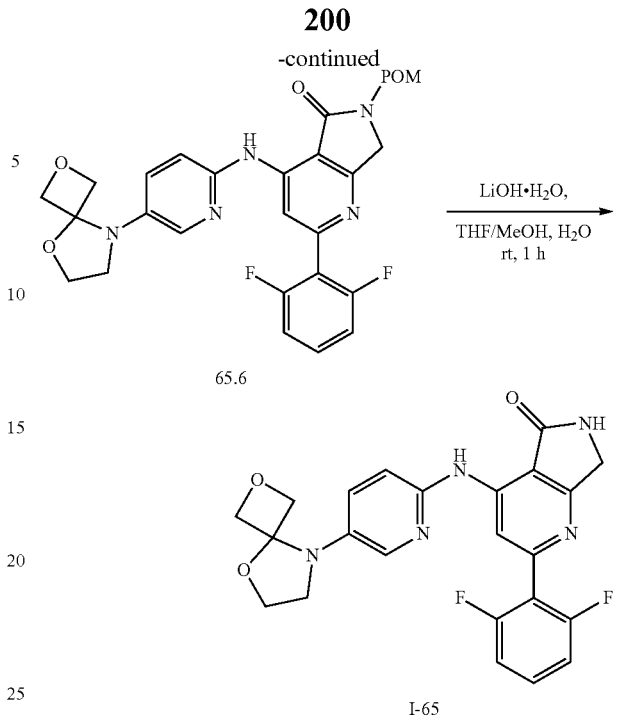

Synthesis of compound 65.2. To a stirred solution of 2-aminoethan-1-ol (1.0 g, 16.37 mmol, 1.0 eq) in CH$_2$Cl$_2$ (10.0 mL) at room temperature was added 65.1 (1.29 g, 18.0 mmol, 1.1 eq), AcOH (0.098 g, 1.64 mmol, 0.1 eq) and molecular sieves (1.0 g). The reaction was stirred at room temperature for 3 hours. After completion of the reaction, mixture was filtered, concentrated under reduced pressure. The crude was purified by column chromatography to provide 65.2 (0.54 g, 33.8%). MS(ES): m/z 115.13 [M+H]⁺.

Synthesis of compound 65.3. To a solution of 20.1 (0.5 g, 2.46 mmol, 1.0 eq) in 1,4-dioxane (8.0 mL) were added compound 65.2 (0.283 g, 2.46 mmol, 1.0 eq) and NaOBu$^t$ (0.472 g, 4.92 mmol, 2.0 eq). The reaction mixture was degassed with argon gas for 15 minutes. Then Pd$_2$(dba)$_3$ (0.023 g, 0.246 mmol, 0.1 eq) and Devphos (0.193 g, 0.492 mmol, 0.2 eq) were added to the reaction mixture. The reaction mixture was irradiated in microwave at 100° C. for 2 hours. After completion of the reaction, mixture was quenched with water and the product was extracted with EtOAc. Organic layers were combined, washed with brine and concentrated under reduced pressure to get crude material. The crude was purified by column chromatography to provide 65.3 (0.165 g, 28.2%). MS(ES): m/z 237.22 [M+H]⁺.

Synthesis of compound 65.4. To a suspension of 10% Pd/C (0.030 g) in MeOH (2.0 mL) was added a solution of 65.3 (0.165 g, 0.695 mmol, 1.0 eq) in MeOH (2.0 mL) under N$_2$. Suspension was purged with hydrogen gas for 1 hour. After completion of the reaction, mixture was filtered through celite, washed with MeOH. Obtained filtrate was concentrated under reduced pressure and triturated with pentane to furnish 65.4 (0.14 g, 97.1%). MS(ES): m/z 207.23 [M+H]⁺.

Synthesis of compound 65.6. To a suspension of 10% Pd/C (0.030 g) in MeOH (2.0 mL) was added a solution of 65.3 (0.165 g, 0.695 mmol, 1.0 eq) in MeOH (2.0 mL) under nitrogen atmosphere. Suspension was purged with H$_2$ gas for 1 hour. After completion of the reaction, mixture was filtered through celite, washed with MeOH. Solvents were removed under a reduced pressure and the crude was triturated with pentane to get pure 65.6 (0.14 g, 97.1%). MS(ES): m/z 207.23 [M+H]$^+$.

Synthesis of compound I-65. Compound 65.6 (0.04 g, 0.07 mmol, 1.0 eq) was dissolved in THF/MeOH mixture (4:1) and LiOH (0.011 g, 0.282 mmol, 4.0 eq) in water (1.0 mL) was added. The reaction was stirred at room temperature for 1 hour. After completion of the reaction, mixture was poured into water, basified with satd/. NaHCO$_3$ solution and product was extracted with EtOAc. Organic layers were combined, washed with brine, dried over Na$_2$SO$_4$ and concentrated under reduced pressure to obtain crude material. The crude was purified by trituration with Et$_2$O to get pure I-65 (0.022 g, 68.9%). MS(ES): m/z 451.43 [M+H]$^+$; $^1$H NMR (DMSO-d$_6$, 400 MHz): δ 9.54 (s,1H), 8.83 (s,1H), 8.38 (s,1H), 8.06 (d,1H), 7.58-7.55 (m,2H), 7.27-7.22 (m,3H), 5.04-5.02 (d,2H), 4.69-4.67 (d,2H), 4.41 (s,2H), 4.05-4.03 (m,2H), 3.47-3.44 (m,2H).

Example 66

Synthesis of 2-(2,6-difluorophenyl)-4-((4-(1,1,1,3,3,3-hexafluoro-2-hydroxy-propan-2-yl)phenyl)amino)-6,7-dihydro-5H-pyrrolo[3,4-b]pyridin-5-one, I-66

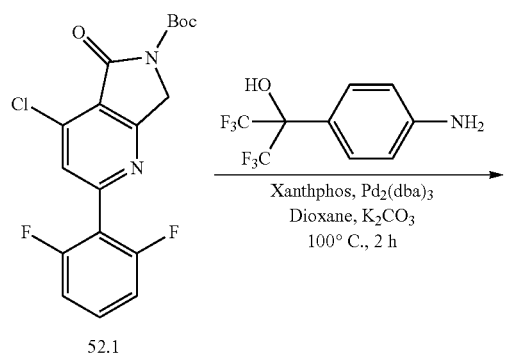

Synthesis of compound 66.1. To a mixture of 52.1 (0.070 g, 0.184 mmol, 1.0 eq) in 1,4-dioxane (3.0 mL) was added 2-(4-aminophenyl)-1,1,1,3,3,3-hexafluoropropan-2-ol (0.048 g, 0.184 mmol, 1.0 eq) and K$_2$CO$_3$ (0.051 g, 0.368 mmol, 2.0 eq). Suspension was degassed for 10 minutes using argon, then Pd$_2$(dba)$_3$ (0.017 g, 0.018 mmol, 0.1 eq) and Xantphos (0.021 g, 0.036 mmol, 0.2 eq) were added. Suspension was degassed for additional 5 minutes. The reaction was stirred 100° C. for 2 hours. After completion of the reaction, mixture was poured into water and product was extracted with EtOAc. Organic layers were combined, washed with brine, dried over Na$_2$SO$_4$ and concentrated under reduced pressure to obtain crude material. The crude was purified by column chromatography to furnish 66.1 (0.064 g, 57.7%). MS(ES): m/z 603.47 [M+H]$^+$.

Synthesis of compound I-66. To a solution of 66.1 (0.064 g, 0.106 mmol, 1.0 eq) in CH$_2$Cl$_2$ (1.5 mL) was added TFA (0.3 mL) at 0° C. Reaction mixture was stirred at room temperature for 1 hour. After completion of the reaction, mixture was poured into water, basified with satd. NaHCO$_3$ and extracted with EtOAc. Organic layers were combined, washed with brine, dried over Na$_2$SO$_4$ and concentrated under reduced pressure to obtain crude which was purified by trituration with Et$_2$O to furnish I-66 (0.038 g, 71.8%). MS(ES): m/z 503.35 [M+H]$^+$; $^1$H NMR (DMSO-d$_6$, 400 MHz): δ 9.22 (s,1H), 8.79 (s,1H), 8.71 (s,1H), 7.69-7.66 (d,2H), 7.58-7.51 (m, 3H), 7.24-7.19 (m,3H), 4.41 (s,2H).

Example 67

Synthesis of 2-(4-((2-(2,6-difluorophenyl)-5-oxo-6,7-dihydro-5H-pyrrolo[3,4-b]pyridin-4-yl)amino)phenyl)-N-ethyl-2-methylpropanamide, I-67

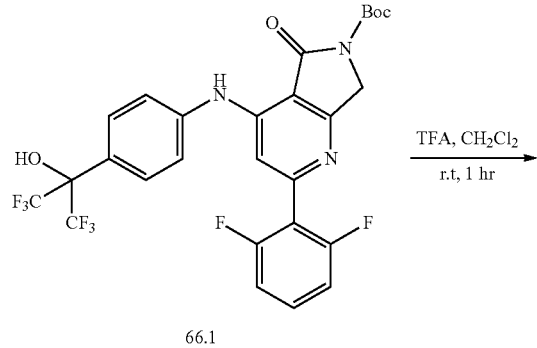

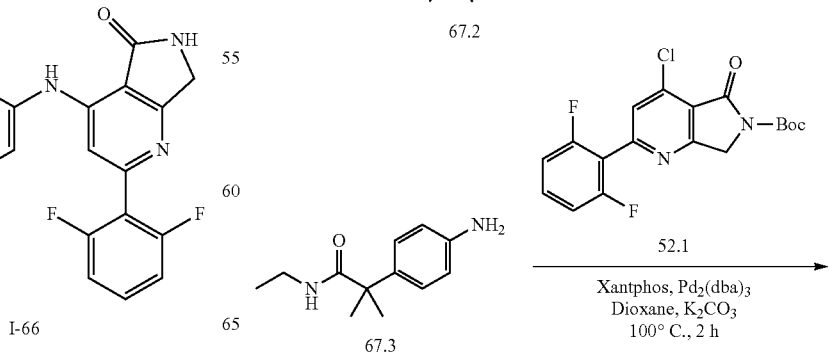

203

-continued

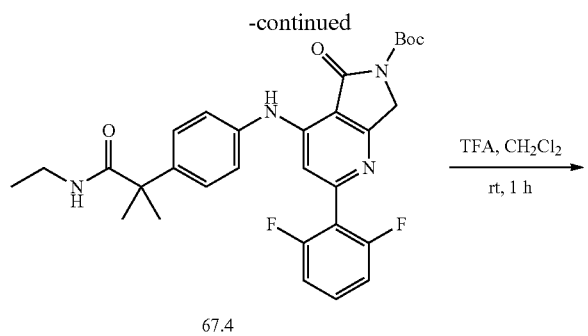

67.4

I-67

Synthesis of compound 67.1. To a solution of NaOBu$^t$ (1.45 g, 15.0 mmol, 1.05 eq) in DMF (50 mL) at 0° C., was added 39.1 (3.0 g, 14.3 mmol, 1.0 eq). After 5 minutes of stirring MeI (2.12 g, 15.0 mmol, 1.05 eq) was added dropwise and the reaction mixture was stirred at 30 minutes at 0° C. After 5 minutes second portion of NaOBu$^t$ (1.45 g, 15.0 mmol, 1.05 eq) was added at 0° C. and the reaction was stirred for 5 minutes. Finally second portion of MeI (2.12 g, 15.0 mmol, 1.05 eq) was added dropwise and the reaction was stirred at 0° C. for 30 minutes. After completion, reaction was quenched with dilute AcOH and the product was extracted with EtOAc. Organic layers were separated, combined, washed with brine solution, dried over Na$_2$SO$_4$ and concentrated under reduced pressure to get crude which was purified by column chromatography to furnish 67.1 (2.0 g, 58.8%). MS (ES): m/z 237.26 [M+H]$^+$.

Synthesis of compound 67.2. To a solution of 67.1 (0.4 g, 1.68 mmol, 1.0 eq) in THF (4.0 mL) was added ethyl amine (1.68 mL, 3.37 mmol, 2.0 eq) and DIPEA (0.6 mL, 3.36 mmol, 2.0 eq). The reaction was cooled to at 0° C. Trimethyl aluminium (4.2 mL, 8.4 mmol, 5.0 eq) was added dropwise at 0° C. to the mixture then the reaction was stirred at reflux temperature for 6 hours. After completion, reaction mixture was quenched with chilled NaHCO$_3$ solution and the product was extracted with EtOAc. Organic layer was separated, washed with brine solution and concentrated under reduced pressure to get crude material. The crude was purified by column chromatography to provide 67.2 (0.24 g, 61.0%). MS(ES): m/z 236.27 [M+H]$^+$.

Synthesis of compound 67.3. To a suspension of 10% Pd/C (0.05 g) in MeOH (2.0 mL) was added a solution of 67.2 (0.243 g, 1.028 mmol, 1.0 eq) in MeOH (2.0 mL) under nitrogen. Hydrogen gas was bubbled into the reaction mixture for 1 hour at room temperature. After completion of thr reaction, mixture was filtered through celite, washed with MeOH and obtained filtrate was concentrated under reduced pressure then triturated with pentane to provide pure 67.3 (0.19 g, 89.6%). MS(ES): m/z 206.29 [M+H]$^+$.

Synthesis of compound 67.4. To a mixture of 67.3 (0.1 g, 0.26 mmol, 1.0 eq) in 1,4-dioxane (3.0 mL) was added

204 compound 67.3 (0.06 g, 0.28 mmol, 1.0 eq) and K$_2$CO$_3$ (0.090 g, 0.65 mmol, 2.5 eq). Reaction mixture was degassed for 10 minutes using argon then Pd$_2$(dba)$_3$ (0.024 g, 0.026 mmol, 0.1 eq) and Xanthpos (0.03 g, 0.052 mmol, 0.2 eq) were added, and again degassed for 5 minutes. The reaction was stirred at 100° C. for 2 hours. After completion of the reaction, mixture was poured into water and product was extracted with EtOAc. Organic layers were combined, washed with brine, dried over Na$_2$SO$_4$ and concentrated under reduced pressure to obtain crude which was purified by column chromatography to provide 67.4 (0.127 g, 87.8%). MS(ES): m/z 550.61 [M+H]$^+$.

Synthesis of compound I-67. To a solution of 67.4 (0.127 g, 0.23 mmol, 1.0 eq) in CH$_2$Cl$_2$ (2.0 mL) TFA (0.5 mL) was added. The reaction mixture was stirred at room temperature for 1 hour. After completion of the reaction, mixture was basified with satd. saturated NaHCO$_3$ solution and extracted with EtOAc. Organic layers were combined, washed with brine, dried over Na$_2$SO$_4$ and concentrated under reduced pressure to obtain crude which was purified by column chromatography and trituration with Et$_2$O to get pure I-67 (0.069 g, 66.4%). MS(ES): m/z 450.49 [M+H]$^+$; $^1$H NMR (DMSO-d$_6$, 400 MHz): δ 8.96 (s,1H), 8.71 (s,1H), 7.52 (m,1H), 7.37-7.31 (m,5H), 7.22-7.18 (t,2H), 7.02 (s,1H), 4.38 (s,2H), 3.05-3.02 (q,2H), 1.42 (s,6H), 0.95-0.92 (t,3H).

Example 68

Synthesis of 4-(benzo[d][1,3]dioxol-5-ylamino)-2-(2,6-difluorophenyl)-6,7-dihydro-5H-pyrrolo[3,4-b]pyridin-5-one, I-68

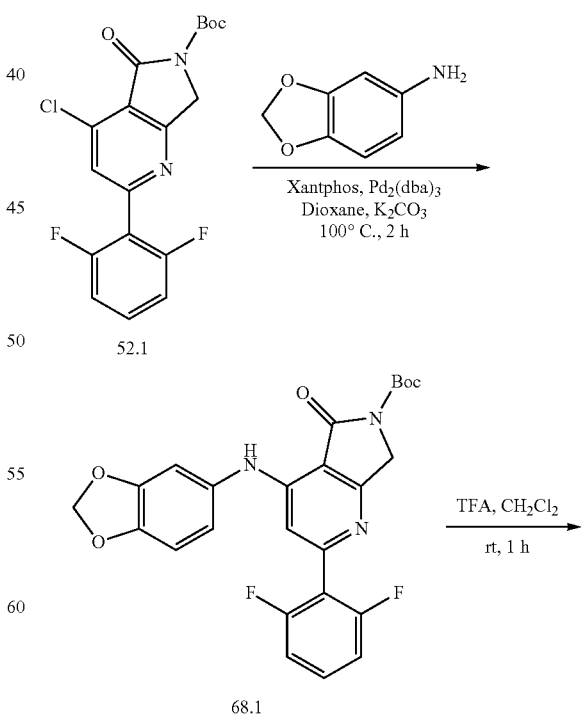

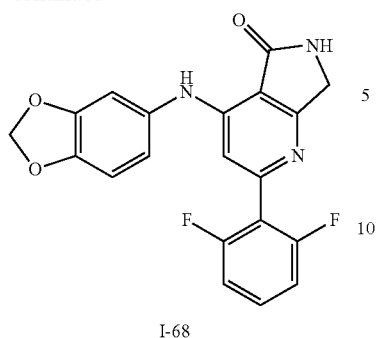

I-68

Synthesis of compound 68.1. To a mixture of 52.1 (0.105 g, 0.394 mmol, 1.0 eq) in 1,4-dioxane (2.0 mL) was added benzo[d][1,3]dioxol-5-amine (0.054 g, 0.394 mmol, 1.0 eq) and $K_2CO_3$ (0.11 g, 0.79 mmol, 2.0 eq). The reaction was degassed using argon, then $Pd_2(dba)_3$ (0.036 g, 0.039 mmol, 0.1 eq) and Xantphos (0.045 g, 0.078 mmol, 0.2 eq) were added. The reaction was stirred at 100° C. for 2 hours. After completion of the reaction, mixture was poured into water and product was extracted with EtOAc. Organic layers were combined, washed with brine, dried over $Na_2SO_4$ and concentrated under reduced pressure to obtain crude material. The crude was purified by column chromatography to provide 68.1 (0.105 g, 55.4%). MS(ES): m/z 481.46 $[M+H]^+$.

Synthesis of compound I-68. To a solution of 68.1 (0.10 g, 0.207 mmol, 1.0 eq) in $CH_2Cl_2$ (2.0 mL) was added TFA (0.3 mL), dropwise at 0° C. under nitrogen. The reaction was stirred at room temperature for 1 hour. After completion of the reaction, mixture was poured into water, basified with satd. $NaHCO_3$ solution and extracted with EtOAc. Organic layers were combined, washed with brine, dried over $Na_2SO_4$ and concentrated under reduced pressure to obtain crude material. The crude was purified by trituration with pentane to get pure I-68 (0.075 g, 94.7%). MS(ES): m/z 381.34 $[M+H]^+$; $^1H$ NMR (DMSO-$d_6$, 400 MHz): δ 8.74 (s,1H), 8.65 (s,1H), 7.53-7.49 (m, 1H), 7.21-7.17 (t,2H), 6.98-6.92 (m,2H), 6.82-6.79 (m,2H), 6.04 (s,2H), 4.37 (s,2H).

Example 69

Synthesis of 4-((2,2-difluorobenzo[d][1,3]dioxol-5-yl)amino)-2-(2,6-difluoro-phenyl)-6,7-dihydro-5H-pyrrolo[3,4-b]pyridin-5-one, I-69

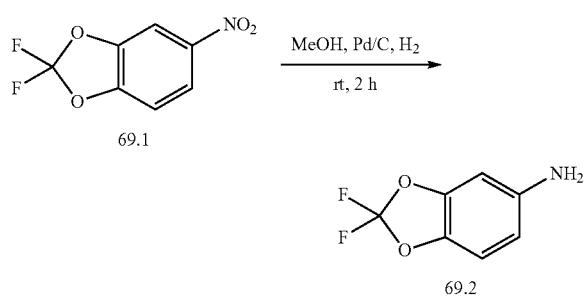

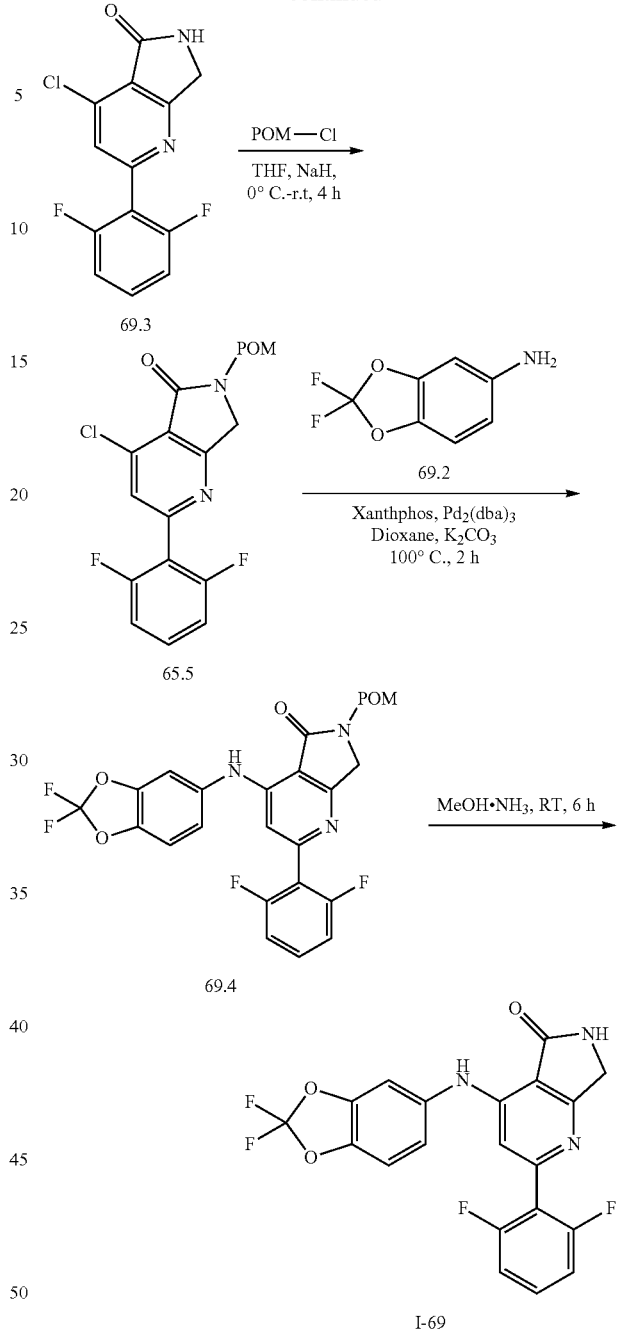

Synthesis of compound 69.2. To a suspension of 10% Pd/C (0.05 g) in MeOH (5.0 mL) was added a solution of 69.1 (0.5 g, 2.46 mmol, 1.0 eq) in MeOH (3.0 mL) under nitrogen. Reaction was purged with $H_2$ gas for 2 hours. After completion of the reaction, mixture was filtered through celite and washed with MeOH. Obtained filtrate was concentrated under reduced pressure to get crude which was purified by trituration with n-hexane to provide 69.2 (0.31 g, 72.5%). MS(ES): m/z 173.12 $[M+H]^+$.

Synthesis of compound 65.5. A solution of NaH (0.01, 3.57 mmol, 2.0 eq) in THF (10 mL) was cooled to 0° C. Compound 69.3 (0.5 g, 1.78 mmol, 1.0 eq) was added and stirred at 0° C. Methyl pivaloyl chloride (0.321 g, 2.14 mmol, 1.2 eq) was added dropwise and the reaction was stirred at room temperature for 4 hours. After completion, the reaction was quenched with water. Product was extracted with EtOAc and washed with NaHCO$_3$ solution. Organic layer was separated, washed with brine, dried over Na$_2$SO$_4$ and concentrated under reduced pressure to get crude. The crude was purified by column chromatography to furnish 65.5 (0.34 g, 58.4%). MS(ES): m/z 326.62 [M+H]$^+$.

Synthesis of compound 69.4. To a solution of compound 65.5 (0.12 g, 0.225 mmol, 1.0 eq) in 1,4-dioxane (3.0 mL) was added compound 69.2 (0.039 g, 0.223 mmol, 1.0 eq) and K$_2$CO$_3$ (0.077 g, 0.564 mmol, 2.5 eq). Suspension was degassed for 10 minutes using argon, then Pd$_2$(dba)$_3$ (0.021 g, 0.023 mmol, 0.1 eq) and Xantphos (0.026 g, 0.045 mmol, 0.2 eq) were added and again degassed for 5 minutes. The reaction was stirred at 100° C. for 2 hours. After completion of the reaction, mixture was poured into water and extracted with EtOAc. Organic layers were combined, washed with brine, dried over Na$_2$SO$_4$ and concentrated under reduced pressure to obtain crude which was purified by column chromatography to provide 69.4 (0.12 g, 69.3%). MS(ES): m/z 463.28 [M+H]$^+$.

Synthesis of compound I-69. To a solution of compound 69.4 (0.12 g, 0.25 mmol, 1.0 eq) in CH$_2$Cl$_2$ (3.0 mL) was added TFA (1.5 mL). The reaction was stirred at room temperature for 1 hour. After completion of the reaction, mixture was poured into water, basified with satd. NaHCO$_3$ solution and product was extracted with ethyl acetate. Organic layer was combined, washed with brine solution, dried over Na$_2$SO$_4$ and concentrated under reduced pressure to obtain crude which was purified by column chromatography and trituration to furnish I-69 (0.037 g, 34.8%). MS(ES): m/z 417.32 [M+H]$^+$; $^1$H NMR (DMSO-d$_6$, 400 MHz): δ 8.98 (s,1H), 8.71 (s,1H), 7.54-7.41 (m,3H), 7.21-7.17 (m,3H), 6.97 (s,1H), 4.39 (s,2H).

Example 70

Synthesis of 2-(2,6-difluorophenyl)-4-((3,3-dimethyl-2,3-dihydrobenzofuran-6-yl)amino)-6,7-dihydro-5H-pyrrolo[3,4-b]pyridin-5-one, I-70

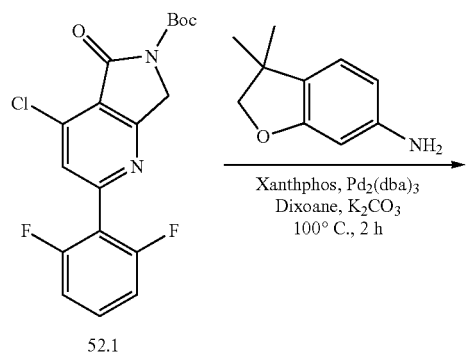

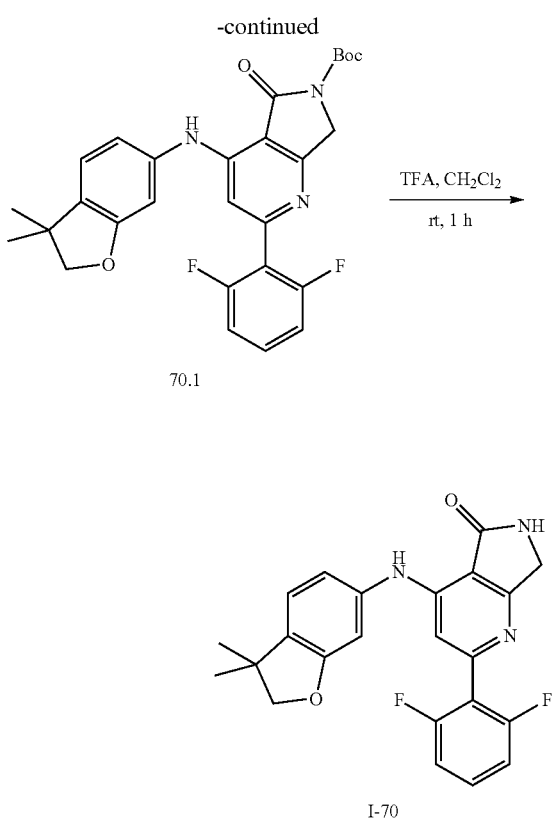

Synthesis of compound 70.1. To a mixture of 52.1 (0.1 g, 0.26 mmol, 1.0 eq) in 1,4-dioxane (3.0 mL) was added 3,3-dimethyl-2,3-dihydrobenzofuran-6-amine (0.042 g, 0.262 mmol, 1.0 eq) and K$_2$CO$_3$ (0.09 g, 0.657 mmol, 2.5 eq). The reaction mixture was degassed for 10 minutes using argon, then Pd$_2$(dba)$_3$ (0.024 g, 0.026 mmol, 0.1 eq) and Xantphos (0.030 g, 0.052 mmol, 0.2 eq) were added. Suspension was then degassed for additional 5 minutes. The reaction was then heated at 100° C. for 2 hours. After completion of the reaction, mixture was poured into water and product was extracted with EtOAc. Organic layers were combined, washed with brine solution, dried over Na$_2$SO$_4$ and concentrated under reduced pressure to obtain crude material. This crude was purified by column chromatography to furnish 70.1 (0.076 g, 57.0%). MS(ES): m/z 507.54 [M+H]$^+$.

Synthesis of compound I-70. A solution of 70.1 (0.076 g, 0.149 mmol, 1.0 eq) in CH$_2$Cl$_2$ (3.0 mL) was added TFA (1.0 mL). The reaction was stirred at room temperature for 1 hour. After completion of the reaction, mixture was poured into water, basified with satd. NaHCO$_3$ solution and product was extracted with EtOAc. Organic layers were combined, washed with brine, dried over Na$_2$SO$_4$ and concentrated under reduced pressure to obtain crude. The crude was purified by column chromatography and trituration to furnish I-70 (0.05 g, 82.0%). MS(ES): m/z 407.42 [M+H]$^+$; $^1$H NMR (DMSO-d$_6$, 400 MHz): δ 8.88 (s,1H), 8.69 (s,1H), 7.56-7.49 (m,1H), 7.23-7.18 (m,3H), 7.00 (s,1H), 6.85-6.82 (dd,1H),6.78-6.77 (d,1H), 4.37 (s,2H) 4.23 (s,2H), 1.28 (s,6H).

Example 71

Synthesis of 2-(2,6-difluorophenyl)-4-((2,2-dimethyl-2,3-dihydrobenzofuran-6-yl)amino)-6,7-dihydro-5H-pyrrolo[3,4-b]pyridin-5-one, I-71

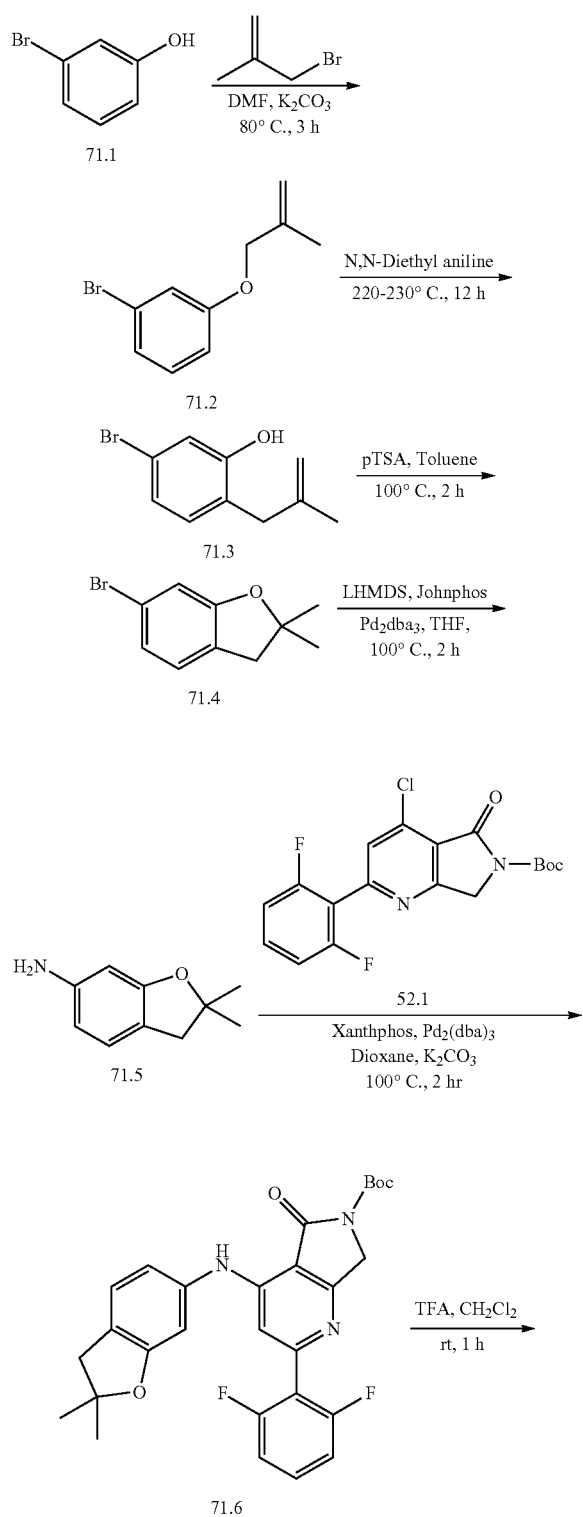

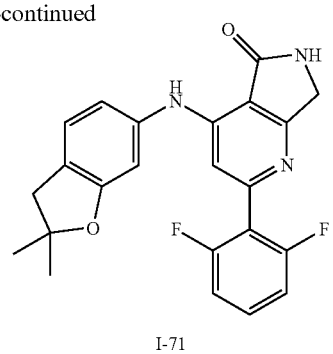

I-71

Synthesis of compound 71.2. To a mixture of 71.1 (2.13 g, 12.3 mmol, 1.0 eq) and K$_2$CO$_3$ (3.4 g, 24.6 mmol, 2.0 eq) in DMF (10 mL) at room temperature, was added 3-bromo-2-methylprop-1-ene (2.0 g, 14.8 mmol, 1.2 eq). Reaction mixture was stirred at 80° C. for 3 hours. After completion of the reaction, mixture was poured into water and extracted with EtOAc. Organic layers were combined, washed with brine, dried over Na$_2$SO$_4$ and concentrated under reduced pressure to provide 71.2 (2.9 g, 99.0%). MS(ES): m/z 227.10 [M+H]$^+$.

Synthesis of compound 71.3. A solution of 71.2 (2.9 g, 12.8 mmol, 1.0 eq) in N,N-diethyl aniline (10 mL) was stirred under argon at 210-220° C. for 12 hours. After completion of the reaction, mixture was cooled to room temperature, acidified with 1N HCl extracted with EtOAc. Organic layers were combined, washed with brine, dried over Na$_2$SO$_4$ and concentrated under reduced pressure to obtain crude material. The crude was purified by column chromatography to provide 71.3 (0.55 g, 18.9%). MS(ES): m/z 227.10 [M+H]$^+$.

Synthesis of compound 71.4. To a solution of compound 71.3 (0.55 g, 2.43 mmol, 1.0 eq) in dry toluene (6.0 mL), p-toluene sulphonic acid (46 mL) was added. Reaction mixture was stirred at 100° C. for 2 hours. After completion of the reaction, mixture was cooled to room temperature and basified with 1N NaOH solution and extracted with EtOAc. Organic layers were combined, washed with brine, dried over Na$_2$SO$_4$ and concentrated under reduced pressure to obtain crude which was purified by column chromatography to provide 71.4 (0.45 g, 81.8%). MS(ES): m/z 227.10 [M+H]$^+$.

Synthesis of compound 71.5. To a solution of 71.4 (0.25 g, 1.10 mmol, 1.0 eq) in THF (5.0 mL) was added CyJohnphos (0.077 g, 0.2 2 mmol, 0.2 eq) and Pd$_2$(dba)$_3$ (0.1 g, 0.11 mmol, 0.1 eq). Suspension was degassed with argon, LHMDS (0.919 g, 5.50 mmol, 5.0 eq) was added and the mixture was stirred at 100° C. for 2 hours. After completion of the reaction, mixture was poured into dilute HCl and extracted with EtOAc. Aqueous fractions were basified with saturated NaHCO$_3$ solution and extracted with EtOAc. Organic layers were combined, washed with brine, dried over Na$_2$SO$_4$ and concentrated under reduced pressure to obtain crude. The crude was purified by column chromatography to provide 71.5 (0.087 g, 48.4%). MS(ES): m/z 163.22 [M+H]$^+$.

Synthesis of compound 71.6. To a mixture of 52.1 (0.11 g, 0.29 mmol, 1.15 eq) in 1,4-dioxane (2.5 mL) was added compound 1.4 (0.042 g, 0.251 mmol, 1.0 eq) and K$_2$CO$_3$ (0.069 g, 0.502 mmol, 2.0 eq). The reaction mixture was degassed for 10 minutes using argone, then Pd$_2$(dba)$_3$ (0.023 g, 0.021 mmol, 0.1 eq) and Xantphos (0.029 g, 0.050 mmol, 0.2 eq) were added, and again degassed for 5 minutes.

Reaction was stirred at 100° C. for 2 hours. After completion of the reaction, mixture was poured into water and extracted with EtOAc. Organic layers were combined, washed with brine, dried over $Na_2SO_4$ and concentrated under reduced pressure to obtain crude material. The crude was purified by column chromatography to furnish 71.6 (0.095 g, 64.8%). MS(ES): m/z 507.54 [M+H]+.

Synthesis of compound I-71. To a solution of compound 71.6 (0.095 g, 0.187 mmol, 1.0 eq) in $CH_2Cl_2$ (2.0 mL) was added TFA (0.5 mL). The reaction was stirred at room temperature for 1 hour. After completion of the reaction, mixture was poured into water, basified with satd. $NaHCO_3$ and extracted with EtOAc. Organic layers were combined, washed with brine, dried over $Na_2SO_4$ and concentrated under reduced pressure to obtain crude which was purified by column chromatography to provide I-71 (0.041 g, 53.8%). MS(ES): m/z 407.42 [M+H]+; $^1H$ NMR ($CDCl_3$, 400 MHz): δ 8.67 (s,1H), 7.39-7.31 (m,1H), 7.14-7.10 (m,2H), 7.02-6.96 (m,2H), 6.77-6.74 (dd,1H), 6.71-6.70 (d,1H), 5.98 (s,1H), 4.50 (s,2H), 3.01 (s,2H), 1.50 (s,6H).

Example 72

Synthesis of 2-(2,6-difluorophenyl)-4-((4-oxochroman-7-yl)amino)-6,7-dihy-dro-5H-pyrrolo[3,4-b]pyridin-5-one, I-72

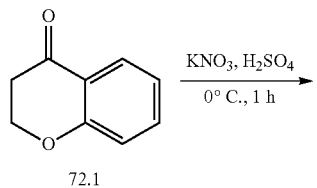

72.1

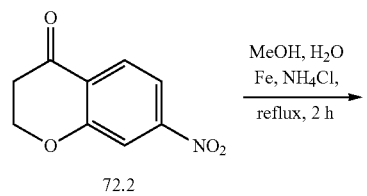

72.2

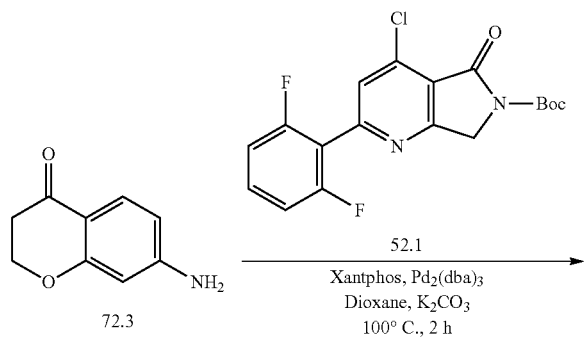

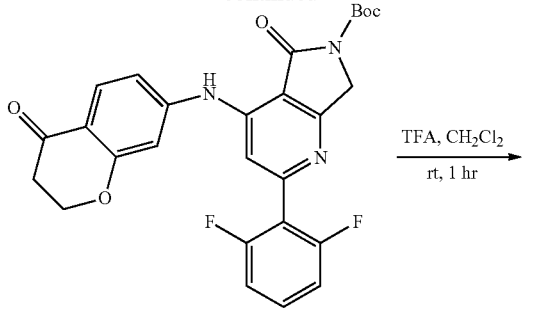

72.3

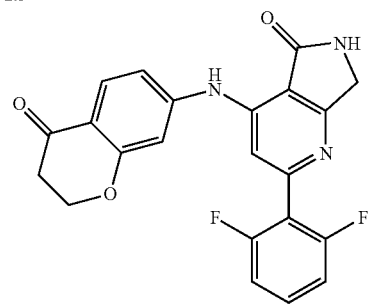

I-72

Synthesis of compound 72.2. To a solution of 72.1 (1.0 g, 6.7 mmol, 1.0 eq) in concentrated $H_2SO_4$ (20 mL) was added a solution of $KNO_3$ (0.75 g, 7.4 mmol, 1.1 eq) in sulphuric acid (13 mL) at 0° C. The reaction was stirred at 0° C. for 1 hour. After completion of the reaction, mixture was poured into ice-water. White precipitate was filtered off, washed with water and dried. Solids were triturated with EtOAc, filtered and driedunder vaccum to get 72.1 (1.0 g, 76.7%). MS(ES): m/z 193.16 [M+H]+.

Synthesis of compound 72.3. To a suspension of compound 72.1 (0.1 g, 0.5 mmol, 1.0 eq) in MeOH (4.0 mL) and water (1.0 mL) was added $NH_4Cl$ (0.26 g, 5.0 mmol, 10 eq) and iron powder (0.28 g, 5 mmol, 10 eq). The reaction was stirred at reflux for 2 hours. After completion of the reaction, mixture was partioned between water and EtOAC, filtered through celite. Organic layer was dried over $Na_2SO_4$ and concentrated under reduced pressure to obtain crude. The crude was purified by column chromatography to provide 72.3 (0.065 g, 76.9%). MS(ES): m/z 163.18 [M+H]+.

Synthesis of compound 72.4. To a mixture of 52.1 (0.1 g, 0.262 mmol, 1.0 eq) in 1,4-dioxane (2.5 mL) was added compound 72.3 (0.051 g, 0.315 mmol, 1.2 eq) and $K_2CO_3$ (0.054 g, 0.363 mmol, 1.5 eq). Mixture was degassed for 10 minutes using argon, then $Pd_2(dba)_3$ (0.024 g, 0.026 mmol, 0.1 eq) and Xantphos (0.03 g, 0.052 mmol, 0.2 eq) were added and again degassed for 5 minutes. The reaction was stirred at 100° C. for 2 hours. After completion of the reaction, mixture was poured into water and product was extracted with EtOAc. Organic layers were combined, washed with brine, dried over $Na_2SO_4$ and concentrated under reduced pressure to obtain crude material. The crude was purified by column chromatography to furnish 72.4 (0.10 g, 77.3%). MS(ES): m/z 507.49 [M+H]+.

Synthesis of compound I-72. To a solution of 72.4 (0.103 g, 0.202 mmol, 1.0 eq) in $CH_2Cl_2$ (3.0 mL) was added TFA (1.0 mL). Reaction mixture was stirred at room temperature for 1 hour. After completion of the reaction, mixture was poured into water, basified with satd. $NaHCO_3$ and extracted with EtOAc. Organic layers were combined, washed with brine, dried over Na₂SO₄ and concentrated under reduced pressure to obtain the crude which was purified by column chromatography to furnish I-72 (0.070 g, 84.7%). MS(ES): m/z 407.38 [M+H]⁺; ¹H NMR (DMSO-d₆, 400 MHz): δ 8.89 (s,1H), 8.67 (s,1H), 7.67-7.66 (d,1H), 7.57-7.47 (m,2H), 7.21-7.17 (t,2H), 7.11-7.08 (d,1H), 6.76 (s,1H), 4.56-4.53 (t,2H), 4.38 (s,2H), 2.81-2.78 (t,2H).

Example 73

Synthesis of 2-(2,6-difluorophenyl)-4-((6-((3aR,6aS)-tetrahydro-1H-furo[3,4-c]pyrrol-5(3H)-yl)pyridin-3-yl)amino)-6,7-dihydro-5H-pyrrolo[3,4-b]pyridin-5-one. I-73

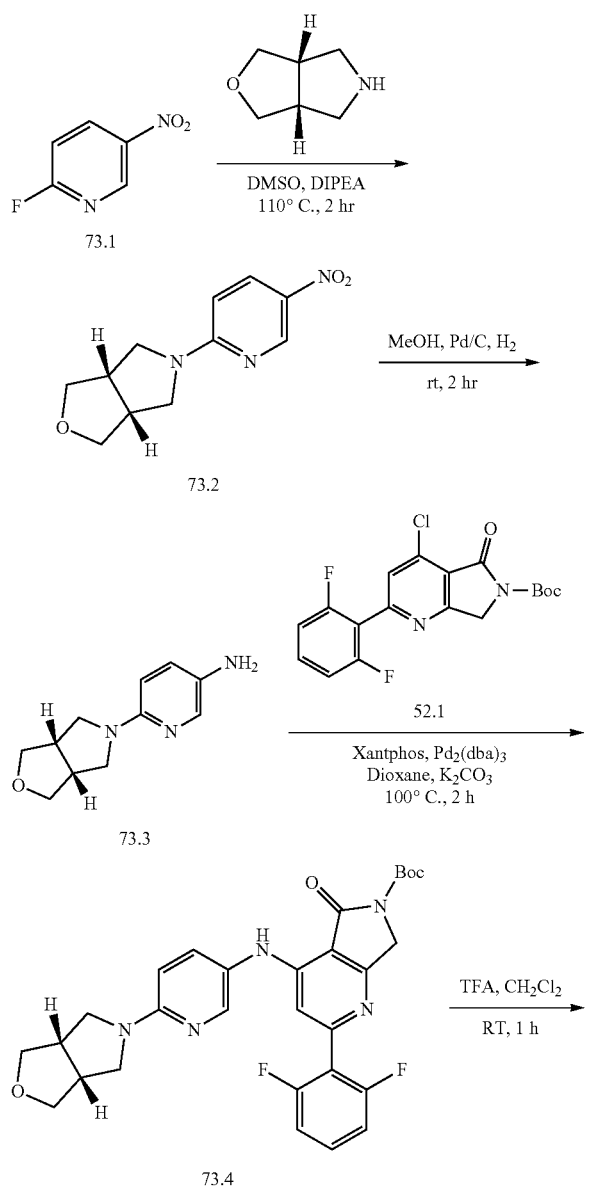

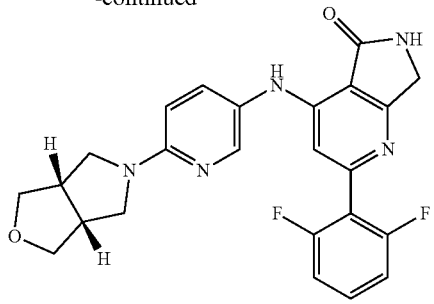

I-73

Synthesis of compound 73.2. To a stirred solution of 73.1 (0.19 g, 1.336 mmol, 1.0 eq) and (3aR,6aS)-hexahydro-1H-furo[3,4-c]pyrrole (0.2 g, 1.34 mmol, 1.0 eq) in dry DMSO (5.0 mL), was added DIPEA (2.37 mL, 13.36 mmol, 10.0 eq). The reaction was stirred at 110° C. for 2 hours. After completion of the reaction, mixture was poured into water and extracted with EtOAc. Organic layers were combined, washed with brine, dried over Na₂SO₄ and concentrated under reduced pressure to obtain crude material. The crude was purified by trituration to afford 73.2 (0.24 g, 76.3%). MS(ES): m/z 235.24 [M+H]⁺.

Synthesis of compound 73.3. To a suspension of 10% Pd/C (0.15 g) in MeOH (2.5 mL) was added a solution of compound 73.2 (0.24 g, 1.02 mmol, 1.0 eq) in MeOH (2.5 mL) under nitrogen. H₂ gas was bubbled into the reaction mixture for 2 hours. After completion of the reaction, mixture was filtered through celite, washed with MeOH. Obtained filtrate was concentrated under reduced pressure to get crude which was purified by column chromatography to furnish 73.3 (0.15 g, 71.6%). MS(ES): m/z 205.26 [M+H]⁺.

Synthesis of compound 73.4. To a mixture of 52.1 (0.1 g, 0.263 mmol, 1.2 eq) in 1,4-dioxane (3.0 mL) was added compound 73.3 (0.045 g, 0.219 mmol, 1.0 eq) and K₂CO₃ (0.06 g, 0.438 mmol, 2.0 eq). The reaction was degassed for 10 minutes using argon, then Pd₂(dba)₃ (0.02 g, 0.021 mmol, 0.1 eq) and Xantphos (0.025 g, 0.043 mmol, 0.2 eq) were added. The reaction was stirred at 100° C. for 2 hours. After completion of the reaction, mixture was poured into the water and product was extracted with EtOAc. Organic layers were combined, washed with brine solution, dried over Na₂SO₄ and concentrated under reduced pressure to obtain crude material which was purified by column chromatography to furnish 73.4 (0.1 g, 69.3%). MS(ES): m/z 549.58 [M+H]⁺.

Synthesis of compound I-73. To a solution of compound 73.4 (0.1 g, 0.18 mmol, 1.0 eq) in CH₂Cl₂ (3.0 mL) was added TFA (0.4 mL). The reaction was stirred at room temperature for 1 hour. After completion of the reaction, mixture was poured into water, basified with satd. NaHCO₃ solution and extracted with EtOAc. Organic layer were combined, washed with brine, dried over Na₂SO₄ and concentrated under reduced pressure to obtain crude material which was purified by trituration with n-pentane and Et₂O to get pure I-73 (0.055 g, 67.3%). MS(ES): m/z 449.46 [M+H]⁺; ¹H NMR (DMSO-d₆, 400 MHz): δ 8.61-8.59 (d,1H), 8.08-8.07(d,1H), 7.53-7.46 (m,2H), 7.19-7.15 (t,2H), 6.56-6.53 (m,2H), 4.36 (s,2H), 3.86-3.82 (m,2H), 3.56-3.51 (m, 4H), 3.33-3.32 (m,2H), 3.00 (m,2H).

Example 74

Synthesis of 3-fluoro-2-(5-oxo-4-((6-((3aR,6aS)-tetrahydro-1H-furo[3,4-c]pyrrol-5(3H)-yl)pyridin-3-yl)amino)-6,7-dihydro-5H-pyrrolo[3,4-b]pyridin-2-yl)benzonitrile, I-74

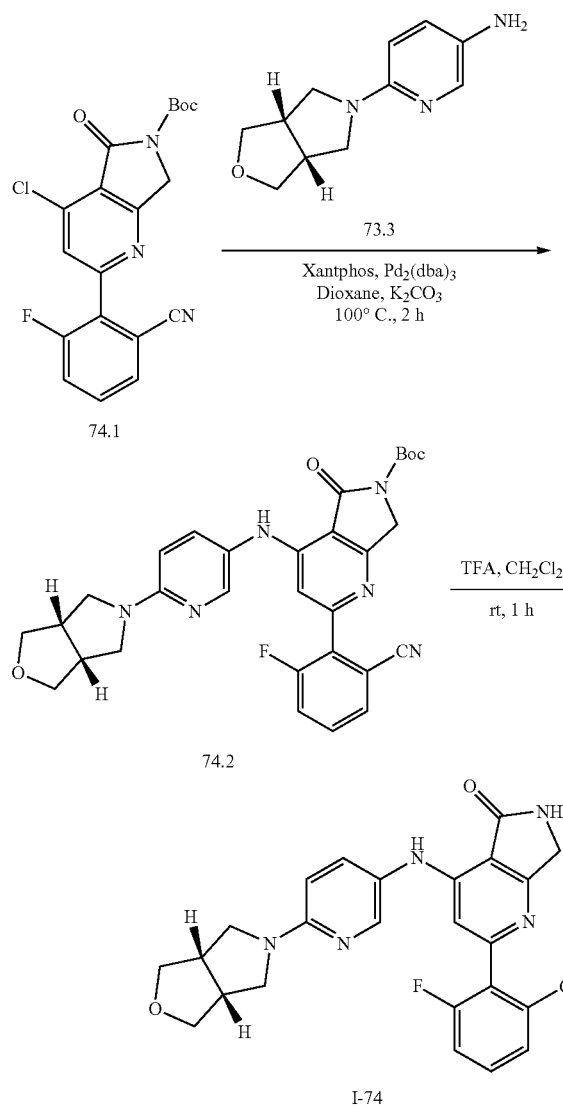

Synthesis of compound 74.2. To a mixture of 74.1 (0.08 g, 0.206 mmol, 1.2 eq) in 1,4-dioxane (2.5 mL) was added 73.3 (0.035 g, 0.172 mmol, 1.0 eq) and $K_2CO_3$ (0.048 g, 0.344 mmol, 2.0 eq). The reaction mixture was degassed for 10 minutes using argon, then $Pd_2(dba)_3$ (0.016 g, 0.017 mmol, 0.1 eq) and Xantphos (0.02 g, 0.034 mmol, 0.2 eq) were added and again degassed for 5 minutes. The reaction was stirred at 100° C. for 2 hours. After completion of the reaction, mixture was poured into water and product was extracted with EtOAc. Organic layers were combined, washed with brine, dried over $Na_2SO_4$ and concentrated under reduced pressure to obtain crude which was purified by column chromatography to furnish 74.2 (0.075 g, 65.3%). MS(ES): m/z 556.60 [M+H]$^+$.

Synthesis of compound I-74. A solution of compound 74.3 (0.075 g, 0.134 mmol, 1.0 eq) in $CH_2Cl_2$ (3.0 mL) was added TFA (0.4 mL). The mixture was stirred at room temperature for 1 hour. After completion of the reaction, mixture was poured into water, basified with satd. $NaHCO_3$ and extracted with EtOAc. Organic layers were combined, washed with brine, dried over $Na_2SO_4$ and concentrated under reduced pressure to obtain crude material. The crude was purified by trituration with n-hexane and $Et_2O$ to provide (0.03 g, 48.8%). MS(ES): m/z 456.48 [M+H]$^+$; $^1$H NMR (MeOD, 400 MHz): δ 8.10 (d,1H), 7.72-7.55 (m,4H), 6.75 (s,1H), 6.67-6.65 (d,1H), 4.48 (s,2H), 4.00-3.96 (m,2H), 3.72-3.65 (m,4H), 3.44-3.43 (m,2H), 3.15-3.12 (m,2H).

Example 75

Synthesis of 2-(4-((5-(6-azaspiro[2.5]octan-6-yl)pyridin-2-yl)amino)-5-oxo-6,7-dihydro-5H-pyrrolo[3,4-b]pyridin-2-yl)-3-fluorobenzonitrile, I-75

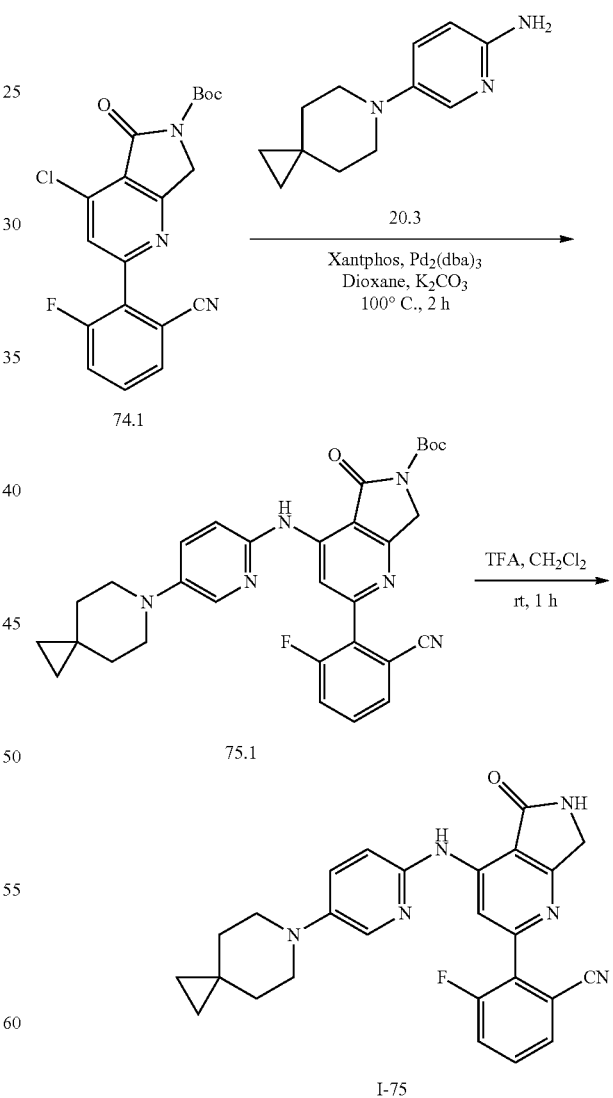

Synthesis of compound 75.1. To a mixture of 74.1 (0.075 g, 0.193 mmol, 1.0 eq) in 1,4-dioxane (2.5 mL) was added compound 20.3 (0.043 g, 0.212 mmol, 1.1 eq) and $K_2CO_3$ (0.080 g, 0.579 mmol, 3.0 eq). The mixture was degassed with argon then Pd$_2$(dba)$_3$ (0.018 g, 0.019 mmol, 0.1 eq) and Xantphos (0.022 g, 0.039 mmol, 0.2 eq) were added, again degassed for 5 min. The reaction was then heated at 100° C. for 0.5 h. After completion of the reaction, mixture was poured into water and extracted with EtOAc. Organic layers were combined, washed with brine solution, dried over Na$_2$SO$_4$ and concentrated under reduced pressure to obtain the crude which was purified by column chromatography to provide 75.1 (0.05 g, 46.6%). MS(ES): m/z 555.6 [M+H]$^+$.

Synthesis of compound I-75. A solution of 75.1 (0.05 g, 0.09 mmol, 1.0 eq) in CH$_2$Cl$_2$ (1.0 mL) was added TFA (0.2 mL). The mixture was stirred at room temperature for 1 hour. After completion of the reaction, mixture was poured into water, basified with satd. NaHCO$_3$ solution and extracted with EtOAc. Organic layers were combined, washed with brine, dried over Na$_2$SO$_4$ and concentrated under reduced pressure to obtain crude which was purified by column chromatography to furnish I-75 (0.04 g, 97.6%). MS(ES): m/z 455.57 [M+H]$^+$; $^1$H NMR (CDCl$_3$, 400 MHz): δ 9.41 (s,1H), 8.65-8.64 (d,1H), 8.07-8.06 (d,1H), 7.64-7.63 (d,1H), 7.55-7.43 (m,2H), 7.35-7.32 (dd,1H), 6.94-6.92 (d,1H), 6.19 (s,1H), 4.55 (s,2H), 3.23-3.20 (t,4H), 1.56-1.53 (t,4H), 0.48 (s,4H).

Example 76

Synthesis of 3-fluoro-2-(5-oxo-4-((5-((3aR,6aS)-tetrahydro-1H-furo[3,4-c]pyrrol-5(3H)-yl)pyridin-2-yl)amino)-6,7-dihydro-5H-pyrrolo[3,4-b]pyridin-2-yl)benzonitrile, I-76

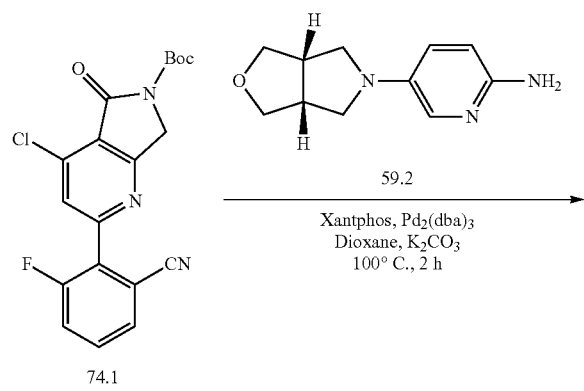

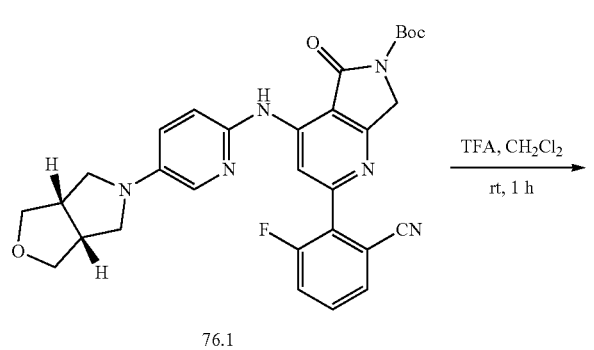

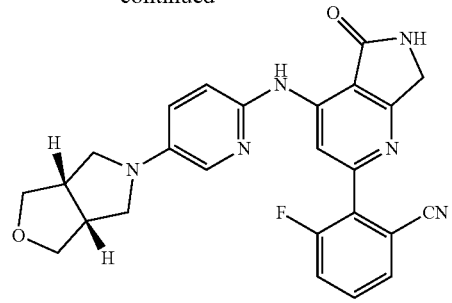

I-76

Synthesis of compound 76.1. To a mixture of 74.1 (0.1 g, 0.258 mmol, 1.0 eq) in 1,4-dioxane (3.0 mL) was added 59.2 (0.052 g, 0.258 mmol, 1.0 eq) and K$_2$CO$_3$ (0.089 g, 0.645 mmol, 2.5 eq). The reaction mixture was degassed for 10 minutes using argon then Pd$_2$(dba)$_3$ (0.023 g, 0.025 mmol, 0.1 eq) and Xantphos (0.029 g, 0.051 mmol, 0.2 eq) were added, and again degassed for 5 minutes. The reaction was stirred at 100° C. for 2 hours. After completion of the reaction, mixture was poured into water and product was extracted with EtOAc. Organic layers were combined, washed with brine solution, dried over Na$_2$SO$_4$ and concentrated under reduced pressure to obtain crude material. The crude was purified by column chromatography to get pure 76.1 (0.075 g, 52.3%). MS(ES): m/z 556.60 [M+H]$^+$.

Synthesis of compound I-76. Compound 76.1 (0.075 g, 0.134 mmol, 1.0 eq) was dissolved in CH$_2$Cl$_2$ (2.0 mL) and TFA (0.3 mL) was added. The reaction was stirred at room temperature for 1 hour. After completion of the reaction, mixture was poured into water, basified with satd. NaHCO$_3$ solution and product was extracted with EtOAc. Organic layers were combined, washed with brine, dried over Na$_2$SO$_4$ and concentrated under reduced pressure to obtain crude material. The crude was purified by column chromatography to get pure I-76 (0.027 g, 43.9%). MS(ES): m/z 456.48 [M+H]$^+$; $^1$H NMR (CDCl$_3$, 400 MHz): δ 9.48 (s,1H), 8.84 (s,1H), 8.39 (s,1H), 7.88-7.86 (dd,1H), 7.80-7.71 (m,3H), 7.18-7.11 (m,2H), 4.41 (s,2H), 3.87-3.83 (dd,2H), 3.53-3.50 (dd,2H), 3.34-3.28 (m,2H), 3.20-3.17 (dd,2H), 2.98 (m, H).

Example 77

Synthesis of 2-(2,6-difluorophenyl)-4-((3-oxo-3H-spiro[benzofuran-2,1'-cyclopropan]-6-yl)amino)-6,7-dihydro-5H-pyrrolo[3,4-b]pyridin-5-one, I-61

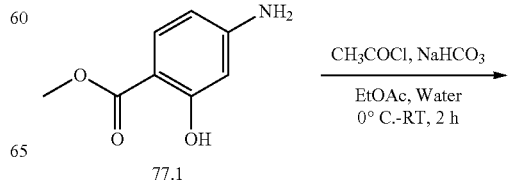

-continued

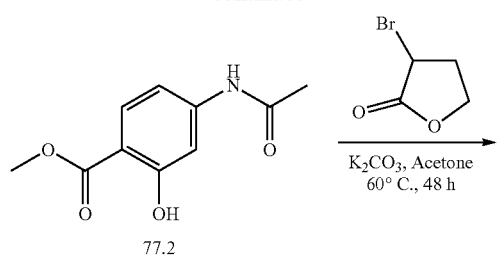

77.2

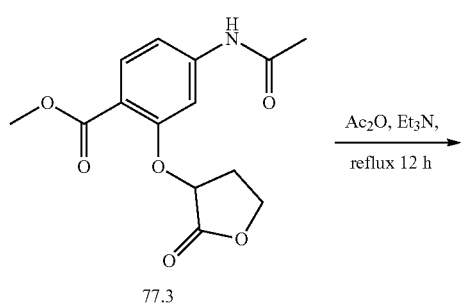

77.3

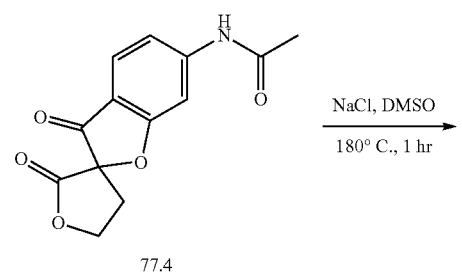

77.4

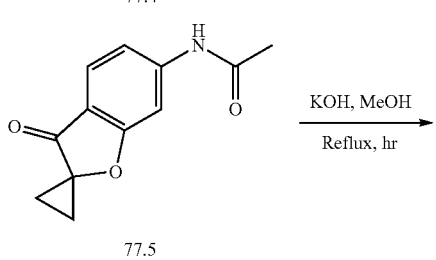

77.5

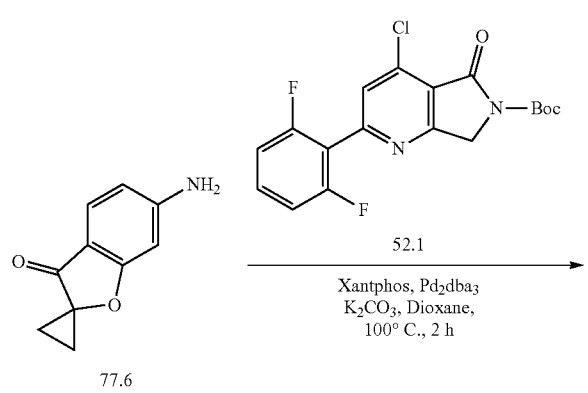

77.6

-continued

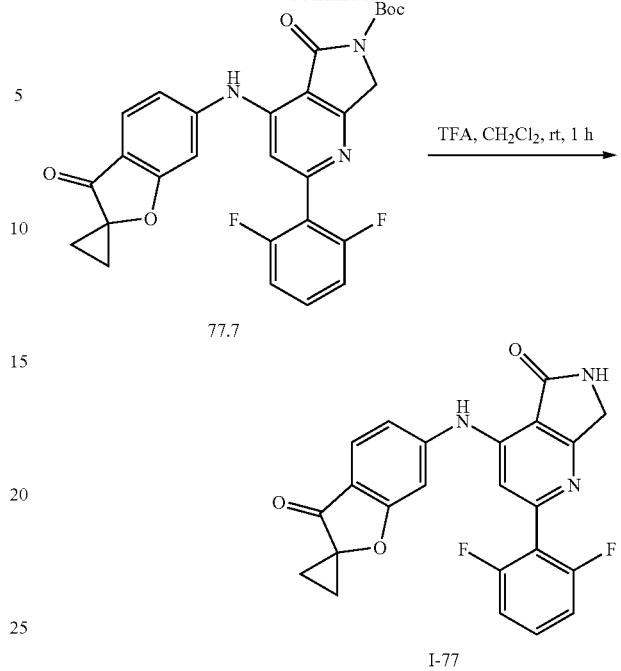

Synthesis of 77.2. Compound 77.1 (2.0 g, 12.0 mmol, 1.0 eq) in EtOAc (30 mL) was added to a cooled solution of NaHCO$_3$ (1.38 g, 16.4 mmol, 1.37 eq) in water (15 mL). The reaction was stirred for 10 minutes. Acetyl chloride (1.28 g, 16.4 mmol, 1.37 eq) was added to the mixture over 15 minutes and the reaction was stirred at room temperature for 2 hours. After completion of the reaction, mixture was quenched with water and extracted with EtOAc. Organic layers were combined, washed with satd. NaHCO$_3$, dried over Na$_2$SO$_4$ and concentrated under reduced pressure to obtain crude material. The crude was purified by trituration with EtOAc and n-hexane to furnish 77.2 (2.2 g, 87.9%). MS(ES): m/z 209.20 [M+H]$^+$.

Synthesis of 77.3. To a solution of compound 77.2 (2.2 g, 10.5 mmol, 1.0 eq) in acetone (5.5 mL) was added K$_2$CO$_3$ (1.8 g, 13.1 mmol, 1.25 eq) and 3-bromodihydrofuran-2 (3H)-one (2.3 g, 14 mmol, 1.33 eq). The reaction was stirred at 60° C. for two days. After completion of the reaction, mixture was cooled to room temperature and the product was filtered through celite. The celite bed was washed with acetone and the filtrate was concentrated under reduced pressure to get crude material. The crude was purified by column chromatography to furnish 77.3 (0.70 g, 22.7%). MS(ES): m/z 294.28 [M+H]$^+$.

Synthesis of 77.4. To the mixture of 77.3 (0.5 g, 1.7 mmol, 1.0 eq) and Ac$_2$O (7.5 mL) was added Et$_3$N (1.5 mL). Reaction was stirred at reflux for 12 hours. After completion of the reaction, mixture was quenched with water and product was extracted with EtOAc. Organic layers were combined, washed with satd. NaHCO$_3$ and brine solutions, dried over Na$_2$SO$_4$ and concentrated under reduced pressure to obtain crude material. The crude was purified by column chromatography to furnish 77.4 (0.21 g, 47.2%). MS(ES): m/z 262.23 [M+H]$^+$.

Synthesis of 77.5. To a solution of 77.4 (0.2 g, 0.76 mmol, 1.0 veq) in DMSO (0.5 mL) was added NaCl (0.009 g, 0.167 mmol, 0.22 eq). Reaction mixture was heated to 150° C. for 1 hour. After completion of the reaction, mixture was quenched with water and product was extracted with EtOAc.

Organic layers were combined, washed with satd. NaHCO₃ and brine solutions, dried over Na₂SO₄ and concentrated under reduced pressure to obtain crude material. The crude was purified by trituration with n-hexane to provide pure 77.5 (0.115 g, 69.2%). MS(ES): m/z 217.22 [M+H]⁺.

Synthesis of 77.6. To a solution of 77.5 (0.1 g, 0.46 mmol, 1.0 eq) in MeOH (2.0 mL) and was added KOH (0.077 g, 1.38 mmol, 3.0 eq). The reaction mixture was stirred at 65° C. for 2 hours. After completion of the reaction, mixture was quenched with water and product was extracted with EtOAc. Organic layers were combined washed with satd. NaHCO₃ and brine solutions, dried over Na₂SO₄ and concentrated under reduced pressure to obtain crude which was purified by trituration with n-hexane to get pure 77.6 (0.074 g, 91.8%). MS(ES): m/z 175.19 [M+H]⁺.

Synthesis of 77.7. To a mixture of 52.1 (0.085 g, 0.22 mmol, 1.0 eq) in 1,4-dioxane (2.0 mL) was added compound 77.6 (0.039 g, 0.22 mmol, 1.0 eq) and K₂CO₃ (0.06 g, 0.44 mmol, 2.0 eq). The reaction mixture was degassed for 10 minutes using argon, then Pd₂(dba)₃ (0.022 g, 0.022 mmol, 0.1 eq) and Xantphos (0.025 g, 0.044 mmol, 0.2 eq) were added. Suspension was degassed for additional 5 minutes. The reaction was stirred at 100° C. for 2 hours. After completion of the reaction, mixture was poured into water and product was extracted with EtOAc. Organic layers were combined, washed with brine solution, dried over Na₂SO₄ and concentrated under reduced pressure to obtain crude which was purified by column chromatography to furnish 77.7 (0.081 g, 69.9%). MS(ES): m/z 519.50 [M+H]⁺.

Synthesis of I-77. To a solution of compound 77.7 (0.081 g, 0.153 mmol, 1.0 eq) in CH₂Cl₂ (1.0 mL) was added TFA (0.5 mL). The reaction was stirred at room temperature for 1 hour. After completion of the reaction, mixture was poured into water, basified with satd. NaHCO₃ solution and extracted with EtOAc. Organic layers were combined, dried over Na₂SO₄ and concentrated under reduced pressure to obtain crude material. The crude was purified by trituration with n-pentane to furnish I-77 (0.049 g, 75.9%). MS(ES): m/z 419.39 [M+H]⁺; ¹H NMR (DMSO-d₆, 400 MHz): δ 9.53 (s,1H), 8.88 (s,1H), 7.67-7.65 (d,1H), 7.58-7.50 (m,2H), 7.32 (d,1H), 7.26-7.16 (m,3H), 4.45 (s,2H), 1.76-1.73 (q,2H), 1.42-1.39 (q,2H).

Example 78

Synthesis of 2-(2,6-difluorophenyl)-4-((5-(1,1,1-trifluoro-2-hydroxypropan-2-yl)pyridin-2-yl)amino)-6,7-dihydro-5H-pyrrolo[3,4-b]pyridin-5-one, I-78

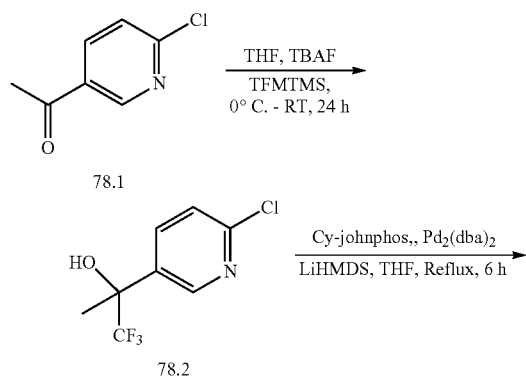

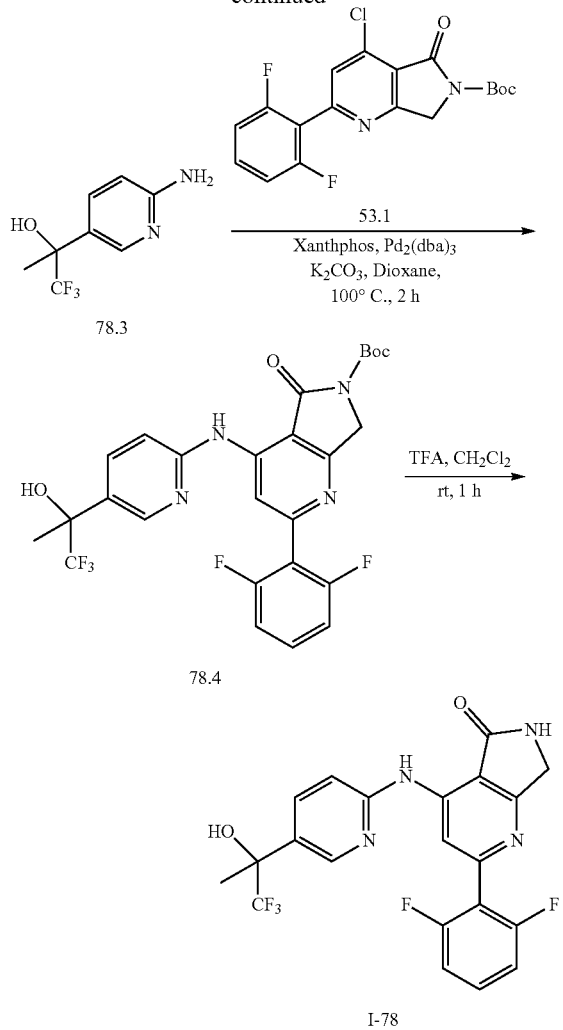

Synthesis of compound 78.2. Compound 78.1 (1.0 g, 6.0 mmol, 1.0 eq) was dissolved in THF (10.0 mL) and cooled to 0° C. Trimethyl (trifluoromethyl) silane (1.27 g, 9.0 mmol, 1.5 eq) and TBAF (0.120 g, 1.2 mmol, 0.02 eq) were added to the mixture. Reaction was stirred at room temperature for 24 hours. After completion of the reaction, mixture was quenched with 2N HCl solution and extracted with EtOAc. Organic layers were combined, washed with brine dried over Na₂SO₄ and concentrated under reduced pressure to obtain crude material. The crude was purified by column chromatography to provide 78.2 (0.95 g, 65.5%). MS(ES): m/z 225.60 [M+H]⁺.

Synthesis of compound 78.3. To a solution of 78.2 (0.45 g, 1.99 mmol, 1.0 eq) in THF (5.0 mL) (2-biphenyl)dicyclohexylphosphine (0.14 g, 0.4 mmol, 0.2 eq) and Pd₂(dba)₃ (0.182 g, 0.2 mmol, 0.1 eq) were added. The reaction was degassed with argon for 30 minutes. LHMDS (, 12 mmol, 6.0 eq) was added and the reaction was stirred at ruflux temperature for 6 hours. After completion of the reaction, mixture was quenched with cold HCl solution and extracted with EtOAc. Aqueous layere were combined, basified with NaHCO₃, and extracted with EtOAc. Organic layer was washed with water, brine and dried over Na₂SO₄ and concentrated under reduced pressure to obtain crude. The crude was purified by trituration with Et₂O to furnish 78.3 (0.52 g, 99.0%). MS(ES): m/z 206.17 [M+H]⁺.

Synthesis of compound 78.4. To a mixture of 53.1 (0.250 g, 0.65 mmol, 1.0 eq) in 1,4-dioxane (2.5 mL) was added 78.3 (0.135 g, 0.65 mmol, 1.0 eq) and K$_2$CO$_3$ (0.180 g, 1.3 mmol, 2.0 eq). The reaction mixture was degassed for 10 minutes using argon, then Pd$_2$(dba)$_3$ (0.060 g, 0.065 mmol, 0.1 eq) and Xantphos (0.075 g, 0.13 mmol, 0.2 eq) were added, and again degassed for 5 minutes. The reaction was stirred at 100° C. for 2 hours. After completion of the reaction, mixture was poured into water and product was extracted with EtOAc. Organic layers were combined, washed with brine, dried over Na$_2$SO$_4$ and concentrated under reduced pressure to obtain crude material. The crude was purified by column chromatography to furnish 78.4 (0.23 g, 63.6%). MS(ES): m/z 550.49 [M+H]$^+$.

Synthesis of compound I-78. To a solution of compound 78.4 (0.21 g, 0.381 mmol, 1.0 eq) in CH$_2$Cl$_2$ (2.0 mL) was added TFA (0.5 mL). The reaction mixture was stirred at room temperature for 1 hour. After completion of the reaction, mixture was poured into water, basified with satd. NaHCO$_3$ solution and product was extracted with EtOAc. Organic layers were combined, washed with brine solution, dried over Na$_2$SO$_4$ and concentrated under reduced pressure to obtain crude which was purified by trituration to furnish I-78 (0.17 g, 98.9%). MS(ES): m/z 450.37 [M+H]$^+$; $^1$H NMR (DMSO-d$_6$, 400 MHz): δ 9.83 (s,1H), 8.93 (s,1H), 8.62 (s, 1H), 8.51 (d,1H), 7.95-7.93 (t,1H), 7.60-7.56 (m,1H), 7.29-7.20 (m,3H), 6.74 (s,1H), 4.45 (s,2H), 1.70 (s,3H).

Example 79

Synthesis of 2-(4-((6-(4-oxa-7-azaspiro[2.5]octan-7-yl)pyridin-3-yl)amino)-5-oxo-6,7-dihydro-5H-pyrrolo[3,4-b]pyridin-2-yl)-3-fluorobenzonitrile, I-79

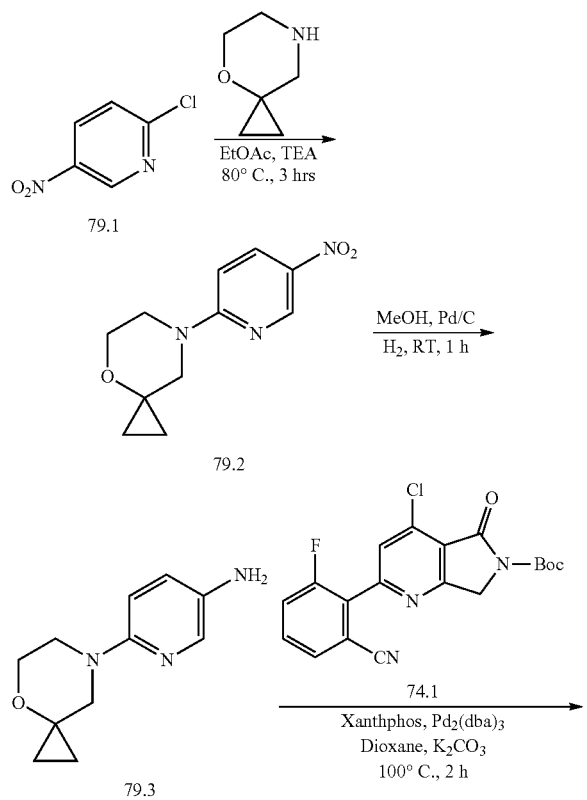

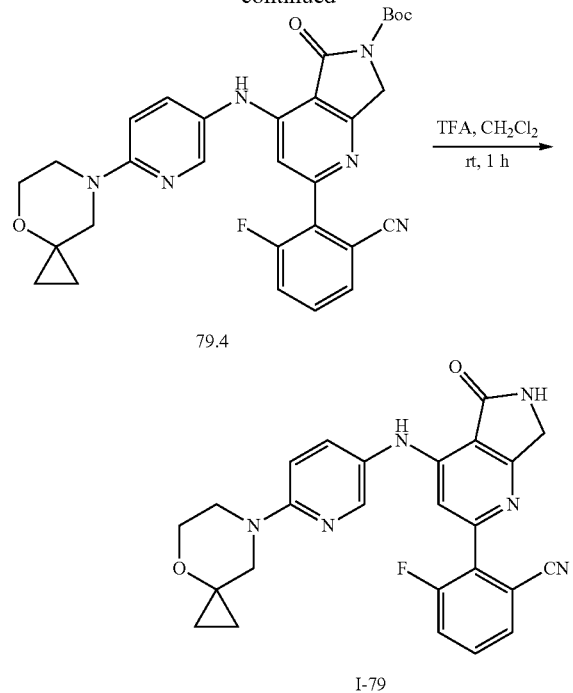

Synthesis of compound 79.2. To a mixture 79.1 (0.019 g, 0.121 mmol, 1.0 eq) in EtOAc (2.0 mL) was added 4-oxa-7-azaspiro[2.5]octane (0.02 g, 0.133 mmol, 1.1 eq) and Et$_3$N (0.031 g, 0.29 mmol, 2.4 eq). The reaction was stirred at 80° C. for 3 hours. After completion of the reaction, solvent was evaporated under reduced pressure. The residue was triturated with 0.2% dichloromethane in hexane to provide 79.2 (0.054 g, 99.0%). MS(ES): m/z 236.27 [M+H]$^+$.

Synthesis of compound 79.3. To a suspension of 10% Pd/C (0.030 g) in MeOH (2.0 mL) was added a solution of compound 79.2 (0.054 g, 0.229 mmol, 1.0 eq) in MeOH (2.0 mL) under nitrogen. Reaction was purged with H$_2$ gas for 1 hour. After completion of the reaction, mixture was filtered through celite, washed with MeOH. Filtrate was concentrated under reduced pressure. The residue was triturated with 0.5% CH$_2$Cl$_2$ in hexane to provide pure 79.3 (0.047 g, 99.0%)

Synthesis of compound 79.4. To a mixture of 74.1 (0.075 g, 0.193 mmol, 1.0 eq) in 1,4-dioxane (3.0 ml) was added 79.3 (0.044 g, 0.212 mmol, 1.0 eq) and K$_2$CO$_3$ (0.08 g, 0.579 mmol, 3.0 eq). Mixture was degassed for 10 minutes using argon, then Pd$_2$(dba)$_3$ (0.017 g, 0.019 mmol, 0.1 eq) and Xantphos (0.022 g, 0.038 mmol, 0.2 eq) were added. Reaction mixture was degassed for additional 5 minutes then stirred at 100° C. for 2 hours. After completion of the reaction, mixture was poured into water and product was extracted with EtOAc. Organic layers were combined, washed with brine, dried over Na$_2$SO$_4$ and concentrated under reduced pressure to obtain crude material. The crude was purified by column chromatography to furnish 79.4 (0.05 g, 46.5%). MS(ES): m/z 557.78 [M+H]$^+$.

Synthesis of compound I-79. To a solution of 79.4 (0.050 g, 0.089 mmol, 1.0 eq) in CH$_2$Cl$_2$ (2.0 mL) was added TFA (0.5 mL) The reaction was stirred at room temperature for 1.5 hours. After completion of the reaction, mixture was poured into water, basified with satd. NaHCO$_3$ and extracted with EtOAc. Organic layers were combined, dried over Na$_2$SO$_4$ and concentrated under reduced pressure to obtain crude. The crude was purified by column chromatography to furnish I-79 (0.025 g, 61.0%). MS(ES): m/z 457.57 [M+H]$^+$; $^1$H NMR (CDCl$_3$, 400 MHz): δ 8.42 (s,1H), 8.22-8.21 (d,1H), 7.60-7.58 (d,1H), 7.54-7.37 (m,3H), 6.81 (s,1H), 6.70-6.68 (d, 1H), 6.18 (s,1H), 4.54 (s,2H), 3.93-3.90 (t,2H), 3.67-3.64 (t,2H), 3.51 (s,2H), 0.86 (t,2H), 0.56 (t, 2H).

Example 80

Synthesis of 2-(4-((3,3-dimethyl-2,3-dihydrobenzofuran-6-yl)amino)-5-oxo-6,7-dihydro-5H-pyrrolo[3,4-b]pyridin-2-yl)-3-fluorobenzonitrile, I-80

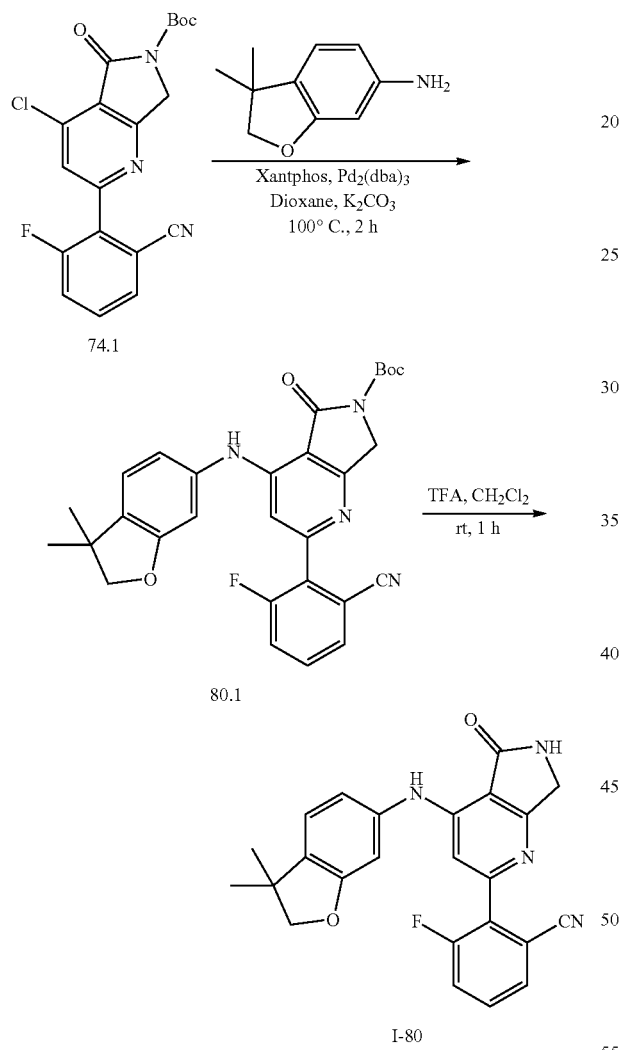

Synthesis of compound 80.1. To a solution of 74.1 (0.1 g, 0.25 mmol, 1.0 eq) in 1,4-dioxane (2.5 mL) was added 3,3-dimethyl-2,3-dihydrobenzofuran-6-amine (0.041 g, 0.25 mmol, 1.0 eq) and K$_2$CO$_3$ (0.069 g, 0.5 mmol, 2.0 eq). After degassing with argon (10 minutes), Pd$_2$(dba)$_3$ (0.022 g, 0.025 mmol, 0.1 eq) and Xantphos (0.029 g, 0.05 mmol, 0.2 eq) were added. Suspension was degassed with argon for addition 5 minutes, then stirred at 100° C. for 2 hours. After completion of the reaction, mixture was poured into water and extracted with EtOAc. Organic layers were combined, washed with brine, dried over Na$_2$SO$_4$ and concentrated under reduced pressure to obtain the crude. The crude was purified by column chromatography to furnish 80.1 (0.065 g, 49.0%). MS(ES): m/z 514.56 [M+H]$^+$.

Synthesis of compound I-80. To a solution of 80.1 (0.065 g, 0.126 mmol, 1.0 eq) in CH$_2$Cl$_2$ (2.0 mL) was added TFA (0.5 mL). The reaction mixture was stirred at room temperature for 1 hour. After completion of the reaction, mixture was poured into iced water, basified with NaHCO$_3$ and extracted with EtOAc. Organic layers were combined, washed with brine, dried over Na$_2$SO$_4$ and concentrated under reduced pressure to obtain crude material. The crude was purified by column chromatography to provide I-80 (0.026 g, 49.7%). MS(ES): m/z 414.44 [M+H]$^+$; $^1$H NMR (DMSO-d$_6$, 400 MHz): δ 8.96 (s,1H), 8.75 (s,1H), 7.85-7.83 (m,1H), 7.72-7.70 (m,2H), 7.22-7.17 (m,2H), 6.88-6.62 (m,2H), 4.40 (s,2H), 4.24 (s,2H), 1.29 (s,6H).

Example 81

Synthesis of 2-(4-((2-(2-cyano-6-fluorophenyl)-5-oxo-6,7-dihydro-5H-pyrrolo[3,4-b]pyridin-4-yl)amino)phenyl)-N-ethyl-2-methylpropanamide, I-81

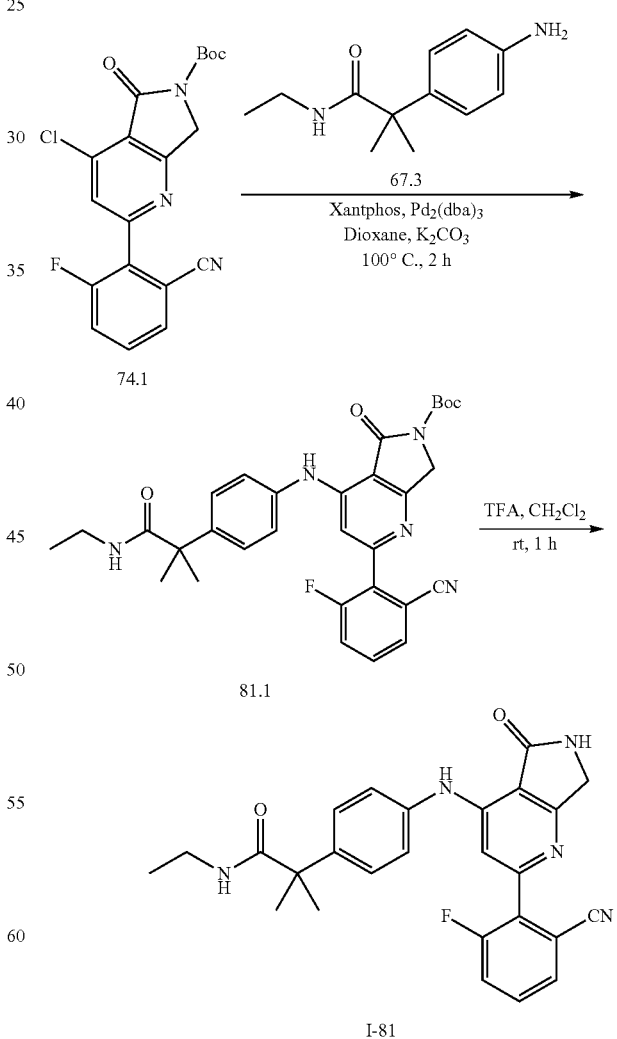

Synthesis of compound 81.1. To a mixture of 74.1 (0.1 g, 0.258 mmol, 1.0 eq) in 1,4-dioxane (2.5 mL) was added 67.3

(0.053 g, 0.258 mmol, 1.0 eq) and K$_2$CO$_3$ (0.089 g, 0.645 mmol, 2.5 eq). After degassing with argon for 10 minutes, Pd$_2$(dba)$_3$ (0.024 g, 0.0258 mmol, 0.1 eq) and Xantphos (0.03 g, 0.052 mmol, 0.2 eq) were added. Suspension was degassed for additional 5 minutes then stirred at 100° C. for 2 hours. After completion of the reaction, mixture was poured into water and product was extracted with EtOAc. Organic layers were combined, washed with brine, dried over Na$_2$SO$_4$ and concentrated under reduced pressure to obtain crude material. The crude was purified by column chromatography to furnish 81.1 (0.09 g, 62.6%). MS(ES): m/z 557.63 [M+H]$^+$.

Synthesis of compound I-81. To a solution of 81.1 (0.09 g, 0.16 mmol, 1.0 eq) in CH$_2$Cl$_2$ (3.0 mL) was added TFA (0.5 mL). The reaction was stirred at room temperature for 1 hour. After completion of the reaction, mixture was poured into iced water, basified with satd. NaHCO$_3$ and extracted with EtOAc. Organic layers were combined, washed with brine, dried over Na$_2$SO$_4$ and concentrated under reduced pressure to obtain crude material. The crude was purified by column chromatography to furnish I-81 (0.04 g, 54.2%). MS(ES): m/z 457.51 [M+H]$^+$; $^1$H NMR (DMSO-d$_6$, 400 MHz): δ 9.04 (s,1H), 8.77 (s,1H), 7.85-7.83 (m,1H), 7.72-7.68 (m,2H), 7.39-7.31 (m,5H), 7.18 (s,1H), 4.40 (s,2H), 3.07-3.01 (m,2H), 1.43 (s,6H), 0.96-0.92 (t, H).

Example 82

Synthesis of compound (S)-2-(2,6-difluorophenyl)-4-((5-(1,1,1-trifluoro-2-hydroxypropan-2-yl)pyridin-2-yl)amino)-6,7-dihydro-5H-pyrrolo[3,4-b]pyridin-5-one, I-82

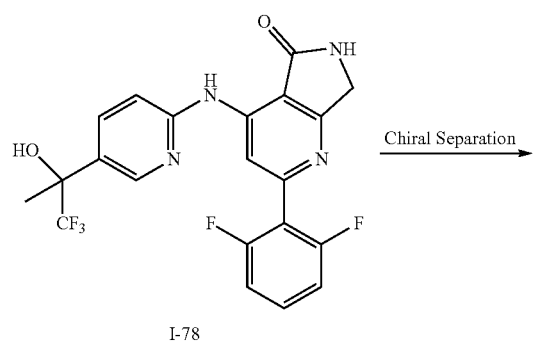

I-78

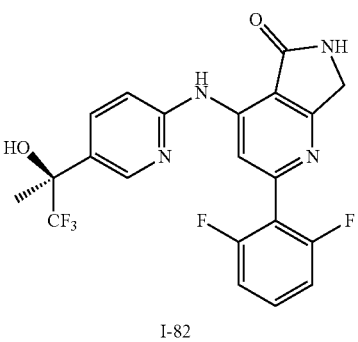

I-82

Compound I-82 was prepared by chiral separation of compound 1.78. MS (ES): m/z 450.37 [M+H]$^+$, $^1$H NMR (MeOD, 400 MHz): δ 8.81(s,1H), 8.56 (d,1H), 8.01-7.98 (m,1H), 7.58-7.53 (m, 1H), 7.19-7.11 (m,3H), 4.51 (s,2H), 1.76 (s,3H).

Example 83

Synthesis of (R)-2-(2,6-difluorophenyl)-4-((5-(1,1,1-trifluoro-2-hydroxy-propan-2-yl)pyridin-2-yl)amino)-6,7-dihydro-5H-pyrrolo[3,4-b]pyridin-5-one, I-83

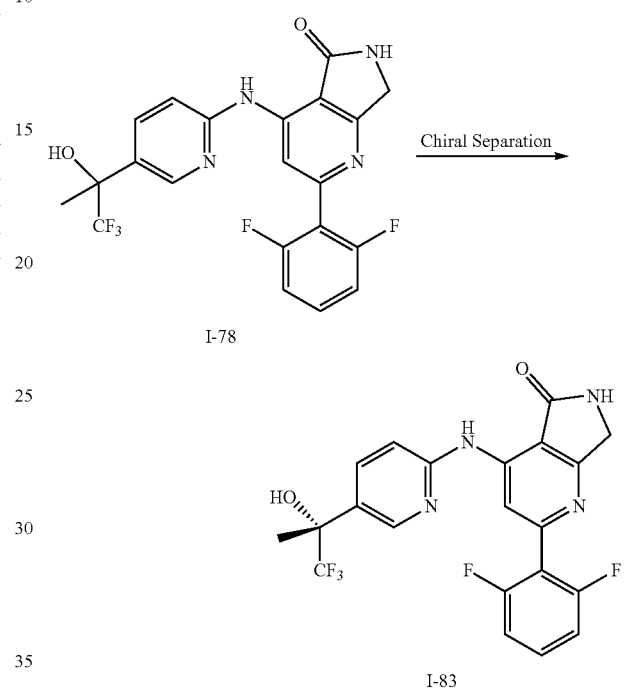

Compound I-83 was prepared by chiral separation of compound 1.78. MS (ES): m/z 450.37 [M+H]$^+$, $^1$H NMR (MeOD, 400 MHz): δ 8.80 (s,1H), 8.56-8.55 (d,1H), 8.00-7.98 (m,1H), 7.55 (m,1H), 7.18-7.10 (m,3H), 4.50 (s,2H), 1.76 (s,3H).

Example 84

Synthesis of 2-(2,6-difluorophenyl)-4-((4-(morpholine-4-carbonyl)phenyl)-amino)-5-oxo-6,7-dihydro-5H-pyrrolo[3,4-b]pyridine 1-oxide, I-84

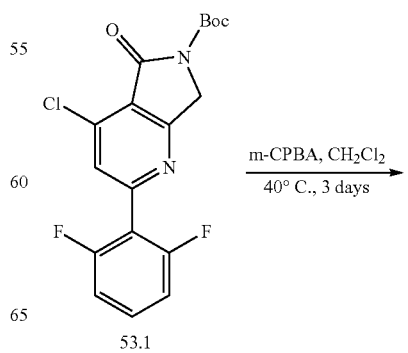

53.1

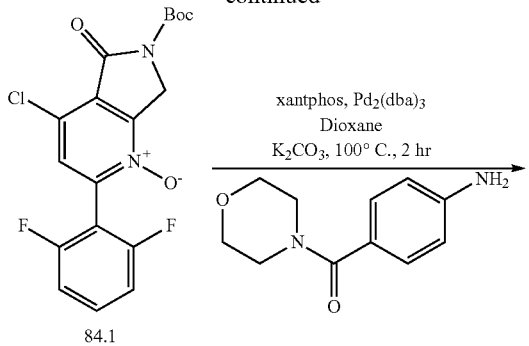

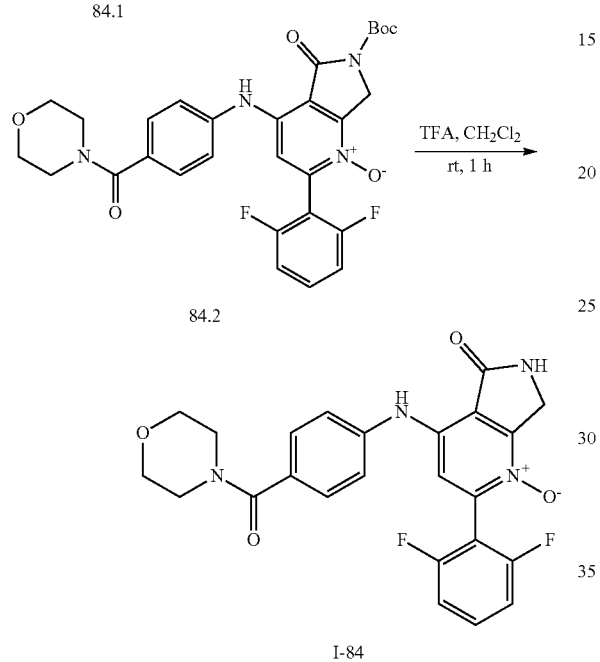

Syntheis of compound 84.1. Compound 53.1 (0.2 g, 0.53 mmol, 1.0 eq) and MCPBA (0.09, 0.53 mmol, 1.0 eq) were dissolved in $CH_2Cl_2$ (5.0 mL). The reaction was stirred at 40° C. for 4 days. After completion of the reaction, mixture was poured into water and product was extracted with EtOAc. Organic layers were combined, washed with brine, dried over $Na_2SO_4$ and concentrated under reduced pressure to obtain crude material. The crude was purified by column chromatography to furnish 84.1 (0.15 g, 72.0%). MS(ES): m/z 396.77 $[M+H]^+$.

Synthesis of compound 84.2. To a suspension of compound 84.1 (0.15 g, 0.38 mmol, 1.0 eq) in 1,4-dioxane (3.0 ml) was added (4-aminophenyl)(morpholino)methanone (0.078 g, 0.378 mmol, 1.0 eq) and $K_2CO_3$ (0.156 g, 1.13 mmol, 3.0 eq). After degassing of the suspension with argon (10 minutes) $Pd_2(dba)_3$ (0.034 g, 0.037 mmol, 0.1 eq) and Xantphos (0.043 g, 0.075 mmol, 0.2 eq) were added. Suspension was degassed for 5 minutes, the heated for 100° C. for 2 hours. After completion of the reaction, mixture was poured into water and product was extracted with EtOAc. Organic layers were combined, washed with brine, dried over $Na_2SO_4$ and concentrated under reduced pressure to obtain crude material. The crude was ourified by column chromatography to provide 84.2 (0.05 g, 23.3%). MS(ES): m/z 566.56 $[M+H]^+$.

Synthesis of compound I-84. To a solution of 84.2 (0.05 g, 0.088 mmol, 1.0 eq) in $CH_2Cl_2$ (2.0 mL) was added TFA (0.5 mL). The reaction was stirred at room temperature for 1 hour. After completion of the reaction, mixture was poured into water, basified with satd. $NaHCO_3$ and extracted with EtOAc. Organic layers were combined, dried over $Na_2SO_4$ and concentrated under reduced pressure to obtain crude which was purified by column chromatography to furnish I-84 (0.020 g, 48.6%). MS(ES): m/z 466.44 $[M+H]^+$; $^1H$ NMR (DMSO-$d_6$, 400 MHz): δ 9.08 (s,1H), 9.05 (s,1H), 7.62 (m,1H), 7.46-7.37 (m,5H), 7.27-7.23 (t,2H), 4.50 (s,2H), 3.58-3.38 (m, 8H).

Example 85

Synthesis of 2-(4-((3,3-dimethyl-2,3-dihydrofuro[2,3-b]pyridin-6-yl)amino)-5-oxo-6,7-dihydro-5H-pyrrolo[3,4-b]pyridin-2-yl)-3-fluorobenzonitrile, I-85

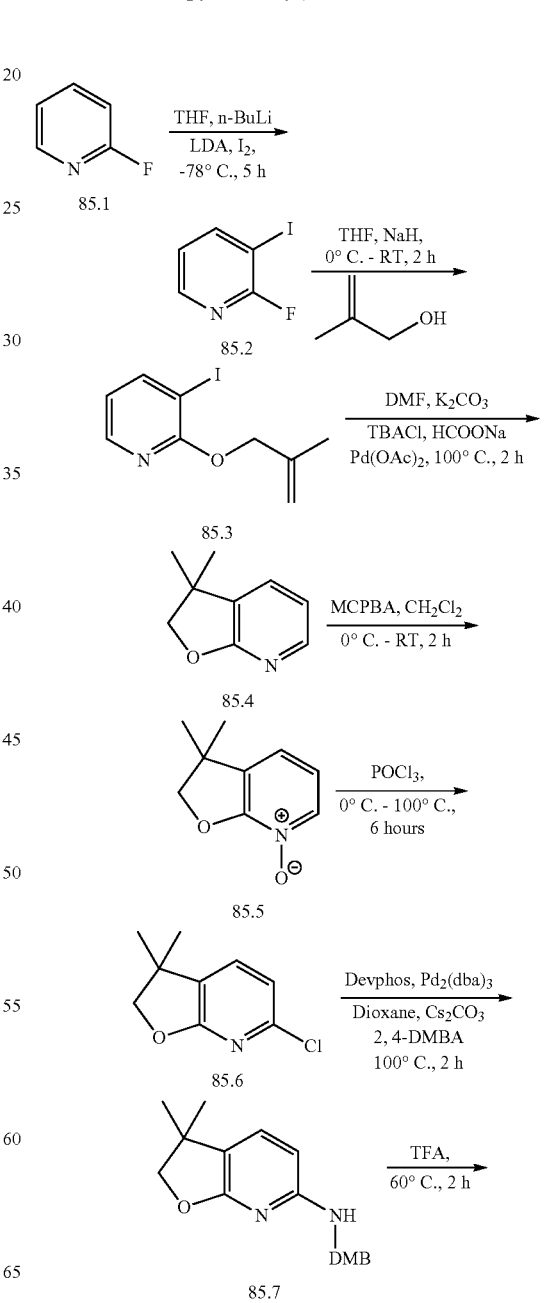

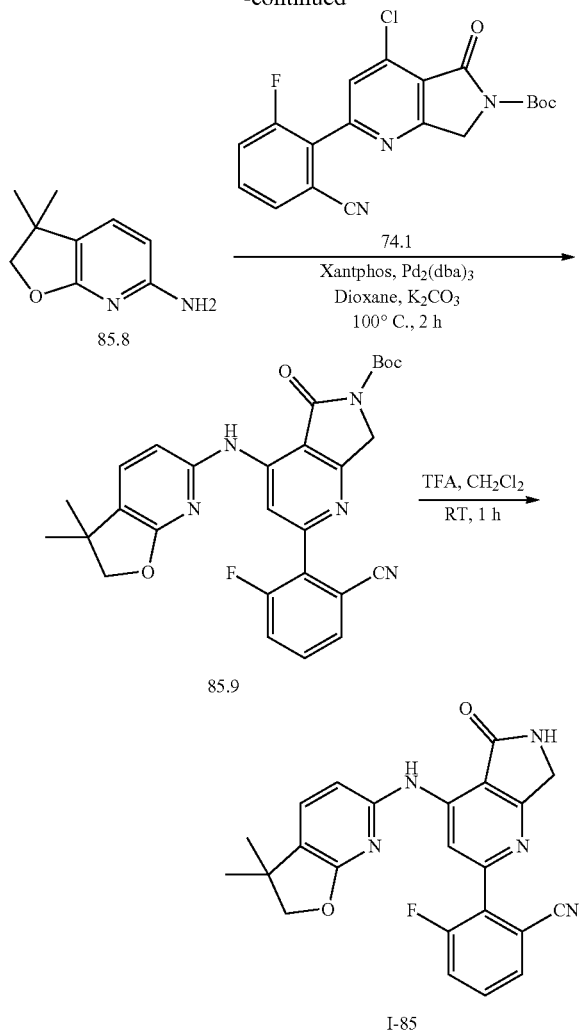

Synthesis of compound 85.2. To a solution of LDA (2.1 g, 21.0 mmol, 1.05 eq) in THF (15.0 mL) was added n-BuLi (8.6 mL, 21.0 mmol, 1.05 eq) at −20° C. The reaction was stirred at same temperature for 1 hour. Compound 85.1 (2.0 g, 20.0 mmol, 1.0 eq) was added at −78° C. and the reaction was stirred for 3 hours. Then a solution of $I_2$ (5.3 g, 21.0 mmol, 1.05 eq) in THF (15.0 mL) was added dropwise to the reaction mixture and the reaction was stirred for 1 hour. After completion of the reaction, mixture was poured into water and product was extracted with EtOAc. Organic layers were combined, washed with brine, dried over $Na_2SO_4$ and concentrated under reduced pressure to obtain pure 85.2 (1.7 g, 37.0%). MS(ES): m/z 222.99 [M+H]$^+$.

Synthesis of compound 85.3. 2-methylprop-2-en-1-ol (0.32 g, 4.5 mmol, 1.0 eq) was added to a solution of NaH (0.2 g, 9.0 mmol, 2.0 eq) in THF (10.0 mL). Compound 85.2 (1.0 g, 4.5 mmol, 1.0 eq) was added to the mixture. Reaction was stirred at room temperature for 2 hours. After completion of the reaction, water was added to the reaction mixture and product was extracted with EtOAc. Organic layers were combined, washed with brine, dried over $Na_2SO_4$ and concentrated under reduced pressure to obtain pure 85.3 (0.3 g, 24.3%). MS(ES): m/z 275.09 [M+H]$^+$.

Synthesis of compound 85.4. Compound 85.3 (1.0 g, 3.6 mmol, 1.0 eq), TBAC (1.0 g, 3.6 mmol, 1.0 eq), sodium formate (0.24 g, 3.6 mmol, 1.0 eq) and $K_2CO_3$ (1.5 g, 10.9 mmol, 3.0 eq) were mixed in DMF (10.0 mL) and suspension was degassed with argon gas for 15 minutes. Pd(OAC)$_2$ (0.08 g, 0.36 mmol, 0.1 eq) was added to the mixture and the reaction was stirred 100° C. for 2 hours. After completion of the reaction, water was added and product was extracted with EtOAc. Organic layers were combined, washed with brine, dried over $Na_2SO_4$ and concentrated under reduced pressure to obtain crude material. The crude was purified by column chromatography to furnish 85.4 (0.3 g, 55.3%). MS(ES): m/z 149.19 [M+H]$^+$.

Synthesis of compound 85.5. To a solution of 85.4 (0.23 g, 1.54 mmol, 1.0 eq) in $CH_2Cl_2$ (5.0 mL) was added m-CPBA (0.39 g, 2.31 mmol, 1.5 eq) 0° C. The reaction was stirred at room temperature for 2 hours. After completion of the reaction, mixture was poured in water and product was extracted with $CH_2Cl_2$. Organic layers were combined, washed with brine solution, dried over $Na_2SO_4$ and concentrated under reduced pressure to obtain crude material. The crude was purified by column chromatography to provide 85.5 (0.1 g, 39.3%). MS(ES): m/z 165.19 [M+H]$^+$.

Synthesis of compound 85.6. Compound 85.5 (0.3 g, 1.81 mmol, 1.0 eq) was dissolved in POCl$_3$ (5.0 mL) and the reaction was stirred at 100° C. for 6 hours. After completion of the reaction, mixture was quenched with satd. NaHCO$_3$ then extracted with EtOAc. Organic layers were combined, washed with brine, dried over $Na_2SO_4$ and concentrated under reduced pressure to obtain crude material. The crude was purified by column chromatography to furnish 85.6 (0.1 g, 30.0%). MS(ES): m/z 183.64 [M+H]$^+$.

Synthesis of compound 85.7. To a solution of compound 85.6 (0.06 g, 0.327 mmol, 1.0 eq) in 1,4-dioxane (1 ml) was added 2,4-dmethoxy benzyl amine (0.082 g, 0.149 mmol, 1.5 eq) and Cs$_2$CO$_3$ (0.319 g, 0.98 mmol, 3.0 eq). The reaction mixture was degassed for 10 minutes with argon, then Pd$_2$(dba)$_3$ (0.03 g, 0.032 mmol, 0.1 eq) and 2-Dicyclo-hexylphosphino-2'-(N,N-dimethylamino)biphenyl (0.025 g, 0.06 5 mmol, 0.2 eq) were added. The reaction was then stirred at 100° C. for 2 hours. After completion of the reaction, mixture was poured into water and product was extracted with EtOAc. Organic layers were combined, dried over $Na_2SO_4$ and concentrated under reduced pressure to obtain crude material. The crude was purified by column chromatography to furnish 85.7 (0.04 g, 43.4%). MS (ES): m/z 282.39 [M+H]$^+$.

Synthesis of compound 85.8. Compound 85.7 (0.03 g, 0.106 mmol, 1.0 eq) was dissolved in TFA (1.0 mL). The reaction was stirred at 60° C. for 2 hours. After completion of the reaction, mixture was quenched with satd. NaHCO$_3$ solution and product was extracted with EtOAc. Organic layers were combined, washed with brine, dried over Na$_2$SO$_4$ and concentrated under reduced pressure to obtain pure 85.8 (0.020 g, 99.0%). MS(ES): m/z 164.21 [M+H]$^+$.

Synthesis of compound 85.9. To a mixture of 74.1 (0.047 g, 0.12 mmol, 1.0 eq) in 1,4-dioxane (3.0 ml) was added compound 85.8 (0.020 g, 0.12 mmol, 1.0 eq) and K$_2$CO$_3$ (0.05 g, 0.36 mmol, 3.0 eq). The reaction mixture was degassed for 10 minutes with argon then Pd$_2$(dba)$_3$ (0.011 g, 0.012 mmol, 0.1 eq) and xantphos (0.013 g, 0.024 mmol, 0.2 eq) were added and again degassed for 5 minutes. The reaction was stirred at 100° C. for 2 hours. After completion of the reaction, mixture was poured into water and product was extracted with EtOAc. Organic layers were combined, washed with brine, dried over Na$_2$SO$_4$ and concentrated under reduced pressure to obtain crude material. The crude was purified by column chromatography to furnish 85.9 (0.04 g, 64.0%). MS(ES): m/z 515.55 [M+H]$^+$.

Synthesis of compound I-85. To a solution of 85.9 (0.04 g, 0.077 mmol, 1.0 eq) in CH$_2$Cl$_2$ (1.0 mL) was added TFA (1.0 mL) The reaction was stirred at room temperature for 1 hour. After completion of the reaction, mixture was poured into water, basified with satd. NaHCO$_3$ and product was extracted with EtOAc. Organic layer were combined and dried over Na$_2$SO$_4$ and concentrated under reduced pressure to obtain crude material. The crude was purified by column chromatography to provide I-85 (0.02 g, 62.1%). MS(ES): m/z 415.43 [M+H]$^+$; $^1$H NMR (DMSO-d$_6$, 400 MHz): δ 9.40 (s,1H), 9.01 (s,1H), 7.93-7.87 (m,2H), 7.77-7.72 (m,2H), 7.58 (s,1H), 7.18-7.16 (d,1H), 4.49 (s,2H), 4.25 (s,2H), 1.49 (s,6H).

Example 86

Synthesis of 2-(2,6-difluorophenyl)-4-((2,2-dioxido-1,3-dihydro-benzo[c]thio-phen-5-yl)amino)-6,7-dihydro-5H-pyrrolo[3,4-b]pyridin-5-one, I-86

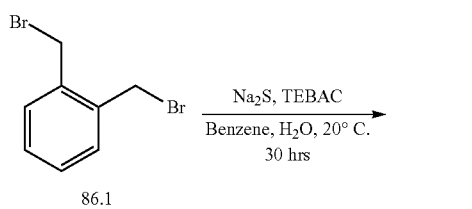

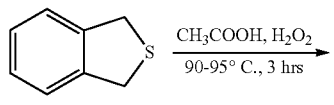

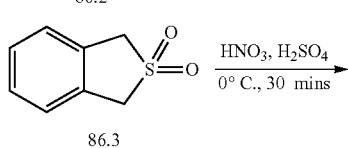

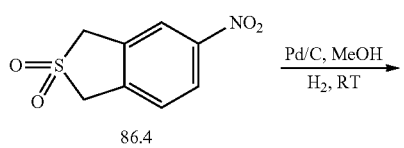

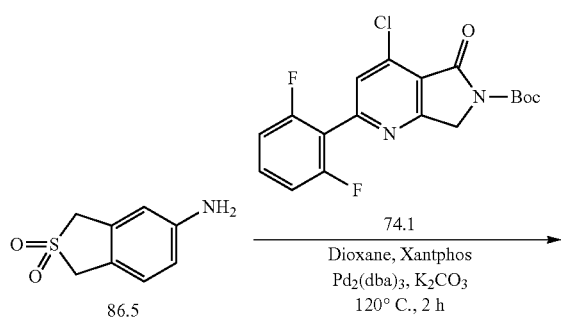

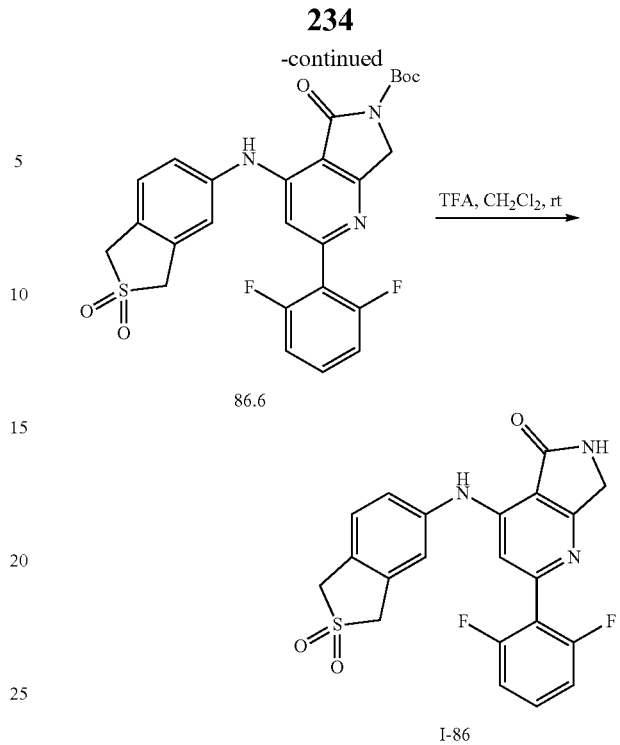

I-86

Synthesis of compound 86.2. To a solution of 86.1 (1.6 g, 6.06 mmol, 1.0 eq) in benzene (8.0 mL) was added solution of sodium sulfide monohydrate (2.9 g, 12.1 mmol, 2.0 eq) in water (30 mL) followed by Benz triethyl ammonium chloride (catalytic). The reaction was stirred at 20° C. for 30 hours. After completion of the reaction, mixture was poured into water and extracted with CH$_2$Cl$_2$. Organic layers were combined, washed with brine, dried over Na$_2$SO$_4$ and concentrated under reduced pressure to obtain 86.2 (0.7 g, 84.7%). Crude product was used for next step without any further purification.

Synthesis of compound 86.3. To 86.2 (0.7 g, 5.14 mmol, 1.0 eq) was added AcOH (4.3 mL) at 5-10° C. Solution was stirred for 1 hour. To this solution was added 30% H$_2$O$_2$ solution (1.2 mL). Reaction mixture stirred at 90-95° C. for 3 hours. After completion of the reaction, mixture waspored into water and product was extracted with EtOAc. Organic layers were combined, washed with brine, dried over Na$_2$SO$_4$ and concentrated under reduced pressure to get crude material. The crude was purified by column chromatography to provide 86.3 (0.3 g, 34.7%). $^1$H NMR (CDCl$_4$, 400 MHz): δ 7.40-7.28 (m,4H), 4.4 (s,4H).

Synthesis of compound 86.4. To a solution of 86.3 (0.2 g, 1.19 mmol, 1.0 eq) in concentrated H$_2$SO$_4$ (2.0 mL) at 0° C. was added HNO$_3$ (1.0 mL) slowly. Reaction was stirred at 0° C. for 30 minutes. After completion of the reaction, mixture was transferred into crushed ice and product was extracted with EtOAc. Organic layers were combined, washed with brine, dried over Na$_2$SO$_4$ and concentrated under reduced pressure to get crude material. The crude was purified by column chromatography to furnish 86.4 (0.12 g, 47.3%). $^1$H NMR (CDCl$_3$, 400 MHz): δ8.3-8.26 (m,2H), 7.58-7.54 (d,1H), 4.51-4.48 (d,4H).

Synthesis of compound 86.5. To the suspension of 10% Pd/C (0.03 g) in MeOH (3.0 mL) was added compound 86.4 (0.12 g, 0.56 mmol, 1.0 eq). Suspension was purged with H$_2$ gas for 1 hour. Reaction mixture filtered through celite and concentrated under reduced pressure to obtain 86.5 (0.08 g, 77.5%). MS(ES): m/z 184.1 [M+H]$^+$.

235

Synthesis of compound 86.6. To a mixture of 74.1 (0.080 g, 0.21 mmol, 1.0 eq) in 1,4-dioxane (3.0 ml) was added 86.5 (0.046 g, 0.21 mmol, 1.0 eq) and K$_2$CO$_3$ (0.073 g, 0.53 mmol, 2.5 eq). The reaction mixture was degassed for 10 minutes using argon then Pd$_2$(dba)$_3$ (0.019 g, 0.021 mmol, 0.1 eq) and Xantphos (0.024 g, 0.042 mmol, 0.2 eq) were added, and again degassed for 5 minutes. The reaction was stirred at 120° C. for 2 hours. After completion of the reaction, mixture was transferred into water and product was extracted with EtOAc. Organic layers were combined, washed with brine, dried over Na$_2$SO$_4$ and concentrated under reduced pressure to obtain crude material. The crude was purified by column chromatography to furnish 86.6 (0.08 g, 72.2%). MS(ES): m/z 528.6 [M+H]$^+$.

Synthesis of compound I-86. Compound 86.6 (0.08 g, 0.151 mmol, 1.0 eq) was dissolved in CH$_2$Cl$_2$ (1.0 mL) and TFA (0.5 mL) was added to the reaction mixture. The reaction was stirred at room temperature for 1 hour. After completion of the reaction, mixture was poured into water, basified with satd. NaHCO$_3$ and product was extracted with EtOAc. Organic layers were combined, dried over Na$_2$SO$_4$ and concentrated under reduced pressure to obtain crude material. The crude was purified by column chromatography to provide (0.05 g, 77.1%). MS(ES): m/z 428.57 [M+H]$^+$; $^1$H NMR (DMSO-d$_6$, 400 MHz): δ 9.10 (s,1H), 8.75 (s,1H), 7.55-7.51 (m,1H), 7.43-7.34 (m,2H), 7.22-7.18 (m,2H), 7.08 (s,1H), 5.76 (s,1H), 4.57-4.46 (d,4H), 4.37 (s,2H).

Example 87

Synthesis of 3-fluoro-2-(4-((5-(4-hydroxy-9-azadispiro[2.1.25.33]decan-9-yl)pyridin-2-yl)amino)-5-oxo-6,7-dihydro-5H-pyrrolo [3,4-b]pyridin-2-yl)benzonitrile, I-87

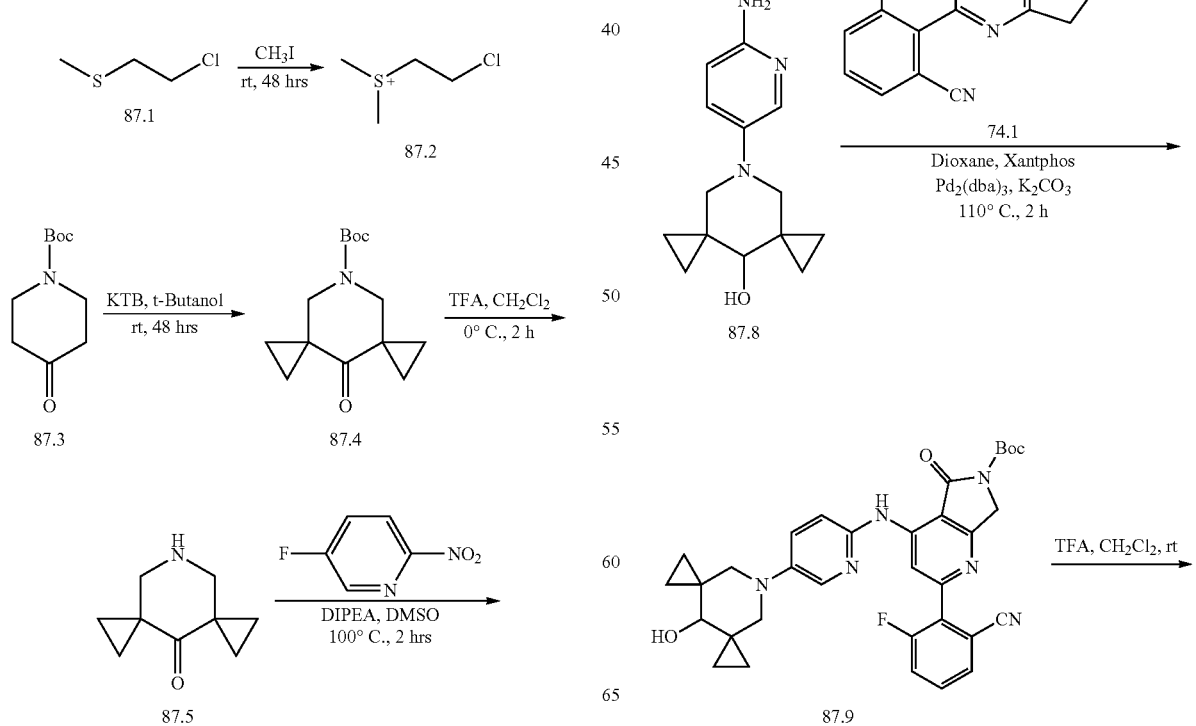

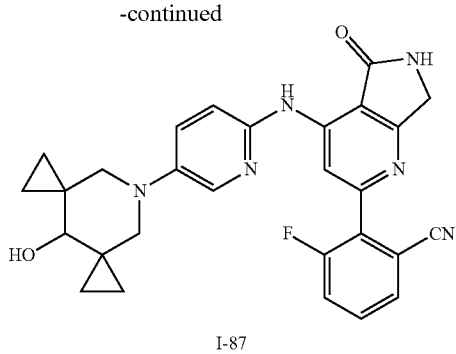

I-87

Synthesis of compound 87.2. Methyl Iodide (46.2 g, 45.2 mmol, 1.0 eq) was added to 87.1 (5.0 g, 325 mmol, 1.1 eq). Reaction mixture was stirred at room temperature for 48 hours. After completion of the reaction, solid were filtered off and washed with Et$_2$O to get pure 87.2 (5.2 g, 91.6%). $^1$H NMR (DMSO-d$_6$, 400 MHz): δ 4.15-4.12 (t,2H), 3.80-3.77 (t,2H), 2.97 (s,6H).

Synthesis of compound 87.4. KOBu$^t$ (0.675 g, 6.03 mmol, 1.0 eq) was added to t-Butanol (10 mL) and heated to 60° C. To this solution was added 87.3 (1.2 g, 6.03 mmol, 1.0 eq) and stirred at room temperature for 1 h. To the mixture was added 87.2 (1.36 g, 5.4 mmol, 0.9 eq) portion wise and resulting mixture was stirred at room temperature for 2 hours. To this mixture was added solution of KOBu$^t$ (0.68 g, 6.03 mmol, 1.0 eq) in t-Butanol (10 mL) and reaction was stirred at room temperature for 48 hours. After completion of the reaction, mixture was poured into water and product was extracted with EtOAc. Organic layers were combined, dried over Na$_2$SO$_4$ and concentrated under reduced pressure to obtain crude material. The crude was purified by column chromatography to provide 87.4 (0.2 g, 13.2%). $^1$H NMR (CDCl$_3$, 400 MHz): δ 3.76 (s,4H), 1.49 (s,9H), 1.3-1.26 (m,4H), 0.87 (bs,4H).

Synthesis of compound 87.5. To a solution of 87.5 (0.2 g, 0.79 mmol, 1.0 eq) in CH$_2$Cl$_2$ (5.0 mL) was added TFA (0.9 g, 7.96 mmol, 10 eq) at 0° C. Reaction was stirred for 2 hours. After completion of the reaction, solvent was concentrated under reduced pressure and neutralised with satd. NaHCO$_3$ solution. Mixture was extracted with CH$_2$Cl$_2$, organic layers were combined, dried over Na$_2$SO$_4$ and concentrated under reduced pressure to obtain 87.5 (0.11 g, 91.4%). $^1$H NMR (CDCl$_3$, 400 MHz): δ 3.12 (s,4H), 1.34-1.31 (m,4H), 0.75-0.73 (m,4H).

Synthesis of compound 87.6. To a solution of 87.5 (0.11 g, 0.728 mmol, 1.0 eq) in DMSO (5.0 mL) was added 5-fluoro-2-nitropyridine (0.103 g, 0.728 mmol, 1.0 eq) followed by DIPEA (0.94 g, 7.28 mmol, 10 eq). Reaction mixture was stirred at 100° C. for 2 hours. After completion of the reaction, mixture was transferred into water and extracted with EtOAc. Organic layers were combined, dried over Na$_2$SO$_4$ and concentrated under reduced pressure to obtain 87.6 (0.1 g, 50.3%). MS(ES): m/z 274.3 [M+H]$^+$.

Synthesis of compound 87.7. To a solution of 87.6 (0.1 g, 0.366 mmol, 1.0 eq) in MeOH (3.0 mL) was added NaBH$_4$ (0.070 g, 1.83 mmol, 5.0 eq) at 0° C. Reaction mixture was stirred at room temperature for 1 hour. After completion, the reaction was quenched with saturated NH$_4$Cl solution and extracted with CH$_2$Cl$_2$. Organic layers were combined, dried over Na$_2$SO$_4$ and concentrated under reduced pressure to obtain crude material which was triturated with n-hexane to provide 87.7 (0.075 g, 79.0%). MS(ES): m/z 276.38 [M+H]$^+$.

Synthesis of compound 87.8. To the suspension of 10% Pd/C (0.05 g) in MeOH (3.0 mL) was added compound 87.7 (0.075 g, 0.272 mmol, 1.0 eq) and purged with H$_2$ gas for 2 hours. Reaction mixture was filtered through celite and concentrated under reduced pressure to obtain 87.8 (0.06 g, 89.8%). MS(ES): m/z 246.37 [M+H]$^+$.

Synthesis of compound 87.9. To a solution 74.1 (0.090 g, 0.232 mmol, 1.0 eq) in 1,4-dioxane (2.0 ml) was added 87.8 (0.051 g, 0.208 mmol, 1.0 eq) and K$_2$CO$_3$ (0.080 g, 0.58 mmol, 2.5 eq). The reaction mixture was degassed for 10 minutes using argon then Pd$_2$(dba)$_3$ (0.021 g, 0.023 mmol, 0.1 eq) and Xantphos (0.026 g, 0.046 mmol, 0.2 eq) were added and again degassed for 5 minutes. The reaction was stirred at 110° C. for 2 hours. After completion of the reaction, mixture was poured into water and product was extracted with EtOAc. Organic layers were combined, dried over Na$_2$SO$_4$ and concentrated under reduced pressure to obtain crude material. The crude was purified by column chromatography to furnish 87.9 (0.07 g, 55.5%). MS(ES): m/z 597.6 [M+H]$^+$.

Synthesis of compound I-87. Compound 87.9 (0.070 g, 0.117 mmol, 1.0 eq) was dissolved in CH$_2$Cl$_2$ (2.0 mL) and TFA (0.5 mL) was added to the reaction mixture. The reaction was stirred at room temperature for 1 hour. After completion of the reaction, mixture was poured into water, basified with satd. NaHCO$_3$ solution and extracted with EtOAc. Organic layers were combined, dried over Na$_2$SO$_4$ and concentrated under reduced pressure to obtain crude. The crude was purified by column chromatography to furnish I-87 (0.030 g, 51.3%). MS (ES): m/z 497.7 [M+H]$^+$; $^1$H NMR (DMSO-d$_6$, 400 MHz): δ 9.52 (s,1H), 8.86 (s,1H), 8.47 (s,1H), 7.96 (d, 1H), 7.89-7.86 (dd,1H), 7.8-7.72 (m,2H), 7.41-7.38 (dd,1H), 7.09-7.07 (d,1H), 4.63 (d,1H), 4.42 (s,2H), 3.23-3.20 (d,2H), 2.79-2.76 (d,2H), 0.46 (s,6H), 0.34-0.32 (d,2H).

Example 88

Synthesis of 3-fluoro-2-(4-((5-((3R,5R)-3-hydroxy-1-oxa-7-azaspiro[4.4]nonan-7-yl)pyridin-2-yl)amino)-5-oxo-6,7-dihydro-5H-pyrrolo[3,4-b]pyridin-2-yl)benzonitrile. I-88

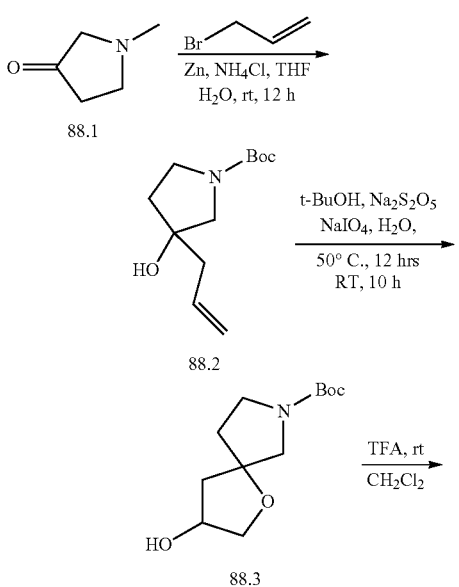

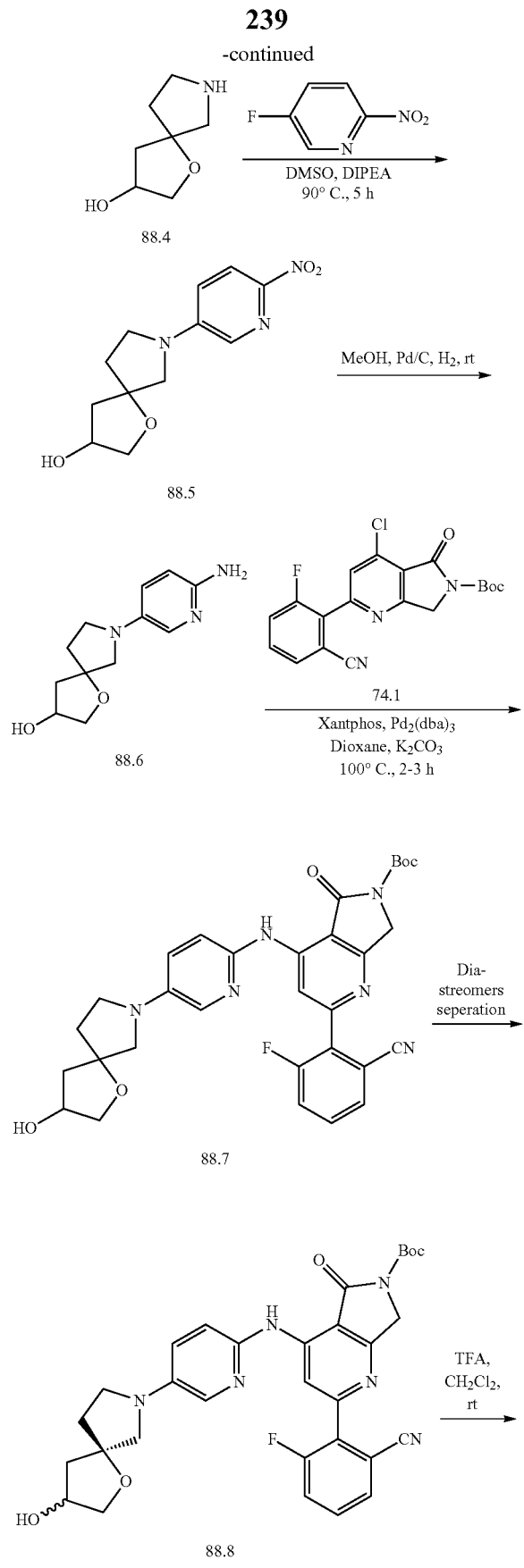

Synthesis of compound 88.2. To a stirred mixture of 88.1 (4.0 g, 21.5 mmol, 1.0 eq) and 3-bromoprop-1-ene (4.7 mL, 53.9 mmol, 2.5 eq) in THF (10.0 mL) was added saturated $NH_4Cl$ solution (20.0 mL). To the suspension was slowly added zinc dust (2.8 g, 43.1 mmol, 2.0 eq) while maintaining temperature below 40° C. The reaction mixture was stirred at room temperature for 12 hours. After completion of the reaction, 10% aq. $H_2SO_4$ was slowly added. Reaction mixture was filtered and the product was extracted with EtOAc. Organic layers were separated, washed with brine solution and dried over $Na_2SO_4$, concentrated under reduced pressure to provide 88.2 (4.3 g 87.6%). $^1$H NMR (DMSO-$d_6$, 400 MHz): δ 5.91-5.83 (m,1H), 5.24-5.19 (m,2H), 3.55-3.48 (m, H), 3.41-3.25 (m,2H), 2.42-2.40 (d,2H), 1.89-1.85 (t,2H), 1.47(s,9H).

Synthesis of compound 88.3. To a stirred mixture of 88.2 (4.3 g, 18.9 mmol, 1.0 eq) and $NaIO_4$ (4.0 g, 18.9 mmol, 1.0 eq) in t-Butanol (28 mL) and water (9.4 mL) was added solution of sodium metabisulphite (3.59 g, 18.9 mmol, 1.0 eq) in water (15.0 mL) at 50° C. Reaction mixture was stirred at 50° C. for 12 hour followed by 10 hours at room temperature. After completion of the reaction, reaction mixture cooled to room temperature and extracted with EtOAc. Organic layers were combined, washed with brine, dried over sodium sulphate and concentrated under reduced pressure to obtain crude material which was purified by column chromatography, to provide 88.3 (1.0 g, 21.7%). MS(ES): m/z 244.3 [M+H]$^+$.

Synthesis of compound 88.4. To a stirred solution of 88.3 (0.38 g, 1.56 mmol, 1.0 eq) in $CH_2Cl_2$ (5.0 mL) was added TFA (1.0 mL) and reaction mixture was stirred at room temperature for 2 hours. Reaction mixture was concentrated under reduced pressure to obtain crude 88.4 (0.3 g, 80.0%), MS(ES): m/z 144.17 [M+H]$^+$.

Synthesis of compound 88.5. To a stirred mixture of 88.4 (0.12 g, 0.84 mmol, 1.2 eq) and 5-fluoro-2-nitropyridine (0.1 g, 0.70 mmol, 1.0 eq) in DMSO (2.0 mL) was added DIPEA (0.92 g, 7.03 mmol, 10.0 eq) and heated at 90° C. for 5 hours. Reaction mixture was cooled to room temperature, poured into water and extracted with EtOAc. Organic layers were combined, washed with brine, dried over $Na_2SO_4$ and concentrated under reduced pressure to obtain crude which was purified by column chromatography to furnish 88.5 (0.125 g, 64.3%). MS(ES): m/z 266.33 [M+H]$^+$.

Synthesis of compound 88.6. To a suspension of 10% Pd/C (0.05 g) in MeOH (5.0 mL) was added compound 88.5 (0.125 g, 0.471 mmol, 1.0 eq). Suspension was purged with $H_2$ gas for 1 hour. Reaction mixture filtered through celite and concentrated under reduced pressure to obtain 88.6 (0.10 g, 94.0%). MS(ES): m/z 236.37 [M+H]$^+$.

Synthesis of compound 88.7. To a mixture of 74.1 (0.075 g, 0.193 mmol, 1.0 eq) in 1,4-dioxane (2.0 mL) was added 88.5 (0.049 g, 0.212 mmol, 1.1 eq) and $K_2CO_3$ (0.079 g, 0.579 mmol, 3.0 eq). The reaction mixture was degassed for 10 minutes using argon then $Pd_2(dba)_3$ (0.017 g, 0.019 mmol, 0.1 eq) and Xantphos (0.022 g, 0.038 mmol, 0.2 eq) were added and again degassed for 5 minutes. The reaction was stirred at 100° C. for 2 hours. After completion of the reaction, mixture was poured into water and product was extracted with EtOAc. Organic layers were combined, washed with brine, dried over $Na_2SO_4$ and concentrated under reduced pressure to obtain crude. This was purified by column chromatography to furnish 88.7 (0.058 g, 23.3%). MS(ES): m/z 587.58 [M+H]$^+$.

Synthesis of compound 88.8. Diastereomeric mixture 88.7 (0.058 g) was separated using reverse phase column (X-BRIDGE C18 250×19 mm, 5μ) to afford to afford pure 88.8 (0.023 g), MS (ES): 587.3 [M+H]$^+$ Synthesis of compound I-88. Compound 88.8 (0.023 g, 0.039 mmol, 1.0 eq) was dissolved in $CH_2Cl_2$ (2.0 mL) and TFA (0.2 mL) was added. The reaction mixture was stirred at room temperature for 2 hours. After completion of the reaction, mixture was poured into water, basified with satd. $NaHCO_3$ and extracted with $CH_2Cl_2$. Organic layers were combined, washed with brine, dried over $Na_2SO_4$ and concentrated under reduced pressure to obtain crude which was purified trituration with n-pentane to get pure I-88 (0.010 g, 52.4%). MS(ES): m/z 487.2 [M+H]$^+$; $^1$H NMR (DMSO-d$_6$, 400 MHz): δ 9.42 (s,1H), 8.81 (s,1H), 8.31 (s,1H), 7.88-7.85 (m, 1H), 7.79-7.69 (m, H), 7.65-7.64 (d, 1H), 7.11-7.09 (d, 1H), 7.01-6.98 (dd,1H), 4.96 (d,1H), 4.40 (s,2H), 4.35 (s,1H), 3.83-3.79 (m,1H), 3.60-3.57 (dd,1H), 3.29 (s,1H), 3.25 (s, H), 2.20-2.13 (m, 2H), 2.08-2.00 (m,1H), 1.88-1.84 (dd,1H).

Example 89

Synthesis of 3-fluoro-2-(4-((5-((3S,5R)-3-hydroxy-1-oxa-7-azaspiro[4.4]nonan-7-yl)pyridin-2-yl)amino)-5-oxo-6,7-dihydro-5H-pyrrolo[3,4-b]pyridin-2-yl)benzonitrile, I-89

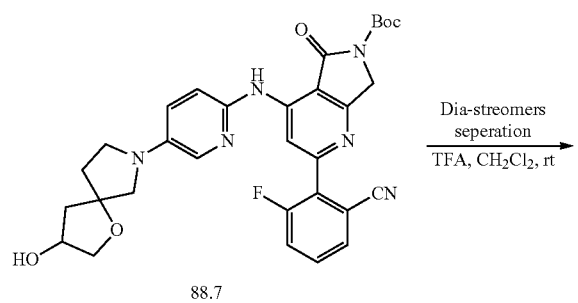

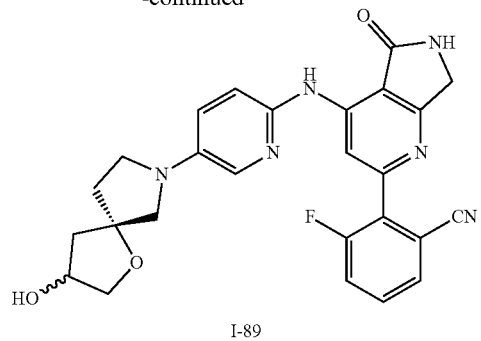

I-89

Compound I-89 was prepared from 88.7 using procedure described in Example 89. MS(ES): m/z 487.2 [M+H]$^+$; $^1$H NMR (DMSO-d$_6$, 400 MHz): δ 9.43 (s,1H), 8.81 (s,1H), 8.31 (s,1H), 7.87-7.85 (m,1H), 7.78-7.70 (m,2H), 7.64 (d,1H), 7.11-7.09 (d,1H), 7.01-6.98 (dd,1H), 4.97 (d,1H), 4.40 (s,2H), 4.35 (s,1H), 3.86-3.82 (m,1H), 3.59-3.56 (dd, 1H), 3.38 (s,1H), 3.26 (s,2H), 2.12-2.08 (m,1H), 2.01-1.98 (m,2H), 1.94-1.90 (dd,1H).

Example 90

Synthesis of 3-fluoro-2-(4-((5-((3R,5R)-3-hydroxy-1-oxa-7-azaspiro[4.4]nonan-7-yl)pyridin-2-yl)amino)-5-oxo-6,7-dihydro-5H-pyrrolo[3,4-c]pyridin-2-yl)benzonitrile, I-90

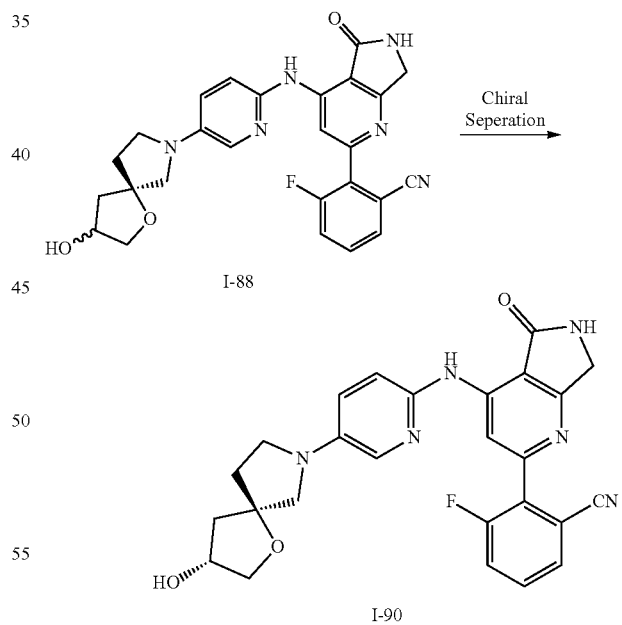

Compound I-90 was prepared by chiral separation of compound I-88. MS(ES): m/z 487.2 [M+H]$^+$; $^1$H NMR (DMSO-d$_6$, 400 MHz): δ 9.43 (s,1H), 8.82 (s,1H), 8.32 (s,1H), 7.88-7.86 (dd, 1H), 7.79-7.71 (m,H), 7.65 (d,1H), 7.12-7.09 (d,1H), 7.02-6.99 (dd,1H), 4.96 (d,1H), 4.41(s, 2H), 4.35 (s,1H), 3.83-3.79 (m,1H), 3.60-3.58 (dd,1H), 3.29 (s,1H), 3.25 (s,2H), 2.18-2.12 (m, 2H), 2.09-2.03 (m,1H), 1.89-1.85 (dd,1H).

Example 91

Synthesis of 3-fluoro-2-(4-((5-((3S,5S)-3-hydroxy-1-oxa-7-azaspiro[4.4]nonan-7-yl)pyridin-2-yl)amino)-5-oxo-6,7-dihydro-5H-pyrrolo[3,4-b]pyridin-2-yl)benzonitrile, I-91

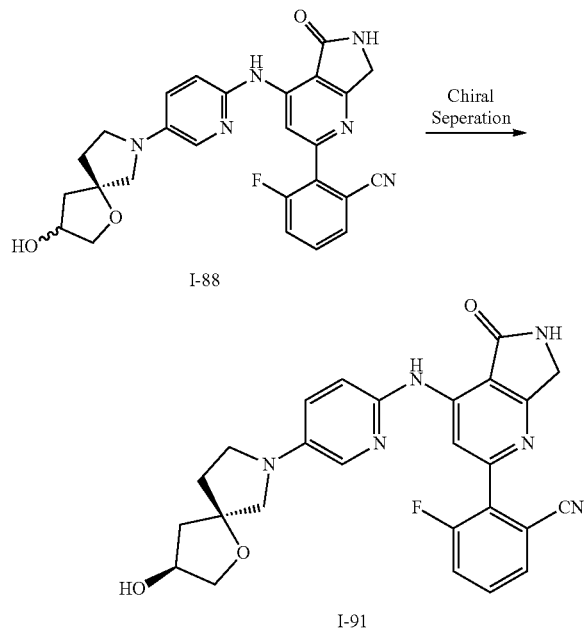

Compound I-91 was prepared by chiral separation of compound I-88. MS(ES): m/z 487.2 [M+H]$^+$; $^1$H NMR (DMSO-d$_6$, 400 MHz): 9.42 (s,1H), 8.82 (s,1H), 8.32 (s,1H), 7.88-7.86 (dd, 1H), 7.79-7.71 (m,2H), 7.65 (d,1H), 7.11-7.09 (d,1H), 7.01-6.98 (dd,1H), 4.98 (s,1H), 4.41(s, 2H), 4.35(s,1H), 3.83-3.80 (m,1H), 3.61-3.58 (dd,1H), 3.29 (s,1H), 3.25 (s,2H), 2.18-2.12 (m, 2H), 2.09-2.03 (m,1H), 1.89-1.85 (dd,1H).

Example 92

Synthesis of 3-fluoro-2-(4-((5-((3R,5S)-3-hydroxy-1-oxa-7-azaspiro[4.4]nonan-7-yl)pyridin-2-yl)amino)-5-oxo-6,7-dihydro-5H-pyrrolo[3,4-b]pyridin-2-yl)benzonitrile, I-92

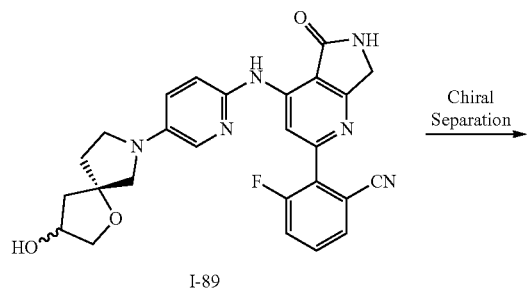

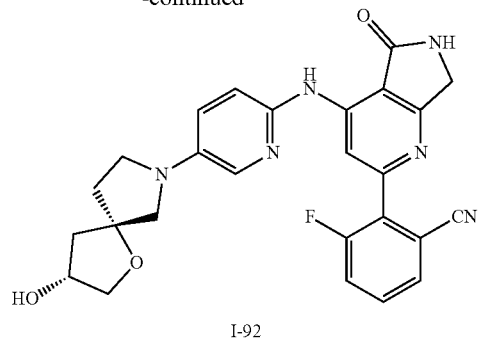

Compound I-92 was prepared by chiral separation of compound I-89. MS(ES): m/z 487.1 [M+H]$^+$; $^1$H NMR (DMSO-d$_6$, 400 MHz): δ 9.43 (s,1H), 8.81 (s,1H), 8.32 (s,1H), 7.88-7.86 (dd, 1H), 7.77-7.71 (m,2H), 7.65-7.64 (d,1H), 7.11-7.09 (d,1H), 7.01-6.98 (dd,1H), 4.98-4.97 (d,1H), 4.41 (s,2H), 4.35 (s,1H), 3.86-3.82 (m,1H), 3.59-3.56 (dd,1H), 3.30 (s,2H), 3.25 (s,2H), 2.13-2.08 (m,1H), 2.02-1.99 (m,2H), 1.94-1.90 (dd,1H).

Example 93

Synthesis of 3-fluoro-2-(4-((5-((3S,5R)-3-hydroxy-1-oxa-7-azaspiro[4.4]nonan-7-yl)pyridin-2-yl)amino)-5-oxo-6,7-dihydro-5H-pyrrolo[3,4-b]pyridin-2-yl)benzonitrile, I-93

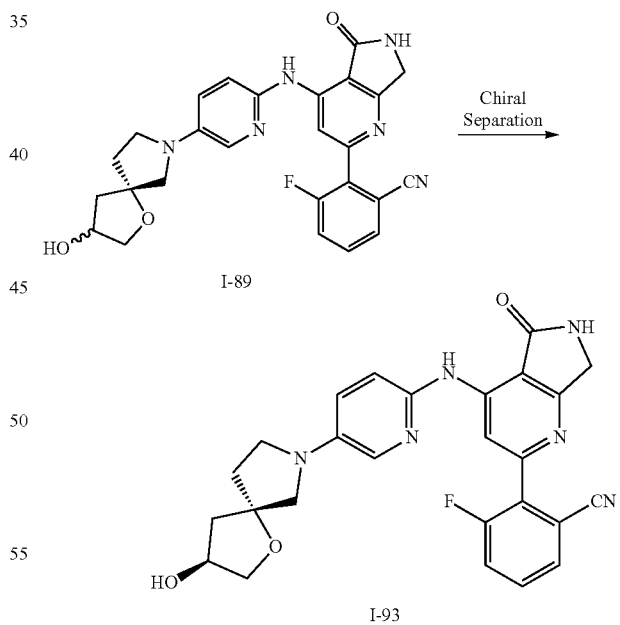

Compound I-93 was prepared by chiral separation of compound I-89. MS(ES): m/z 487.2 [M+H]$^+$; $^1$H NMR (DMSO-d$_6$, 400 MHz): δ 9.43 (s,1H), 8.81 (s,1H), 8.32 (s, 1H), 7.87-7.85 (d,1H), 7.77-7.71 (m,2H), 7.65-7.64 (d,1H), 7.11-7.09 (d,1H), 7.01-6.98 (dd,1H), 4.97 (s,1H), 4.41 (s,2H), 4.36 (s,1H), 3.86-3.83 (m,1H), 3.59-3.57 (dd,1H), 3.29 (s,1H), 3.26 (s, 2H), 2.13-2.08 (m,1H), 2.02-2.00 (m,2H), 1.94-1.91 (dd,1H).

Example 94

Tyk2 & JAK2 Radioactive Kinase Assay

Peptide substrate, [KKSRGDYMTMQIG], (20 μM) is prepared in reaction buffer (20 mM Hepes pH 7.5, 10 mM $MgCl_2$, 1 mM EGTA, 0.02% Brij35, 0.02 mg/mL BSA, 0.1 mM $Na_3PO_4$, 2 mM DTT, 1% DMSO. TYK2 (Invitrogen) kinase is added, followed by compounds in DMSO. 33PATP is added to initiate the reaction in ATP at 10 μM. Kinase reaction is incubated for 120 min at room temp and reactions are spotted onto P81 ion exchange paper (Whatman #3698-915), and then washed extensively in 0.75% phosphoric acid, prior to reading the radioactivity counts. For JAK2 (Invitrogen) kinase assay the peptide substrate poly[Glu: Tyr] (4:1), 0.2 mg/ml is used, in the reaction carried out the same as for TYK2.

Example 95

Tyk2 & JAK2 Caliper Assay

The caliper machine employs an off chip mobility shift assay to detect phosphorylated peptide substrates from kinase assays, using microfluidics technology. The assays are carried out at ATP concentration equivalent to the ATP Km, and at 1 mM ATP. Compounds are serially diluted in DMSO then further diluted in assay buffer (25 mM HEPES, pH 7.5, 0.01% Brij-35, 0.01% Triton, 0.5 mM EGTA). 5 ul of diluted compound was added into wells first, then 10 ul of enzyme mix was added into wells, followed by 10 uL of substrate mix (peptide and ATP in 10 mM $MgCl_2$) to start reaction. Reaction was incubated at 28° C. for 25 min and then added 25 ul stop buffer (100 mM HEPES, 0.015% Brij-35, 50 mM EDTA), followed by reading with Caliper. JAK2 at 1 nM final concentration and TYK2 at 9.75 nM are from Carna, and substrates used are ATP at 20 and 16 uM, respectively. JAK2 assay uses peptide 22 and TYK2 uses peptide 30 (Caliper), each at 3 uM.

Table 2 shows the activity of selected compounds of this invention in the Tyk2 and JAK2 activity inhibition assay. The compound numbers correspond to the compound numbers in Table 1. Compounds having an activity designated as "A" provided an Ki≤0.01 μM; compounds having an activity designated as "B" provided an Ki of 0.01-0.1 μM; compounds having an activity designated as "C" provided an Ki of 0.1-1.0 μM; and compounds having an activity designated as "D" provided an Ki≥1.0 μM.

TABLE 2

Tyk2 & JAK2 Activity Inhibition Data

| Compound # | Tyk2 Ki | JAK2 Ki |
|---|---|---|
| I-1 | A | C |
| I-2 | A | B |
| I-3 | A | C |
| I-4 | A | B |
| I-5 | A | C |
| I-6 | A | C |
| I-7 | A | C |
| I-8 | A | C |
| I-9 | B | B |
| I-10 | A | B |
| I-12 | A | C |
| I-13 | B | C |
| I-14 | A | C |
| I-15 | A | B |
| I-16 | A | C |
| I-17 | A | B |
| I-18 | A | B |
| I-19 | B | D |
| I-20 | A | B |
| I-21 | A | B |
| I-22 | A | B |
| I-23 | A | C |
| I-24 | A | A |
| I-25 | A | B |
| I-26 | A | C |
| I-27 | A | B |
| I-28 | A | C |
| I-29 | A | C |
| I-30 | A | C |
| I-31 | A | B |
| I-32 | A | D |
| I-33 | A | C |
| I-34 | A | B |
| I-35 | A | C |
| I-36 | A | B |
| I-37 | A | A |
| I-38 | A | A |
| I-39 | A | C |
| I-40 | C | D |
| I-41 | C | C |
| I-42 | A | B |
| I-43 | A | B |
| I-44 | A | C |
| I-45 | A | C |
| I-46 | B | C |
| I-47 | A | A |
| I-48 | B | C |
| I-48 | A | B |
| I-50 | A | B |
| I-51 | A | A |
| I-52 | A | A |
| I-53 | A | B |
| I-54 | A | B |
| I-55 | A | A |
| I-56 | B | C |
| I-57 | A | B |
| I-58 | A | A |
| I-59 | A | B |
| I-60 | A | B |
| I-61 | B | D |
| I-62 | A | B |
| I-63 | A | B |
| I-64 | A | B |
| I-65 | A | A |
| I-66 | A | B |
| I-67 | A | A |
| I-68 | B | C |
| I-69 | B | D |
| I-70 | A | C |
| I-71 | B | C |
| I-72 | B | D |
| I-73 | B | D |
| I-74 | A | C |
| I-75 | A | A |
| I-76 | A | B |
| I-77 | A | B |
| I-78 | A | B |
| I-79 | A | B |
| I-80 | A | B |
| I-81 | A | A |
| I-82 | A | A |
| I-83 | A | A |
| I-84 | B | D |
| I-85 | D | D |
| I-86 | A | B |
| I-87 | A | A |
| I-88 | A | A |
| I-89 | A | A |
| I-90 | A | A |

TABLE 2-continued

Tyk2 & JAK2 Activity Inhibition Data

| Compound # | Tyk2 Ki | JAK2 Ki |
|---|---|---|
| I-91 | A | A |
| I-92 | A | B |
| I-93 | A | B |

IL-12 Induced pSTAT4 in human PBMC. Human PBMC are isolated from buffy coat and are stored frozen for assays as needed. Cells for assay are thawed and resuspended in complete media containing serum, then cells are diluted to 1.67 E6 cells/ml so that 120 µl per well is 200,000 cells. 15 µl of compound or DMSO is added to the well at the desired concentrations and incubated at 1 hr at 37 C. 15 µl of stimulus (final concentration of 1.7 ng/mL IL-12) is added for 30 minutes prior to pSTAT4 and total STAT4 analysis using cell lysates prepared and analyzed by MSD reagents as per manufacturer protocol. The final DMSO concentration of compound in the assay is 0.1%.

GM-CSF Induced pSTAT5 in human PBMC. Cells are prepared for analysis as in the above procedure and 15 µl of GM-CSF (final concentration 5 ng/mL) is added for 20 minutes prior to pSTAT5 and total STAT5 analysis using cell lysates prepared and analyzed by MSD reagents as per manufacturer protocol. The final DMSO concentration of compound in the assay is 0.1%.

Table 3 shows the activity of selected compounds of this invention in the IL-12 induced pSTAT4 and GM-CSF induced pSTAT5 inhibition assays in human PBMC. The compound numbers correspond to the compound numbers in Table 1. Compounds having an activity designated as "A" provided an $EC_{50} \leq 2$ µM; compounds having an activity designated as "B" provided a $EC_{50}$ of 2-20 µM, and compounds having an activity designated as "C" provided an $EC_{50} > 20$ µM.

TABLE 3

Cell activity data

| Compound # | Tyk2-pSTAT4 $EC_{50}$ | JAK2-pSTAT5 $EC_{50}$ |
|---|---|---|
| I-1 | A | B |
| I-2 | A | B |
| I-4 | A | A |
| I-10 | A | A |
| I-15 | A | B |
| I-17 | A | B |
| I-18 | A | B |
| I-20 | A | C |
| I-25 | A | B |
| I-34 | A | B |
| I-36 | A | B |
| I-52 | A | A |
| I-58 | A | B |
| I-59 | A | B |
| I-60 | A | B |
| I-62 | A | A |
| I-65 | A | B |
| I-67 | A | B |
| I-70 | A | C |
| I-72 | C | C |
| I-75 | A | B |
| I-79 | A | B |
| I-84 | C | C |
| I-88 | A | A |
| I-89 | A | A |

TABLE 3-continued

Cell activity data

| Compound # | Tyk2-pSTAT4 $EC_{50}$ | JAK2-pSTAT5 $EC_{50}$ |
|---|---|---|
| I-91 | A | A |
| I-93 | A | B |

Acute Mouse Model for IL-12/IL-18 Induced IFNγ in serum—C57BL/6 mice mice are dosed PO or SC with test compound at various doses or vehicle (n=9 or 10 per group) and then, 30 minutes later, injected IP with 10 ng IL-12 and 1 µg IL-18. Three hours after IL-12/IL-18 injection, mice are bled and serum isolated. Concentration of cytokines in serum are determined using CBA analysis.

Certain compounds of the invention inhibit ~50% of the IL-12/IL-18 induced IFNγ production in vivo.

Ex vivo Mouse IL-12 induced IFNγ Studies C57/BL6 mice are given a single oral dose of either vehicle or different doses of compound at a volume of 10 mL/kg. 30 minutes to 1 hour after dosing, animals are euthanized and blood was collected via vena cava into sodium heparin blood collection tubes and inverted several times. Blood is then plated on anti-CD3 coated plates and stimulated with 2 ng/ml of mouse IL-12 in RPMI media for 24 hours at 37° C. in humidified incubator with 5% $CO_2$. At the end of the incubation, blood is centrifuged at 260 g for 5 minutes to collect supernatant. IFNγ concentration in the supernatant is determined with mouse IFNγ MSD kit per manufacture's instruction (Meso Scale Discovery). At the time of the blood collection, plasma is collected for drug level analysis by LC-MS/MS.

Certain compounds of the invention inhibit IL-12 induced IFNγ production in the ex-vivo mouse model.

T-ALL Cell Proliferation Assay T-ALL cell lines KOPT-K1, HPB-ALL, DND-41, PEER, and CCRF-CEM are cultured in RPMI-1640 medium with 10% fetal bovine serum and penicillin/streptomycin. Cells are plated in triplicate at $1 \times 10^4$ cells per well in 96-well plates. T-ALL cell lines DU.528, LOUCY, and SUP-T13 are cultured in the same medium and plated at a density of $1.5 \times 10^4$ cells per well. The cells are treated with DMSO or different concentrations of each compound of the invention. Cell viability at 72 hour exposure to the drug is assessed by CellTiter-Glo Luminescent Cell Viability Assay (Promega). CellTiter-Glo Reagent is added into the well and incubated for 10 minutes. Luminescence is measured subsequently using a 96-well plate luminescence reader. Cell viability is calculated by using the DMSO treated samples as 100%. $IC_{50}$ value is calculated by nonlinear regression using GraphPad Prism software.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A method of inhibiting TYK2 in a biological sample comprising contacting the sample with a compound of formula I, or a pharmaceutically acceptable salt thereof:

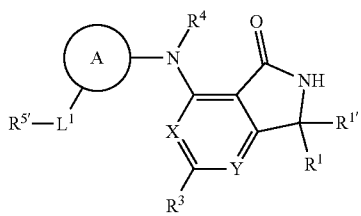

wherein:
each of X and Y is independently =C(R⁶)—, =N—, or =N⁺(→O⁻)—, provided that X and Y are not simultaneously =C(R⁶)—;
Ring A is phenyl; a 5-6 membered heteroaryl ring having 1-4 heteroatoms independently selected from nitrogen, oxygen, and sulfur; a 3-6 membered saturated or partially unsaturated heterocyclic ring having 1-2 heteroatoms independently selected from nitrogen, oxygen, and sulfur; or a 4-6 membered saturated or partially unsaturated carbocyclic ring; wherein Ring A is substituted with m instances of $R^7$;
each of $R^1$ and $R^{1'}$ is independently hydrogen, —$R^2$, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R; or
$R^1$ and $R^{1'}$ are taken together to form an oxo group or with their intervening atoms to form an optionally substituted 3-7 membered spiro-fused ring having 0-2 heteroatoms independently selected from nitrogen, oxygen, and sulfur;
each $R^2$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
$R^3$ is a group selected from $C_{1-6}$ alkyl, phenyl, a 3-7 membered saturated or partially unsaturated carbocyclic ring, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein $R^3$ is substituted with n instances of $R^8$;
$R^4$ is hydrogen or optionally substituted $C_{1-6}$ aliphatic; or $R^4$ and one instance of $R^7$ are taken together with their intervening atoms to form a 5-6 membered partially unsaturated or aromatic ring having 1-4 heteroatoms independently selected from nitrogen, oxygen and sulfur;
$R^{5'}$ is an 8-14 membered saturated or partially unsaturated heterocyclic ring having 1-4 heteroatoms independently selected from nitrogen, oxygen, and sulfur; wherein $R^{5'}$ is substituted with p instances of $R^9$;
$R^6$ is hydrogen, —$R^2$, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

each instance of $R^7$, $R^8$, $R^{10}$, and $R^{11}$ is independently oxo, —$R^2$, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;
each instance of $R^9$ is independently oxo, $C_{1-6}$ hydroxyaliphatic, —$R^2$, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;
$L^1$ is a covalent bond or a $C_{1-6}$ bivalent saturated or unsaturated, straight or branched hydrocarbon chain wherein one or two methylene units of the chain are optionally and independently replaced by —C(R¹⁰)₂—, —N(R)—, —N(R)C(O)—, —C(O)N(R)—, —N(R)S(O)₂—, —S(O)₂N(R)—, —O—, —C(O)—, —OC(O)—, —C(O)O—, —S—, —S(O)— or —S(O)₂—; or
$L^1$ and one instance of $R^7$ are taken together with their intervening atoms to form a 5-10 membered partially unsaturated or aromatic ring having 1-4 heteroatoms independently selected from nitrogen, oxygen, sulfur, and boron; wherein said ring is substituted by q instances of $R^{11}$; and $R^{5'}$ is attached to any position of the ring formed by $L^1$ and $R^7$;
m is 0-4;
n is 0-4;
p is 0-6;
q is 0-4; and
each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

2. A method of treating a TYK2-mediated disorder, disease, or condition in a patient wherein the disorder, disease, or condition is an autoimmune disorder selected from the group consisting of psoriasis, Crohn's disease, ulcerative colitis, and inflammatory bowel disease, comprising administering to said patient a compound of formula I, or a pharmaceutical composition thereof:

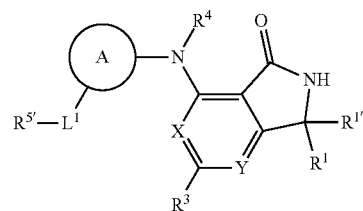

or a pharmaceutically acceptable salt thereof, wherein:
each of X and Y is independently =C(R⁶)—, =N—, or =N⁺(→O⁻)—, provided that X and Y are not simultaneously =C(R⁶)—;

Ring A is phenyl; a 5-6 membered heteroaryl ring having 1-4 heteroatoms independently selected from nitrogen, oxygen, and sulfur; a 3-6 membered saturated or partially unsaturated heterocyclic ring having 1-2 heteroatoms independently selected from nitrogen, oxygen, and sulfur; or a 4-6 membered saturated or partially unsaturated carbocyclic ring; wherein Ring A is substituted with m instances of $R^7$;

each of $R^1$ and $R^{1'}$ is independently hydrogen, $-R^2$, halogen, $-CN$, $-NO_2$, $-OR$, $-SR$, $-NR_2$, $-S(O)_2R$, $-S(O)_2NR_2$, $-S(O)R$, $-C(O)R$, $-C(O)OR$, $-C(O)NR_2$, $-C(O)N(R)OR$, $-OC(O)R$, $-OC(O)NR_2$, $-N(R)C(O)OR$, $-N(R)C(O)R$, $-N(R)C(O)NR_2$, or $-N(R)S(O)_2R$; or $R^1$ and $R^{1'}$ are taken together to form an oxo group or with their intervening atoms to form an optionally substituted 3-7 membered spiro-fused ring having 0-2 heteroatoms independently selected from nitrogen, oxygen, and sulfur;

each $R^2$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$R^3$ is a group selected from $C_{1-6}$ alkyl, phenyl, a 3-7 membered saturated or partially unsaturated carbocyclic ring, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein $R^3$ is substituted with n instances of $R^8$;

$R^4$ is hydrogen or optionally substituted C1-6 aliphatic; or $R^4$ and one instance of $R^7$ are taken together with their intervening atoms to form a 5-6 membered partially unsaturated or aromatic ring having 1-4 heteroatoms independently selected from nitrogen, oxygen and sulfur;

$R^{5'}$ is an 8-14 membered saturated or partially unsaturated heterocyclic ring having 1-4 heteroatoms independently selected from nitrogen, oxygen, and sulfur; wherein $R^{5'}$ is substituted with p instances of $R^9$;

$R^6$ is hydrogen, $-R^2$, halogen, $-CN$, $-NO_2$, $-OR$, $-SR$, $-NR_2$, $-S(O)_2R$, $-S(O)_2NR_2$, $-S(O)R$, $-C(O)R$, $-C(O)OR$, $-C(O)NR_2$, $-C(O)N(R)OR$, $-OC(O)R$, $-OC(O)NR_2$, $-N(R)C(O)OR$, $-N(R)C(O)R$, $-N(R)C(O)NR_2$, or $-N(R)S(O)_2R$;

each instance of $R^7$, $R^8$, $R^{10}$, and $R_{11}$ is independently oxo, $-R^2$, halogen, $-CN$, $-NO_2$, $-OR$, $-SR$, $-NR_2$, $-S(O)_2R$, $-S(O)_2NR_2$, $-S(O)R$, $-C(O)R$, $-C(O)OR$, $-C(O)NR_2$, $-C(O)N(R)OR$, $-OC(O)R$, $-OC(O)NR_2$, $-N(R)C(O)OR$, $-N(R)C(O)R$, $-N(R)C(O)NR_2$, or $-N(R)S(O)_2R$;

each instance of $R^9$ is independently oxo, $C_{1-6}$ hydroxyaliphatic, $-R^2$, halogen, $-CN$, $-NO_2$, $-OR$, $-SR$, $-NR_2$, $-S(O)_2R$, $-S(O)_2NR_2$, $-S(O)R$, $-C(O)R$, $-C(O)OR$, $-C(O)NR_2$, $-C(O)N(R)OR$, $-OC(O)R$, $-OC(O)NR_2$, $-N(R)C(O)OR$, $-N(R)C(O)R$, $-N(R)C(O)NR_2$, or $-N(R)S(O)_2R$;

$L^1$ is a covalent bond or a $C_{1-6}$ bivalent saturated or unsaturated, straight or branched hydrocarbon chain wherein one or two methylene units of the chain are optionally and independently replaced by $-C(R^{10})_2-$, $-N(R)-$, $-N(R)C(O)-$, $-C(O)N(R)-$, $-N(R)S(O)_2-$, $-S(O)_2N(R)-$, $-O-$, $-C(O)-$, $-OC(O)-$, $-C(O)O-$, $-S-$, $-S(O)-$ or $-S(O)_2-$; or $L^1$ and one instance of $R^7$ are taken together with their intervening atoms to form a 5-10 membered partially unsaturated or aromatic ring having 1-4 heteroatoms independently selected from nitrogen, oxygen, sulfur, and boron; wherein said ring is substituted by q instances of $R^{11}$; and $R^{5'}$ is attached to any position of the ring formed by $L^1$ and $R^7$;

m is 0-4;

n is 0-4;

p is 0-6;

q is 0-4; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

3. A method of treating a TYK2-mediated disorder, disease, or condition in a patient wherein the disorder, disease, or condition is an inflammatory disorder selected from the group consisting of rheumatoid arthritis, asthma, chronic obstructive pulmonary disease, psoriasis, Crohn's disease, ulcerative colitis, and inflammatory bowel disease, comprising administering to said patient a compound of formula I, or a pharmaceutical composition thereof:

or a pharmaceutically acceptable salt thereof, wherein:

each of X and Y is independently $=C(R^6)-$, $=N-$, or $=N^+(\rightarrow O^-)-$, provided that X and Y are not simultaneously $=C(R^6)-$;

Ring A is phenyl; a 5-6 membered heteroaryl ring having 1-4 heteroatoms independently selected from nitrogen, oxygen, and sulfur; a 3-6 membered saturated or partially unsaturated heterocyclic ring having 1-2 heteroatoms independently selected from nitrogen, oxygen, and sulfur; or a 4-6 membered saturated or partially unsaturated carbocyclic ring; wherein Ring A is substituted with m instances of $R^7$;

each of $R^1$ and $R^{1'}$ is independently hydrogen, $-R^2$, halogen, $-CN$, $-NO_2$, $-OR$, $-SR$, $-NR_2$, $-S(O)_2R$, $-S(O)_2NR_2$, $-S(O)R$, $-C(O)R$, $-C(O)OR$, $-C(O)NR_2$, $-C(O)N(R)OR$, $-OC(O)R$, $-OC(O)NR_2$, $-N(R)C(O)OR$, $-N(R)C(O)R$, $-N(R)C(O)NR_2$, or $-N(R)S(O)_2R$; or R¹ and R¹' are taken together to form an oxo group or with their intervening atoms to form an optionally substituted 3-7 membered spiro-fused ring having 0-2 heteroatoms independently selected from nitrogen, oxygen, and sulfur;

each R² is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

R³ is a group selected from $C_{1-6}$ alkyl, phenyl, a 3-7 membered saturated or partially unsaturated carbocyclic ring, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein R³ is substituted with n instances of R⁸;

R⁴ is hydrogen or optionally substituted $C_{1-6}$ aliphatic; or R⁴ and one instance of R⁷ are taken together with their intervening atoms to form a 5-6 membered partially unsaturated or aromatic ring having 1-4 heteroatoms independently selected from nitrogen, oxygen and sulfur;

R⁵' is an 8-14 membered saturated or partially unsaturated heterocyclic ring having 1-4 heteroatoms independently selected from nitrogen, oxygen, and sulfur; wherein R⁵' is substituted with p instances of R⁹;

R⁶ is hydrogen, —R², halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

each instance of R⁷, R⁸, R¹⁰, and R¹¹ is independently oxo, —R², halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

each instance of R⁹ is independently oxo, $C_{1-6}$ hydroxyaliphatic, —R², halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

L¹ is a covalent bond or a $C_{1-6}$ bivalent saturated or unsaturated, straight or branched hydrocarbon chain wherein one or two methylene units of the chain are optionally and independently replaced by —C(R¹⁰)₂—, —N(R)—, —N(R)C(O)—, —C(O)N(R)—, —N(R)S(O)₂—, —S(O)₂N(R)—, —O—, —C(O)—, —OC(O)—, —C(O)O—, —S—, —S(O)— or —S(O)₂—; or L¹ and one instance of R⁷ are taken together with their intervening atoms to form a 5-10 membered partially unsaturated or aromatic ring having 1-4 heteroatoms independently selected from nitrogen, oxygen, sulfur, and boron; wherein said ring is substituted by q instances of R¹¹; and R⁵' is attached to any position of the ring formed by L¹ and R⁷;

m is 0-4;
n is 0-4;
p is 0-6;
q is 0-4; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

4. A method of treating a TYK2-mediated disorder, disease, or condition in a patient wherein the disorder, disease or condition is transplant rejection or graft versus host disease, comprising administering to said patient a compound of formula I, or a pharmaceutical composition thereof:

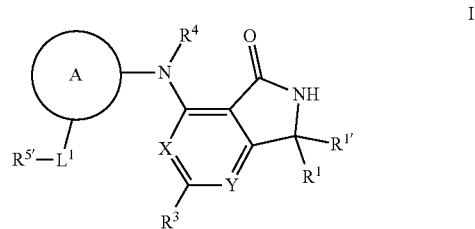

or a pharmaceutically acceptable salt thereof, wherein:
each of X and Y is independently =C(R⁶)—, =N—, or =N⁺(→O⁻)—, provided that X and Y are not simultaneously =C(R⁶)—;

Ring A is phenyl; a 5-6 membered heteroaryl ring having 1-4 heteroatoms independently selected from nitrogen, oxygen, and sulfur; a 3-6 membered saturated or partially unsaturated heterocyclic ring having 1-2 heteroatoms independently selected from nitrogen, oxygen, and sulfur; or a 4-6 membered saturated or partially unsaturated carbocyclic ring; wherein Ring A is substituted with m instances of R⁷;

each of R¹ and R¹' is independently hydrogen, —R², halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R; or R¹ and R¹' are taken together to form an oxo group or with their intervening atoms to form an optionally substituted 3-7 membered spiro-fused ring having 0-2 heteroatoms independently selected from nitrogen, oxygen, and sulfur;

each R² is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

R³ is a group selected from $C_{1-6}$ alkyl, phenyl, a 3-7 membered saturated or partially unsaturated carbocyclic ring, a 3-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; wherein $R^3$ is substituted with n instances of $R^8$;

$R^4$ is hydrogen or optionally substituted $C_{1-6}$ aliphatic; or $R^4$ and one instance of $R^7$ are taken together with their intervening atoms to form a 5-6 membered partially unsaturated or aromatic ring having 1-4 heteroatoms independently selected from nitrogen, oxygen and sulfur;

$R^{5'}$ is an 8-14 membered saturated or partially unsaturated heterocyclic ring having 1-4 heteroatoms independently selected from nitrogen, oxygen, and sulfur; wherein $R^{5'}$ is substituted with p instances of $R^9$;

$R^6$ is hydrogen, —$R^2$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

each instance of $R^7$, $R^8$, $R^{10}$, and $R^{11}$ is independently oxo, —$R^2$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

each instance of $R^9$ is independently oxo, $C_{1-6}$ hydroxyaliphatic, —$R^2$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$L^1$ is a covalent bond or a $C_{1-6}$ bivalent saturated or unsaturated, straight or branched hydrocarbon chain wherein one or two methylene units of the chain are optionally and independently replaced by —C(R$^{10}$)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—; or $L^1$ and one instance of $R^7$ are taken together with their intervening atoms to form a 5-10 membered partially unsaturated or aromatic ring having 1-4 heteroatoms independently selected from nitrogen, oxygen, sulfur, and boron; wherein said ring is substituted by q instances of $R^{11}$; and $R^{5'}$ is attached to any position of the ring formed by $L^1$ and $R^7$;

m is 0-4;

n is 0-4;

p is 0-6;

q is 0-4; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

5. The method of claim 2, wherein Ring A is phenyl, pyridin-2-yl, pyridine-3-yl, or pyrazol-4-yl.

6. The method of claim 5, wherein Ring A is pyridin-2-yl.

7. The method of claim 2, wherein X is =C(R$^6$)—; and Y is =N—.

8. The method of claim 7, wherein $R^6$ is hydrogen.

9. The method of claim 2, wherein $L^1$ is —CH$_2$C(O)—, —C(O)—, or a covalent bond.

10. The method of claim 9, wherein $L^1$ is a covalent bond.

11. The method of claim 2, wherein $R^3$ is phenyl, pyrrolidinyl, or piperidinyl.

12. The method of claim 11, wherein $R^3$ is phenyl.

13. The method of claim 2, wherein n is 2, and at least one $R^8$ is fluoro.

14. The method of claim 3, wherein Ring A is phenyl, pyridin-2-yl, pyridine-3-yl, or pyrazol-4-yl.

* * * * *